United States Patent
Uchikawa et al.

(10) Patent No.: US 6,949,648 B2
(45) Date of Patent: Sep. 27, 2005

(54) CONDENSED PYRAZOLE DERIVATIVES, PROCESS FOR PRODUCING THE SAME AND USE THEREOF

(75) Inventors: Osamu Uchikawa, Kobe (JP); Keita Mitsui, Suita (JP); Akiko Asakawa, Takatsuki (JP); Shigeru Morimoto, Tondabayashi (JP); Masataka Yamamoto, Osaka (JP); Hiroyuki Kimura, Sakai (JP); Takeo Moriya, Mino (JP); Masahiro Mizuno, Mishima-gun (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/239,978

(22) PCT Filed: Mar. 27, 2001

(86) PCT No.: PCT/JP01/02439

§ 371 (c)(1),
(2), (4) Date: Sep. 25, 2002

(87) PCT Pub. No.: WO01/72749

PCT Pub. Date: Oct. 4, 2001

(65) Prior Publication Data

US 2003/0187014 A1 Oct. 2, 2003

(30) Foreign Application Priority Data

Mar. 27, 2000 (JP) ........................ 2000-086313
Mar. 27, 2000 (JP) ........................ 2000-086524

(51) Int. Cl.[7] ...................... C07D 401/14; C07D 413/14
(52) U.S. Cl. ...................... 546/82; 544/126; 544/333; 546/83
(58) Field of Search ........................... 546/82, 83, 119; 544/126, 333; 514/293, 256, 303

(56) References Cited

U.S. PATENT DOCUMENTS

| | | | |
|---|---|---|---|
| 3,855,675 A | 12/1974 | Denzel et al. | |
| 3,903,096 A | 9/1975 | Denzel et al. | |
| 3,935,222 A | 1/1976 | Hoehn | |
| 4,111,940 A | 9/1978 | Hoehn et al. | 260/293.6 |
| 4,179,564 A | 12/1979 | Hoehn et al. | 546/64 |
| 4,920,128 A | 4/1990 | Bell et al. | 514/293 |
| 5,506,236 A | 4/1996 | Afonso et al. | 514/293 |
| 5,595,998 A * | 1/1997 | Wolin et al. | 514/293 |
| 5,597,821 A | 1/1997 | Wolin et al. | 514/126 |

FOREIGN PATENT DOCUMENTS

| | | |
|---|---|---|
| EP | 0 254 241 | 1/1988 |
| EP | 0 339 358 | 11/1989 |
| JP | 62230782 | 10/1987 |
| JP | 01190681 | 7/1989 |
| JP | 3271289 | 12/1991 |
| JP | 07002786 | 1/1995 |

OTHER PUBLICATIONS

Compounds with RN 113576–39–9 and 114072–97–8 ( disclosed in a Russian Journal, Vysokochistye Veshchestva (1987 ).*
Ostrovskaya, V., et al.,"Analytically ready forms and reagents for their preparation. I. Immobilization of pyrazolyl–containing formazans and hydrazones on a paper base for rapid tests as a means for achieving . . . ", *Vysokochistye Veshchestva* (1987), vol. 4, pp. 178–182 (English Abstract Only).
Harry R. Snyder, Jr., "1H–Pyrazolo[3,4–b]pyridines" J. Heterocycle Chem. 12(6):1303–1304 (1975).
Wolin, et al. "Sythesis and Evaluation of Pyrazolo[a3,4–b] Quinoline Ribofuranosides and Their Derivatives as Inhibitors of Oncogenic Ras" Bioorganic & Medicinal Chemistry Letters 6(2): 195–200(1966).
Y. Tominaga, et al. "Synthesis and Chemiluminescence of 1,3–Disubstituted Pyrazolo[4',3':5,6]Pyrido[2,3–d]Pyridazine–5,8(6H,7H)–Diones and Related Compounds" Tetrahedron Letters 36(47): 8641–8644(1995).
Farghaly, et al. "Synthesis of Some Thiazole–, 1,34–Thiadiazole–, and 4H–1,2,4–Triazole Derivatives of Pyrazolo[3, 4–b]quinoline".
Nielsen, et al. "Synthesis of 4–Arylamino–5,6,7, 8–tetrahydro–1H–pyrazolo[3,4–b]quinolines and the Corresponding N–Mannich Bases" Liebigs Ann. Chem. 1728–1735(1986).
Tomasik, et al. "Friedländer Condensation of 1H–Pyrazolin–5–ones with o–Aminobenzaldehydes. Synthesis of 1H–Pyrazolo[3,4–b]quinolines" J. Heterocyclic Chem. 20: 1539–1543 (1983).
Kidwai, et al. "Synthesis of Some Novel Substituted Quinolines as Potent Analgesic Agents" Monatshefte Fur Chemie 128: 85–89(1997).

* cited by examiner

*Primary Examiner*—Charanjit S. Aulakh
(74) *Attorney, Agent, or Firm*—Elaine M. Ramesh; Mark Chao

(57) ABSTRACT

Novel pharmaceutical compositions for inhibiting Th2-selective immune response and pharmaceutical compositions for inhibiting cyclooxygenase comprising condensed pyrazole derivatives represented by the general formula (I):

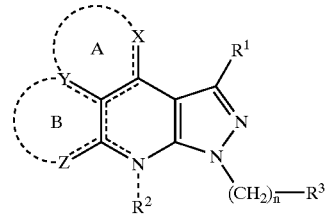

or salts thereof.

7 Claims, No Drawings

CONDENSED PYRAZOLE DERIVATIVES, PROCESS FOR PRODUCING THE SAME AND USE THEREOF

This application is the National Phase filing of International Patent Application No. PCT/JP01/02439, filed Mar. 27, 2001, now WO 01/72749.

FIELD OF THE INVENTION

The present invention relates to a novel condensed pyrazole derivative, which is useful as a preventive and/or therapeutic agent for diseases caused by immune malfunction and accompanied by immune malfunction, and for graft rejection and graft versus host diseases associated with transplantation of organs and bone marrow, and which has excellent anti-inflammatory and analgesic and antipyretic activities, a process for producing the same, and the use thereof.

BACKGROUND ART

Mosmann et al., proposed that helper T cells (Th), lymphocytes playing a central role in immune responses, could be classified into two subsets, Th1 and Th2 cells, according to secretion patterns of cytokines [J. Immunol., vol. 136, p. 2348 (1986)]. Since then, several reports indicating that abnormality in the balance of Th1 and Th2 cells is closely involved in onset and aggravation of diseases caused by immune malfunction such as allergic diseases and autoimmune diseases and of diseases associated with immune malfunction have been published [Medical Immunology, vol. 15, p. 401 (1988); Annual Review of Immunology, vol. 12, p. 227 (1994); and Immunology Today, vol. 17, p. 138 (1996)].

Among the diseases above, allergic diseases are believed to be caused mainly by an increase in the number and the accentuation of Th2 cells, and an increase in production of IgE antibodies, IL-4 and IL-5 are said to be one of the aggravation factors. IL-4, one of cytokines produced in Th2 cell, accelerates production of IgE antibodies, while IL-5 accelerates differentiation, proliferation and migration of acidocytes, and also has a life-extending effect on the cells. Therefore, a medicine to suppress the functions of Th2 cell has a potential to relieve symptoms of the allergic diseases. Antiallegic drugs currently available, mainly suppressing immediate allergic responses, are not so effective for late-onset allergic diseases such as severe asthma and atopic dermatitis in the allergic diseases. Steroid drugs are often used for that purpose, but various side effects associated with taking such drugs for a long period of time (such as steroid skin diseases, adrenal cortical incompetence, etc.) are cited as the disadvantage.

Additionally, cyclosporin and tacrolimus are also used as the immunosuppressive drugs, but these drugs are non-specific, i.e., suppressing immune responses of Th2 side as well as Th1 side, and thus the administration thereof often lead to deterioration in resistance to infection and cause severe side effects such as nephrotoxicity and hepatotoxicity. Condensed heterocyclic compounds having suppressive activities to the Th2 immune responses have been described in JP 10-298181 A, JP 10-324631 A, JP 10-330369 A, WO98/47899 and J. Immunol., 162, 7470 (1999), but hitherto, no condensed pyrazole derivatives having the suppressive activity to the Th2 immune responses have been reported.

Pyrazolo[3,4-b]pyridine derivatives relevant to the present invention have been described in JP 48-57995 A (1973), JP 48-81891 A, U.S. Pat. No. 3,840,546 (1974), and Arch. Pharma., vol. 307, p. 117 (1974).

Non-steroidal anti-inflammatory drugs (NSAIDs) have been widely used for treatment of the inflammatory diseases such as inflammation, pain, fever, but these drugs also have clinical disadvantage in that they are not free from the side effect of gastrointestinal disorders adequately.

Recently, a hypothesis that cyclooxygenase (COX), the site of action of the non-steroidal anti-inflammatory agents, has two isozymes, COX-1 and COX-2, and inhibition of the COX-1, the constitutive enzyme thereof, could trigger gastrointestinal disorders was proposed. Since then, development of a COX-2 selective inhibitor has been intensively carried out to overcome the problems of gastrointestinal disorders. Consequently, Celecoxib and Rofecoxib are brought on the market in 1999, from Searle and Merck respectively, as NSAIDs that have fewer problems of the gastrointestinal disorders. But, a fact that a COX-1 knock-out mouse does not have gastric disorder was pointed out, for example, in Cell, vol. 83, p. 483 (1995), and a fact that even the COX-1 selective inhibitors have fewer cases of stomach disorders if they do not induce apoptosis of the gastric mucosal cells was also reported in Eur. J. Pharm., vol. 380, p. 271 (1998), and thus there is still doubt in that the COX-2 selective inhibitor can completely conquer the problem of the gastrointestinal disorders.

DISCLOSURE OF THE INVENTION

An object of the present invention is to provide a novel Th2-selective immune response suppressant which can be used, effectively and with fewer side effects, for prevention and/or treatment of allergic diseases by selectively suppressing Th2 side immune responses typified by production of cytokines such as IL-4 and 1L-5 and IgE antibodies both of which are involved in the allergic responses, and by controlling the balance of Th1 and Th2 cells.

As described above, the conventional NSAIDs have potent medicinal activities, but also the inevitable problem of gastrointestinal disorders, and thus had a disadvantage in that the administration thereof to a patient over a long period of time or to the elderly was difficult. Development of a novel compound satisfactory as the drug for the diseases described above has been highly desired. On the other hand, development of a new COX inhibitor, having no carboxyl groups characteristic in the conventional NSAIDs, and thus having a basic chemical structure completely different from those of the conventional anti-inflammatory drugs, is also desirable since the COX inhibitor has a potential to be a drug having excellent anti-inflammatory, analgesic and antipyretic actions and having fewer problems of gastrointestinal disorders.

Another object of the present invention is to develop such a COX inhibitor.

After an intensive study, the present inventors have found that a condensed pyrazole derivative represented by the formula (I):

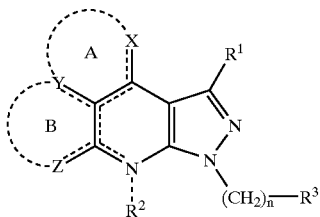

wherein, $R^1$ is a hydrogen atom, a hydrocarbon group which may be optionally substituted, an amino group which may be optionally substituted, a thiol group which may be optionally substituted, or a carboxyl group which may be optionally esterified or amidated; $R^2$ is unsubstituted, or a hydrogen atom or a hydrocarbon group which may be optionally substituted; $R^3$ is a heterocyclic group which may be optionally substituted; X, Y, and Z are, respectively, hydrogen, halogen, nitrile, a hydrocarbon group which may be optionally substituted, a carboxyl group which may be esterified or amidated, an acyl group which may be optionally substituted, —$NR^4R^5$, an oxygen atom, $OR^4$, a sulfur atom, or $SR^4$ ($R^4$ and $R^5$ are, respectively, a hydrogen atom, a hydrocarbon group which may be optionally substituted, or a heterocyclic group which may be optionally substituted, or may bind each other to form a cyclic amino group or a heterocyclic group with the nitrogen bound thereto), or X and Y may bind each other to form ring A, or Y and Z may bind each other to form ring B; bond portions indicated by both solid and broken lines are, respectively, a single bond or a double bond, and bond portions indicated by a broken line are, respectively, a single bond or unsubstituted; ring A is a homocyclic or heterocyclic 5- to 7-membered ring which may be optionally substituted; ring B is a homocyclic or heterocyclic 5- to 7-membered ring which may be optionally substituted; and n is an integer of 0 or 1, or a salt thereof suppresses selectively the Th2 side immune responses by inhibiting production of cytokines such as IL-4 and IL-5 and the production of IgE antibodies, but has no influence on IFN-γ, a cytokine of Th1 side, and on the basis of the finding, the present invention was completed after further studies.

The present invention provides a pharmaceutical composition for selectively suppressing the Th2 immune responses comprising a condensed pyrazole derivative represented by the formula (I) [hereinafter, occasionally referred to as compound (I)] or a salt thereof. The pharmaceutical composition of the present invention is useful, especially, as a preventive and/or therapeutic agent for diseases caused by immune malfunction or associated with immune malfunction, as a preventive and/or therapeutic agent for graft rejection, as a preventive and/or therapeutic agent for graft versus host diseases, as a preventive and/or therapeutic agent for allergic diseases, and as a regulator of Th1/Th2 balance.

The present invention also provides a process for producing a novel compound, a condensed pyrazole derivative, represented by the formula (I'):

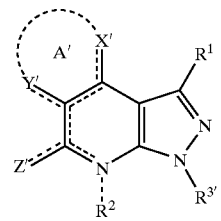

wherein, $R^1$ is a hydrogen atom, a hydrocarbon group which may be optionally substituted, an amino group which may be optionally substituted, a thiol group which may be optionally substituted, or a carboxyl group which may be optionally esterified or amidated; $R^2$ is unsubstituted, a hydrogen atom, or a hydrocarbon group which may be optionally substituted; $R^{3'}$ is an unsaturated heterocyclic group having only a nitrogen atom as the hetero atom, which may be optionally substituted; X', Y', and Z' are respectively, hydrogen, halogen, nitrile, a hydrocarbon group which may be optionally substituted, a carboxyl group which may be optionally esterified or amidated, an acyl group which may be optionally substituted, —$CON_3$, —$NR^4R^5$, =N—N=$R^4$, —$N_3$, an oxygen atom, —$OR^4$, a sulfur atom, or —$SR^4$ ($R^4$ and $R^5$ are, respectively, a hydrogen atom, a hydrocarbon group which may be optionally substituted, a heterocyclic group which may be optionally substituted, or may bind each other to form a cyclic amino group or a heterocyclic group with the nitrogen bound thereto), or X' and Y' may bind each other to form ring A', while one of X' and Z' is an oxygen atom or —$OR^4$; bond portions indicated by solid and broken lines are, respectively, a single bond or a double bond, and a bond portion indicated by a broken line is a single bond or unsubstituted; and ring A' is a homocyclic or heterocyclic 5- to 7-membered ring which may be optionally substituted [hereinafter, occasionally referred to as compound (I')], or a salt thereof, useful as an active component for the pharmaceutical compositions described above or an intermediate for the production thereof.

Additionally, after an intensive study, the present inventors have found that a compound (I) or a salt thereof, especially, a pyrazoloquinoline derivative represented by the formula:

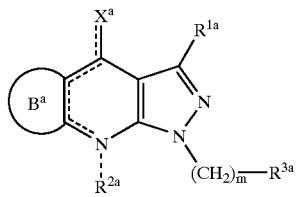

wherein, $R^{1a}$ is a hydrogen atom, a hydrocarbon group which may be optionally substituted, or a carboxyl group which may be optionally esterified or amidated; $R^{2a}$ is unsubstituted, a hydrogen atom, or a hydrocarbon group which may be optionally substituted; $R^{3a}$ is a heterocyclic group which may be optionally substituted; $X^a$ is hydrogen, halogen, nitrile, a hydrocarbon group which may be optionally substituted, a carboxyl group which may be optionally esterified or amidated, an acyl group which may be optionally substituted, —$NR^{4a}R^{5a}$, an oxygen atom, —$OR^{4a}$, a sulfur atom, or —$SR^{4a}$ ($R^{4a}$ and $R^{5a}$ are, respectively, a hydrogen atom, a hydrocarbon group which may be optionally substituted, or may bind each other to form a cyclic amino group or a heterocyclic group with the nitrogen atom bound thereto); bond portions indicated by solid and broken lines are, respectively, a single bond or a double bond, and bond portions indicated by a broken line are, respectively, a single bond or unsubstituted; $B^a$ ring is a homocyclic or heterocyclic 5- to 7-membered ring which may be optionally substituted; and m is an integer of 0 or 1, or a salt thereof has the desired COX inhibition activity, and the present invention was completed.

Meanwhile, a pyrazoloquinoline derivative represented by the formula:

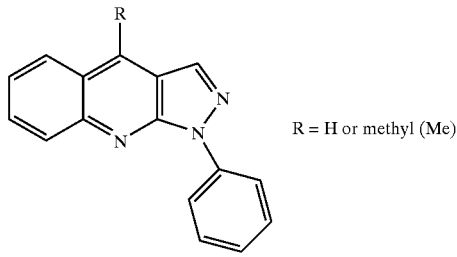

R = H or methyl (Me)

was described to have an analgesic activity in Monatsh. Chem., vol. 128, p. 85 (1997).

Therefore, the present invention provides a pharmaceutical composition comprising a pyrazole derivative represented by the formula (I) or a salt thereof, useful as a pharmaceutical composition for inhibiting COX, especially as a preventive and/or therapeutic agent of inflammatory diseases, as a preventive and/or therapeutic agent of arthritis, as a preventive and/or therapeutic agent of rheumatism, and as a preventive and/or therapeutic agent of chronic rheumatoid arthritis.

A pyrazoloquinoline derivative represented by the formula (Ia'):

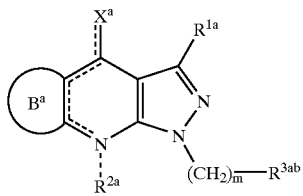

wherein, $R^{1a}$ is a hydrogen atom, a hydrocarbon group which may be optionally substituted, or a carboxyl group which may be optionally esterified or amidated; $R^{2a}$ is unsubstituted, a hydrogen atom, or a hydrocarbon group which may be optionally substituted; $R^{3ab}$ is an unsaturated heterocyclic group having 2 or less nitrogen atoms as the hetero atoms which may be optionally substituted, or an unsaturated monocyclic heterocyclic group having a nitrogen atom and a sulfur atom as the hetero atoms; $X^a$ is hydrogen, halogen, nitrile and a hydrocarbon group which may be optionally substituted, a carboxyl group which may be optionally esterified or amidated, an acyl group which may be optionally substituted, —$NR^{4a}R^{5a}$, an oxygen atom, —$OR^{4a}$, a sulfur atom, or —$SR^{4a}$ ($R^{4a}$ and $R^{5a}$ are, respectively, a hydrogen atom, a hydrocarbon group which may be optionally substituted, or may bind each other to form a cyclic amino group or a heterocyclic group with the nitrogen atom bound thereto); bond portions indicated by solid and broken lines are, respectively, a single bond or a double bond, and bond portions indicated by a broken line are, respectively, a single bond or unsubstituted; ring $B^a$ is a homocyclic or heterocyclic 5- to 7-membered ring which may be optionally substituted; and m is an integer of 0 or 1, or a salt thereof is a novel compound that has not been described in literature. The present invention also provides a process for producing the novel pyrazoloquinoline derivative represented by the formula (Ia') or the salt thereof.

DETAILED DESCRIPTION OF THE INVENTION

Each of the condensed pyrazole derivatives represented by formulas (I), (I'), (Ia), and (Ia') may be present as forms of various isomers, but it should be construed that both isolated isomers and mixture of isomers are included in the compounds represented by formulas (I), (I'), (Ia), and (Ia') in the present specification.

The terms, "Th1" and "Th2", indicate, respectively, "type 1 helper T cell" and "type 2 helper T cell" in the present specification.

The "hydrocarbon groups", in the phrase "a hydrocarbon group which may be optionally substituted" used in the present specification, are, for example, an aliphatic hydrocarbon group, a saturated monocyclic hydrocarbon group, an aromatic hydrocarbon group, etc., preferably the group having 1 to 16 carbons. More specifically, examples of the hydrocarbon group are alkyl groups, alkenyl groups, alkynyl groups, cycloalkyl groups, and aryl groups, etc.

Preferred examples of "the alkyl group" include a lower alkyl group or the like, more specifically, $C_{1-6}$ alkyl groups such as methyl, ethyl, propyl, isopropyl, butyl, isobutyl, sec-butyl, and tert-butyl, pentyl, hexyl, etc.

Preferred examples of "the alkenyl group" are lower alkenyl groups or the like, more specifically $C_{2-6}$ alkenyl groups such as vinyl, 1-propenyl, allyl, isopropenyl, butenyl, and isobutenyl, etc.

Preferred examples of "the alkynyl group" are lower alkynyl groups or the like, more specifically a $C_{2-6}$ alkynyl group such as ethynyl, propargyl, and 1-propynyl, etc.

Preferred examples of "the cycloalkyl group" are lower cycloalkyl groups or the like, more specifically $C_{3-6}$ cycloalkyl groups such as cyclopropyl, cyclobutyl, cyclopentyl, and cyclohexyl, etc.

Preferred examples of "the aryl group" are $C_{6-14}$ aryl groups or the like, such as phenyl, 1-naphthyl, 2-naphthyl, biphenylyl, 2-indenyl, and 2-anthryl, etc., more preferably phenyl group, etc.

Examples of the substituent of "the hydrocarbon group" in "the hydrocarbon group which may be optionally substituted" include halogen atoms (e.g., fluorine, chlorine, bromine, iodine, etc.); a nitro group; a cyano group; a hydroxyl group; lower alkyl groups which may be optionally halogenated (e.g., $C_{1-6}$ alkyl groups which may be optionally halogenated such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, etc.); lower alkoxy groups (e.g., $C_{1-6}$ alkoxy groups such as methoxy, ethoxy, propoxy, isopropoxy, cyclopropoxy, butoxy, isobutoxy, cyclobutoxy, pentyloxy, cyclopentyloxy, hexyloxy, cyclohexyloxy, etc.); an amino group; mono-lower alkylamino groups (e.g., mono-$C_{1-6}$ alkylamino groups such as methylamino, ethylamino, etc.); di-lower alkylamino groups (e.g., di-$C_{1-6}$ alkylamino groups such as dimethylamino, diethylamino, etc.); a carboxyl group; lower alkyl carbonyl groups (e.g., $C_{1-6}$ alkylcarbonyl groups such as acetyl, propionyl, etc.); lower alkoxycarbonyl groups (e.g., $C_{1-6}$ alkoxycarbonyl groups such as methoxycarbonyl, ethoxycarbonyl, propoxycarbonyl, butoxycarbonyl, etc.); a carbamoyl group; mono-lower alkylcarbamoyl groups (e.g., mono-$C_{1-6}$ alkylcarbamoyl groups such as methylcarbamoyl, ethylcarbamoyl, etc.); di-lower alkylcarbamoyl groups (e.g., di-$C_{1-6}$ alkylcarbamoyl groups such as dimethylcarbamoyl, diethylcarbamoyl, etc.); arylcarbamoyl groups (e.g., $C_{6-10}$ arylcarbamoyl groups such as phenylcarbamoyl, naphthylcarbamoyl, etc.); aryl groups (e.g., $C_{6-10}$ aryl groups such as phenyl, naphthyl, etc.); aryloxy groups (e.g., $C_{6-10}$ aryloxy group such as phenyloxy, naphthyloxy, etc.); and lower alkylcarbonylamino groups which may be optionally halogenated (e.g., $C_{1-6}$ alkylcarbonylamino groups which may be optionally halogenated such as acetylamino, trifluoroacetylamino, etc.)

"The hydrocarbon group" of "the hydrocarbon group which may be optionally substituted" may have 1 to 5, preferably 1 to 3, substituents described above at places where the substitution is possible, and in the case of the hydrocarbon group having 2 or more substituents, the substituents may be same or different.

Examples of the term "the heterocyclic group" in "a heterocyclic group which may be optionally substituted" of the present specification include 5- to 14-membered, preferably 5- to 10-membered, (monocyclic to tricyclic, preferably monocyclic to bicyclic) heterocyclic groups having 1 to 4, preferably 1 to 3 atoms which are 1 or 2 kinds of hetero atoms selected from the group consisting of nitrogen, oxygen and sulfur atoms as well as carbon atoms. More specifically, examples of the heterocyclic group include 5-membered ring groups having 1 to 4 hetero atoms selected from the group consisting of oxygen, sulfur and nitrogen atoms as well as carbon atoms such as 2- or 3-thienyl, 3-furyl, 1-, 2-, or 3-pyrrolyl, 1-, 2-, or 3-pyrrolidinyl, 2-, 4-, or 5-oxazolyl, 3-, 4-, or 5-isoxazolyl, 2-, 4-, or 5-thiazolyl, 3-, 4-, or 5-isothiazolyl, 3-, 4-, or 5-pyrazolyl, 2-, 3-, or 4-pyrazolidinyl, 2-, 4-, or 5-imidazolyl, 1,2,3-triazolyl, 1,2,4-triazolyl, 1H- or 2H-tetrazolyl, etc.; 6-membered ring groups having 1 to 4 hetero atoms selected from the group consisting of oxygen, sulfur and nitrogen atoms as well as carbon atoms such as 2-, 3-, or 4-pyridinyl, N-oxide-2-, 3-, or 4-pyridinyl, 2-, 4-, or 5-pyrimidinyl, N-oxide-2-, 4-, or 5-pyrimidinyl, thiomorpholinyl, morpholinyl, piperidino, 2-, 3-, or 4-piperidyl, thiopyranyl, 1,4-oxazinyl, 1,4-thiazinyl, 1,3-thiazinyl, piperazinyl, triazinyl, 3- or 4-pyridazinyl, pyrazinyl, N-oxide-3- or 4-pyridazinyl, etc.; and bicyclic or tricyclic condensed ring groups having 1 to 4 hetero atoms selected from the group consisting of oxygen, sulfur and nitrogen atoms as well as carbon atoms (preferably, groups which are formed by the condensation of the 5 or 6-membered ring groups described above and 1 or 2 of 5- or 6-membered rings having 1 to 4 hetero atoms selected from the group consisting of oxygen, sulfur and nitrogen atoms as well as carbon atoms) such as indolyl, benzofuryl, benzoxazolyl, benzimidazolyl, quinolinyl, isoquinolinyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl, etc. The heterocyclic group is preferably a 5- to 7-membered (preferably 5- or 6-membered) heterocyclic ring having 1 to 3 hetero atoms selected from the group consisting of oxygen, sulfur and nitrogen atoms as well as carbon atoms.

Examples of the substituent of "the heterocyclic group" of "the heterocyclic group which may be optionally substituted" include halogen atoms (e.g., fluorine, chlorine, bromine, iodine, etc.); lower alkyl groups (e.g., $C_{1-6}$ alkyl groups such as methyl, ethyl, propyl, isopropyl, butyl, isobutyl, sec-butyl, tert-butyl, pentyl, hexyl, etc.); cycloalkyl groups (e.g., $C_{3-6}$ cycloalkyl groups such as cyclopropyl, cyclobutyl, cyclopentyl, cyclohexyl, etc.); lower alkynyl groups (e.g., $C_{2-6}$ alkynyl groups such as ethynyl, 1-propynyl, propargyl, etc.); lower alkenyl groups (e.g., $C_{2-6}$ alkenyl groups such as vinyl, allyl, isopropenyl, butenyl, isobutenyl, etc.); aralkyl groups (e.g., $C_{7-11}$ aralkyl groups such as benzyl, α-methylbenzyl, phenethyl, etc.); aryl groups (e.g., $C_{6-10}$ aryl groups such as phenyl, naphthyl, etc., preferably phenyl group); lower alkoxy groups (e.g., $C_{1-6}$ alkoxy groups such as methoxy, ethoxy, propoxy, isopropoxy, butoxy, isobutoxy, sec-butoxy, tert-butoxy, etc.) ; aryloxy groups (e.g., $C_{6-10}$ aryloxy groups such as phenoxy, etc.); lower alkanoyl groups (e.g., $C_{1-6}$ alkanoyl groups such as formyl, acetyl, propionyl, butyryl, isobutyryl, etc.); arylcarbonyl (e.g., $C_{6-10}$ arylcarbonyl groups such as benzoyl group, naphthoyl group, etc.); lower alkanoyloxy groups (e.g., $C_{1-6}$ alkanoyloxy groups such as formyloxy, acetyloxy, propionyloxy, butyryloxy, isobutyryloxy, etc.); arylcarbonyloxy groups (e.g., $C_{6-10}$ arylcarbonyloxy groups such as benzoyloxy, naphthoyloxy, etc.); a carboxyl group; lower alkoxycarbonyl groups (e.g., $C_{1-6}$ alkoxy-carbonyl groups such as methoxycarbonyl, ethoxycarbonyl, propoxycarbonyl, isopropoxycarbonyl, butoxycarbonyl, isobutoxycarbonyl, tert-butoxycarbonyl, etc.); aralkyloxy-carbonyl groups (e.g., $C_{7-11}$ aralkyloxycarbonyl groups such as benzyloxycarbonyl, etc.); a carbamoyl group; mono-, di- or tri-halogeno-lower alkyl groups (e.g., mono-, di-, or tri-halogeno-$C_{1-4}$ alkyl groups such as chloromethyl, dichloromethyl, trifluoromethyl, 2,2,2-trifluoroethyl, etc.); an oxo group; an amidino group; an imino group; an amino group; mono-lower alkylamino groups (e.g., mono-$C_{1-4}$ alkylamino groups such as methylamino, ethylamino, propylamino, isopropylamino, butylamino, etc.); di-lower alkylamino groups (e.g., di-$C_{1-4}$ alkylamino groups such as dimethylamino, diethylamino, dipropylamino, diisopropylamino, dibutylamino, etc.); 3- to 6-membered cyclic amino groups having 1 to 3 hetero atoms selected from the group consisting of oxygen, sulfur, and nitrogen atoms as well as carbon atoms and a nitrogen atom (e.g., 3- to 6-membered cyclic amino groups such as aziridinyl, azetidinyl, pyrrolidinyl, pyrrolinyl, pyrrolyl, imidazolyl, pyrazolyl, imidazolidinyl, piperidinyl, morpholinyl, dihydropyridinyl, pyridinyl, N-methylpiperazinyl, N-ethylpiperazinyl, etc.), alkylenedioxy groups (e.g., $C_{1-3}$ alkylenedioxy groups such as methylenedioxy, ethylenedioxy, etc.); a hydroxyl group; a nitro group; a cyano group; a mercapto group; a sulfo group, a sulfino group, a phosphono group, a sulfamoyl group, monoalkylsulfamoyl groups (e.g., mono-$C_{1-6}$ alkylsulfamoyl groups such as N-methylsulfamoyl, N-ethylsulfamoyl, N-propylsulfamoyl, N-isopropylsulfamoyl, N-butylsulfamoyl, etc.); dialkylsulfamoyl groups (e.g., di-$C_{1-6}$ alkylsulfamoyl groups such as N,N-dimethylsulfamoyl, N,N-diethylsulfamoyl, N,N-dipropylsulfamoyl, N,N-dibutylsulfamoyl, etc.); alkylthio groups (e.g., $C_{1-6}$ alkylthio groups such as methylthio, ethylthio, propylthio, isopropylthio, butylthio, sec-butylthio, tert-butylthio, etc.); arylthio groups (e.g., $C_{6-10}$ arylthio groups such as phenylthio, naphthylthio, etc.); lower alkylsulfinyl groups (e.g., $C_{1-6}$ alkylsulfinyl groups such as methylsulfinyl, ethylsulfinyl, propylsulfinyl, isopropylsulfinyl, butylsulfinyl, etc.); arylsulfinyl groups (e.g., $C_{6-10}$ arylsulfinyl groups such as phenylsulfinyl, naphthylsulfinyl, etc.); lower alkylsulfonyl groups (e.g., $C_{1-6}$ alkylsulfonyl groups such as methylsulfonyl, ethylsulfonyl, propylsulfonyl, isopropylsulfonyl, butylsulfonyl, etc.); and arylsulfonyl groups (e.g., $C_{6-10}$ arylsulfonyl groups such as phenylsulfonyl, naphthylsulfonyl, etc.).

The "heterocyclic group" of the "heterocyclic group which may be optionally substituted" may have 1 to 5, preferably 1 to 3, substituent described above at the positions of the heterocyclic ring where the substitution is possible, and in the case of the ring having 2 or more substituents, the substituents may be same or different.

An example of the term "the amino group which may be optionally substituted" of the present specification, is an amino group which may have 1 or 2 "hydrocarbon groups which may be optionally substituted" described above. Preferred examples of the substituent of the "amino group" include $C_{1-6}$ alkyl groups which may be optionally substituted, and $C_{6-10}$ aryl groups which may be optionally substituted. The substituents which the "$C_{1-6}$ alkyl group" and the "$C_{6-10}$ aryl group" may have are similar to the substituents of the "hydrocarbon groups" described above.

Examples of the term "the cyclic amino group or the heterocyclic group", in the phrase "$R^4$ and $R^5$ may bind each other to form an cyclic amino group or a heterocyclic group with the nitrogen atom bound thereto", of the present specification include 3- to 6-membered cyclic amino groups having 1 to 3 hetero atoms selected from the group consisting of oxygen, sulfur, and nitrogen atoms as well as carbon atoms and a nitrogen atom (e.g., aziridinyl, azetidinyl, pyrrolidinyl, pyrrolinyl, pyrrolyl, imidazolyl, pyrazolyl, imidazolidinyl, piperidyl, morpholinyl, dihydropyridinyl, pyridinyl, N-methylpiperazinyl, N-ethylpiperazinyl, etc.).

Examples of the term "the thiol group which may be optionally substituted" of the present specification include thiol groups which may have the "hydrocarbon group which may be optionally substituted" as substituents. Preferred examples of the substituent which the "thiol group" may have include $C_{1-6}$ alkyl groups which may be optionally substituted, $C_{6-10}$ aryl groups which may be optionally substituted, etc. Examples of the substituent which the "$C_{1-6}$ alkyl group" and the "$C_{6-10}$ aryl group" may have are similar to the substituents of the "hydrocarbon group" described above.

Examples of the term "lower alkyl group", in the phrase "lower alkyl group which may be optionally substituted", of the present specification include $C_{1-6}$ alkyl groups such as methyl, ethyl, propyl, isopropyl, butyl, isobutyl, sec-butyl, tert-butyl, and the lower alkyl group may have 1 to 3 substituents similar to those of the "hydrocarbon group" described above.

Examples of the term "lower alkoxy group", in the phrase "lower alkoxy group which may be optionally substituted", of the present specification include $C_{1-6}$ alkoxy groups such as methoxy, ethoxy, propoxy, isopropoxy, butoxy, isobutoxy, sec-butoxy, tert-butoxy, etc. and the lower alkoxy group may have 1 to 3 substituents similar to those of the "hydrocarbon group" described above.

Examples of the term "benzene ring which may be optionally substituted" of the present specification include benzene rings having, at the position where the substitution is possible, 1 to 3 (preferably 1 or 2) same or different substituents selected from the group of substituents consisting of halogen atoms (e.g., fluorine, chlorine, bromine, iodine, etc.); hydrocarbon groups which may be optionally substituted; amino groups which may be optionally substituted; amide groups (e.g., $C_{1-6}$ acylamino groups such as acetamide, etc., preferably $C_{1-6}$ alkanoylamino groups, etc.); lower alkoxy groups which may be optionally substituted; lower alkylenedioxy groups (e.g., $C_{1-6}$ alkylenedioxy groups such as methylenedioxy, ethylenedioxy, etc.); and substituents similar to those which the "heterocyclic group" in "heterocycle group which may be optionally substituted" may have.

Examples of the term "hydrocarbon group which may be optionally substituted", the "amino group which may be optionally substituted" and the "lower alkoxy group which may be optionally substituted" are similar to those described above in detail. In the case of the "hydrocarbon group", the "amino group" and the "lower alkoxy group" having 2 or more substituents, the substituents may be same or different.

The "benzene ring which may be optionally substituted" is preferably a benzene ring which is substituted by 1 to 3 substituents selected, for example, from the group consisting of halogen atoms (e.g., fluorine, chlorine, etc.), $C_{1-6}$ alkyl groups (e.g., methyl, ethyl, etc.), and mono-$C_{1-6}$ alkylamino groups.

The "carboxyl group which may be optionally esterified" of $R^1$, X, Y, Z, $R^{1a}$, $X^a$, X', Y', and Z' in the compound (I), (I'), (Ia) and (Ia'), is a group represented by —$COOR^4$. Here, $R^4$ is a hydrogen atom or a hydrocarbon group which may be optionally substituted. The "carboxyl group which may be optionally amidated" of $R^1$, X, Y, Z, $R^{1a}$, $X^a$, X', Y' and Z' is a group represented by —$CONR^4R^5$. Here, $R^4$ and $R^5$ are, respectively, a hydrogen atom, a hydrocarbon group which may be optionally substituted, or may bind each other to form a cyclic amino group or a heterocyclic group with the nitrogen atom bound thereto.

The "acyl group which may be optionally substituted" of X, Y, Z, $X^a$, X', Y' and Z' is a group represented by $COR^6$, $SOR^6$ or $SO_2R^6$. Here, $R^6$ is the "hydrocarbon group which may be optionally substituted", or the "heterocycle group which may be optionally substituted", both of which are described above.

Preferably, the heterocyclic group of $R^3$ is a nitrogen-containing aromatic heterocyclic group, especially, a 6-membered nitrogen-containing aromatic heterocycle group, for example, a pyridine ring. The substituents thereof are those of the "heterocyclic group which may be optionally substituted" described above, and $R^3$ may be a quinoline ring which is formed by the condensation of the nitrogen-containing heterocyclic group and a benzene ring. The unsaturated heterocyclic group of $R^{3'}$ having only a nitrogen atom as the hetero atom is preferably an 6-membered unsaturated heterocyclic group having only a nitrogen atom, for example, a pyridine ring. The substituents thereof may be those of the "heterocyclic group which may be optionally substituted" described above, and $R^{3'}$ may be a quinoline ring which is formed by the condensation of the nitrogen-containing heterocyclic group and a benzene ring.

X and X' are, respectively, preferably a hydrogen atom, an oxygen atom, $OR^4$ ($R^4$ is a hydrogen atom or a hydrocarbon group which may be optionally substituted), or a hydrocarbon group which may be optionally substituted.

Y and Y' are, respectively, preferably a hydrogen atom, a hydrocarbon group which may be optionally substituted, $COR^4$ or $COOR^4$, more preferably $COR^4$ or $COOR^4$. Z is preferably a hydrogen atom, an oxygen atom, $OR^4$ or a hydrocarbon group which may be optionally substituted (herein, $R^4$ is a hydrogen atom or a hydrocarbon group which may be optionally substituted).

Examples of the homocyclic ring of the "5- to 7-membered homocyclic or heterocyclic ring which may be optionally substituted" represented by ring A or ring B include cyclopentane, cyclohexane, cycloheptane, cyclopentene, cyclopentadiene, cyclohexene, cyclohexadiene, benzene, cycloheptene, cycloheptadiene, etc., preferably benzene, cyclopentane, cyclohexane, cycloheptane, and most preferably benzene.

Examples of the heterocyclic ring of the "5- to 7-membered homocyclic or heterocyclic ring which may be optionally substituted" represented by ring A or ring B include aromatic heterocyclic rings such as furan, thiophene, pyrrole, oxazole, isoxazole, thiazole, isothiazole, imidazole, pyrazole, oxadiazole, furazan, thiadiazole, triazole, pyridine, pyridazine, pyrimidine, pyrazine, triazine; non-aromatic heterocyclic rings (aliphatic heterocycles) such as azetidine, oxetane, pyrrolidine, piperidine, tetrahydropyran, morpholine, thiomorpholine, piperazine; and non-aromatic heterocyclic rings wherein part or all of the double bonds in aromatic heterocyclic rings are saturated; etc.

The substituents of the "5- to 7-membered homocyclic or heterocyclic ring which may be optionally substituted" are those which the "heterocyclic ring which may be optionally substituted" described above may have, and the number of substitution is also same as that of the heterocyclic ring.

n is preferably 0.

Preferred specific examples of the compound (I) and (I') of the present invention include 4-hydroxy-3-methyl-1-(2-pyridinyl)-pyrazolo[3,4-b]pyridine-5-carboxylic acid or an ester thereof, especially, ethylester.

The heterocyclic group of $R^{3a}$ is preferably an unsaturated heterocyclic group having 2 or less nitrogen atoms as the hetero atoms, or an unsaturated monocyclic heterocyclic group having a nitrogen atom and a sulfur atom as the hetero atoms, more preferably a nitrogen-containing aromatic heterocyclic group, especially, a nitrogen-containing 6-membered aromatic heterocyclic group, for example, a pyridine ring. Substituents thereof may be those of the "heterocyclic group which may be optionally substituted" described above, and $R^{3a}$ may be a quinoline ring which is formed by the condensation of the nitrogen-containing heterocyclic group and a benzene ring. Examples of the unsaturated heterocyclic groups of $R^{3ab}$ having 2 or less nitrogen atoms as the hetero atoms or the unsaturated monocyclic heterocyclic groups having a nitrogen atom and a sulfur atom as the hetero atoms include preferably nitrogen-containing aromatic heterocyclic groups, especially, 6-membered nitrogen-containing aromatic heterocyclic groups, for example, a pyridine ring. The substituents thereof may be those of the "heterocyclic group which may be optionally substituted" described above, and $R^{3ab}$ may be a quinoline ring which is formed by the condensation of the nitrogen-containing heterocyclic and a benzene ring.

Further, $X^a$ is preferably an oxygen atom or $OR^{4a}$ ($R^{4a}$ is a hydrogen atom or a hydrocarbon group which may be optionally substituted), and ring $B^a$ is preferably a benzene ring which may be optionally substituted. Especially, a compound (Ia) or (Ia') having a nitrogen-containing aromatic heterocyclic group which may be optionally substituted as $R^{3a}$ or $R^{3ab}$ and a benzene ring which may be optionally substituted as ring $B^a$ is favorable.

m is preferably 0.

Especially preferred examples of the compound (Ia) or (Ia') include 6,7-difluoro-3-methyl-1-(2-pyridinyl)-1,9-dihydro-4H-pyrazolo[3,4-b]quinolin-4-one, 3-methyl-1-(2-pyridinyl)-6-(trifluoromethyl)-1,9-dihydro-4H-pyrazolo[3,4-b]quinolin-4-one, 6-fluoro-3-methyl-1-(2-pyridinyl)-1,9-dihydro-4H-pyrazolo[3,4-b]quinolin-4-one, 7-fluoro-3-methyl-1-(2-pyridinyl)-1,9-dihydro-4H-pyrazolo[3,4-b]quinolin-4-one, 3-ethyl-6,7-difluoro-1-(2-pyridinyl)-1,9-dihydro-4H-pyrazolo[3,4-b]quinolin-4-one, 6,7-difluoro-3-methyl-1-(3-pyridinyl)-1,9-dihydro-4H-pyrazolo[3,4-b]quinolin-4-one, 6,7-difluoro-3-methyl-1-(6-methyl-2-pyridinyl)-1,9-dihydro-4H-pyrazolo[3,4-b]quinolin-4-one, 6,7-difluoro-3-methyl-1-(6-phenyl-2-pyridinyl)-1,9-dihydro-4H-pyrazolo[3,4-b]quinolin-4-one, 5-fluoro-3-methyl-1-(2-pyridinyl)-1,9-dihydro-4H-pyrazolo[3,4-b]quinolin-4-one, and 1-(2-pyridinyl)-1,9-dihydro-4H-pyrazolo[3,4-b]quinolin-4-one.

As the salts of the compound (I), (I'), (Ia) and (Ia') of the present invention, for example, pharmaceutically acceptable salts are used. Examples of the salt include salts with inorganic bases, with organic bases, with inorganic acids, with organic acids, with basic or acidic amino acids, etc. Suitable examples of the salt with an inorganic base include alkali metal salts such as sodium salt, potassium salt, etc., alkali-earth metal salts such as calcium salt, magnesium salt, etc., and aluminum salt, ammonium salt, etc. Preferred examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N-dibenzylethylene diamine, etc. Preferred examples of the salt with an inorganic acid include salts with hydrochloric acid, hydrobromic acid, nitric acid, sulfuric acid, phosphoric acid, etc. Preferred examples of the salt with an organic acid include salts such as formate, acetate, trifluoroacetate, phthalate, fumarate, oxalate, tartrate, maleate, citrate, succinate, malate, methanesulfonate, benzenesulfonate, p-toluenesulfonate, etc. Preferred examples of the salt with a basic amino acid include salts with arginine, lysine, ornithine, etc., and examples of the salt with an acidic amino acid include salts with aspartic acid, glutamic acid, etc.

The salt is preferably a pharmaceutically acceptable salt, and in the case of the compound (I), (I'), (Ia) or (Ia') having a basic functional group, preferred examples of the salt include salts with inorganic acids such as hydrochloride, hydrobromide, nitrate, sulfate, phosphate, etc., and salts with organic acids such as acetate, phthalate, fumarate, tartrate, maleate, citrate, succinate, methanesulfonate, p-toluenesulfonate, etc., and in the case of the compound (I), (I'), (Ia) or (Ia') having an acidic functional group, examples of the salt include alkali metal salts such as sodium salt, potassium salt, etc., alkali-earth metal salts such as calcium salt, magnesium salt, etc., ammonium salt, etc.

Compounds (I) and (I') or the salts thereof of the present invention may be produced according to a similar method, and therefore, a process for producing a compound (I') having unsubstituted as $R^2$ will be described below as an example of the process.

The compound (I') of the present invention can be prepared, for example, according to a method represented by the reaction formula 1 or a modified method thereof.

Each of the compounds (II) to (IV) in the reaction formula may be present as a salt, and in such a case, a salt is similar to the salts of the compounds (I) and (I') is used.

Each of the symbols in reaction formula 1 has the same meaning as described above.

[Reaction Formula 1]

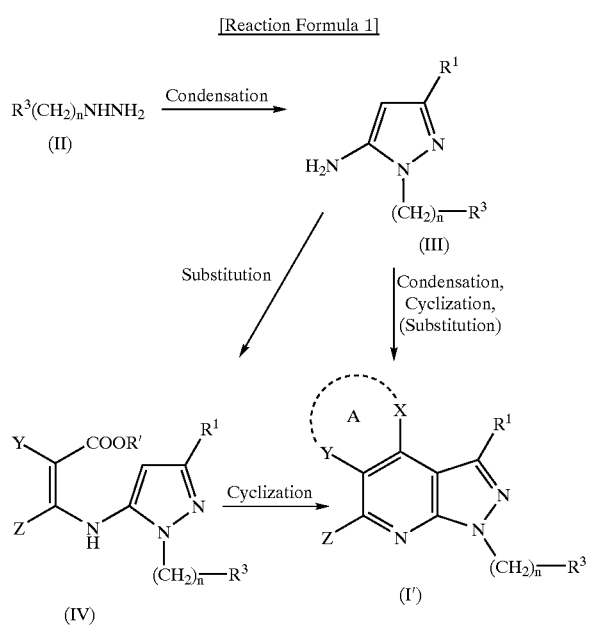

The compound (II) can be prepared according to methods known in the art, for example, the methods described in Shin Jikken Kagaku Koza, vol. 14, p. 1573–1585, Jikken Kagaku Koza (4th Ed.), vol. 20, p. 338–342, (Chem. Soc. Japan, Ed.), J. Med. Chem., vol. 28, p. 1394 (1985), Eur. J. Med. Chem., vol. 24, p. 435 (1989), J. Amer. Chem. Soc., vol. 81, p. 2456 (1959), Japanese Patent Laid-open Publication No. H02 (1990)-229168, Japanese Patent Laid-open Publication No. H02 (1990)-229169, Japanese Patent Publication No. S56 (1981)-37231, U.S. Pat. No. 4,260,767, Can. J. Chem., vol. 48, p. 3554 (1970), J. Chem. Soc., p. 3830 (1959), and Yakugaku Zasshi, vol. 73, p. 598 (1953), with or without slight modifications.

The compound (III) can be prepared according to methods known in the art, for example, the methods described in U.S. Pat. Nos. 3,414,580, 3,755,340, EP389189, Japanese Patent Publication No.S56 (1981)-37231 (1981), U.S. Pat. No. 4,260,767 (1981), Eur. J. Med. Chem., vol. 24, p. 435 (1989), J. Amer. Chem. Soc., vol. 81, p. 2456, 2460 (1959), and Synthesis, p. 337 (1997), with or without slight modifications.

The compound (IV) can be prepared from the compound (III) and a β-ketoester derivative. Substituted β-ketoester derivative can be prepared according to methods known in the art, for example, the methods described in U.S. Pat. Nos. 4,804,760, 4,994,610, Org. Synth., vol. 28, p. 60 (1948), and Org. Synth. Coll. IV, p. 285 (1963), with or without slight modifications. The β-ketoester derivative is used in an amount of about 0.8 to 10.0 moles, preferably about 1.0 to 3.0 moles per mole of the compound (III). The reaction may be favorably carried out in the absence of a solvent, or in a solution using a solvent which does not interfere with the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, halogenated hydrocarbons such as dichloromethane, chloroform, carbon tetrachloride, 1,2-dichloroethane, etc., nitriles such as acetonitrile, propionitrile, etc., sulfoxides such as dimethylsulfoxide, etc., or a mixture thereof. The reaction period may vary according to the reagents used and the solvent, but is usually 10 minutes to 12 hours, preferably 20 minutes to 8 hours. The reaction temperature is usually 0 to 200° C., preferably 0 to 150° C.

The compound (I'; X=OH) can be prepared by subjecting the compound (IV) to a cyclization reaction known in the art. The cyclization reaction may be carried out according to methods, for example, by heating, by the use of an acidic compound, or the modified method thereof.

The cyclization by heating is favorably carried out in the absence of a solvent, or in a solution using a solvent inactive to the reaction. Preferred examples of the solvent include, but not limited to so far as the reaction can proceed, high-boiling point hydrocarbons such as 1,2,3,4-tetrahydronaphthalene, etc., and high-boiling point ethers such as diphenylether, diethyleneglycol dimethylether, etc., or a mixture thereof. The reaction period is usually 5 minutes to 24 hours, preferably 10 minutes to 6 hours. The reaction temperature is usually 80 to 300° C., preferably 100 to 250° C.

In the case of the cyclization being carried out by using an acidic compound, an acidic compound, e.g., methanesulfonic acid, phosphorus pentoxide, phosphorus oxychloride, phosphorus pentachloride, phosphorus trichloride, thionyl chloride, hydrochloric acid, sulfuric acid, polyphosphoric acid, p-toluenesulfonic acid, etc., or a mixture thereof, is used. The acidic compound is used in an amount of about 0.5 to 100 moles, preferably about 1.0 to 20 moles per mole of the compound (IV). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., acid anhydrides such as acetic anhydride, etc., and sulfoxides such as dimethylsulfoxide, etc., or a mixed solvent thereof. The reaction period is usually 5 minutes to 12 hours, preferably 10 minutes to 6 hours. The reaction temperature is usually 0 to 250° C., preferably 0 to 200° C. The product of the cyclization reaction (I'; X=OH) may be used in the following reaction as it is in the reaction mixture or as a crude product, but also isolated from the reaction mixture by the common methods, and can be easily purified by separation means such as recrystallization, distillation, chromatography, etc.

The compound (I'; X=OH) can be prepared by subjecting the compound (III) to a cyclization reaction with a β-ketoester derivative known in the art, for example, the methods described in Japanese Patent Laid-open Publication No. H06 (1994)-199855, Japanese Patent Laid-open Publication No. S58 (1983)-67685, and Angew. Chem., Int. Ed. Engl., p. 958 (1967), with or without slight modifications. The cyclization reaction may be carried out according to methods, for example, by heating and by the use of an acidic compound, or the modified method thereof. The cyclization by heating is favorably carried out in a solution using a solvent inactive to the reaction. Preferred examples of the solvent include, but not limited to so far as the reaction can proceed, high-boiling point hydrocarbons such as 1,2,3,4-tetrahydronaphthalene, etc., and high-boiling point ethers such as diphenylether, diethyleneglycol dimethylether, etc., or a mixture thereof. The reaction period is usually 5 minutes to 24 hours, preferably 10 minutes to 6 hours. The reaction temperature is usually 50 to 300° C., preferably 100 to 250° C. In the case of the cyclization being carried out by using an acidic compound, an acidic compound, e.g., methanesulfonic acid, phosphorus pentoxide, phosphorus oxychloride, phosphorus pentachloride, phosphorus trichloride, thionyl chloride, hydrochloric acid, sulfuric acid, polyphosphoric acid, p-toluenesulfonic acid, trifluoroacetic anhydride, trifluoroacetic acid, acetic acid, acetic anhydride, etc., or a mixture thereof is used. The acidic compound is used in an amount of about 0.5 to 100 moles, preferably about 1.0 to 20 moles per mole of the compound (III). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., acid anhydrides such as acetic anhydride, etc., and sulfoxides such as dimethylsulfoxide, etc., or a mixed solvent thereof. The β-ketoester derivative is used in an amount of about 0.8 to 10 moles, preferably about 1.0 to 3.0 moles per mole of compound (III). The reaction period may vary according to the reagents used and the solvent, but is usually about 5 minutes to 24 hours, preferably 10 minutes to 12 hours. The reaction temperature is usually 0 to 300° C., preferably 50 to 200° C. The product of the cyclization reaction (I'; X=OH) may be used in the following reaction as it is in the reaction mixture or as a crude product, but also isolated from the reaction mixture by the common methods, and can be easily purified by separation means such as recrystallization, distillation, chromatography, etc.

The compound (I'; Z=OH) may be prepared by subjecting the compound (III) to a cyclization reaction with a β-ketoester derivative, known in the art, for example, the methods described in J. Heterocycl. Chem., vol. 12, p. 517 (1975), and J. Chem. Soc., Perkin Trans. 1, p. 938 (1980), with or without slight modification. The cyclization reaction may be carried out according to methods, for example, by the use of an acidic compound, or the modified method thereof. Examples of the acidic compound include acidic compounds such as methanesulfonic acid, phosphorus pentoxide, phosphorus oxychloride, phosphorus pentachloride, phosphorus trichloride, thionyl chloride, hydrochloric acid, sulfuric acid, polyphosphoric acid, p-toluenesulfonic acid, trifluoroacetic anhydride, trifluoroacetic acid, acetic acid, acetic anhydride, or a mixture thereof. The acidic compound is used in an amount of about 0.5 to 100 moles, preferably about 1.0 to 20 moles per mole of the compound (III). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., acid anhydrides such as acetic anhydride, etc., and sulfoxides such as dimethylsulfoxide, etc., or a mixed solvent thereof. The β-ketoester derivative is used in an amount of about 0.8 to 10 moles, preferably about 1.0 to 3.0 moles per mole of the compound (III). The reaction period may vary according to the reagents used and the solvent, but is usually about 1 minute to 120 hours, preferably 5 minutes to 60 hours. The reaction temperature is usually 0 to 300° C., preferably 50 to 200° C. The product of the cyclization reaction (I'; Z=OH) may be used in the following reaction as it is in the reaction mixture or as a crude product, but also isolated from the reaction mixture by the common methods, and can be easily purified by separation means such as recrystallization, distillation, chromatography, etc.

The compound (I'; X=Cl) can be prepared by subjecting the compound (I'; X=OH) to a halogenation reaction in the presence of an acidic compound known in the art. The acidic compounds include, for example, phosphorus oxychloride, phosphorus pentachloride, phosphorus trichloride, thionyl chloride, etc. The acidic compound is used in an amount of about 0.2 to 100 moles, preferably about 0.3 to 30 moles per mole of compound (I'; X=OH). The reaction may be favorably carried out in the absence of a solvent or in a solution using a solvent which is inactive to the reaction. Preferred examples of the solvent include, is but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., and sulfoxides such as dimethylsulfoxide, etc., or a mixture thereof. The reaction period is usually 10 minutes to 12 hours, preferably 30 minutes to 6 hours. The reaction temperature is usually 0 to 200° C., preferably 0 to 150° C. The product (I'; X=Cl) may be used in the following reaction as it is in the reaction mixture or as a crude product, but also isolated from the reaction mixture by the common methods, and can be easily purified by separation means such as recrystallization, distillation, chromatography, etc.

The compound (I'; X=alkoxy) can be prepared by a reaction of the compound (I'; X=OH) and a corresponding alkylating agent (e.g., substituted alkyl halides, substituted alcohol sulfonic esters, etc.) in the presence of a base. The alkylating agent is used in an amount of about 0.8 to 50 moles, preferably about 1.0 to 10 moles per mole of the compound (I'; X=OH). Examples of the base include inorganic bases such as sodium carbonate, potassium carbonate, sodium bicarbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., and metal alkoxides such as sodium methoxide, sodium ethoxide, potassium tert-butoxide, etc. The base is used in an amount of about 0.8 to 10 moles, preferably about 1.0 to 3.0 moles per mole of the compound (I'; X=OH). The reaction may be favorably carried out in a solution using a solvent which is inactive to the reaction. Preferred examples of the solvent include, but not limited to so far as the reaction can proceed, ethers such as diethylether tetrahydrofuran, dioxane, 1,2-dimethoxyethane, etc., hydrocarbons such as benzene, toluene, cyclohexane, hexane, etc., amides such as N,N- dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixed solvent thereof. The reaction period is usually 30 minutes to 24 hours, preferably 1 to 12 hours. The reaction temperature is usually −20 to 200° C., preferably 0 to 150° C. The product (I':X=alkoxy) may be used in the following reaction as it is in the reaction mixture or as a crude product, but also isolated from the reaction mixture by the common methods, and can be easily purified by separation means such as recrystallization, distillation, chromatography, etc.

The compound (I'; X=alkoxy) can also be prepared in a reaction of the compound (I'; X=Cl) and a corresponding substituted alcohol in the presence of a base. Examples of the base include inorganic bases such as sodium carbonate, potassium carbonate, sodium bicarbonate, etc., alkali metal hydrides such as sodium hydride, potassium hydride, etc., metal amides such as sodium amide, lithium diisopropylamide, lithium hexamethyldisilazide, etc., and metal alkoxides such as sodium methoxide, sodium ethoxide, potassium tert-butoxide, etc. The base is used in an amount of about 0.8 to 5.0 moles, preferably about 1.0 to 3.0 moles per mole of the compound (I'; X=Cl). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., and sulfoxides such as dimethylsulfoxide, etc., or a mixed solvent thereof. The reaction period is usually 10 minutes to 48 hours, preferably 15 minutes to 12 hours. The reaction temperature is usually 0 to 200° C., preferably 40 to 120° C. The product (I'; X=alkoxy) may be used in the following reaction as it is in the reaction mixture or as a crude product, but also isolated from the reaction mixture by the common methods, and can be easily purified by separation means such as recrystallization, distillation, chromatography, etc.

The compound (I'; X=NH$_2$) can be prepared in a reaction of the compound (I'; X=Cl) and sodium azide and subsequent catalytic reduction of the resulting azide. Sodium azide is used in an amount of about 0.8 to 10 moles, preferably about 1.0 to 3.0 moles per mole of the compound (I'; X=Cl). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., pyridine, hydrocarbons such as benzene, toluene, cyclohexane, hexane, etc., halogenated hydrocarbons such as dichloromethane, chloroform, carbon tetrachloride, 1,2-dichloroethane, etc., amides such as N,N-dimethylformamide, N,N-dimethylacetamide, etc., and sulfoxides such as dimethylsulfoxide, etc., or a mixture thereof. The reaction period is usually 5 minutes to 12 hours, preferably 10 minutes to 3 hours. The reaction temperature is usually 0 to 200° C., preferably 20 to 150° C. The azide product thus obtained may be used in the following reaction as it is in the reaction mixture or as a crude product, but also isolated from the reaction mixture by the common methods, and can be easily purified by separation means such as recrystallization, distillation, chromatography, etc.

Subsequently, by subjecting the azide thus obtained to a catalytic reduction reaction under hydrogen atmosphere in the presence of a variety of catalysts, the compound (I'; X=NH$_2$) can be prepared. Examples of the catalyst used include platinum oxide, platinum on activated carbon, palladium on activated carbon, palladium on barium sulfate, nickel, copper-chromium oxide, rhodium, cobalt, ruthenium, etc. The catalyst is used in an amount of about 1.0 to 1000% by weight, preferably about 5.0 to 300% by weight per the azide. The reaction may be favorably carried out in a solution using a solvent which is inactive to the reaction. Preferred examples of the solvent include, but not limited to so far as the reaction can proceed, alcohols such as methanol, ethanol, propanol, etc., ethers such as diethylether, tetrahydrofuran, dioxane, 1,2-dimethoxyethane, etc., saturated hydrocarbons such as cyclohexane, hexane, etc., amides such as N,N-dimethylformamide, N,N-dimethylacetamide, etc., organic acids such as formic acid, acetic acid, etc., and water, or a mixture thereof. The reaction period may vary according to the activity and the quantity of the catalyst used, but is usually 15 minutes to 24 hours, preferably 30 minutes to 6 hours. The reaction temperature is usually 0 to 120° C., preferably 20 to 80° C. The reaction pressure is usually 1 to 100 atm. An additive (an accelerator) may be added into the reaction system to increase the activity of the catalyst. Preferred examples of the acidic additive include inorganic acids such as hydrochloric acid, sulfuric acid, nitric acid, perchloric acid, hydrobromic acid, phosphoric acid, etc., and organic acids such as acetic acid, trifluoroacetic acid, oxalic acid, phthalic acid, fumaric acid, tartaric acid, citric acid, succinic acid, methanesulfonic acid, p-toluenesulfonic acid, 10-camphorsulfonic acid, etc. Preferred examples of the basic additive include sodium hydroxide, potassium hydroxide, etc. The product (I'; X=NH$_2$) may be used in the following reaction as it is in the reaction mixture or as a crude product, but also isolated from the reaction mixture by the common methods, and can be easily purified by separation means such as recrystallization, distillation, chromatography, etc.

The compound (I'; X=alkylamine) can be prepared in a reaction of the compound (I'; X=Cl) and an alkyl amine, in the presence of a base if desired. The alkyl amine is used in an amount of about 0.1 to 1000 moles, preferably about 1.0 to 200 moles per mole of the compound (I'; X=Cl). Example of the base include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The base is used in an amount of about 0.1 to 50 moles, preferably about 1.0 to 10 moles per mole of the compound (I'; X=Cl). The reaction may be favorably carried out in a solution using a solvent which is inactive to the reaction. Preferred examples of the solvent include, but not limited to so far as the reaction can proceed, alcohols such as methanol, ethanol, propanol, etc., hydrocarbons such as benzene, toluene, cyclohexane, hexane, etc., amides such as N,N-dimethylformamide, N'N-dimethylacetamide, etc., halogenated hydrocarbons such as dichloromethane, chloroform, carbon tetrachloride, 1,2-dichloroethane, etc., nitrites such as acetonitrile, propionitrile, etc., water, etc., or a mixture thereof. The reaction period may vary according to the reagents used and the solvent, but is usually 10 minutes to 48 hours, preferably 30 minutes to 20 hours. The reaction temperature is usually 0 to 250° C., preferably 20 to 150° C. In the case where a reaction reagent has a low boiling point, the substitution reaction can be carried out in a similar condition by heating and stirring the reaction mixture under pressure, for example in an autoclave. The product (I'; X=alkylamine) may be used in the following reaction as it is in the reaction mixture or as a crude product, but also isolated from the reaction mixture by the common methods, and can be easily purified by separation means such as recrystallization, distillation, chromatography, etc.

The compound (I'; Y=COOH) can be prepared in a hydrolysis reaction known in the art of the compound (I'; Y=ester) in the presence of an acid or a base. For the acid-catalyzed hydrolysis, mineral acids such as hydrochloric acid, sulfuric acid, etc., Lewis acids such as boron trichloride, boron tribromide, etc., a mixture of a Lewis acid and a thiol or a sulfide, and organic acids such as trifluoroacetic acid, p-toluenesulfonic acid, etc., are commonly used as the catalyst. For the base-catalyzed hydrolysis, metal hydroxides such as sodium hydroxide, potassium hydroxide, barium hydroxide, etc., metal carbonates such as sodium carbonate, potassium carbonate, etc., metal alkoxides such as sodium methoxide, sodium ethoxide, potassium tert-butoxide, etc., and organic bases such as triethylamine, imidazole, formamidine, etc., are commonly used as the catalyst. The acid and the base are used, respectively, in an amount of about 0.1 to 100 moles, preferably about 0.5 to 10 moles per mole of the compound (I'). The reaction may be favorably carried out in the absence of a solvent or in a solution using a solvent which is inactive to the reaction. Preferred examples of the solvent include, but not limited to so far as the reaction can proceed, alcohols such as methanol, ethanol, propanol, etc., aromatic hydrocarbons such as benzene, toluene, etc., saturated hydrocarbons such as cyclohexane, hexane, etc., organic acids such as formic acid, acetic acid, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., ketones such as acetone, methylethylketone, etc., sulfoxides such as dimethylsulfoxide, etc., and water, etc., or a mixed solvent thereof. The reaction period is usually 5 minutes to 24 hours, preferably 10 minutes to 12 hours. The reaction temperature is usually −10 to 200° C., preferably 0 to 150° C. The product (I'; Y=COOH) may be used in the following reaction as it is in the reaction mixture or as a crude product, but also isolated from the reaction mixture by the common methods, and can be easily purified by separation means such as recrystallization, distillation, chromatography, etc.

The compound (I'; Y=H) can be prepared by subjecting the compound (I'; Y=COOH, ester) to a decarboxylation reaction known in the art. The reaction can be carried out, according to methods, for example, by heating and by the use of an acidic compound, or the modified methods thereof. In the case where the cyclization is conducted by heating, the reaction may be favorably carried out in the absence of a solvent or in a solution using a solvent which is inactive to the reaction. Preferred examples of the solvent include, but not limited to so far as the reaction can proceed, high-boiling point hydrocarbons such as 1,2,3,4-tetrahydronaphthalene, etc., high-boiling point ethers such as diphenylether, diethyleneglycol dimethylether, etc., anilines such as N,N-dimethylaniline, N-methylaniline, etc., and nitrogen-containing aromatic compounds such as pyridine, quinoline, etc., or a mixture thereof. The reaction period is usually 5 minutes to 12 hours, preferably 10 minutes to 10 hours. The reaction temperature is usually 100 to 300° C., preferably 100 to 250° C. In the case where an acidic compound is used for cyclization, an acidic compound, e.g., methanesulfonic acid, phosphorus pentoxide, phosphorus oxychloride, phosphorus pentachloride, phosphorus trichloride, thionyl chloride, hydrochloric acid, sulfuric acid, polyphosphoric acid, p-toluenesulfonic acid, etc, or a mixture thereof is commonly used. The acidic compound is used in an amount of about 0.5 to 100 moles, preferably about 1.0 to 20 moles per mole of the compound (I'; Y=COOH, ester). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., acid anhydrides such as acetic anhydride, etc., and sulfoxides such as dimethylsulfoxide, etc., or a mixed solvent thereof. The reaction period is usually 5 minute to 12 hours, preferably 10 minutes to 6 hours. The reaction temperature is usually 0 to 250° C., preferably 10 to 200° C. The product of the cyclization reaction (I'; Y=H) may be used in the following reaction as it is in the reaction mixture or as a crude product, but also isolated from the reaction mixture by the common methods, and can be easily purified by separation means such as recrystallization, distillation, chromatography, etc.

The compound (I'; Y=CO-alkyl, CO-aryl) can be prepared in a reaction of the compound (I'; Y=reactive derivative of carboxylic acid) with an alkylating or an arylating agent known in the art (e.g., Grignard reagents, organolithium reagents, organocerium reagents, organotitanium reagents, organozinc reagents, organoaluminum reagents, and organocopper reagents). Examples of the reactive derivative of the carboxylic acid include acid halides (e.g., acid chlorides, acid bromides, etc.); acid amides (e.g., acid amides with pyrazole, imidazole, benzotriazole, etc.); mixed acid anhydrides [e.g., mono $C_{1-4}$ alkylcarbonate mixed acid anhydrides such as monomethylcarbonate, monoethylcarbonate, monoisopropylcarbonate, mono-tert-butylcarbonate; mono-$C_{7-10}$ aralkylcarbonate mixed acid anhydrides such as monobenzylcarbonate, mono(p-nitrobenzyl)carbonate, monoallylcarbonate; $C_{1-6}$ aliphatic carboxylate mixed acid anhydrides such as acetate, cyanoacetate, propionate, butyrate, isobutyrate, valerate, isovalerate, pivalate, trifluoroacetate, trichloroacetate, acetoacetate; $C_{7-11}$ aromatic carboxylate mixed acid anhydrides such as benzoate, p-toluate, p-chlorobenzoate; organic sulfonate mixed acid anhydrides such as methanesulfonate, ethanesulfonate, benzenesulfonate, p-toluenesulfonate, etc.)]; acid azides; activated esters (e.g., diethoxyphosphoric ester, diphenoxyphosphoric ester, p-nitrophenylester, 2,4-dinitrophenylester, cyanomethylester, pentachlorophenylester, ester with N-hydroxysuccimide, ester with N-hydroxyphthalimide, ester with 1-hydroxybenzotriazole, ester with 6-chloro-1-hydroxybenzotriazole, ester with 1-hydroxy-1H-2-pyridone, etc.); and activated thioesters (e.g., 2-pyridylthioester, 2-benzothiazolylthioester, etc.); etc. The alkylating agent or the arylating agent is used in an amount of about 0.8 to 20 moles, preferably about 1.0 to 5.0 moles per mole of the compound (I'; Y=reactive derivative of carboxylic acid).

Preferred examples of the solvent to be used for dilution include, but not limited to so far as the reaction can proceed, aromatic hydrocarbons such as benzene, toluene, etc., saturated hydrocarbons such as cyclohexane, hexane, etc., halogenated hydrocarbons such as chlorotoluene, etc., and ethers such as diethylether, tetrahydrofuran, dioxane, 1,2-dimethoxyethane, etc., or a mixture thereof. The reaction period is usually 10 minutes to 20 hours, preferably 15 minutes to 6 hours. The reaction temperature is usually −78 to 200° C., preferably −78 to 100° C. In the case where an acid halide is used as the reactive derivative of the carboxylic acid, the reaction may be carried out in the presence of a deacidifying agent to be used for the purpose of removing hydrogen halide released in the reaction system. Examples of the deacidifying agent include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.

Instead of using the reactive derivative, the carboxylic acid or the salt thereof may be directly reacted with an alkylating agent or an arylating agent in the presence of a proper condensing agent. Examples of the condensing agent include N,N-disubstituted carbodiimides such as N,N-dicyclohexylcarbodiimide, 1-ethyl-3-(3-dimethylaminopropyl)carbodiimide (WSC) hydrochloride, etc., azolides such as N,N-carbonyldiimidazole, etc., dehydrating agents such as N-ethoxycarbonyl-2-ethoxy-1,2-dihydroquinoline, phosphorus oxychloride, alkoxyacetylene, etc., and 2-halogenopyridinium salts such as 2-chloromethylpyridinium iodide, 2-fluoro-1-methylpyridinium iodide, etc. When the condensing agent is used, the reaction seems to proceed via a reactive derivative of carboxylic acid. The condensing agent is used in an amount of about 0.8 to 5.0 moles, preferably about 1.0 to 2.0 moles per mole of compound (I'; Y=carboxylic acid). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., and sulfoxides such as dimethylsulfoxide, etc., or a mixture thereof. The reaction period may vary according to the reagents and the solvent used, but is usually 10 minute to 24 hours, preferably 30 minutes to 4 hours. The reaction temperature is usually −78 to 100° C., preferably −78 to 70° C. The product (I'; Y=CO-alkyl, CO-aryl) may be used in the following reaction as it is in the reaction mixture or as a crude product, but also isolated from the reaction mixture by the common methods, and can be easily purified by separation means such as recrystallization, distillation, chromatography, etc.

The compound (I'; Y=carboxamide) can be prepared by condensing the compound (I'; Y=ester) and an amine derivative. The amine derivative is used in an amount of about 0.8 to 100 moles, preferably about 1.0 to 50 moles per mole of the compound (I'; Y=ester). The reaction may be favorably carried out in the absence of a solvent or in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, xylene, decalin, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., and sulfoxides such as dimethylsulfoxide, etc., or a mixture thereof. The reaction period may vary according to the reagents used and the solvent, but is usually 5 minutes to 48 hours, preferably 10 minutes to 24 hours. The reaction temperature is usually 0 to 300° C., preferably 20 to 250° C. In the case where a reaction reagent has a low boiling point, the condensation reaction can be carried out in a similar condition by heating and stirring the reaction mixture under pressure, for example in an autoclave. The product (I'; Y=carboxamide) may be used in the following reaction as it is in the reaction mixture or as a crude product, but also isolated from the reaction mixture by the common methods, and can be easily purified by separation means such as recrystallization, distillation, chromatography, etc.

The compound (I'; Y=carboxamide) can also be prepared by condensing the compound (I'; Y=reactive derivative of carboxylic acid) and an amine derivative. Examples of the reactive derivative of carboxylic acid include acid halides (e.g., acid chlorides, acid bromides, etc.); acid amides (e.g., acid amides with pyrazole, imidazole, benzotriazole, etc.); mixed acid anhydrides [e.g., mono $C_{1-4}$ alkylcarbonate-mixed acid anhydrides such as monomethylcarbonate, monoethylcarbonate, monoisopropylcarbonate, mono-tert-butylcarbonate; mono-$C_{7-10}$-aralkylcarbonate mixed acid anhydrides such as monobenzylcarbonate, mono (p-nitrobenzyl) carbonate, monoallylcarbonate; $C_{1-6}$ aliphatic carboxylate mixed acid anhydrides such as acetate, cyanoacetate, propionate, butyrate, isobutyrate, valerate, isovalerate, pivalate, trifluoroacetate, trichloroacetate, acetoacetate; $C_{7-11}$ aromatic carboxylate mixed acid anhydrides such as benzoate, p-toluate, p-chlorobenzoate; organic sulfonate mixed acid anhydrides such as methanesulfonate, ethanesulfonate, benzenesulfonate, p-toluenesulfonate, etc.]; acid azides; activated esters (e.g., diethoxyphosphoric ester, diphenoxyphosphoric ester, p-nitrophenylester, 2,4-dinitrophenylester, cyanomethylester, pentachlorophenylester, ester with N-hydroxysuccimide, ester with N-hydroxyphthalimide, ester with 1-hydroxybenzotriazole, ester with 6-chloro-1-hydroxybenzotriazole, ester with 1-hydroxy-1H-2-pyridone, etc.); and activated thioesters (e.g., 2-pyridylthioester, 2-benzothiazolylthioester, etc.). The amine derivative is used in an amount of about 0.8 to 10 moles, preferably about 1.0 to 5.0 moles per mole of compound (I'; Y=reactive derivative of carboxylic acid). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixture thereof. In the case where an acid halide is used as the reactive derivative of the carboxylic acid, the reaction may be carried out in the presence of a deacidifying agent to be used for the purpose of removing hydrogen halide released from the reaction system. Examples of the deacidifying agent include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The reaction period may vary according to the reagents used and the solvent, but is usually 10 minutes to 24 hours, preferably 30 minutes to 6 hours. The reaction temperature is usually 0 to 200° C., preferably 20 to 120° C.

Instead of using the reactive derivative, the carboxylic acid or the salt thereof may be reacted directly with an amine derivative in the presence of a proper condensing agent. Examples of the condensing agent include N,N-disubstituted carbodiimides such as N,N-dicyclohexylcarbodiimide, 1-ethyl-3-(3-dimethylaminopropyl)carbodiimide (WSC) hydrochloride, etc., azolides such as N,N-carbonyldiimidazole, etc., dehydrating agents such as N-ethoxycarbonyl-2-ethoxy-1,2-dihydroquinoline, phosphorus oxychloride, alkoxyacetylenes, etc., and 2-halogenopyridinium salts such as 2-chloromethylpyridinium iodide, 2-fluoro-1-methylpyridinium iodide, etc. When the condensing agent is used, the reaction seems to proceed via a reactive derivative of carboxylic acid. The condensing agent is used in an amount of about 0.8 to 5.0 moles, preferably about 1.0 to 2.0 moles per mole of compound (I'; Y=carboxylic acid). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixture thereof. The reaction period may vary according to the reagents used and the solvent, but is usually 10 minutes to 24 hours, preferably 30 minutes to 4 hours. The reaction temperature is usually −78 to 100° C., preferably 0 to 70° C. The product (I'; Y=carboxamide) may be used in the following reaction as it is in the reaction mixture or as a crude product, but also isolated from the reaction mixture by the common methods, and can be easily purified by separation means such as recrystallization, distillation, chromatography, etc.

The compounds (Ia) and (Ia') of the present invention or the salts thereof can also be prepared according to the method similar to those described above, and hereinafter, a process for producing a compound represented by the formula (Ia) will be described as an example. The compound (Ia) of the present invention can be prepared, for example, according to methods represented by reaction formulas 2 and 3, or the modified method thereof.

Each of the compounds, (IIa), (IIIa), (V) to (X), in the reaction formulas may be present as a salt, and in such a case, a salt similar to the salts of the compounds (Ia) is used.

Each of the symbols in the reaction formulas 2 and 3 has the same meaning as described above.

Reaction Formula 2

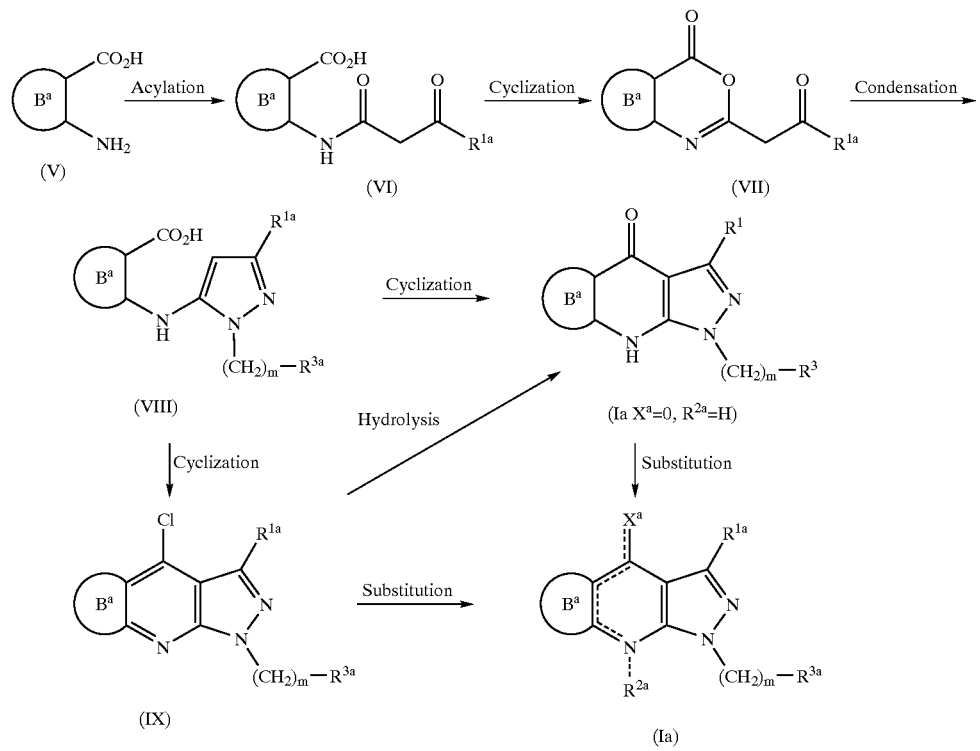

The compound (V) in the reaction formula 2 can be prepared according to methods known in the art, for example, the methods described in J. Amer. Chem. Soc., vol.

106, p. 7195 (1984), ibid., vol. 99, p. 3734 (1976), ibid., vol. 94, p. 498 (1972), J. Chem. Soc. Perkin Trans. 2, p. 291 (1994), J. Heterocyclic. Chem. vol. 27, p. 2151 (1990), and J. Med. Chem., vol. 26, p. 420 (1983), with or without slight modifications.

The compound (VI) having a methyl group as $R^{1a}$ can be prepared from the compound (V) and diketene according to methods known in the art, for example, the method described in J. Med. Chem., vol. 38, p. 1330 (1995), with or without slight modifications. Diketene is used in an amount of about 1.0 to 20.0 moles, preferably about 1.0 to 10.0 moles per mole of the compound (V).

The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixture thereof. The reaction period may vary according to the reagents used and the solvent, but is usually 30 minutes to 72 hours, preferably 30 minutes to 16 hours. The reaction temperature is usually 0 to 100° C., preferably 0 to 70° C.

The compounds (VI) except the compound (VI) having a methyl group as $R^{1a}$ can be prepared in reactions of the compound (V) with an acylated Meldrum's acid derivative and a carboxylic acid, the salt thereof, or the reactive derivative thereof. The acylated Meldrum's acid derivative can be prepared according to the methods known in the art, for example, the methods described in Synthesis, p. 1213 (1992), and Org. Synth., vol. 63, p. 198 (1985), with or without slight modifications. The carboxylic acid is, for example, a compound represented by the formula $R^{1a}$—COCH$_2$COOH (wherein, $R^{1a}$ has the same meaning as described above). Examples of the reactive derivative of the carboxylic acid include acid halides (e.g., acid chlorides, acid bromides, etc.); acid amides (e.g., acid amides with pyrazole, imidazole, benzotriazole, etc.,); mixed acid anhydrides [e.g., mono $C_{1-4}$ alkylcarbonate-mixed acid anhydrides such as monomethylcarbonate, monoethylcarbonate, monoisopropylcarbonate, mono-tert-butylcarbonate; mono-$C_{7-10}$ aralkylcarbonate mixed acid anhydrides such as monobenzylcarbonate, mono(p-nitrobenzyl)carbonate, monoallylcarbonate; $C_{1-6}$ aliphatic carboxylate mixed acid anhydrides such as acetate, cyanoacetate, propionate, butyrate, isobutyrate, valerate, isovalerate, pivalate, trifluoroacetate, trichloroacetate, acetoacetate; $C_{7-11}$ aromatic carboxylate mixed acid anhydrides such as benzoate, p-toluate, p-chlorobenzoate, etc.; organic sulfonate mixed acid anhydrides such as methanesulfonate, ethanesulfonate, benzenesulfonate, p-toluenesulfonate]; acid azides; activated esters (e.g., diethoxyphosphoric ester, diphenoxyphosphoric ester, p-nitrophenylester, 2,4-dinitrophenylester, cyanomethylester, pentachlorophenylester, ester with N-hydroxysuccimide, ester with N-hydroxyphthalimide, ester with 1-hydroxybenzotriazole, ester with 6-chloro-1-hydroxybenzotriazole, ester with 1-hydroxy-1H-2-pyridone, etc.); and activated thioesters (e.g., 2-pyridylthioester, 2-benzothiazolylthioester, etc.). The acylated Meldrum's acid derivative and the carboxylic acid or the reactive derivative thereof are used, respectively, in an amount of about 1.0 to 10.0 moles, preferably about 1.0 to 2.0 moles per mole of the compound (V).

The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., ketones such as acetone, methylethylketone, etc., and sulfoxides such as dimethylsulfoxide, etc., or a mixture thereof. In the case where an acid halide is used as the reactive derivative of the carboxylic acid, the reaction may be carried out in the presence of a deacidifying agent to be used for the purpose of removing hydrogen halide released from the reaction system. Examples of the deacidifying agent include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The reaction period may vary according to the reagents used and the solvent, but is usually 30 minutes to 24 hours, preferably 30 minutes to 6 hours. The reaction temperature is usually 0 to 200° C., preferably 20 to 120° C.

Instead of using the reactive derivative, the carboxylic acid or the salt thereof may be reacted directly with the compound (V) in the presence of a proper condensing agent. Examples of the condensing agent include N,N-disubstituted carbodiimides such as N,N-dicyclohexylcarbodiimide, 1-ethyl-3-(3-dimethylaminopropyl)carbodiimide (WSC) hydrochloride, etc., azolides such as N,N-carbonyldiimidazole, etc., dehydrating agents such as N-ethoxycarbonyl-2-ethoxy-1,2-dihydroquinoline, phosphorus oxychloride, alkoxyacetylene, etc., and 2-halogenopyridinium salts such as 2-chloromethyl pyridinium iodide, 2-fluoro-1-methyl pyridinium iodide, etc. When the condensing agent is used, the reaction seems to proceed via a reactive derivative of carboxylic acid. The carboxylic acid represented by the formula $R^{1a}$—COCH$_2$COOH ($R^{1a}$ has the same meaning as described above) or the reactive derivative thereof is used in an amount of about 1.0 to 5.0 moles, preferably about 1.0 to 2.0 moles per mole of the compound (II).

The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixture thereof. In the case where an acid halide is used as the reactive derivative of the carboxylic acid, the reaction may be carried out in the presence of a deacidifying agent to be used for the purpose of removing hydrogen halide released in the reaction. Examples of the deacidifying agent include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The reaction period may vary according to the reagents used and the solvent, but is usually 30 minutes to 24 hours, preferably 30 minutes to 4 hours. The reaction temperature is usually 0 to 100° C., preferably 0 to 70° C.

The compound (VII) can be prepared by dehydration cyclization of the compound (VI). Examples of catalyst used for the dehydration reaction include acidic catalysts such as hydrochloric acid, sulfuric acid, phosphoric acid, potassium hydrogensulfate, oxalic acid, p-toluenesulfonic acid, 10-camphorsulfonic acid, boron trifluoride ether complex, etc., and basic catalysts such as sodium hydroxide, potassium hydroxide, etc., and further include dehydrating agents such as acetic anhydride, N,N-dicyclohexylcarbodiimide, etc., alumina, sodium oxide, phosphorus oxychloride, thionyl chloride, methanesulfonyl chloride, etc. The reaction may be favorably carried out in the absence of a solvent or in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., sulfoxides such as dimethylsulfoxide, etc., or a mixture thereof. The reaction period is usually 30 minutes to 24 hours, preferably 30 minutes to 12 hours. The reaction temperature is usually 0 to 200° C., preferably 0 to 150° C.

The compound (VIII) can be prepared by a reaction of the compound (VII) with a hydrazine derivative. The hydrazine derivative can be prepared according to methods known in the art, for example, the methods described in Shin Jikken Kagaku Koza, vol. 14, p. 1573–1585, Jikken Kagaku Koza (4th Ed), vol. 20, p. 338–342 (Chem. Soc. Japan, Ed.), J. Med. Chem., vol. 28, p. 1394 (1985), Eur. J. Med. Chem., vol. 24, p. 435 (1989), J. Amer. Chem. Soc., vol. 81, p. 2456 (1959), Japanese Patent Laid-open Publication No. H02 (1990)-229168, Japanese Patent Laid-open Publication No. H02 (1990)-229169, Japanese Patent Publication No.S56 (1981)-37231, U.S. Pat. No. 4,260,767, Can. J. Chem., vol. 48, p. 3554 (1970), J. Chem. Soc., p. 3830 (1959), Yakugaku Zasshi, vol. 73, p. 598 (1953), with or without slight modifications. The hydrazine derivative is used in an amount of about 0.8 to 5.0 moles, preferably about 0.9 to 2.0 moles per mole of compound (VII). The reaction may be favorably carried out in a solution using a solvent which is inactive to the reaction. Preferred examples of the solvent include, but not limited to so far as the reaction can proceed, alcohols such as methanol, ethanol, propanol, etc., ethers such as diethylether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixture thereof. The reaction period may vary according to the reagents used and the solvent, but is usually 30 minutes to 12 hours, preferably 30 minutes to 6 hours. The reaction temperature is usually 0 to 200° C., preferably 0 to 120° C.

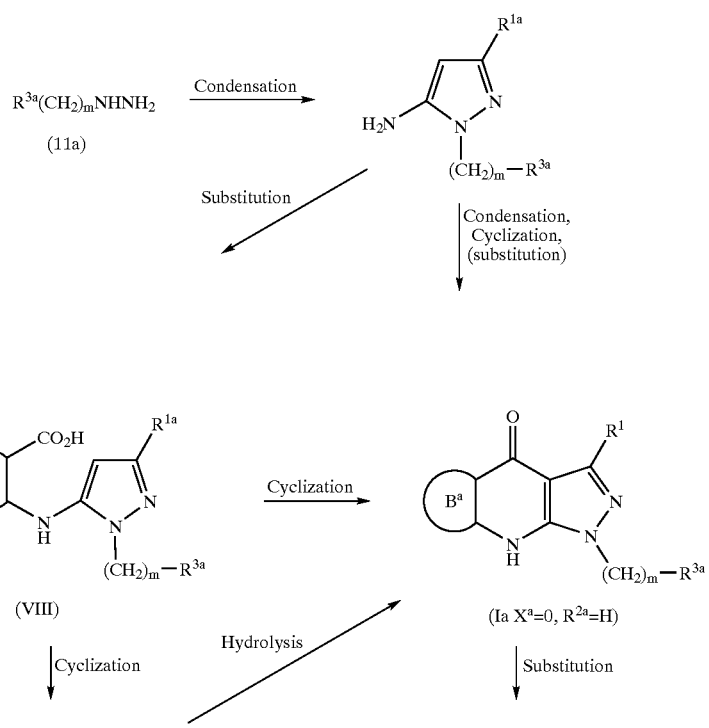

Reaction Formula 3

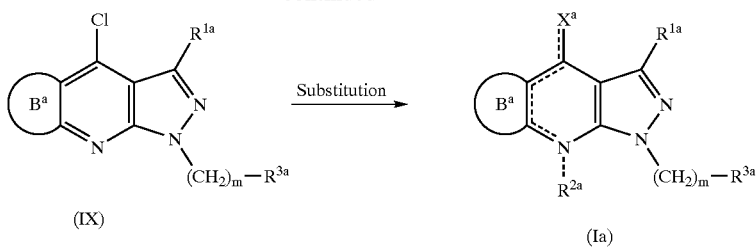

The compound (VIII) can be prepared, according to reaction formula 3, in the Ullman condensation reaction of the compound (IIIa) with a halogenated benzoic acid derivative, a halogenated picolinic acid derivative, a halogenated nicotinic acid derivative, a halogenated isonicotinic acid derivative, a halogenated thiphenecarboxylic acid or the like in the presence of a base. The Ullman condensation reaction can be carried out according to methods known in the art, for example, the methods described in Chem. Pham. Bull., vol. 45, p. 719 (1997), Organic Reactions, vol. 2, p. 243 (1943), vol. 14, p. 19 (1965), and WO-28446 (1996), with or without slight modifications. The halogenated benzoic acid derivative can be prepared according to method known in the art, for example, the methods described in EP389189, Tetrahedron Letters, vol. 37, p. 2767 (1996), Japanese Patent Laid-open Publication No. S63 (1988)-287756, Japanese Patent Laid-open Publication No. H07 (1995)-165638, and Collection Czechoslov. Chem. Commun., vol. 40, p. 719 (1975), with or without slight modifications. The halogenated picolinic acid derivative, the halogenated nicotinic acid derivative, and the halogenated isonicotinic acid derivative can be prepared according to method known in the art, for example, the methods described in J. Med. Chem., vol. 41, p. 1828 (1998), Chem. Pharm. Bull., vol. 38, p. 2466 (1990), Synth. Commun., vol. 27, p. 1075 (1997), with or without slight modifications. The halogenated benzoic acid derivative, the halogenated picolinic acid derivative, the halogenated nicotinic acid derivative, the halogenated isonicotinic acid derivative, and the halogenated thiphenecarboxylic acid are used, respectively, in an amount of about 1.0 to 5.0 moles, preferably about 1.0 to 2.0 moles per mole of compound (IIIa). Example of the base include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The base is used in an amount of about 0.1 to 5.0 moles, preferably about 0.3 to 2.0 moles per mole of compound (IIIa). The reaction may be favorably carried out in a solution using a solvent which is inactive to the reaction. Preferred examples of the solvent include, but not limited to so far as the reaction can proceed, hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., and hexamethylphosphoramide, or a mixture thereof. The reaction period may vary according to the reagents used and the solvent, but is usually 30 minutes to 24 hours, preferably 30 minutes to 6 hours. The reaction temperature is usually 0 to 250° C., preferably 20 to 180° C. An additive (an accelerator) may be added into the reaction mixture for the purpose of increasing the catalytic activity. Preferred examples of the additive include powdery copper, copper acetate (II), copper bromide (I), copper bromide (II), copper chloride (I), copper chloride (II), copper iodide (I), copper oxide (I), etc. The additive is used in an amount of about 0.01 to 5.0 moles, preferably about 0.05 to 1.0 moles per mole of compound (IIIa). Examples of the additive also include phase transfer catalysts and crown ethers. The compound (VIII) may be used in the following reaction as it is in the reaction mixture or as a crude product, but also isolated from the reaction mixture by the common methods, and can be easily purified by separation means such as recrystallization, distillation, chromatography, etc.

The compound (IX) can be prepared in a cyclization reaction of the compound (VIII) in the presence of an acidic compound known in the art. Examples of the acidic compound include phosphorus oxychloride, phosphorus pentachloride, phosphorus trichloride, thionyl chloride, etc. The acidic compound is used in an amount of about 0.5 to 100 moles, preferably about 1.0 to 30 moles per mole of compound (VIII). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., and sulfoxides such as dimethylsulfoxide, etc., or a mixed solvent thereof. The reaction period is usually 10 minutes to 12 hours, preferably 30 minutes to 6 hours. The reaction temperature is usually 0 to 200° C., preferably 0 to 150° C. The compound (IX) thus obtained may be used in the following reaction as it is in the reaction mixture or as a crude product, but also isolated from the reaction mixture by the common methods, and can be easily purified by separation means such as recrystallization, distillation, chromatography, etc.

The compound (Ia; X=O, $R^{2a}$=H) can be prepared in a cyclization reaction known in the art of the compound (VIII). The reaction can be carried out, for example, according to methods, for example, by heating and by the use of an acidic compound, by halogenation and subsequent cyclization in the presence of Lewis acid, or the modified method thereof.

In the case where the cyclization is conducted by heating, the reaction may be favorably carried out in the absence of a solvent or in a solution using a solvent which is inactive to the reaction. Preferred examples of the solvent include, but not limited to so far as the reaction can proceed, high-boiling point hydrocarbons such as 1,2,3,4- tetrahydronaphthalene, etc., and high-boiling point ethers such as diphenylether, diethyleneglycol dimethylether, etc., or a mixture thereof. The reaction period is usually 10 minutes to 24 hours, preferably 10 minutes to 6 hours. The reaction temperature is usually 100 to 300° C., preferably 100 to 250° C.

In the case where an acidic compound is used for cyclization, an acidic compound, e.g., methanesulfonic acid, phosphorus pentoxide, phosphorus oxychloride, phosphorus pentachloride, phosphorus trichloride, thionyl chloride, hydrochloric acid, sulfuric acid, polyphosphoric acid, p-toluenesulfonic acid, etc., or a mixture thereof is commonly used. The acidic compound is used in an amount of about 0.5 to 100 moles, preferably about 1.0 to 20 moles per mole of compound (VIII). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., acid anhydrides such as acetic anhydride, etc., and sulfoxides such as dimethylsulfoxide, etc., or a mixture thereof. The reaction period is usually 5 minutes to 12 hours, preferably 10 minutes to 3 hours. The reaction temperature is usually 0 to 250° C., preferably 0 to 150° C.

In the case where the compound (VIII) is halogenated and subsequently cyclized in the presence of a Lewis acid, examples of the halogenating agent to be used include thionyl halides such as thionyl chloride, thionyl bromide, etc., phosphoryl halides such as phosphoryl chloride, phosphoryl bromide, etc., phosphorus halides such as phosphorus pentachloride, phosphorus trichloride, phosphorus pentabromide, phosphorus tribromide, etc., oxalyl halides such as oxalyl chloride, etc., phosgene, etc. The halogenating agent is used in an amount of about 1.0 to 30 moles, preferably about 1.0 to 10 moles per mole of compound (VIII). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., and halogenated hydrocarbons such as dichloromethane, chloroform, carbon tetrachloride, 1,2-dichloroethane, etc., or a mixture thereof. The reaction period is usually 10 minutes to 12 hours, preferably 10 minutes to 6 hours. The reaction temperature is usually −10 to 200° C., preferably −10 to 120° C. The product may be used in the following reaction as it is in the reaction mixture or as a crude product, but also isolated from the reaction mixture by the common methods, and can be easily purified by separation means such as recrystallization, distillation, chromatography, etc. Examples of the Lewis acid used in the following cyclization reaction include anhydrous aluminum chloride, anhydrous zinc chloride, anhydrous iron chloride, etc. The Lewis acid is used in an amount of about 0.1 to 20 moles, preferably about 0.2 to 5.0 moles per mole of compound (VIII). The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., and halogenated hydrocarbons such as monochlorobenzene, o-dichlorobenzene, 1,2,4-trichlorobenzene, dichloromethane, chloroform, carbon tetrachloride, 1,2-dichloroethane, or a mixture thereof. The reaction period is usually 30 minutes to 12 hours, preferably 30 minutes to 6 hours. The reaction temperature is usually −20 to 200° C., preferably −5 to 120° C. The product (Ia; X=O, $R^{2a}$=H) of the cyclization reaction described above may be used in the following reaction as it is in the reaction mixture or as a crude product, but also isolated from the reaction mixture by the common methods, and can be easily purified by separation means such as recrystallization, distillation, chromatography, etc.

The compound (Ia; X=O, $R^{2a}$=H) can be prepared in a hydrolysis reaction known in the art in the presence of an acid or a base of the compound (IX), or according to methods known in the art, for example, the method described in U.S. Pat. No. 5,459,146 (1995), and J. Org. Chem., vol. 38, p. 3740 (1973), with or without slight modifications. Examples of the acid used for the acid-catalyzed hydrolysis include mineral acids such as hydrochloric acid, sulfuric acid, etc., Lewis acids such as boron trichloride, boron tribromide, etc., a mixture of a Lewis acid and a thiol or a sulfide, and organic acids such as trifluoroacetic acid, p-toluenesulfonic acid, etc. are commonly used as the catalyst. Examples of the base used for the base-catalyzed hydrolysis include metal hydroxides such as sodium hydroxide, potassium hydroxide, barium hydroxide, etc., metal carbonates such as sodium carbonate, potassium carbonate, etc., metal alkoxides such as sodium methoxide, sodium ethoxide, potassium tert-butoxide, etc., and organic bases such as triethylamine, imidazole, formamidine, etc. are commonly used as the catalyst. The acid and the base are used, respectively, in an amount of about 0.5 to 100 moles, preferably about 0.5 to 10 moles per mole of compound (IX). The reaction may be favorably carried out in the absence of a solvent or in a solution using a solvent which is inactive to the reaction. Preferred examples of the solvent include, but not limited to so far as the reaction can proceed, alcohols such as methanol, ethanol, propanol, etc., aromatic hydrocarbons such as benzene, toluene, etc., saturated hydrocarbons such as cyclohexane, hexane, etc., organic acids such as formic acid, acetic acid, etc., ethers such as diethylether, tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., ketones such as acetone, methylethylketone, etc., sulfoxides such as dimethylsulfoxide, etc., and water, etc., or a mixture thereof. The reaction period is usually 10 minutes to 60 hours, preferably 10 minutes to 12 hours. The reaction temperature is usually −10 to 200° C., preferably 0 to 150° C. The product (Ia; X=O, $R^{2a}$=H) may be used in the following reaction as it is in the reaction mixture or as a crude product, but also isolated from the reaction mixture by the common methods, and can be easily purified by separation means such as recrystallization, distillation, chromatography, etc.

The compound (Ia) having hydrogen as $X^a$ can be prepared by subjecting the compound (IX) to a catalytic reduction reaction in the presence of a variety of catalysts under hydrogen atmosphere. Examples of the catalyst used include platinum oxide, platinum on activated carbon, palladium on activated carbon, palladium on barium sulfate, nickel, copper-chromium oxide, rhodium, cobalt, ruthenium, etc. The catalyst is used in an amount of about 1.0 to 1000% by weight, preferably about 5.0 to 300% by weight per the compound (VI). The reaction may be favorably carried out in a solution using a solvent which is inactive to the reaction. Preferred examples of the solvent include, but not limited to so far as the reaction can proceed, alcohols such as methanol, ethanol, propanol, etc., ethers such as diethylether, tetrahydrofuran, dioxane, 1,2-dimethoxyethane, etc., saturated hydrocarbons such as cyclohexane, hexane, etc., amides such as N,N-dimethylformamide, N,N-dimethylacetamide, etc., organic acids such as formic acid, acetic acid, etc., and water, etc., or a mixture thereof. The reaction period may vary according to activity and quantity of the catalyst used, but is usually 30 minutes to 24 hours, preferably 30 minutes to 6 hours. The reaction temperature is usually 0 to 120° C., preferably 20 to 80° C. The reaction pressure is usually 1 to 100 atm. An additive (an accelerator) may be added into the reaction mixture for the purpose of increasing the catalytic activity. Preferred examples of the acidic additive include inorganic acids such as hydrochloric acid, sulfuric acid, nitric acid, perchloric acid, hydrobromic acid, phosphoric acid, etc., and organic acids such as acetic acid, trifluoroacetic acid, oxalic acid, phthalic acid, fumaric acid, tartaric acid, citric acid, succinic acid, methanesulfonic acid, p-toluenesulfonic acid, 10-camphorsulfonic acid, etc. Preferred examples of the basic additive include sodium hydroxide, potassium hydroxide, etc. The compound (Ia) thus obtained may be used in the following reaction as it is in the reaction mixture or as a crude product, but also isolated from the reaction mixture by the common methods, and can be easily purified by separation means such as recrystallization, distillation, chromatography, etc.

The compound (Ia) having nitrile as $X^a$ can be prepared in a reaction of the compound (IX) with a metal cyanide [e.g., sodium cyanide, potassium cyanide, or copper cyanide (I)] or benzyltrimethylammonium cyanide. The metal cyanide or benzyltrimethylammonium cyanide is used in an amount of about 1.0 to 5.0 moles, preferably about 1.0 to 2.0 moles per mole of compound (IX). The reaction may be favorably carried out in a solution using a solvent which is inactive to the reaction. Preferred examples of the solvent include, but not limited to so far as the reaction can proceed, hydrocarbons such as benzene, toluene, cyclohexane, hexane, etc., amides such as N,N-dimethylformamide, N,N-dimethylacetamide, N-methylpyrrolidone, etc., halogenated hydrocarbons such as dichloromethane, chloroform, carbon tetrachloride, 1,2-dichloroethane, etc., nitrites such as acetonitrile, propionitrile, etc., and hexamethylphosphoramide or a mixture thereof. The reaction period may vary according to the reagents used and the solvent, but is usually 30 minutes to 24 hours, preferably 30 minutes to 8 hours. The reaction temperature is usually 0 to 250° C., preferably 20 to 180° C. An additive (an accelerator) may be added into the reaction mixture for the purpose of increasing the catalytic activity. Examples of the additive include sodium iodide, phase transfer catalysts, crown ethers. The compound (Ia) thus obtained may be used in the following reaction as it is in the reaction mixture or as a crude product, but also isolated from the reaction mixture by the common methods, and can be easily purified by separation means such as recrystallization, distillation, chromatography, etc.

The compound (Ia) having an alkyl group as $X^a$ can be prepared in a reaction of the compound (IX) with a corresponding alkylating agent known in the art (e.g., Grignard reagents, organolithium reagents, organocerium reagents, organotitanium reagents, organozinc reagents, organoaluminum reagents, and organocopper reagents). The alkylating agent is used in an amount of about 0.8 to 20 moles, preferably about 1.0 to 5.0 moles per mole of compound (IX). Examples of the solvent used for dilution include, but not limited to so far as the reaction can proceed, aromatic hydrocarbons such as benzene, toluene, etc., saturated hydrocarbons such as cyclohexane, hexane, etc., halogenated hydrocarbons such as chlorotoluene, etc., and ethers such as tetrahydrofuran, dioxane, 1,2-dimethoxyethane, etc., or a mixture thereof. The reaction period is usually 10 minutes to 20 hours, preferably 15 minutes to 6 hours. The reaction temperature is usually −20 to 150° C., preferably 0 to 100° C. The compound (Ia) thus obtained may be used in the following reaction as it is in the reaction mixture or as a crude product, but also isolated from the reaction mixture by the common methods, and can be easily purified by separation means such as recrystallization, distillation, chromatography, etc.

The compound (Ia) having an alkoxy group as $X^a$ or a hydroxyl group as $X^a$ and an alkyl group as $R^{2a}$ can be prepared in a reaction of the compound (Ia; X=O, $R^{2a}$=H) with a corresponding alkylating agent (e.g., substituted alkyl halides, substituted alcohol sulfonic esters, etc.) in the presence of a base. The alkylating agent is used in an amount of about 1.0 to 100 moles, preferably about 1.0 to 30 moles per mole of the compound (Ia; X=O, $R^{2a}$=H). Example of the base include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., metal hydrides such as sodium hydride, potassium hydride, etc., metal amides such as sodium amide, lithium diisopropylamide, lithium hexamethyldisilazide, etc., and metal alkoxides such as sodium methoxide, sodium ethoxide, potassium tert-butoxide, etc. The base is used in an amount of about 1.0 to 10 moles, preferably about 1.0 to 3.0 moles per mole of the compound (Ia; X=O, $R^{2a}$=H). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixture thereof. The reaction period is usually 30 minutes to 72 hours, preferably 1 to 24 hours. The reaction temperature is usually −20 to 200° C., preferably 0 to 150° C. The compound (Ia) may be used in the following reaction as it is in the reaction mixture or as a crude product, but also isolated from the reaction mixture by the common methods, and can be easily purified by separation means such as recrystallization, distillation, chromatography, etc.

The compound (Ia) having an amino group as $X^a$ can be prepared in a reaction of the compound (IX) with sodium azide and by subsequent catalytic reduction of the resulting azide. Sodium azide is used in an amount of about 0.8 to 10 moles, preferably about 1.0 to 3.0 moles per mole of compound (IX). The reaction may be favorably carried out in a solution using a solvent which is inactive to the reaction.

Preferred examples of the solvent include, but not limited to so far as the reaction can proceed, ethers such as diethylether, tetrahydrofuran, dioxane, 1,2-dimethoxyethane, etc., pyridine, hydrocarbons such as benzene, toluene, cyclohexane, hexane, etc., halogenated hydrocarbons such as dichloromethane, chloroform, carbon tetrachloride, 1,2-dichloroethane, etc., amides such as N,N-dimethylformamide, N,N-dimethylacetamide, etc., and sulfoxides such as dimethylsulfoxide, etc., or a mixture thereof. The reaction period is usually 5 minutes to 12 hours, preferably 10 minutes to 3 hours. The reaction temperature is usually 0 to 200° C., preferably 20 to 150° C. The azide derivative thus obtained may be used in the following reaction as it is in the reaction mixture or as a crude product, but also isolated from the reaction mixture by the common methods, and can be easily purified by separation means such as recrystallization, distillation, chromatography, etc.

The compound (Ia) can be prepared by subjecting the azide thus obtained to a catalytic reduction reaction in the presence of a variety of catalysts under hydrogen atmosphere. Examples of the catalyst used include platinum oxide, platinum on activated carbon, palladium on activated carbon, palladium on barium sulfate, nickel, copper-chromium oxide, rhodium, cobalt, ruthenium, etc. The catalyst is used in an amount of about 1.0 to 1000% by weight, preferably about 5.0 to 300% by weight per the compound (IX). The reaction may be favorably carried out in a solution using a solvent which is inactive to the reaction. Preferred examples of the solvent include, but not limited to so far as the reaction can proceed, alcohols such as methanol, ethanol, propanol, etc., ethers such as diethylether, tetrahydrofuran, dioxane, 1,2-dimethoxyethane, etc., saturated hydrocarbons such as cyclohexane, hexane, etc., amides such as N,N-dimethylformamide, N,N-dimethylacetamide, etc., organic acids such as formic acid, acetic acid, etc., and water, etc., or a mixture thereof. The reaction period may vary according to the activity and the quality of the catalyst used and the solvent, but is usually 30 minutes to 24 hours, preferably 30 minutes to 6 hours. The reaction temperature is usually 0 to 120° C., preferably 20 to 80° C. The reaction pressure is usually 1 to 100 atm. An additive (an accelerator) may be added into the reaction mixture for the purpose of increasing the catalytic activity. Preferred examples of the acidic additive include inorganic acids such as hydrochloric acid, sulfuric acid, nitric acid, perchloric acid, hydrobromic acid, phosphoric acid, etc., and organic acids such as acetic acid, trifluoroacetic acid, oxalic acid, phthalic acid, fumaric acid, tartaric acid, citric acid, succinic acid, methanesulfonic acid, p-toluenesulfonic acid, 10-camphorsulfonic acid, etc. Preferred examples of the basic additive include sodium hydroxide, potassium hydroxide, etc. The compound (Ia) thus obtained may be used in the following reaction as it is in the reaction mixture or as a crude product, but also isolated from the reaction mixture by the common methods, and can be easily purified by separation means such as recrystallization, distillation, chromatography, etc.

The compound (Ia) having a substituted alkylthio group as $X^a$ can be prepared by treating the compound (Ia; X=O, $R^{2a}$=H) in the presence of a sulfidizing agent (e.g., phosphorus pentasulfide, Lawesson's reagent, Davy reagent) and by subjecting the resulting compound to an alkylation reaction subsequently. The sulfidizing agent is used in an amount of about 0.5 to 10 moles, preferably about 1.0 to 3.0 moles per mole of the compound (Ia; X=O, $R^{2a}$=H). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., aromatic amines such as pyridine, lutidine, etc., hydrocarbons such as benzene, toluene, cyclohexane, hexane, etc., halogenated hydrocarbons such as dichloromethane, chloroform, carbon tetrachloride, 1,2-dichloroethane, etc., nitrites such as acetonitrile, propionitrile, etc., and sulfoxides such as dimethylsulfoxide, etc., or a mixture thereof. The reaction period is usually 30 minutes to 24 hours, preferably 1 to 12 hours. The reaction temperature is usually 0 to 200° C., preferably 0 to 150° C. The compound (Ia) may be used in the following reaction as it is in the reaction mixture or as a crude product, but also isolated from the reaction mixture by the common methods, and can be easily purified by separation means such as recrystallization, distillation, chromatography, etc.

The compound (Ia) having a substituted alkoxy group or a substituted alkylthio group as $X^a$ can be prepared in a reaction of the compound (IX) with a substituted alkyl alcohol or a substituted alkyl thiol in the presence of a base. The substituted alkyl alcohol and the substituted alkyl thiol are used, respectively, in an amount of about 1.0 to 50.0 moles, preferably about 1.0 to 30.0 moles per mole of the compound (IX). Example of the base include inorganic bases such as sodium carbonate, potassium carbonate, sodium bicarbonate, etc., metal hydrides such as sodium hydride, potassium hydride, etc., metal amides such as sodium amide, lithium diisopropylamide, lithium hexamethyldisilazide, etc., and metal alkoxides such as sodium methoxide, sodium ethoxide, potassium tert-butoxide, etc. The base is used in an amount of about 1.0 to 50.0 moles, preferably about 1.0 to 15 moles per mole of compound (IX). The reaction may be favorably carried out in a solution using a solvent which is inactive to the reaction. Preferred examples of the solvent include, but not limited to so far as the reaction can proceed, ethers such as diethylether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., and sulfoxides such as dimethylsulfoxide, etc., or a mixture thereof. The reaction period is usually 10 minutes to 48 hours, preferably 15 minutes to 12 hours. The reaction temperature is usually 0 to 200° C., preferably 40 to 120° C. The compound (Ia) may be used in the following reaction as it is in the reaction mixture or as a crude product, but also isolated from the reaction mixture by the common methods, and can be easily purified by separation means such as recrystallization, distillation, chromatography, etc.

The compound (Ia) having a sulfinyl group as $X^a$ can be prepared by oxidizing the corresponding sulfide compound (Ia). Examples of the oxidizing agent include hydrogen peroxide, peracids such as peracetic acid, perbenzoic acid, m-chloroperbenzoic acid, etc., sodium metaperiodate, hydroperoxide, ozone, selenium dioxide, chromic acid, dinitrogen tetraoxide, acyl nitrate, iodine, bromine, N-bromosuccinimide, iodosylbenzene, sulfuryl chloride and silica gel hydrate, tert-butyl hypochlorite, etc. The oxidizing agent is used in an amount of about 0.5 to 5.0 moles, preferably about 1.0 to 1.5 moles per mole of the compound (Ia). The reaction may be favorably carried out in a solution using a solvent which is inactive to the reaction. Preferred examples of the solvent include, but not limited to so far as the reaction can proceed, alcohols such as methanol, ethanol, propanol, etc., ethers such as diethylether, tetrahydrofuran, dioxane, 1,2-dimethoxyethane, etc., ketones such as acetone, methylethylketone, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., sulfoxides such as dimethylsulfoxide, etc., organic acids such as formic acid, acetic acid, etc., and water, etc., or a mixture thereof. The reaction period is usually 5 minutes to 48 hours, preferably 10 minutes to 12 hours. The reaction temperature is usually −40 to 200° C., preferably −10 to 120° C. The compound (Ia) may be used in the following reaction as it is in the reaction mixture or as a crude product, but also isolated from the reaction mixture by the common methods, and can be easily purified by separation means such as recrystallization, distillation, chromatography, etc.

The compound (Ia) having a substituted alkyl amino group as $X^a$ can be prepared in a reaction of the compound (IX) with a substituted alkylamine, in the presence of a base if desired. The substituted alkylamine is used in an amount of about 1.0 to 1000 moles, preferably about 1.0 to 200 moles per mole of compound (IX). Example of the base include inorganic bases such as sodium carbonate, potassium carbonate, sodium bicarbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The base is used in an amount of about 0.1 to 50 moles, preferably about 1.0 to 10 moles per mole of compound (IX). The reaction may be favorably carried out in the absence of a solvent or in a solution using a solvent which is inactive to the reaction. Preferred examples of the solvent include, but not limited to so far as the reaction can proceed, alcohols such as methanol, ethanol, propanol, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitrites such as acetonitrile, propionitrile, etc., and water, etc., or a mixture thereof. The reaction period may vary according to the reagents used and the solvent, but is usually 10 minutes to 48 hours, preferably 30 minutes to 20 hours. The reaction temperature is usually 0 to 250° C., preferably 20 to 150° C. In the case where a reaction reagent has a low boiling point, the substitution reaction can be carried out in a similar condition by heating and stirring the reaction mixture under pressure, for example in an autoclave. The compound (Ia) may be used in the following reaction as it is in the reaction mixture or as a crude product, but also isolated from the reaction mixture by the common methods, and can be easily purified by separation means such as recrystallization, distillation, chromatography, etc.

The compound (Ia) having a cycloalkane ring as ring $B^a$ can be prepared in a reaction of the compound (IIIa) in the presence of an acidic compound, with an 2-oxocycloalkanecarboxylic ester represented by the formula (X).

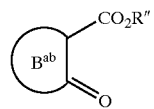

[Formula (X)]

[wherein, R″ is a hydrocarbon group which may be optionally substituted; and ring $B^{ab}$ is a 5- to 7-membered cycloalkane ring which may be optionally substituted]. In the case where an acidic compound is used for cyclization, an acidic compound, e.g., phosphorus oxychloride, phosphorus pentachloride, phosphorus trichloride, thionyl chloride, hydrochloric acid, sulfuric acid, polyphosphoric acid, p-toluenesulfonic acid, or the like, is used. The acidic compound is used in an amount of about 0.5 to 200 moles, preferably about 5.0 to 50 moles per mole of compound (IIIa), or about 1.0 to 10000% by weight, preferably about 2.0 to 1000% by weight. The reaction may be favorably carried out in the absence of a solvent or in a solution using a solvent which is inactive to the reaction. Preferred examples of the solvent include, but not limited to so far as the reaction can proceed, aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., and sulfoxides such as dimethylsulfoxide, etc., or a mixture thereof. The reaction period is usually 30 minutes to 12 hours, preferably 30 minutes to 6 hours. The reaction temperature is usually 0 to 200° C., preferably 0 to 150° C. The compound (Ia) thus obtained may be used in the following reaction as it is in the reaction mixture or as a crude product, but also isolated from the reaction mixture by the common methods, and can be easily purified by separation means such as recrystallization, distillation, chromatography, etc.

The compounds (IIa) and (IIIa) can be prepared according to the method similar to those for the compounds (II) and (III).

The compounds (I) and (Ia) can also be prepared in the reaction processes described above in combination with another or 2 or more other reactions known in the art, including hydrolysis, deprotection, acylation, alkylation, hydrogenation, oxidation, reduction, carbon chain elongation, and exchange of substituent group. These reactions can be carried out according to the methods, described, for example, in "Shin Jikken Kagaku Koza, vol. 14 and 15 (Chem. Soc. Japan, Ed.), 1977, and 1978".

In each of the reactions of the present invention described above and of reactions for preparing a raw compounds, if the starting compound has amino, carboxyl, or hydroxyl groups as the substituents thereof, each of these groups may be protected by a protecting group commonly used in peptide chemistry, and the protecting group can be removed after the reaction to obtain the desired compound is completed.

Examples of the protecting group for an amino group include a formyl group, $C_{1-6}$ alkylcarbonyl groups (e.g., acetyl, ethylcarbonyl, etc.), $C_{1-6}$ alkyloxycarbonyl groups (e.g., methoxycarbonyl, ethoxycarbonyl, etc.), a benzoyl group, $C_{7-10}$ aralkyl-carbonyl groups (e.g., benzylcarbonyl, etc.), a trityl group, a phthaloyl group, a N,N-dimethylaminomethylene group, etc. These groups may be further substituted by 1 to 3 substituents such as halogen atoms (e.g., fluorine, chlorine, bromine, iodine, etc.) and a nitro group.

Examples of the protecting group for a carboxyl group include $C_{1-6}$ alkyl groups (e.g., methyl, ethyl, propyl, isopropyl, butyl, tert-butyl, etc.), a phenyl group, a trityl group, a silyl group, etc. These groups may be further substituted by 1 to 3 substituents including halogen atoms (e.g., fluorine, chlorine, bromine, iodine, etc.), a formyl group, $C_{1-6}$ alkyl-carbonyl groups (e.g., acetyl, propionyl, butylcarbonyl, etc.), a nitro group, etc.

Examples of the protecting group for a hydroxyl group include $C_{1-6}$ alkyl groups (e.g., methyl, ethyl, propyl, isopropyl, butyl, tert-butyl, etc.), a phenyl group, $C_{7-10}$ aralkyl groups (e.g., benzyl, etc.), $C_{1-6}$ alkyl-carbonyl groups (e.g., acetyl, propionyl, etc.), a benzoyl group, $C_{7-10}$ aralkyl-carbonyl groups (e.g., benzylcarbonyl, etc.), a tetrahydropyranyl group, a tetrahydrofuranyl group, a silyl group, etc. These groups may be further substituted by 1 to 3 substituents including halogen atoms (e.g., fluorine, chlorine, bromine, iodine, etc.), $C_{1-6}$ alkyl groups (e.g., methyl, ethyl, propyl, etc.), a phenyl group, $C_{7-10}$ aralkyl groups (e.g., benzyl, etc.), a nitro group, etc.

Removal of the protecting group can be performed according to methods known in the art or the modified methods thereof, for example, methods by the use of an acid, a base, a reducing agent, UV light, hydrazine, phenylhydrazine, sodium N-methyldithiocarbamate, tetrabutylammonium fluoride, and palladium acetate, etc.

The compounds, (I), (I'), (Ia) and (Ia'), of the present invention can be isolated and purified according to methods known in the art, such as solvent extraction, liquid conversion, solvent exchange, crystallization, recrystallization, chromatography, etc. The starting compounds or the salts thereof of the compound (I), (I'), (Ia) and (Ia') of the present invention may be isolated and purified according to the methods known in the art described above, or used in the following process as they are in the reaction mixtures without isolation.

In the case where the compounds (I), (I'), (Ia) and (Ia') are purified by recrystallization, solvents which may be used for the recrystallization are, for example, water, alcohols (e.g., methanol, ethanol, n-propanol, isopropanol, etc.), aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethylether, isopropylether, tetrahydrofuran, dioxane, etc.), ketones (e.g., acetone, methylethylketone, etc.), nitrites (e.g., acetonitrile, etc.), sulfoxides (e.g., dimethylsulfoxide, etc.), acid amides (e.g., N,N-dimethylformamide, etc.), esters (e.g., ethyl acetate, etc.), carboxylic acids (e.g., acetic acid, propionic acid, etc.), etc. These solvents may be used as a single solvent, or a mixture of 2 solvents in an appropriate proportion of, for example, 1:1 to 1:10, or a mixture of more solvents.

When a desired product is obtained as a free state, the desired product may be converted to the salt or the hydrate according to common methods, meanwhile when a product is obtained as a salt or a hydrate, the product may be converted to the free state or another salt thereof. The compounds (I), (I'), (Ia) and (Ia') thus obtained can be isolated from the reaction solution and purified according to methods known in the art, for example, solvent exchange, concentration, solvent extraction, distillation, crystallization, recrystallization, chromatography, etc.

When the compounds (I), (I'), (Ia) and (Ia') are present as a mixture of configurational isomers, diastereomers, conformers, etc., desired isomers or conformers can be isolated according to isolation and purification means described above if desired. Further, when the compounds (I), (I'), (Ia) and (Ia') are optically active compounds, + and − optical isomers can be separated according to optical separation means commonly practiced.

The compound (I) of the present invention or the salt thereof is useful as a preventive and therapeutic agent of a variety of diseases of human and animals (such as mouse, rat, guinea pig, cat, dog, sheep, horse, cow, monkey, etc.), including diseases associated with allergic reactions, autoimmune diseases (e.g., allergic asthma, atopic dermatitis, urticaria, allergic conjunctivitis, allergic rhinitis, pollinosis, chronic rheumatoid arthritis, systemic lupus erythematosus, multiple sclerosis, chronic obstructive pulmonary diseases, malignant anaemia, idiopathic thrombocytopenic purpura, myasthenia gravis, pachyderms, uveitis, chronic thyroiditis, Sjoegren's syndromes, Addison's disease, Basedow's disease, agranulocytosis, etc.), shocks (e.g., septic shock, anaphylactic shock, adult respiratory distress syndromes, etc.), arteriosclerosis, thrombotic diseases, ischemic diseases (e.g., ischemic heart diseases, ischemic brain diseases, cardiac infarction, angina pectoris, etc.), cerebrovascular convulsion, erosive arthritis, polymyositis, ileus, organ failures induced by progress of the shocks and the like (e.g., lung failure, renal failure, hepatic failure, gut hemorrhage, etc.), etc., and as a preventive and therapeutic agent for graft rejections or graft versus host diseases associated with organ transplantation.

The compound (I) of the present invention is low in toxicity, and thus can be safely administered, as it is or as it is mixed with a pharmaceutically acceptable carrier according to methods known in the art, as a pharmaceutical composition in a variety of forms, such as tablets (including sugar coated tablet, film coated tablet), powder, granule, capsule (including soft capsule), liquid, injection, suppository, sustained-release drug, patch, etc., and furthermore as chewing gum, etc., orally or parenterally (e.g., local, rectal, intravenous administration, etc.). The content of the compound (I) of the present invention in the composition is about 0.01 to 100% by weight of the composition. The dosage may vary according to the administration object, the administration route, and the disease, but is, for example, about 0.1 to 100 mg/kg body weight, preferably about 0.2 to 50 mg/kg body weight, more preferably about 0.5 to 30 mg/kg body weight as the compound (I) when the composition is administered orally, and the composition may be administered once a day or divided several times a day.

The compound (I) or the salt thereof can be used as a preventive and therapeutic agent for a variety of diseases owing to its excellent COX inhibitory activity. For example, the pharmaceutical composition of the present invention can be used as a preventive and therapeutic agent for diseases including inflammatory diseases (e.g., diabetic complications such as algesic fervescence, retinopathy, nephropathy, nerve disorders, great vessel disorder, etc.; arthritides such as rheumatism, chronic rheumatism, osteoarthritis, rheumatoid myelitis, urarthritis, periostitis, etc.; lumbago; gout; postoperative and posttraumatic inflammation; remission of puffiness; neuralgia; pharyngitis; cystitis; chronic hepatitis; acute pancreatitis; chronic pancreatitis; Crohn disease; inflammatory enteropathy such as ulcerative colitis, etc.; meningitides; inflammatory ophthalmic diseases; inflammatory pulmonary diseases such as pneumonia, silicosis, pulmonary sarcoidosis, tuberculosis, etc., etc.); allergic diseases (e.g., asthma, atopic dermatitis, chronic obstructive pulmonary diseases, etc.); supraneural disorders (e.g., cerebrovascular diseases such as cerebral hemorrhage and brain infarction, etc., cephalic trauma, spine damage, brain edema, multiple sclerosis, etc.); neurodegenerative diseases (e.g., Alzheimer's disease, Parkinson's disease, amyotrophic lateral sclerosis, AIDS encephalopathy, etc.); systemic erythematosus; psoriasis; bladder cancer; breast cancer; uterocervical cancer; chronic lymphemia; chronic myelocytic leukemia; colon cancer; colic cancer; rectal cancer; *Helicobacter pylori* infection disease; Hodgkin disease; insulin-dependent diabetes; malignant melanoma; multiple myeloma; non-Hodgkin's lymphoma; non-small cell lung cancer; ovarian cancer; peptic ulcer; prostatic cancer; infertility; Behet's disease; systemic fungal infection disease; acute bacteria meningitides; acute myocardial infarction; acute viral encephalitis; adult respiratory distress syndrome; bacteria pneumonia; herpes simplex virus infection disease; varicella zoster virus infection disease; AIDS; human papilloma virus infection disease; influenza; invasive staphylococcal infection disease; septicaemia; interstitial hepatic disease situational ileitis; circulatory diseases (e.g., angina pectoris, cardiac infarction, static cardiac failure, disseminated intravascular coagulation syndrome, arteriosclerosis, peripheral vascular diseases, etc.); etc.

When the compound (I) is used for prevention and treatment of a variety of diseases using its COX inhibitory activity, the compound (I) of the present invention may be safely administered as a pharmaceutical composition containing a pharmaceutically acceptable carrier, formulated in a similar manner as described above. The dosage may be vary according to the administration object, the administration route, and the disease, but, is, for example, is about 0.1 to 20 mg/kg body weight, preferably about 0.2 to 10 mg/kg body weight, more preferably about 0.5 to 10 mg/kg body weight as the compound (I) when the composition is administered orally, and the composition may be administered once a day or divided several times a day.

Examples of the pharmaceutically acceptable carrier used for the production of the pharmaceutical composition of the present invention include various organic or inorganic carriers commonly used for such formulations, for example, diluents, lubricants, binders, disintegrants, etc., for solid formulations, and solvents, solubilizing agents, suspending agents, isotonic agents, buffer agents, smoothing agents, etc., for liquid formulations. Additionally, other additives may also be used, if desired, such as antiseptic substances, antioxidants, coloring agents, sweeteners, absorbents, humectants, as well as the carriers above.

Examples of the diluent include lactose, sucrose, D-mannitol, starch, cornstarch, crystalline cellulose, light silica anhydrate, etc.

Examples of the lubricant include magnesium stearate, calcium stearate, talc, colloidal silica, etc.

Examples of the binder include crystalline cellulose, sucrose, D-mannitol, dextrin, hydroxypropylcellulose, hydroxypropylmethylcelulose, polyvinylpyrrolidone, starch, sucrose, gelatin, methylcellulose, carboxymethylcellulose sodium, etc.

Examples of the disintegrant include starch, carboxymethylcellulose, carboxymethylcellulose calcium, sodium croscarmellose, carboxymethylstarch sodium, L-hydroxypropylcellulose, etc.

Examples of the solvent include injection solvents, alcohol, propyleneglycol, macrogol, benne oil, corn oil, olive oil, etc.

Examples of the solubilizing agent include polyethyleneglycol, propyleneglycol, D-mannitol, benzyl benzoate, ethanol, trisaminomethane, cholesterol, triethanolamine, sodium carbonate, sodium citrate, etc.

Examples of the suspending agent include surfactants such as stearyltriethanolamine, sodium laurylsulfate, laurylaminopropionate, lecithin, benzalkonium chloride, benzethonium chloride, glycerol monostearate, etc, and hydrophilic polymers such as polyvinylalcohol, polyvinylpyrrolidone, carboxymethylcellulose sodium, methylcellulose, hydroxymethylcellulose, hydroxyethylcellulose, hydroxypropylcellulose, etc.

Examples of the isotonic agent include glucose, D-sorbitol, sodium chloride, glycerol, D-mannitol, etc.

Examples of the buffer agent include buffer solutions of the salts such as phosphate, acetate, carbonate, citrate, etc.

Examples of the smoothing agent include benzyl alcohol, etc.

Examples of the antiseptic substance include paraoxybenzoate esters, chlorobutanol, benzyl alcohol, phenethyl alcohol, dehydroacetic acid, sorbic acid, etc.

Examples of the antioxidant include sulfites, ascorbic acid, α-tocopherol, etc.

Hereinafter, the present invention is described in more detail by reference to Reference Examples, Examples and Formulation Examples and Experimental Examples, which however are not intended to limit the present invention, and may be modified within the scope of the present invention.

The term "room temperature" in the following Reference Examples and Examples refers to a temperature of about 10 to 35° C. The term "%" refers to % by weight unless it is explicitly indicated otherwise. Silica gel used is Kieselgel 60, 0.063–0.200 mm (Merck) unless it is explicitly indicated otherwise, and basic silica gel is Chromatorex NH-DM1020, 0.100–0.200 mm, (Fuji Silysia Chemical).

The meanings of abbreviations used in the description are as follows
s: singlet
d: doublet
t: triplet
q: quartet
m: multiplet
br: broad
J: coupling constant
Hz: Hertz
$CDCl_3$: deuterated chloroform
$DMSO-d_6$: deuterated dimethylsulfoxide
NMR: Proton Nuclear Magnetic Resonance REFERENCE EXAMPLE 1-1
3-Methyl-1-(2-pyridinyl)-1H-pyrazol-5-amine To an ice-cold solution of aminocrotononitrile (82 g, 1.0 mol) and 2-hydrazinopyridine (120 g, 1.1 mol) in ethanol (300 mL) was added acetic acid (132 g, 2.2 mol), and the mixture was heated under reflux for 3.5 hours. After the mixture was allowed to cool to room temperature, the reaction solvent was evaporated under reduced pressure and water was added to the residue. After the solution was made basic by the addition of an aqueous sodium hydroxide solution, organic matter was extracted with ethyl acetate. The extract was washed with saturated brine and water and dried over anhydrous magnesium sulfate, and the solvent was evaporated under reduced pressure. Purification of the residue by silica gel column chromatography (ethyl acetate) gave the title compound (156.3 g, 90% yield).

mp: 103–104° C. (recrystallized from ethyl acetate).
NMR ($CDCl_3$) δ: 2.25 (3H, s), 5.37 (1H, s), 5.92 (2H, br s), 7.07 (1H, m), 7.76 (1H, m), 7.94 (1H, d, J=7.0 Hz), 8.32 (1H, d, J=6.0 Hz).

REFERENCE EXAMPLE 1-2

Diethyl 2-([[3-methyl-1-(2-pyridinyl)-1H-pyrazol-5-yl]amino]methylene)malonate

A mixture of diethyl ethoxymethylenemalonate (32.5 g, 0.15 mol) and 3-methyl-1-(2-pyridinyl)-1H-pyrazol-5- amine (23.8 g, 0.137 mol) was heated under reflux at 120° C. for 1 hour. After the mixture was allowed to cool to room temperature, the reaction solvent was evaporated under reduced pressure. The crude crystals thus obtained were filtered and washed with diethylether to give the title compound (45 g, 96% yield).

mp: 128–131° C. (recrystallized from ethyl acetate/hexane). NMR (CDCl$_3$) δ: 1.33 (3H, t, J=7.0 Hz), 1.39 (3H, t, J=7.0 Hz), 2.31 (3H, s), 4.27 (2H, q, J=7.0 Hz), 4.38 (2H, q, J=7.0 Hz), 6.03 (1H, s), 7.13–7.23 (1H, m), 7.77–7.96 (2H, m), 8.25 (1H, d, J=13.9 Hz), 8.49–8.56 (1H, m), hidden (1H). Elementary Analysis: for C$_{17}$H$_{20}$N$_4$O$_4$ Calcd.: C, 59.29; H, 5.85; N, 16.27. Found: C, 59.31; H, 5.91; N, 16.38.

REFERENCE EXAMPLE 1-3

Ethyl 2-benzoyl-3-[[3-methyl-1-(2-pyridinyl)-1H-pyrazol-5-yl]amino]-2-propenoate Following the procedure described in Reference Example 1-2, the title compound was prepared from 3-methyl-1-(2-pyridinyl)-1H-pyrazol-5-amine and ethyl 2-benzoyl-3-ethoxy-2-propenoate (91% yield).

mp: 94–97° C. (recrystallized from methanol). NMR (CDCl$_3$) δ: 0.94, 0.96 (3H, t, J=7.0 Hz), 2.31, 2.31 (3H, s), 4.04, 4.12 (2H, q, J=7.0 Hz), 6.02, 6.14 (1H, s), 7.15–8.30 (9H, m), 8.53–8.70 (1H, m), hidden (1H).

REFERENCE EXAMPLE 1-4

Diethyl 2-([[1-(2-pyridinyl)-1H-pyrazol-5-yl]amino]methylene)malonate

Following the procedure described in Reference Example 1-2, the title compound was prepared from 1-(2-pyridinyl)-1H-pyrazol-5-amine and diethyl ethoxymethylenemalonate (98% yield).

mp: 124–127° C. (recrystallized from ethyl acetate). NMR (CDCl$_3$) δ: 1.34 (3H, t, J=7.0 Hz), 1.39 (3H, t, J=7.0 Hz), 4.27 (2H, q, J=7.0 Hz), 4.38 (2H, q, J=7.0 Hz), 6.21 (1H, d, J=1.8 Hz), 7.20–7.30 (1H, m), 7.58 (1H, d, J=1.8 Hz), 7.81–7.93 (1H, m), 7.99 (1H, d, J=8.4 Hz), 8.29 (1H, d, J=13.6 Hz), 8.53–8.60 (1H, m), hidden (1H). Elementary Analysis: for C$_{16}$H$_{18}$N$_4$O$_4$ Calcd.: C, 58.17; H, 5.49; N, 16.96. Found: C, 58.11; H, 5.41; N, 17.03.

REFERENCE EXAMPLE 1-5

Ethyl 4-chloro-3-methyl-1-(2-pyridinyl)-1H-pyrazolo[3,4-b]pyridine-5-carboxylate A solution of ethyl 4-hydroxy-3-methyl-1-(2-pyridinyl)-1H-pyrazolo[3,4-b]pyridine-5-carboxylate (3.0 g, 0.01 mol) in phosphorous oxychloride (7.7 g, 0.05 mol) was heated and stirred at 100° C. for 1 hour. After the solution was allowed to cool to room temperature, the reaction solvent was evaporated under reduced pressure, and the residue water was added to iced water. After neutralization by the addition of an aqueous sodium hydroxide solution, organic matter was extracted with chloroform. The extract was washed with saturated brine and water, and dried over anhydrous magnesium sulfate, and the solvent was evaporated under reduced pressure. Purification of the residue by silica gel chromatography (ethyl acetate) gave the title compound (1.72 g, 54% yield).

mp: 121–123° C. (recrystallized from ethyl acetate). NMR (CDCl$_3$) δ: 1.45 (3H, t, J=7.3 Hz), 2.90 (3H, s), 4.48 (2H, q, J=7.3 Hz), 7.26–7.34 (1H, m), 7.87–7.97 (1H, m), 8.33–8.41 (1H, m), 8.67–8.73 (1H, m), 9.10 (1H, s). Elementary Analysis: for C$_{15}$H$_{13}$N$_4$O$_2$Cl Calcd.: C, 56.88; H, 4.14; N, 17.69. Found: C, 56.89; H, 3.98; N, 17.79.

REFERENCE EXAMPLE 1-6

4-Chloro-N,3-dimethyl-N-phenyl-1-(2-pyridinyl)-1H-pyrazolo[3,4-b]pyridine-5-carboxamide A solution of 4-hydroxy-3-methyl-1-(2-pyridinyl)-1H-pyrazolo[3,4-b]pyridine-5-carboxylic acid (2.0 g, 7.4 mmol) in phosphorous oxychloride (15 mL, 63 mmol) was heated and stirred at 100° C. for 3 hours. After the solution was cooled to room temperature, the solvent was evaporated under reduced pressure. The residue was dissolved in tetrahydrofuran (50 mL). To the solution, a solution of N-methylaniline (1.0 mL, 9.2 mmol) and triethylamine (5.2 mL, 37 mmol) in tetrahydrofuran (10 mL) was added at 0° C. After the mixture was stirred at room temperature for 1.5 hours, the reaction solvent was evaporated under reduced pressure. Purification of the residue thus obtained by silica gel chromatography (chloroform:methanol=50:1 to 20:1) gave the title compound (2.14 g, 76% yield).

mp: 154–155° C. (recrystallized from hexane/diethylether). NMR (CDCl$_3$) δ: 2.79 (3H, s), 3.57 (3H, s), 7.11–7.27 (6H, m), 7.85 (1H, td, J=7.3, 1.4 Hz), 8.22 (1H, d, J=8.4 Hz), 8.35 (1H, s), 8.62–8.66 (1H, m). Elementary Analysis: for C$_{20}$H$_{16}$N$_5$OCl Calcd.: C, 63.58; H, 4.27; N, 18.54. Found: C, 63.32; H, 4.36; N, 18.24.

REFERENCE EXAMPLE 1-7

4-Chloro-3-methyl-1-(2-pyridinyl)-1H-pyrazolo[3,4-b]pyridine

Following the procedure described in Reference Example 1-5, the title compound was prepared from 4-hydroxy-3-methyl-1-(2-pyridinyl)-1H-pyrazolo[3,4-b]pyridine (59% yield).

mp: 124–125° C. (recrystallized from ethyl acetate). NMR (CDCl$_3$) δ: 2.86 (3H, s), 7.50 (1H, d, J=5.3 Hz), 7.63–7.70 (1H, m), 8.43–8.52 (1H, m), 8.63 (1H, d, J=5.3 Hz), 8.75–8.83 (2H, m). Elementary Analysis: for C$_{12}$H$_9$N$_4$Cl Calcd.: C, 58.91; H, 3.71; N, 22.90. Found: C, 58.93; H, 3.83; N, 22.83.

REFERENCE EXAMPLE 1-8

[4-Chloro-3-methyl-1-(2-pyridinyl)-1H-pyrazolo[3,4-b]pyridin-5-yl]phenylmethanone A solution of 4-hydroxy-3-methyl-1-(2-pyridinyl)-1H-pyrazolo[3,4-b]pyridine-5-carboxylic acid (2.0 g, 7.4 mmol) in phosphorous oxychloride (19 mL, 200 mmol) was heated and stirred at 100° C. for 1.5 hours. After the solution was cooled to room temperature, the solvent was evaporated under reduced pressure. The residue was dissolved in tetrahydrofuran (50 mL) and cooled to −78° C. To the solution, a solution of phenylmagnesium bromide (1M tetrahydrofuran solution, 30 mL, 30 mmol) was added dropwise at the same temperature, and the mixture was stirred for 1 hour, and at room temperature further for 0.5 hour. The mixture was poured into an aqueous saturated ammonium chloride solution and organic matter was extracted with ethyl acetate. The extract was washed with saturated brine and dried over anhydrous sodium sulfate, and the solvent was evaporated under reduced pressure. Purification of the residue by silica gel chromatography (hexane:chloroform:ethyl acetate=2:1:1 to 1:1:1) gave the title compound (0.83 g, 38% yield).

mp: 177–178° C. (recrystallized from hexane/diethylether). NMR (CDCl$_3$) δ: 2.89 (3H, s), 7.26–7.33 (1H, m), 7.47–7.55 (2H, m), 7.62–7.70 (1H, m), 7.84–7.97 (3H, m), 8.37 (1H, d, J=8.4 Hz), 8.63 (1H, s), 8.69–8.72 (1H, m). Elementary Analysis: for C$_{19}$H$_{13}$N$_4$OCl Calcd.: C, 65.43; H, 3.76; N, 16.06. Found: C, 65.20; H, 3.72; N, 15.95

REFERENCE EXAMPLE 1-9

2-Hydrazinopyridine

The title compound was prepared from the following procedure described in J. Med. Chem., vol. 28, p. 1394 (1985). A mixture of 2-chloropyridine (200 mL, 2.1 mol) and hydrazine monohydrate (400 mL, 8.2 mol) was heated under reflux for 20 hours. After the solution was cooled to room temperature, excess hydrazine hydrate was removed under reduced pressure, and the residue was added to water. After the solution was made basic by the addition of a sodium hydroxide solution, organic matter was extracted with chloroform. The extract was washed with saturated brine and water, and dried over anhydrous magnesium sulfate, and the solvent was evaporated under reduced pressure to give the title compound (157 g, 68% yield). The compound was used in the following process, without further purification.

REFERENCE EXAMPLE 1-10

2-[[3-Methyl-1-(2-pyridinyl)-1H-pyrazol-5-yl]amino]benzoic acid

A solution of 2-(2-oxopropyl)-4H-3,1-benzoxazin-4-one (68.2 g, 0.34 mol) and 2-hydrazinopyridine (37.1 g, 0.34 mol) in ethanol (500 mL) was heated under reflux for 1 hour. After the solution was cooled to room temperature, the resulting crude crystals were filtered. The crystals were washed with ethanol and air-dried to give the title compound (50.2 g, 51% yield).

mp: 190–193° C. (recrystallized from methanol). NMR (DMSO-d$_6$) δ: 2.35 (3H, s), 6.15 (1H, s), 6.87–6.97 (1H, m), 7.05–7.15 (1H, m), 7.46–7.56 (1H, m), 7.69 (1H, d, J=8.4 Hz), 7.73–7.82 (1H, m), 7.92 (1H, d, J=8.4 Hz), 8.14 (1H, dd, J=8.1 Hz, 1.5 Hz), 8.45–8.50 (1H, m), 12.25 (1H, br s).

REFERENCE EXAMPLE 1-11

2-[[3-Methyl-1-(2-pyridinyl)-1H-pyrazol-5-yl]amino]benzoic acid

A solution of 3-methyl-1-(2-pyridinyl)-1H-pyrazol-5-ylamine (5.23 g, 30 mmol), o-iodobenzoic acid (8.93 g, 36 mmol), copper acetate (II) (0.654 g, 3.6 mmol), and potassium carbonate (4.98 g, 36 mmol) in N,N-dimethylformamide (30 mL) was heated under reflux for 1 hour under an argon atmosphere. After the solution was cooled to room temperature, the mixture was added to water. The solution was made weakly acidic by the addition of acetic acid, and the resulting crude crystals were collected by filtration. The crystals were washed with water and air dried to give the title compound (8.64 g, 98% yield).

REFERENCE EXAMPLE 1-12

2-(2-Oxopropyl)-4H-3,1-benzoxazin-4-one

To a solution of anthranilic acid (290 g, 2.1 mol) in acetone (1000 mL), diketene (460 mL, 6.0 mol) was added dropwise at room temperature. The mixture was stirred at room temperature for 16 hours. The resulting crystals were collected by filtration, washed with acetone and diethylether, and air dried (170 g). The crude crystals were suspended in a mixture of acetic anhydride (320 mL, 3.4 mol) and tetrahydrofuran (1000 mL), and the mixture was heated and stirred at 80° C. for 12 hours. After the mixture was cooled to room temperature, the reaction solvents were evaporated under reduced pressure, and the resulting crude crystals were filtered. The crystals were washed with acetonitrile and air dried to give the title compound (244 g, 57% yield).

mp: 120–122° C. (recrystallized from acetonitrile).

REFERENCE EXAMPLE 1-13

8-Methyl-2-(2-oxopropyl)-4H-3,1-benzoxazin-4-one

Following the procedure described in Reference Example 1-12, the title compound was prepared from 2-amino-3-methylbenzoic acid (88% yield).

mp: 150–152° C. (recrystallized from ethanol). Elementary Analysis: for C$_{12}$H$_{11}$NO$_3$ Calcd.: C, 66.35; H, 5.10; N, 6.45. Found: C, 66.36; H, 5.12; N, 6.38.

REFERENCE EXAMPLE 1-14

8-Methoxy-2-(2-oxopropyl)-4H-3,1-benzoxazin-4-one

Following the procedure described in Reference Example 1-12, the title compound was prepared from 2-amino-3-methoxybenzoic acid (92% yield).

mp: 177–180° C. (recrystallized from methanol/ethyl acetate). Elementary Analysis: for C$_{12}$H$_{11}$NO$_4$ Calcd.: C, 61.80; H, 4.75; N, 6.01. Found: C, 61.81; H, 4.72; N, 6.01.

REFERENCE EXAMPLE 1-15

6,7-Dimethoxy-2-(2-oxopropyl)-4H-3,1-benzoxazin-4-one

Following the procedure described in Reference Example 1-12, the title compound was prepared from 2-amino-4,5-dimethoxybenzoic acid (65% yield).

mp: 200–202° C. (recrystallized from acetonitrile). Elementary Analysis: for C$_{13}$H$_{13}$NO$_5$ Calcd.: C, 59.31; H, 4,98; N, 5.32. Found: C, 59.28; H, 4.91; N, 5.56.

REFERENCE EXAMPLE 1-16

4,5-Dimethoxy-2-[[3-methyl-1-(2-pyridinyl)-1H-pyrazol-5-yl]amino]benzoic acid Following the procedure described in Reference Example 1-10, the title compound was prepared from 6,7-dimethoxy-2-(2-oxopropyl)-4H-3,1-benzoxazin-4-one and 2-hydrazinopyridine (64% yield).

NMR (DMSO-d$_6$) δ: 2.24 (3H, s), 3.75 (3H, s), 3.86 (3H, s), 6.27 (1H, s), 7.14 (1H, s), 7.26–7.33 (1H, m), 7.41 (1H, s), 7.83 (1H, d, J=8.0 Hz), 7.97 (1H, dt, J=1.8 Hz, 8.4 Hz), 8.41–8.45 (1H, m), hidden (2H).

REFERENCE EXAMPLE 1-17

6-(Methylsulfanyl)-2-(2-oxopropyl)-4H-3,1-benzoxazin-4-one

Following the procedure described in Reference Example 1-12, the title compound was prepared from 2-amino-5-(methylsulfanyl)benzoic acid (68% yield).

mp: 137–140° C. (recrystallized from ethyl acetate/hexane). Elementary Analysis: for C$_{12}$H$_{11}$NO$_3$S Calcd.: C, 57.82; H, 4.45; N, 5.62. Found: C, 57.80; H, 4.61; N, 5.48.

REFERENCE EXAMPLE 1-18

5-(Methylsulfanyl)-2-[[3-methyl-1-(2-pyridinyl)-1H-pyrazol-5-yl]amino]benzoic acid Following the procedure described in Reference Example 1-10, the title compound was prepared from 6-(methylsulfanyl)-2-(2-oxopropyl)-4H-3,1-benzoxazin-4-one and 2-hydrazinopyridine (67% yield).

NMR (DMSO-$d_6$) δ: 2.24 (3H, s), 2.47 (3H, s), 6.21 (1H, s), 7.31 (1H, ddd, J=1.0 Hz, 4.8 Hz, 7.4 Hz), 7.48 (1H, dd, J=2.2 Hz, 8.8 Hz), 7.60 (1H, d, J=8.8 Hz), 7.81–7.86 (2H, m), 7.98 (1H, ddd, J=1.8 Hz, 7.4 Hz, 8.4 Hz), 8.44 (1H, ddd, J=0.8 Hz, 1.8 Hz, 4.8 Hz), 12.18 (1H, s), hidden (1H).

REFERENCE EXAMPLE 1-19

6-Chloro-2-(2-oxopropyl)-4H-3,1-benzoxazin-4-one

Following the procedure described in Reference Example 1-12, the title compound was prepared from 2-amino-5-chlorobenzoic acid (46% yield).

mp: 159–160° C. (recrystallized from acetonitrile). Elementary Analysis: for $C_{11}H_8ClNO_3$ Calcd.: C, 57.82; H, 4.45; N, 5.62. Found: C, 57.80; H, 4.61; N, 5.48.

REFERENCE EXAMPLE 1-20

2-Amino-5-fluorobenzoic acid

A mixture of 5-fluoro-2-nitrotoluene (25.0 g, 161 mmol), potassium permanganate (102 g, 645 mmol) and water (500 mL) was heated and stirred at 100° C. for 3 hours. The solution was cooled to room temperature, and insoluble matter derived from potassium permanganate was removed by celite filtration. The filtrate was washed with diethylether, made acidic by the addition of conc. hydrochloric acid, and organic matter was extracted with diethyl ether. The extract was washed with saturated brine and dried over anhydrous magnesium sulfate, and the solvent was evaporated under reduced pressure to give 5-fluoro-2-nitrobenzoic acid. To a solution of 5-fluoro-2-nitro benzoic acid thus obtained in ethanol (100 mL) was added 10% palladium-carbon (0.5 g, 50% hydrate), and the mixture was stirred at room temperature under hydrogen atmosphere for 4 hours. The solution was filtered to remove the catalyst, and the filtrate was concentrated under reduced pressure to give the title compound (6.25 g, 25% yield).

NMR (CDCl$_3$) δ: 5.94 (3H, br s), 6.64 (1H, dd, J=4.6 Hz, 9.0 Hz), 7.04–7.15 (1H, m), 7.60 (1H, dd, J=3.0 Hz, 9.6 Hz).

REFERENCE EXAMPLE 1-21

5-Fluoro-2-iodobenzoic acid

The title compound was prepared from the following procedure described in Collection Czechoslov. Chem. Commun., vol. 40, p. 719 (1975). To an ice-cold mixture of 2-amino-5-fluorobenzoic acid (9.0 g, 58.0 mmol) and conc. hydrochloric acid (50 mL) was added dropwise a solution of sodium nitrite (4.42 g, 64.1 mmol) in water (10 mL). Subsequently, a solution of potassium iodide (14.5 g, 87.5 mmol) and conc. sulfuric acid (4 mL) in water (30 mL) was added at the same temperature, and the mixture was heated to 100° C. and stirred for 2 hours. After the solution was cooled to room temperature, the mixture was poured into an aqueous solution of sodium thiosulfate, and organic matter was extracted with ethyl acetate. The extract was washed with saturated brine and water, dried over anhydrous magnesium sulfate, and concentrated under reduced pressure to give crude crystals. The crystals were collected by filtration, washed with hexane/diethylether, and air dried to give the title compound (6.33 g, 41% yield).

NMR (CDCl$_3$) δ: 6.99 (1H, ddd, J=3.0 Hz, 5.4 Hz, 8.8 Hz), 7.76 (1H, dd, J=3.0 Hz, 8.8 Hz), 8.02 (1H, dd, J=5.4 Hz, 8.8 Hz), hidden (1H).

REFERENCE EXAMPLE 1-22

2-Hydrazino-3-methylpyridine

The title compound was prepared according to the procedure described in U.S. Pat. No. 4,260,767 (1981). A mixture of 2-bromo-3-methylpyridine (29.0 g, 169 mmol) and hydrazine monohydrate (60 mL, 1.24 mol) was heated and stirred at 100° C. for 4 hours. The mixture was ice cooled, and the resulting crude crystals were filtered. The crystals were washed with cold water and air dried, and recrystallized from chloroform/hexane to give the title compound (12.5 g, 60% yield).

NMR (DMSO-$d_6$) δ: 2.03 (3H, s), 4.10 (2H, br s), 6.53 (1H, dd, J=5.2 Hz, 7.4 Hz), 7.09 (1H, br s), 7.23 (1H, dd, J=1.0 Hz, 7.4 Hz), 7.94 (1H, dd, J=1.0 Hz, 5.2 Hz).

REFERENCE EXAMPLE 1-23

3-Hydrazinopyridine dihydrochloride

To a mixture of 3-aminopyridine (9.41 g, 100 mmol) and conc. hydrochloric acid (100 mL) was cooled to a temperature of lower than –5° C., a solution of sodium nitrite (7.20 g, 105 mmol) in water (60 mL) was added dropwise thereto. Subsequently, a solution of tin chloride (II) (56.9 g, 300 mmol) in conc. hydrochloric acid (50 mL) was added to the solution so that the temperature of the solution does not exceed –5° C., and the solution was stirred at a temperature of less than –5° C. for 3 hours, and the resulting crystals were collected by filtration. The crystals were washed with diethylether/methanol and air dried to give the title compound (15.6 g, 85% yield). The compound was used in the following process without further purification.

REFERENCE EXAMPLE 1-24

2-[[3-Methyl-1-(3-pyridinyl)-1H-pyrazol-5-yl]amino]benzoic acid

A solution of 2-(2-oxopropyl)-4H-3,1-benzoxazin-4-one (10.2 g, 50.0 mmol), 3-hydrazinopyridine dihydrochloride (9.10 g, 50.0 mmol) and sodium acetate (9.84 g, 120 mmol) in ethanol (100 mL) was heated under reflux for 1 hour. The solution was cooled to room temperature, and the reaction solvent was evaporated under reduced pressure. The residue was poured into water, and organic matter was extracted with a mixed solvent of chloroform/methanol. The extract was washed with saturated brine and dried over anhydrous magnesium sulfate, and the solvent was evaporated under reduced pressure. The residue was crystallized from ethyl acetate/diethylether/hexane to give the title compound (10.1 g, 69% yield).

NMR (DMSO-$d_6$) δ: 2.27 (3H, s), 6.27 (1H, s), 6.77–6.84 (1H, m), 6.91 (1H, d, J=8.2 Hz), 7.38 (1H, t, J=7.6 Hz), 7.45–7.52 (1H, m), 7.88 (1H, d, J=7.6 Hz), 7.97 (1H, d, J=7.6 Hz), 8.50–8.53 (1H, m), 8.79 (1H, s), 9.94 (1H, br s), hidden (1H).

REFERENCE EXAMPLE 1-25

2-Hydrazinopyrimidine

The title compound was prepared according to the procedure described in Yakugaku Zasshi, vol. 73, p. 598 (1953).

A mixture of 2-chloropyrimidine (25.0 g, 218 mmol), potassium carbonate (25.0 g, 181 mmol), and hydrazine monohydrate (50 mL, 1.01 mol) was heated and stirred at 100° C. for 20 minutes. The solution was ice cooled and the resulting crude crystals were collected by filtration. The crystals were washed with cold water and air dried, and recrystallized from benzene to give the title compound (19.7 g, 82% yield).

NMR (DMSO-$d_6$) δ: 4.12 (2H, br s), 6.60 (1H, t, J=4.8 Hz), 8.10 (1H, br s), 8.31 (2H, d, J=4.8 Hz).

REFERENCE EXAMPLE 1-26

Ethyl 5-amino-1-(2-pyridinyl)-1H-pyrazole-4-carboxylate

A solution of ethyl 2-(ethoxymethylene)-2-cyanacetate (33.8 g, 200 mmol) and 2-hydrazinopyridine (21.8 g, 200 mmol) in ethanol (100 mL) was heated under reflux for 20 minutes. The solution was cooled to room temperature, and the resulting crystals were collected by filtration. The crystals were washed with ethanol and air dried to give the title compound (33.8 g, 73% yield).

mp: 103–104° C. (recrystallized from ethyl acetate). NMR (CDCl$_3$) δ: 1.37 (3H, t, J=7.0 Hz), 4.31 (2H, q, J=7.0 Hz), 7.12–7.18 (1H, m), 7.48 (2H, br s), 7.76 (1H, s), 7.77–7.87 (1H, m), 7.95 (1H, d, J=8.4 Hz), 8.35–8.38 (1H, m).

REFERENCE EXAMPLE 1-27

1-(2-Pyridinyl)-1H-pyrazol-5-ylamine

A suspension of ethyl 5-amino-1-(2-pyridinyl)-1H-pyrazole-4-carboxylate (27.9 g, 120 mmol) in 4N sodium hydroxide (300 mL) solution was heated under reflux for 1 hour. The mixture was cooled to room temperature, neutralized with conc. hydrochloric acid, and made acidic with acetic acid. The resulting crystals were collected by filtration, washed with ethanol, and air dried. The crystals was subjected to heat at a temperature of 200° C., and then washed with diethylether to give the title compound (6.02 g, 31% yield).

NMR (CDCl$_3$) δ: 5.51 (1H, d, J=1.8 Hz), 5.95 (2H, br s), 7.07–7.13 (1H, m), 7.42 (1H, d, J=1.8 Hz), 7.75–7.84 (1H, m), 7.98 (1H, d, J=8.4 Hz), 8.33 (1H, dd, J=1.6 Hz, 4.6 Hz).

REFERENCE EXAMPLE 1-28

2-[[1-(2-Pyridinyl)-1H-pyrazol-5-yl]amino]benzoic acid

Following the procedure described in Reference Example 1-11, the title compound was prepared from o-iodobenzoic acid and 1-(2-pyridinyl)-1H-pyrazol-5-ylamine (90% yield).

mp: 216–218° C. (recrystallized from ethanol). NMR (DMSO-$d_6$) δ: 6.40 (1H, d, J=2.2 Hz), 6.90–6.98 (1H, m), 7.37 (1H, ddd, J=1.2Hz, 5.0 Hz, 7.2 Hz), 7.48–7.57 (1H, m), 7.61 (1H, dd, J=1.0 Hz, 8.4 Hz), 7.69 (1H, d, J=2.2 Hz), 7.88–8.08 (3H, m), 8.49 (1H, dd, J=1.0 Hz, 5.0 Hz), 12.20 (1H, br s), hidden (1H). Elementary Analysis: for $C_{15}H_{12}N_4O_2$ Calcd.: C, 64.28; H, 4.32; N, 19.99. Found: C, 64.44; H, 4.26; N, 20.11.

EXAMPLE 1-1

Ethyl 4-hydroxy-3-methyl-1-(2-pyridinyl)-1H-pyrazolo[3,4-b]pyridine-5-carboxylate A solution of diethyl 2-([[3-methyl-1-(2-pyridinyl)-1H-pyrazol-5-yl]amino]methylene)malonate (2.0 g, 5.8 mmol) in polyphosphoric acid (10 g) was heated and stirred at 100° C. for 2 hours. The solution was cooled to room temperature, and iced water was added thereto. The solution was neutralized by the addition of an aqueous sodium hydroxide solution, and organic matter was extracted with 10% methanol/chloroform. The extract was washed with saturated brine and water, dried over anhydrous magnesium sulfate, and the solvent was evaporated under reduced pressure. Purification of the residue by silica gel column chromatography (chloroform) gave the title compound (0.98 g, 57% yield).

mp: 166–169° C. (recrystallized from ethyl acetate). NMR (CDCl$_3$) δ: 1.46 (3H, t, J=7.3 Hz), 2.79 (3H, s), 4.49 (2H, q, J=7.3 Hz), 7.20–7.33 (1H, m), 7.83–7.95 (1H, m), 8.36 (1H, d, J=8.4 Hz), 8.67 (1H, d, J=4.0 Hz), 8.97 (1H, s), 12.25 (1H, s). Elementary Analysis: for $C_{15}H_{14}N_4O_3$ Calcd.: C, 60.40; H, 4.73; N, 18.78. Found: C, 60.28; H, 4.54; N, 18.79.

EXAMPLE 1-2

4-Hydroxy-3-methyl-1-(2-pyridinyl)-1H-pyrazolo[3,4-b]pyridine-5-carboxylic acid

A suspension of ethyl 4-hydroxy-3-methyl-1-(2-pyridinyl)-1H-pyrazolo[3,4-b]pyridine-5-carboxylate (2.0 g, 6.7 mmol) in 6N hydrochloric acid solution (10 mL) was heated and stirred at 100° C. for 1 hour. The solution was cooled to room temperature, made weakly acidic by the addition of an aqueous sodium hydroxide solution, and the resulting precipitate was collected by filtration. The crude crystals thus obtained were washed with water and dried to give the title compound (0.6 g, 33% yield).

mp: 248–251° C. NMR (DMSO-$d_6$) δ: 2.60 (3H, s), 3.32 (1H, br s), 7.44 (1H, t, J=6.6 Hz), 7.90 (1H, d, J=8.4 Hz), 8.08 (1H, t, J=6.6 Hz), 8.48–8.63 (2H, m), hidden (1H).

EXAMPLE 1-3

3-Methyl-1-(2-pyridinyl)-1H-pyrazolo[3,4-b]pyridin-4-ol

A suspension of 4-hydroxy-3-methyl-1-(2-pyridinyl)-1H-pyrazolo[3,4-b]pyridine-5-carboxylic acid (2.0 g, 6.7 mmol) in phosphoric acid (10 mL) was heated and stirred at 180° C. for 12 hours. The reaction solution was cooled to room temperature, neutralized by the addition of an aqueous sodium hydroxide solution, and organic matter was extracted with chloroform. The extract was washed with saturated brine and water, and dried over anhydrous magnesium sulfate, and the solvent was evaporated under reduced pressure. Purification of the residue by silica gel column chromatography (chloroform:methanol=95:5) gave the title compound (230 mg, 15% yield).

mp: 241–243° C. (recrystallized from ethanol). NMR (CDCl$_3$) δ: 2.70 (3H, s), 6.21 (1H, d, J=7.3 Hz), 7.17–7.25 (1H, m), 7.49 (1H, d, J=7.3 Hz), 7.83–8.02 (2H, m), 8.40–8.45 (1H, m), 11.56 (1H, br s).

EXAMPLE 1-4

[4-Hydroxy-3-methyl-1-(2-pyridinyl)-1H-pyrazolo[3,4-b]pyridin-5-yl]phenylmethanone A mixture of methanesulfonic acid (30 mL) and phosphorus pentoxide (6 g) was heated at 100° C. The mixture was stirred thoroughly at the temperature, with gradual addition of powdery ethyl 2-benzoyl-3-[[3-methyl-1-(2-pyridinyl)-1H-pyrazol-5-yl]amino]-2-propenoate (3.0 g, 8.0 mmol). The mixture was further heated and stirred at the temperature for 30 minutes. The solution was cooled to room temperature, iced water was added thereto. The solution was neutralized by the addition of an aqueous sodium hydroxide solution, and organic matter was extracted with chloroform. The extract was washed with saturated brine and water, and dried over anhydrous magnesium sulfate, and the solvent was evaporated under reduced pressure. Purification of the residue by basic silica gel column chromatography (chloroform) gave the title compound (880 mg, 34% yield).

mp: 224–226° C. (recrystallized from ethyl acetate/methanol). NMR (CDCl$_3$) δ: 2.83 (3H, s), 7.20–8.00 (10H, m), 8.82 (1H, br s). Elementary Analysis: for $C_{19}H_{14}N_4O_2$ Calcd.: C, 69.08; H, 4.27; N, 16.96. Found: C, 68.82; H, 4.31; N, 17.13.

EXAMPLE 1-5

[1-(6-Ethoxy-2-pyridinyl)-4-hydroxy-3-methyl-1H-pyrazolo[3,4-b]pyridin-5-yl]phenylmethanone Following the procedure described in Reference Example 1-1, 3-methyl-1-(6-ethoxy-2-pyridinyl)-1H-pyrazol-5-amine was prepared from aminocrotononitrile and 6-ethoxy-2-hydrazinopyridine. Following the procedure described in Reference Example 1-2, the compound was subjected to a reaction with ethyl 2-benzoyl-3-ethoxy-2-propenoate to give ethyl 2-benzoyl-3-[[3-methyl-1-(6-ethoxy-2-pyridinyl)-1H-pyrazol-5-yl]amino)-2-propenoate. The compound was treated following the method described in Example 1-4 to give the title compound (35% cyclization yield).

mp: 160–162° C. (recrystallized from ethyl acetate). NMR (CDCl$_3$) δ: 1.45 (3H, t, J=7.0 Hz), 2.78 (3H, s), 4.44 (2H, q, J=7.0 Hz), 6.71 (1H, d, J=8.1 Hz), 7.45–7.85 (8H, m), 8.73 (1H, br s).

EXAMPLE 1-6

Ethyl 4-hydroxy-1-(2-pyridinyl)-1H-pyrazolo[3,4-b]pyridine-5-carboxylate

Following the procedure described in Example 1-1, the title compound was prepared from diethyl 2-([[1-(2-pyridinyl)-1H-pyrazol-5-yl]amino]methylene)malonate (41% yield).

mp: 195–197° C. (recrystallized from chloroform/methanol). NMR (CDCl$_3$) δ: 1.46 (3H, t, J=7.0 Hz), 4.50 (2H, q, J=7.0 Hz), 7.25–7.35 (1H, m), 7.87–7.98 (1H, m), 8.31 (1H, d, J=8.1 Hz), 8.40 (1H, s), 8.68 (1H, br s), 9.03 (1H, s), 12.25 (1H, br s). Elementary Analysis: for $C_{14}H_{12}N_4O_3$ Calcd.: C, 59.15; H, 4.25; N, 19.71. Found: C, 59.00; H, 4.30; N, 19.80.

EXAMPLE 1-7

1-(2-Pyridinyl)-1H-pyrazolo[3,4-b]pyridin-4-ol

Following the procedure described in Example 1-3, the title compound was prepared from ethyl 4-hydroxy-1-(2-pyridinyl)-1H-pyrazolo[3,4-b]pyridine-5-carboxylate (99% yield).

mp: 192–194° C. (recrystallized from ethyl acetate/methanol). NMR (CDCl$_3$) δ: 6.28 (1H, d, J=7.3 Hz), 7.23–7.30 (1H, m), 7.53 (1H, d, J=7.7 Hz), 7.88–7.99 (1H, m), 8.05 (1H, br, d, J=8.4 Hz), 8.26 (1H, s), 8.43–8.48 (1H, m), 11.56 (1H, br s). Elementary Analysis: for $C_{11}H_8N_4O.H_2O$ Calcd.: C, 57.39; H, 4.38; N, 24.34. Found: C, 57.51; H, 4.24; N, 24.29.

EXAMPLE 1-8

N-Cyclohexyl-4-hydroxy-3-methyl-1-(2-pyridinyl)-1H-pyrazolo[3,4-b]pyridine-5-carboxamide A mixed solution of ethyl 4-hydroxy-3-methyl-1-(2-pyridinyl)-1H-pyrazolo[3,4-b]pyridine-5-carboxylate (1.5 g, 5.0 mmol) and cyclohexylamine (2.2 g, 22 mmol) in xylene (5.0 mL) and dimethylsulfoxide (5.0 mL) was stirred at 130° C. for 28 hours. The solution was cooled to room temperature and water was added thereto. Subsequently, organic matter was extracted with ethyl acetate. The extract was washed with saturated brine and dried over anhydrous sodium sulfate, and the solvent was evaporated under reduced pressure. Purification of the residue by silica gel column chromatography (chloroform:methanol=50:1 to 20:1) gave crude crystals. The crude crystals were recrystallized from ethyl acetate/ethanol to give the title compound (0.17 g, 10% yield).

mp: >300° C. (recrystallized from ethyl acetate/ethanol). NMR (CDCl$_3$) δ: 1.22–1.46 (4H, m), 1.52–1.80 (4H, m), 1.94–2.04 (2H, m), 2.73 (3H, s), 3.98 (1H, br), 7.22–7.28 (1H, m), 7.87–8.02 (2H, m), 8.45 (1H, d, J=4.4 Hz), 8.72 (1H, d, J=5.8 Hz), 9.99 (1H, d, J=8.0 Hz), 11.84 (1H, br s). Elementary Analysis: for $C_{19}H_{21}N_5O_2$ Calcd.: C, 64.94; H, 6.02; N, 19.93. Found: C, 64.82; H, 6.18; N, 19.69.

EXAMPLE 1-9

N-Benzyl-4-hydroxy-3-methyl-1-(2-pyridinyl)-1H-pyrazolo[3,4-b]pyridine-5-carboxamide A mixture of ethyl 4-hydroxy-3-methyl-1-(2-pyridinyl)-1H-pyrazolo[3,4-b]pyridine-5-carboxylate (2.0 g, 6.7 mmol) and benzylamine (8.0 mL, 73 mmol) was stirred at 180° C. for 16 hours under an argon atmosphere. The mixture was cooled to room temperature, ethyl acetate was added thereto. The resulting crude crystals were collected by filtration, and washed with ethyl acetate. The crude crystals thus obtained were purified by silica gel column chromatography (chloroform:methanol=20:1 to 5:1), and recrystallized from ethanol to give the title compound (1.5 g, 60% yield).

mp: >300° C. (recrystallized from ethanol). NMR (CDCl$_3$/CF$_3$CO$_2$D, 50:1) δ: 2.80 (3H, s), 4.66 (2H, s), 7.33–7.44 (6H, m), 8.04–8.07 (2H, m), 8.48–8.51 (1H, m), 9.11 (1H, s), hidden (2H). Elementary Analysis: for $C_{20}H_{17}N_5O_2$ Calcd.: C, 66.84; H, 4.77; N, 19.49. Found: C, 66.77; H, 4.72; N, 19.38.

EXAMPLE 1-10

[4-Hydroxy-3-methyl-1-(2-pyridinyl)-1H-pyrazolo[3,4-b]pyridin-5-yl](1-piperidinyl)methanone Following the procedure described in Example 1-9, the title compound was prepared from ethyl 4-hydroxy-3-methyl-1-(2-pyridinyl)-1H-pyrazolo[3,4-b]pyridine-5-carboxylate and piperidine (32% yield).

mp: 264–266° C. (recrystallized from ethyl acetate/ethanol). NMR (CDCl$_3$) δ: 1.65 (6H, br), 2.66 (3H, s), 3.39 (2H, br), 3.72 (2H, br), 7.18–7.24 (1H, m), 7.74 (1H, d, J=5.2 Hz), 7.83–7.98 (2H, m), 8.41 (1H, d, J=5.2 Hz), 11.62 (1H, br). Elementary Analysis: for $C_{18}H_{19}N_5O_2$ Calcd.: C, 64.08; H, 5.68; N, 20.76. Found: C, 64.08; H, 5.93; N, 20.79

EXAMPLE 1-11

4-Hydroxy-3-methyl-N-phenyl-1-(2-pyridinyl)-1H-pyrazolo[3,4-b]pyridine-5-carboxamide Following the procedure described in Example 1-9, the title compound was prepared from ethyl 4-hydroxy-3- methyl-1-(2-pyridinyl)-1H-pyrazolo[3,4-b]pyridine-5-carboxylate and aniline (16% yield).

mp: >300° C. (recrystallized from ethanol). NMR (CDCl$_3$/CF$_3$CO$_2$D, 50:1) δ: 2.83 (3H, s), 7.26–7.33 (1H, m), 7.40–7.47 (3H, m), 7.60 (2H, d, J=8.2 Hz), 8.06–8.10 (2H, m), 8.53 (1H, d, J=5.2 Hz), 9.27 (1H, s), hidden (2H). Elementary Analysis: for C$_{19}$H$_{15}$N$_5$O$_2$ Calcd.: C, 66.08; H, 4.38; N, 20.28. Found: C, 65.81; H, 4.37; N, 20.31

EXAMPLE 1-12

N-(2-Fluorophenyl)-4-hydroxy-3-methyl-1-(2-pyridinyl)-1H-pyrazolo[3,4-b]pyridine-5-carboxamide Following the procedure described in Example 1-9, the title compound was prepared from ethyl 4-hydroxy-3-methyl-1-(2-pyridinyl)-1H-pyrazolo[3,4-b]pyridine-5-carboxylate and 2-fluoroaniline (23% yield).

mp: >300° C. (recrystallized from ethanol). NMR (CDCl$_3$/CF$_3$CO$_2$D, 50:1) δ: 2.79 (3H, s), 7.13–7.29 (3H, m), 7.37–7.43 (1H, m), 7.86–7.95 (1H, m), 8.01–8.10 (2H, m), 8.53 (1H, d, J=5.4 Hz), 9.19 (1H, s), hidden (2H). Elementary Analysis: for C$_{19}$H$_{14}$N$_5$O$_2$F Calcd.: C, 62.81; H, 3.88; N, 19.27. Found: C, 62.62; H, 4.08; N, 19.31.

EXAMPLE 1-13

N-(3-Fluorophenyl)-4-hydroxy-3-methyl-1-(2-pyridinyl)-1H-pyrazolo[3,4-b]pyridine-5-carboxamide Following the procedure described in Example 1-9, the title compound was prepared from ethyl 4-hydroxy-3-methyl-1-(2-pyridinyl)-1H-pyrazolo[3,4-b]pyridine-5-carboxylate and 3-fluoroaniline (19% yield).

mp: >300° C. (recrystallized from ethanol). NMR (CDCl$_3$) δ: 2.83 (3H s), 6.96–7.04 (1H, m), 7.31–7.54 (4H, m), 8.10–8.16 (2H, m), 8.54 (1H, dd, J=5.3, 1.6 Hz), 9.25 (1H, s), 11.18 (2H, br s). Elementary Analysis: for C$_{19}$H$_{14}$N$_5$O$_2$F Calcd.: C, 62.81; H, 3.88; N, 19.27. Found: C, 62.62; H, 4.08; N, 19.31.

EXAMPLE 1-14

N-(4-Fluorophenyl)-4-hydroxy-3-methyl-1-(2-pyridinyl)-1H-pyrazolo[3,4-b]pyridine-5-carboxamide Following the procedure described in Example 1-9, the title compound was prepared from ethyl 4-hydroxy-3-methyl-1-(2-pyridinyl)-1H-pyrazolo[3,4-b]pyridine-5-carboxylate and 4-fluoroaniline (14% yield).

mp: >300° C. (recrystallized from ethanol). NMR (CDCl$_3$/CF$_3$CO$_2$D, 50:1) δ: 2.81 (3H, s), 7.07–7.16 (2H, m), 7.36–7.45 (1H, m), 7.56–7.63 (2H, m), 8.06–8.09 (2H, m), 8.52–8.55 (1H, m), 9.24 (1H, s), hidden (2H). Elementary Analysis: for C$_{19}$H$_{14}$N$_5$O$_2$F Calcd.: C, 62.81; H, 3.88; N, 19.27. Found: C, 62.88; H, 3.87; N, 19.31.

EXAMPLE 1-15

N-(3,4-Difluorophenyl)-4-hydroxy-3-methyl-1-(2-pyridinyl)-1H-pyrazolo[3,4-b]pyridine-5-carboxamide Following the procedure described in Example 1-9, the title compound was prepared from ethyl 4-hydroxy-3-methyl-1-(2-pyridinyl)-1H-pyrazolo[3,4-b]pyridine-5-carboxylate and 3,4-difluoroaniline (7% yield).

mp: >300° C. (recrystallized from ethanol). NMR (CDCl$_3$/CF$_3$CO$_2$D, 10:1) δ: 2.84 (3H, s), 7.14–7.28 (2H, m), 7.44–7.51 (1H, m), 7.57–7.67 (1H, m), 8.12–8.14 (2H, m), 8.53–8.55 (1H, m), 9.23 (1H, s), 10.21 (1H, br s), hidden (1H). Elementary Analysis: for C$_{19}$H$_{13}$N$_5$O$_2$F$_2$ Calcd.: C, 59.84; H, 3.44; N, 18.36. Found: C, 59.66; H, 3.43; N, 18.26.

EXAMPLE 1-16

N-[(3,5-Bis(trifluoromethyl)phenyl]-4-hydroxy-3-methyl-1-(2-pyridinyl)-1H-pyrazolo[3,4-b]pyridine-5-carboxamide Following the procedure described in Example 1-9, the title compound was prepared from ethyl 4-hydroxy-3-methyl-1-(2-pyridinyl)-1H-pyrazolo[3,4-b]pyridine-5-carboxylate and 3,5-bis(trifluoromethyl)aniline (49% yield).

mp: 283–285° C. (recrystallized from ethanol). NMR (CDCl$_3$) δ: 2.77 (3H, s), 7.23–7.30 (1H, m), 7.57 (1H, s), 7.88–8.03 (2H, m), 8.27 (2H, s), 8.44–8.47 (1H, m), 8.79 (1H, d, J=6.2 Hz), 12.16 (1H, br), 12.80 (1H, br s). Elementary Analysis: for C$_{21}$H$_{13}$N$_5$O$_2$F$_6$·H$_2$O Calcd.: C, 50.51; H, 3.03; N, 14.02. Found: C, 50.28; H, 2.86; N, 14.05.

EXAMPLE 1-17

4-(Benzyloxy)-N,3-dimethyl-N-phenyl-1-(2-pyridinyl)-1H-pyrazolo[3,4-b]pyridine-5-carboxamide To a solution of benzyl alcohol (0.40 g, 3.7 mmol) in N,N-dimethylformamide (10 mL), sodium hydride (0.16 g, 40 mmol, 60% oil) was added at room temperature, and the resulting mixture was stirred at the same temperature for 30 minutes. To the solution, a solution of 4-chloro-N,3-dimethyl-N-phenyl-1-(2-pyridinyl)-1H-pyrazolo[3,4-b]pyridine-5-carboxamide (1.0 g, 2.8 mmol) in N,N-dimethylformamide (10 mL) solution was added at room temperature, and stirred at 100° C. for 11.5 hours. The mixture was concentrated under reduced pressure, and the residue was poured into water. Organic matter was extracted with ethyl acetate. The extract was washed with saturated brine and dried over anhydrous sodium sulfate, and the solvent was evaporated under reduced pressure. Purification of the resulting residue by silica gel chromatography (hexane:chloroform:ethyl acetate=2:1:1 to 1:1:1 to 1:2:2) gave the title compound (0.99 g, 80% yield).

mp: 92–93° C. (crystallized from hexane/chloroform/ethyl acetate). NMR (CDCl$_3$) δ: 2.53 (3H, s), 3.56 (3H, s), 5.43 (2H, s), 7.01–7.23 (5H, m), 7.27–7.51 (6H, m), 7.83 (1H, td, J=7.7, 2.2 Hz), 8.28 (1H, d, J=8.4 Hz), 8.39 (1H, s), 8.62 (1H, d, J=3.8 Hz). Elementary Analysis: for C$_{27}$H$_{23}$N$_5$O$_2$·1.6CHCl$_3$ Calcd.: C, 53.63; H, 3.87; N, 10.93. Found: C, 53.42; H, 3.77; N, 10.92.

EXAMPLE 1-18

3,6-Dimethyl-1-(2-pyridinyl)-1H-pyrazolo[3,4-b]pyridin-4-ol

A mixture of 3-methyl-1-(2-pyridinyl)-1H-pyrazol-5-amine (1.8 g, 10 mmol) and polyphosphoric acid (4.2 g) was heated at 130° C. The mixture was stirred thoroughly at the same temperature, while ethyl acetoacetate (1.3 mL, 10 mmol) was added dropwise thereto, and the resulting mixture was stirred at the same temperature for 1 hour. The mixture was cooled to room temperature, iced water was added thereto. The mixture was neutralized with an aqueous sodium hydroxide solution, and organic matter was extracted with chloroform. The extract was washed with saturated brine and dried over anhydrous sodium sulfate, and the solvent was evaporated under reduced pressure. The residue thus obtained was purified by silica gel column chromatography (chloroform:methanol=50:1 to 20:1), and recrystallized from ethyl acetate to give the title compound (0.72 g, 30% yield).

mp: 175–176° C. (recrystallized from ethyl acetate). NMR (CDCl$_3$) δ: 2.43 (3H, s), 2.68 (3H, s), 6.03 (1H, d, J=1.0 Hz), 7.17–7.23 (1H, m), 7.88 (1H, td, J=8.5, 2.0 Hz), 7.98 (1H, d, J=8.5 Hz), 8.40–8.43 (1H, m), 11.13 (1H, br). Elementary Analysis: for C$_{13}$H$_{12}$N$_4$O.1.5H$_2$O Calcd.: C, 58.42; H, 5.66; N, 20.96.
Found: C, 58.97; H, 5.63; N, 21.11.

EXAMPLE 1-19

3,5,6-Trimethyl-1-(2-pyridinyl)-1H-pyrazolo[3,4-b]pyridin-4-ol

Following the procedure described in Example 1-18, a mixture containing the title compound as the main component was prepared from 3-methyl-1-(2-pyridinyl)-1H-pyrazol-5-amine and ethyl 2-methylacetoacetate (16% yield).

mp: 187–188° C. (recrystallized from ethyl acetate). NMR (CDCl$_3$) δ: 2.08 (3H, s), 2.44 (3H, s), 2.70 (3H, s), 7.14–7.21 (1H, m), 7.82–7.98 (2H, m), 8.39–8.43 (1H, m), 10.98 (1H, br).

EXAMPLE 1-20

5-Benzyl-3,6-dimethyl-1-(2-pyridinyl)-1H-pyrazolo[3,4-b]pyridin-4-ol

Following the procedure described in Example 1-18, the title compound was prepared from 3-methyl-1-(2-pyridinyl)-1H-pyrazol-5-amine and ethyl 2-benzylacetoacetate (15% yield).

mp: 181–182° C. (recrystallized from ethyl acetate). NMR (CDCl$_3$) δ: 2.41 (3H, s), 2.72 (3H, s), 4.00 (2H, s), 7.14–7.30 (6H, m), 7.86 (1H, td, J=7.9, 1.8 Hz), 7.97 (1H, d, J=8.4 Hz), 8.40 (1H, d, J=4.0 Hz), 11.03 (1H, br). Elementary Analysis: for C$_{20}$H$_{18}$N$_4$O Calcd.: C, 72.71; H, 5.49; N, 16.96. Found: C, 72.67; H, 5.49; N, 17.02.

EXAMPLE 1-21

6-Benzyl-3-methyl-1-(2-pyridinyl)-1H-pyrazolo[3,4-b]pyridin-4-ol

Following the procedure described in Example 1-18, the title compound was prepared from 3-methyl-1-(2-pyridinyl)-1H-pyrazol-5-amine and ethyl 3-oxo-4-phenylbutanoate (14% yield).

mp: 168–169° C. (recrystallized from ethyl acetate). NMR (CDCl$_3$) δ: 2.67 (3H, s), 4.02 (2H, s), 6.14 (1H, t, J=0.8 Hz), 7.08–7.14 (1H, m), 7.32–7.47 (5H, m), 7.77–7.92 (2H, m), 8.09–8.13 (1H, m), 11.11 (1H, br). Elementary Analysis: for C$_{19}$H$_{16}$N$_4$O Calcd.: C, 72.14; H, 5.10; N, 17.71. Found: C, 71.91; H, 5.16; N, 17.53.

EXAMPLE 1-22

3-Methyl-6-phenyl-1-(2-pyridinyl)-1H-pyrazolo[3,4-b]pyridin-4-ol

Following the procedure described in Example 1-18, the title compound was prepared from 3-methyl-1-(2-pyridinyl)-1H-pyrazol-5-amine and ethyl benzoylacetate (32% yield).

mp: 198–199° C. (recrystallized from ethyl acetate). NMR (CDCl$_3$) δ: 2.73 (3H, s), 6.52 (1H, d, J=1.8 Hz), 7.21 (1H, t, J=6.2 Hz), 7.54–7.58 (3H, m), 7.69–7.74 (2H, m), 7.86–7.95 (1H, m), 8.02 (1H, d, J=8.4 Hz), 8.43 (1H, d, J=5.0 Hz), 11.73 (1H, br). Elementary Analysis: for C$_{18}$H$_{14}$N$_4$O.H$_2$O Calcd.: C, 67.49; H, 5.03; N, 17.49. Found: C, 67.83; H, 5.18; N, 17.69.

EXAMPLE 1-23

3,4-Dimethyl-1-(2-pyridinyl)-1H-pyrazolo[3,4-b]pyridin-6-ol

A solution of 3-methyl-1-(2-pyridinyl)-1H-pyrazol-5-amine (5.1 g, 29 mmol) and ethyl acetoacetate (3.8 g, 30 mmol) in acetic acid (14 mL) was stirred at 100° C. for 4 hours. The solution was cooled to room temperature and ethyl acetate was added thereto. The resulting crude crystals were collected by filtration, and recrystallized from ethanol to give the title compound (4.4 g, 62% yield).

mp: 254–255° C. (recrystallized from ethanol). NMR (CDCl$_3$) δ: 2.46 (3H, s), 2.56 (3H, s), 6.13 (1H, s), 7.15–7.22 (1H, m), 7.80–7.95 (2H, m), 8.39 (1H, d, J=4.8 Hz), 11.52 (1H, br). Elementary Analysis: for C$_{13}$H$_{12}$N$_4$O Calcd.: C, 64.99; H, 5.03; N, 23.32. Found: C, 65.06; H, 5.15; N, 23.24.

EXAMPLE 1-24

3,4,5-Trimethyl-1-(2-pyridinyl)-1H-pyrazolo[3,4-b]pyridin-6-ol

Following the procedure described in Example 1-19, the title compound as the by-product was prepared from 3-methyl-1-(2-pyridinyl)-1H-pyrazol-5-amine and ethyl 2-methylacetoacetate (7% yield).

mp: 226–228° C. (recrystallized from ethyl acetate). NMR (CDCl$_3$) δ: 2.16 (3H, s), 2.46 (3H, s), 2.59 (3H, s), 7.13–7.20 (1H, m), 7.79–7.95 (2H, m), 8.41–8.43 (1H, m), 11.54 (1H, br). Elementary Analysis: for C$_{14}$H$_{14}$N$_4$O Calcd.: C, 66.13; H, 5.55; N, 22.03. Found: C, 66.11; H, 5.35; N, 21.94.

EXAMPLE 1-25

5-Benzyl-3,4-dimethyl-1-(2-pyridinyl)-1H-pyrazolo[3,4-b]pyridin-6-ol

Following the procedure described in Example 1-23, the title compound was prepared from 3-methyl-1-(2-pyridinyl)-1H-pyrazol-5-amine and ethyl 2-benzylacetoacetate (24% yield).

mp: 208–209° C. (recrystallized from ethyl acetate). NMR (CDCl$_3$) δ: 2.46 (3H, s), 2.57 (3H, s), 4.07 (2H, s), 7.15–7.30 (6H, m), 7.84 (1H, td, J=8.4, 1.8 Hz), 7.92 (1H, d, J=8.4 Hz), 8.40 (1H, d, J=5.0 Hz), 11.60 (1H, br). Elementary Analysis: for C$_{20}$H$_{18}$N$_4$O Calcd.: C, 72.71; H, 5.49; N, 16.96. Found: C, 72.83; H, 5.34; N, 16.90.

EXAMPLE 1-26

4-Benzyl-3-methyl-1-(2-pyridinyl)-1H-pyrazolo[3,4-b]pyridin-6-ol

Following the procedure described in Example 1-23, the title compound was prepared from 3-methyl-1-(2-pyridinyl)-1H-pyrazol-5-amine and ethyl 3-oxo-4-phenylbutanoate (37% yield).

mp: 222–224° C. (recrystallized from ethyl acetate). NMR (CDCl$_3$) δ: 2.41 (3H, s), 4.14 (2H, s), 7.17–7.37 (7H, m), 7.80–7.91 (2H, m), 8.39–8.42 (1H, m), 11.65 (1H, br) Elementary Analysis: for $C_{19}H_{16}N_4$). Calcd.: C, 72.14; H, 5.10; N, 17.71. Found: C, 72.29; H, 4.93; N, 17.86.

EXAMPLE 1-27

3-Methyl-4-phenyl-1-(2-pyridinyl)-1H-pyrazolo[3,4-b]pyridin-6-ol

Following the procedure described in Example 1-23, the title compound was prepared from 3-methyl-1-(2-pyridinyl)-1H-pyrazol-5-amine and ethyl benzoylacetate (13% yield).

mp: 195–196° C (recrystallized from ethanol). NMR (CDCl$_3$) δ: 2.06 (3H, s), 6.26 (1H, s), 7.18–7.51 (6H, m), 7.87 (1H, td, J=8.4, 2.0 Hz), 7.96 (1H, d, J=8.4 Hz), 8.43 (1H, d, J=4.8 Hz), 11.78 (1H, br). Elementary Analysis: for $C_{18}H_{14}N_4O$ Calcd.: C, 71.51; H, 4.67; N, 18.53. Found: C, 71.55; H, 4.70; N, 18.36.

EXAMPLE 1-28

1-Methyl-3-(2-pyridinyl)-3,6,7,8-tetrahydrocyclopenta[d]pyrazolo[3,4-b]pyridin-5-ol Following the procedure described in Example 1-23, the title compound was prepared from 3-methyl-1-(2-pyridinyl)-1H-pyrazol-5-amine and ethyl 2-oxocyclopentanecarboxylate (17% yield).

mp: 255–256° C. (recrystallized from ethyl acetate). NMR (CDCl$_3$) δ: 2.15–2.27 (2H, m), 2.50 (3H, s), 2.88 (2H, t, J=7.6 Hz), 3.12 (2H, t, J=8.1 Hz), 7.14–7.21 (1H, m), 7.79–7.95 (2H, m), 8.39–8.43 (1H, m), 11.51 (1H, br). Elementary Analysis: for $C_{15}H_{14}N_4O$ Calcd.: C, 67.65; H, 5.30; N, 21.04. Found: C, 67.69; H, 5.31; N, 20.93.

EXAMPLE 1-29

1-Methyl-3-(2-pyridinyl)-6,7,8,9-tetrahydro-3H-pyrazolo[3,4-c]isoquinolin-5-ol

Following the procedure described in Example 1-18, the title compound was prepared from 3-methyl-1-(2-pyridinyl)-1H-pyrazol-5-amine and ethyl 2-cyclohexanonecarboxylate (19% yield).

mp: 248–249° C. (recrystallized from ethyl acetate). NMR (CDCl$_3$) δ: 1.82 (4H, br), 2.56 (3H, s), 2.58 (2H, br), 2.90 (2H, br), 7.13–7.19 (1H, m), 7.78–7.94 (2H, m), 8.40 (1H, dd, J=5.8, 0.8 Hz), 11.47 (1H, br). Elementary Analysis: for $C_{16}H_{16}N_4O$ Calcd.: C, 68.55; H, 5.75; N, 19.99. Found: C, 68.42; H, 5.70; N, 19.99.

EXAMPLE 1-30

1-Methyl-3-(2-pyridinyl)-3,6,7,8,9,10-hexahydrocyclohepta[d]pyrazolo[3,4-b]pyridin-5-ol Following the procedure described in Example 1-18, the title compound was prepared from 3-methyl-1-(2-pyridinyl)-1H-pyrazol-5-amine and methyl 2-oxocycloheptanecarboxylate (8% yield).

mp: 243–244° C. (recrystallized from ethyl acetate/hexane). NMR (CDCl$_3$) δ: 1.59 (2H, br), 1.65–1.73 (2H, m), 1.86–1.96 (2H, m), 2.58 (3H, s), 2.89–2.95 (2H, m), 2.99–3.05 (2H, m), 7.13–7.20 (1H, m), 7.79–7.95 (2H, m), 8.40–8.43 (1H, m), 11.58 (1H, br). Elementary Analysis: for $C_{17}H_{18}N_4O$ Calcd.: C, 69.37; H, 6.16; N, 19.03. Found: C, 69.36; H, 6.18; N, 19.15.

EXAMPLE 1-31

Ethyl 4-amino-3-methyl-1-(2-pyridinyl)-1H-pyrazolo[3,4-b]pyridine-5-carboxylate

A solution of ethyl 4-chloro-3-methyl-1-(2-pyridinyl)-1H-pyrazolo[3,4-b]pyridine-5-carboxylate (1.0 g, 3.2 mmol) and sodium azide (0.23 g, 3.5 mmol) in N,N-dimethylformamide (5 mL) was heated and stirred at 100° C. for 30 minutes. The solution was cooled to room temperature, and poured into water, and the resulting solution was made basic by the addition of an aqueous sodium hydroxide solution, and organic matter was extracted with chloroform. The extract was washed with saturated brine and dried over anhydrous sodium sulfate, and the solvent was evaporated under reduced pressure to give ethyl 4-azido-3-methyl-1-(2-pyridinyl)-1H-pyrazolo[3,4-b]pyridine-5-carboxylate. To a solution of the ethyl 4-azido-3-methyl-1-(2-pyridinyl)-1H-pyrazolo[3,4-b]pyridine-5-carboxylate in ethanol (150 mL) was added 10% palladium-carbon (1.2 g, 50% hydrate), and the mixture was stirred at room temperature for 1 hour under hydrogen atmosphere. The catalyst was removed by filtration, and the filtrate was concentrated under reduced pressure. Purification of the residue by silica gel column chromatography (basic silica gel, ethyl acetate:methanol=93:7) gave the title compound (900 mg, 96% yield).

mp: 147–149° C. (recrystallized from ethyl acetate/hexane). NMR (CDCl$_3$) δ: 1.41 (3H, t, J=7.3 Hz), 2.80 (3H, s), 4.38 (2H, q, J=7.3 Hz), 7.19–7.30 (1H, m), 7.81–7.93 (1H, m), 8.41 (1H, d, J=8.1 Hz), 8.60–8.70 (1H m), 8.96 (1H s), hidden (2H). Elementary Analysis: for $C_{15}H_{15}N_5O_2 \cdot 0.3H_2O$ Calcd.: C, 59.52; H, 5.19; N, 23.13. Found: C, 59.40; H, 5.16; N, 23.30.

EXAMPLE 1-32

4-(Benzyloxy)-3-methyl-1-(2-pyridinyl)-1H-pyrazolo[3,4-b]pyridine

Following the procedure described in Example 1-17, the title compound was prepared from 4-chloro-3-methyl-1-(2-pyridinyl)-1H-pyrazolo[3,4-b]pyridine and benzyl alcohol (54% yield).

mp: 108–110° C. (crystallized from hexane/diethylether). NMR (CDCl$_3$) δ: 2.77 (3H, s), 5.31 (2H, s), 6.65 (1H, d, J=5.6 Hz), 7.16–7.23 (1H, m), 7.37–7.51 (5H, m), 7.81–7.90 (1H, m), 8.42 (1H, dd, J=8.2, 0.8 Hz), 8.48 (1H, d, J=5.6 Hz), 8.64–8.67 (1H, m). Elementary Analysis: for $C_{19}H_{16}N_4O$ Calcd.: C, 72.14; H, 5.10; N, 17.71. Found: C, 72.11; H, 5.15; N, 17.80.

EXAMPLE 1-33

4-Hydroxy-3-methyl-1-(2-pyridinyl)-1H-pyrazolo[3,4-b]pyridin-5-yl]phenylmethanone A solution of [4-chloro-3-methyl-1-(2-pyridinyl)-1H-pyrazolo[3,4-b]pyridin-5-yl]phenylmethanone (0.51 g, 1.5 mmol) and 6N hydrochloric acid (5.0 mL) in methanol (10 mL) was heated under reflux for 14 hours. The solution was cooled to room temperature, neutralized by the addition of a 1N sodium hydroxide solution, and organic matter was extracted with chloroform. The extract was washed with saturated brine and dried over anhydrous sodium sulfate, and the solvent was evaporated under reduced pressure. The residue was recrystallized from ethyl acetate/methanol to give the title compound (0.36 g, 75% yield).

NMR (CDCl$_3$) δ: 2.83 (3H, s), 7.20–8.00 (10H, m), 8.82 (1H, br s).

Chemical structures of the compounds obtained in Examples 1-1 to 1-33 are summarized in the following Table 1 and Table 2.

TABLE 1

| Example Number | R³ | R¹ | X | Y | Z |
|---|---|---|---|---|---|
| 1-1 | 2-Py | Me | OH | CO₂Et | H |
| 1-2 | 2-Py | Me | OH | CO₂H | H |
| 1-3 | 2-Py | Me | OH | H | H |
| 1-4 | 2-Py | Me | OH | PhCO | H |
| 1-5 | 6-EtO-2-Py | Me | OH | PhCO | H |
| 1-6 | 2-Py | H | OH | CO₂Et | H |
| 1-7 | 2-Py | H | OH | H | H |
| 1-8 | 2-Py | Me | OH | cyclohexyl-NHCO | H |
| 1-9 | 2-Py | Me | OH | PhCH₂NHCO | H |
| 1-10 | 2-Py | Me | OH | 1-piperidinyl-CO | H |
| 1-11 | 2-Py | Me | OH | PhNHCO | H |
| 1-12 | 2-Py | Me | OH | 2-F-PhNHCO | H |
| 1-13 | 2-Py | Me | OH | 3-F-PhNHCO | H |
| 1-14 | 2-Py | Me | OH | 4-F-PhNHCO | H |
| 1-15 | 2-Py | Me | OH | 3,4-F-PhNHCO | H |
| 1-16 | 2-Py | Me | OH | 3,5-CF₃-PhNHCO | H |
| 1-17 | 2-Py | Me | PhCH₂O | PhNMeCO | H |
| 1-18 | 2-Py | Me | OH | H | Me |
| 1-19 | 2-Py | Me | OH | Me | Me |
| 1-20 | 2-Py | Me | OH | PhCH₂ | Me |
| 1-21 | 2-Py | Me | OH | H | PhCH₂ |
| 1-22 | 2-Py | Me | OH | H | Ph |
| 1-23 | 2-Py | Me | Me | H | OH |
| 1-24 | 2-Py | Me | Me | Me | OH |
| 1-25 | 2-Py | Me | Me | PhCH₂ | OH |
| 1-26 | 2-Py | Me | PhCH₂ | H | OH |
| 1-27 | 2-Py | Me | Ph | H | OH |
| 1-31 | 2-Py | Me | NH₂ | COOEt | H |
| 1-32 | 2-Py | Me | PhCH₂O | H | H |
| 1-33 | 2-Py | Me | OH | PhCO | H |

TABLE 2

| Example Number | R³ | R¹ | Ring A |
|---|---|---|---|
| 1-28 | 2-Py | Me | (5-membered ring) |
| 1-29 | 2-Py | Me | (6-membered ring) |
| 1-30 | 2-Py | Me | (7-membered ring) |

EXAMPLE 1-34

4-Chloro-3-methyl-1-(2-pyridinyl)-1H-pyrazolo[3,4-b]quinoline

A solution of 2-[[3-methyl-1-(2-pyridinyl)-1H-pyrazol-5-yl]amino]benzoic acid (50.2 g, 0.17 mol) in phosphorous oxychloride (120 mL, 1.27 mol) was heated under reflux for 1 hour. After the solution was cooled to room temperature, the solvent was evaporated under reduced pressure and the residue was poured into iced water. The solution was made basic by the addition of a sodium hydroxide solution, and organic matter was extracted with chloroform. The extract was washed with saturated brine and water, dried over anhydrous magnesium sulfate, and the solvent was evaporated under reduced pressure. Purification of the residue thus obtained by silica gel column chromatography (chloroform:methanol=98:2) gave the title compound (21.5 g, 43% yield).

mp: 157–159° C. (recrystallized from ethyl acetate/hexane). NMR (CDCl₃) δ: 3.00 (3H, s), 7.21–7.25 (1H, m), 7.60–7.64 (1H, m), 7.78–7.87 (1H, m), 7.90–7.99 (1H, m), 8.18 (1H, dd, J=0.8 Hz, 8.4 Hz), 8.41 (1H, dt, J=0.8 Hz, 7.6 Hz), 8.68 (1H, d, J=4.8 Hz), 8.85 (1H, d, J=8.4 Hz). Elementary Analysis: for $C_{16}H_{11}ClN_4$ Calcd.: C, 65.20; H, 3.76; N, 19.01; Cl, 12.03. Found: C, 65.22; H, 3.73; N, 19.13; Cl, 11.76.

EXAMPLE 1-35

3-Methyl-1-(2-pyridinyl)-1H-pyrazolo[3,4-b]quinolin-4-ylamine

A solution of 4-chloro-3-methyl-1-(2-pyridinyl)-1H-pyrazolo[3,4-b]quinoline (1.44 g, 4.89 mmol) and sodium azide (0.35 g, 5.37 mmol) in N,N-dimethylformamide (10 mL) was heated and stirred at 100° C. for 30 minutes. The solution was cooled to room temperature and poured into water, and organic matter was extracted with chloroform. The extract was washed with saturated brine and water, dried over anhydrous magnesium sulfate, and the solvent was evaporated under reduced pressure. To a solution of the residue thus obtained in ethanol (70 mL) was added 10% palladium-carbon (2 g, 50% hydrate), and the mixture was stirred at room temperature for 1 hour under an hydrogen atmosphere. The catalyst was removed by filtration, and the filtrate was concentrated under reduced pressure. The resulting residue was purified by basic silica gel column chromatography (ethyl acetate:methanol=95:5) to give the title compound (760 mg, 57% yield).

mp: 210–213° C. (recrystallized from methanol/ethyl acetate/hexane). NMR (CDCl₃) δ: 2.80 (3H, s), 5.60 (2H, br s), 7.13–7.22 (1H, m), 7.29–7.40 (1H, m), 7.63–7.75 (1H, m), 7.80–7.95 (2H, m), 7.98–8.05 (1H, m), 8.60–8.67 (1H, m), 8.90–8.98 (1H, m). Elementary Analysis: for $C_{16}H_{13}N_5$ Calcd.: C, 69.80; H, 4.76; N, 25.44. Found: C, 69.61; H, 4.70; N, 25.30.

EXAMPLE 1-36

3-Methyl-1-(2-pyridinyl)-1H-pyrazolo[3,4-b]quinolin-4-ylamine hydrochloride

To a solution of 3-methyl-1-(2-pyridinyl)-1H-pyrazolo[3,4-b]quinolin-4-ylamine (1.56 g, 5.65 mmol) in ethanol (5 mL) was added a 4N hydrochloric acid/ethyl acetate solution (10 mL), and the solution was concentrated under reduced pressure. The residue thus obtained was recrystallized from ethanol to give the title compound (1.41 g, 80% yield).

mp: 268–271° C. (recrystallized from ethanol). NMR (DMSO-$d_6$) δ: 2.85 (3H, s), 7.46–7.52 (1H, m), 7.59–7.67 (1H, m), 7.92–8.04 (2H, m), 8.09–8.18 (1H, m), 8.44 (1H, d, J=8.4 Hz), 8.68–8.70 (1H, m), 8.82–8.87 (2H, m), 9.85 (2H, br s). Elementary Analysis: for $C_{16}H_{13}N_5$.HCl.1.6$H_2O$ Calcd.: C, 56.42; H, 5.09; N, 20.56; Cl, 10.41. Found: C, 56.20; H, 5.01; N, 20.60; Cl, 10.39.

EXAMPLE 1-37

N-Methyl-N-[3-methyl-1-(2-pyridinyl)-1H-pyrazolo [3,4-b]quinolin-4-yl]amine hydrochloride A solution of 4-chloro-3-methyl-1-(2-pyridinyl)-1H-pyrazolo[3,4-b]quinoline (0.8 g, 2.71 mmol) in 40% methylamine methanol (21 mL, 0.27 mol) solution was heated and stirred at 100° C. for 4 hours in a sealed stainless tube. After the solution was cooled to room temperature, the reaction solvents were evaporated under reduced pressure. Purification of the residue thus obtained by silica gel column chromatography (chloroform:methanol=98:2) gave an oil of N-methyl-N-[3-methyl-1-(2-pyridinyl)-1H-pyrazolo[3,4-b] quinolin-4-yl]amine. To a solution of the oil in ethanol (10 mL), was added a saturated hydrochloric acid/ethanol solution (10 mL), and the solution was concentrated under reduced pressure. The residue thus obtained was recrystallized from methanol/ethyl acetate to give the title compound (0.63 g, 64% yield).

mp: 229–232° C. (recrystallized from ethyl acetate/ methanol). NMR (DMSO-$d_6$) δ: 2.84 (3H, s), 3.57 (3H, s), 7.45–7.62 (2H, m), 7.87–8.00 (2H, m), 8.14 (1H, d, J=7.3 Hz, 1.8 Hz), 8.34 (1H, d, J=8.1 Hz), 8.55–8.71 (1H, m), 8.72–8.82 (1H, m), 10.40 (1H, br s). Elementary Analysis: for $C_{17}H_{15}N_5$.1.5HCl.$H_2O$ Calcd.: C, 56.40; H, 5.15; N, 19.34. Found: C, 56.29; H, 5.10; N, 19.08.

EXAMPLE 1-38

N,N-Dimethyl-N-[3-methyl-1-(2-pyridinyl)-1H-pyrazolo[3,4-b]quinolin-4-yl]amine

4-Chloro-3-methyl-1-(2-pyridinyl)-1H-pyrazolo[3,4-b] quinoline (1.00 g, 3.39 mmol) was added to a 2M dimethylamine tetrahydrofuran (5.00 mL, 10.0 mmol) solution, and the mixture was heated at 100° C. overnight in a sealed tube. The reaction mixture was cooled to room temperature and poured into water, and organic matter was extracted with ethyl acetate. The extract was washed with saturated brine and dried over anhydrous magnesium sulfate, and the solvent was evaporated under reduced pressure. The residue thus obtained was purified by silica gel column chromatography (ethyl acetate to ethyl acetate:methanol=9:1) to give the title compound (1.00 g, 97% yield).

mp: 98–101° C. (recrystallized from ethyl acetate/ hexane). NMR (CDCl$_3$) δ: 2.89 (3H, s), 3.39 (6H, s), 7.16–7.22 (1H, m), 7.37–7.45 (1H, m), 7.66–7.74 (1H, m), 7.87–7.96 (1H, m), 8.12 (1H, d, J=9.0 Hz), 8.22 (1H, d, J=7.3 Hz), 8.64–8.67 (1H, m), 8.94 (1H, d, J=8.4 Hz). Elementary Analysis: for $C_{18}H_{17}N_5$ Calcd.: C, 71.27; H, 5.65; N, 23.09. Found: C, 71.25; H, 5.64; N, 23.02.

EXAMPLE 1-39

3-Methyl-1-(2-pyridinyl)-1,9-dihydro-4H-pyrazolo [3,4-b]quinolin-4-one

A mixture of methanesulfonic acid (120 mL, 0.84 mol) and phosphorus pentoxide (24.0 g, 0.17 mol) was heated at 100° C. The mixture was stirred thoroughly at the same temperature, with the gradual addition of powdery 2-[[3-methyl-1-(2-pyridinyl)-1H-pyrazol-5-yl]amino]benzoic acid (24.0 g, 82 mmol). The reaction mixture was heated and stirred at the same temperature further for 15 minutes. The mixture was allowed to cool to room temperature, and water was added thereto. The solution was made basic by the addition of an aqueous sodium hydroxide solution, and organic matter was extracted with chloroform. The extract was washed with saturated brine and water, dried over anhydrous magnesium sulfate, and the solvent was evaporated under reduced pressure. The residue thus obtained was purified by basic silica gel column chromatography (chloroform). The crystals thus obtained we dissolved in a mixture of ethyl acetate (300 mL) and methanol (300 mL) under heating, and heated under reflux for 30 minutes after the addition of activated carbon (2.5 g). The hot solution was filtered, and the solvents were evaporated under reduced pressure. The residue was recrystallized from ethyl acetate to give the title compound (15.1 g, 67% yield).

mp: 199–200° C. (recrystallized from ethyl acetate). NMR (CDCl$_3$) δ: 2.77 (3H, s), 7.19–7.26 (1H, m), 7.33 (1H, td, J=1.2 Hz, 8.0 Hz), 7.44 (1H, d, J=8.0 Hz), 7.61–7.70 (1H, m), 7.90 (1H, td, J=8.4 Hz, 1.6 Hz), 8.02 (1H, d, J=8.4 Hz), 8.46–8.50 (2H, m), 11.45 (1H, br s). Elementary Analysis: for $C_{16}H_{12}N_4O$ Calcd.: C, 69.55; H, 4.38; N, 20.28. Found: C, 69.47; H, 4.26; N, 20.33.

EXAMPLE 1-40

3-Methyl-1-(2-pyridinyl)-1,9-dihydro-4H-pyrazolo [3,4-b]quinolin-4-one

To a solution of 4-chloro-3-methyl-1-(2-pyridinyl)-1H-pyrazolo[3,4-b]quinoline (34.9 g, 0.12 mol) in ethanol (500 mL) was added 6N hydrochloric acid (50 mL, 0.30 mol), and the mixture was heated and under reflux for 2 hours. The solution was cooled to room temperature, and the reaction solvent was concentrated and evaporated under reduced pressure. The residue was made basic by the addition of an aqueous sodium hydroxide solution, and organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform:methanol= 95:5) to give the title compound (25.8 g, 79% yield).

EXAMPLE 1-41

4-Butoxy-3-methyl-1-(2-pyridinyl)-1H-pyrazolo[3, 4-b]quinoline

To an ice-cold solution of 1-butanol (5.0 g, 68 mmol) in tetrahydrofuran (15 mL) was added sodium hydride (oiliness, content 60%, 0.41 g, 17 mmol), and the mixture was stirred at room temperature for 15 minutes. After 4-chloro-3-methyl-1-(2-pyridinyl)-1H-pyrazolo[3,4-b] quinoline (1.0 g, 3.39 mmol) was added thereto at 0° C., the mixture was heated under reflux further for 1 hour. The reaction mixture was allowed to cool to room temperature, and the solvent was evaporated and concentrated under reduced pressure. Iced water was added to the residue and the mixture was neutralized with dilute hydrochloric acid, and organic matter was extracted with ethyl acetate. The extract was washed with saturated brine and water, dried over anhydrous magnesium sulfate, and the solvent was evaporated under reduced pressure. The residue thus obtained was purified by silica gel column chromatography (ethyl acetate) to give the title compound (0.29 g, 26% yield).

mp: 59–61° C. (recrystallized from petroleum ether/hexane). NMR (CDCl$_3$) δ: 1.06 (3H, t, J=7.3 Hz), 1.56–1.75 (2H, m), 1.95–2.10 (2H, m), 2.91 (3H, s), 4.37 (2H, t, J=6.6 Hz), 7.16–7.26 (1H, m), 7.43–7.54 (1H, m), 7.72–7.84 (1H, m), 7.88–7.98 (1H, m), 8.15 (1H, d, J=8.4 Hz), 8.31 (1H, d, J=8.4 Hz), 8.64–8.70 (1H, m), 8.92 (1H, d, J=8.4 Hz).

EXAMPLE 1-42

3-Methyl-1-(2-pyridinyl)-1,9-dihydro-4H-pyrazolo[3,4-b]quinolin-4-thione

A solution of 3-methyl-1-(2-pyridinyl)-1,9-dihydro-4H-pyrazolo[3,4-b]quinolin-4-one (13.94 g, 50.5 mmol) and Lawesson's Reagent (12.5 g, 30.9 mmol) in toluene (750 mL) was heated under reflux for 1 hour. The solution was cooled to room temperature, and the resulting crude crystals were collected by filtration. The crystals were recrystallized from ethyl acetate to give the title compound (13.11 g, 89% yield).

mp: 252–253° C. (recrystallized from ethyl acetate). NMR (CDCl$_3$) δ: 2.96 (3H, s), 7.23–7.28 (1H, m), 7.37–7.50 (2H, m), 7.65–7.73 (1H, m), 7.88–7.97 (1H, m), 8.05 (1H, d, J=7.6 Hz), 8.51 (1H, d, J=4.2 Hz), 9.08 (1H, d, J=8.6 Hz), 12.01 (1H, br s). Elementary Analysis: for C$_{16}$H$_{12}$N$_4$S Calcd.: C, 65.73; H, 4.14; N, 19.16. Found: C, 65.53; H, 4.10; N, 19.04.

EXAMPLE 1-43

4-Chloro-3,5-dimethyl-1-(2-pyridinyl)-1H-pyrazolo[3,4-b]quinoline

To a solution of 2-amino-6-methylbenzoic acid (20 g, 0.132 mol) in acetone (100 mL), diketene (15.3 mL, 0.198 mol) was added dropwise at room temperature, and the mixture was stirred overnight at room temperature. The reaction solvent and excess diketene was evaporated under reduced pressure. To the residue, carbon tetrachloride (80 mL) and subsequently acetic anhydride (27 g, 0.265 mol) were added, and the mixture was heated under reflux for 3 hours. The reaction solvent and excess acetic anhydride were evaporated and concentrated under reduced pressure, and the resulting powder was collected by filtration and washed with diethylether to give crude 5-methyl-2-(2-oxopropyl)-4H-3,1-benzoxazin-4-one (13.75 g, 48% yield). A solution of the compound (12.99 g, 0.06 mol) and 2-hydrazinopyridine (7.18 g, 0.066 mol) in ethanol (100 mL) was heated under reflux for 1 hour. The reaction solution was allowed to cool to room temperature, and the reaction solvent was evaporated and concentrated under reduced pressure. A solution of the residue in phosphorous oxychloride (45.8 g, 0.3 mol) was heated and stirred at 100° C. for 1 hour. After the reaction solution was cooled to room temperature, the reaction solvent was evaporated and concentrated under reduced pressure, and the residue was poured into iced water, which was made basic by the addition of a sodium hydroxide solution, and organic matter was extracted with chloroform. The extract was washed with saturated brine and water, and dried over anhydrous magnesium sulfate, and the solvent was evaporated under reduced pressure. The residue thus obtained was purified by silica gel column chromatography (ethyl acetate:methanol=98:2) to give the title compound (4.4 g, 24% yield).

mp: 167–169° C. (recrystallized from ethyl acetate/methanol). NMR (CDCl$_3$) δ: 2.98 (3H, s), 3.08 (3H, s), 7.18–7.33 (2H, m), 7.60 (1H, q, J=7.1 Hz), 7.87–7.97 (1H, m), 8.01 (1H, d, J=8.1 Hz), 8.64–8.70 (1H, m), 8.83 (1H, d, J=8.4 Hz). Elementary Analysis: for C$_{17}$H$_{13}$ClN$_4$ Calcd.: C, 66.13; H, 4.24; N, 18.15; Cl, 11.48. Found: C, 66.18; H, 4.22; N, 18.17; Cl, 11.54.

EXAMPLE 1-44

3,5-Dimethyl-1-(2-pyridinyl)-1H-pyrazolo[3,4-b]quinolin-4-ylamine

Following the procedure described in Example 1-35, the title compound was prepared from 4-chloro-3,5-dimethyl-1-(2-pyridinyl)-1H-pyrazolo[3,4-b]quinoline and sodium azide (58% yield).

mp: 252–255° C. (recrystallized from methanol). NMR (DMSO-d$_6$) δ: 2.82 (3H, s), 2.99 (3H, s), 6.73 (2H, br s), 7.04 (1H, d, J=6.2 Hz), 7.22–7.31 (1H, m), 7.47 (1H, t, J=7.3 Hz), 7.63 (1H, d, J=8.8 Hz), 7.93–8.07 (1H, m), 8.50–8.56 (1H, m), 8.71 (1H, d, J=8.4 Hz). Elementary Analysis: for C$_{17}$H$_{15}$N$_5$ Calcd.: C, 70.57; H, 5.23; N, 24.21. Found: C, 70.79; H, 5.17; N, 23.81.

EXAMPLE 1-45

3,5-Dimethyl-1-(2-pyridinyl)-1,9-dihydro-4H-pyrazolo[3,4-b]quinolin-4-one

A solution of 4-chloro-3,5-dimethyl-1-(2-pyridinyl)-1H-pyrazolo[3,4-b]quinoline (1.65 g, 5.34 mmol), sodium iodide (0.96 g, 6.41 mmol) and conc. hydrochloric acid (1 mL) in dimethylsulfoxide (20 mL) was heated and stirred at 100° C. for 2 hours. The solution was cooled to room temperature, and the residue was poured into water. The mixture was made basic by the addition of a sodium hydroxide solution, and organic matter was extracted with 10% methanol/chloroform. The extract was washed with saturated brine and water, and dried over anhydrous magnesium sulfate, and the solvents were evaporated under reduced pressure. The residue thus obtained was purified by silica gel column chromatography (ethyl acetate:hexane=90:10) to give the title compound (1.13 g, 73% yield).

mp: 183–186° C. (recrystallized from ethyl acetate). NMR (CDCl$_3$) δ: 2.73 (3H, s), 2.99 (3H, s), 7.01 (1H, d, J=7.3 Hz), 7.15–7.28 (2H, m), 7.44 (1H, t, J=7.9 Hz), 7.82–8.02 (2H, m), 8.43–8.49 (1H, m), 11.18 (1H, br s). Elementary Analysis: for C$_{17}$H$_{14}$N$_4$O Calcd.: C, 70.33; H, 4.86; N, 19.36. Found: C, 70.46; H, 4.87; N, 19.27.

EXAMPLE 1-46

3,8-Dimethyl-1-(2-pyridinyl)-1H-pyrazolo[3,4-b]quinolin-4-ylamine hydrochloride Following the procedure described in Example 1-36, the title compound was prepared from 3,8-dimethyl-1-(2-pyridinyl)-1H-pyrazolo[3,4-b]quinolin-4-ylamine (57% yield).

mp: 283–286° C. (recrystallized from ethanol). NMR (DMSO-d$_6$) δ: 2.59 (3H, s), 2.77 (3H, s), 3.36 (2H, br s), 7.30–7.55 (2H, m), 7.62–7.82 (1H, m), 8.00–8.20 (2H, m), 8.50–8.70 (2H, m). Elementary Analysis: for C$_{17}$H$_{15}$N$_5$.HCl.0.5H$_2$O Calcd.: C, 60.99; H, 5.12; N, 20.92; Cl, 10.59. Found: C, 61.38; H, 4.96; N, 20.71; Cl, 10.64.

EXAMPLE 1-47

3,8-Dimethyl-1-(2-pyridinyl)-1,9-dihydro-4H-pyrazolo[3,4-b]quinolin-4-one

Following the procedure described in Example 1-40, the title compound was prepared from 4-chloro-3,8-dimethyl-1-(2-pyridinyl)-1H-pyrazolo[3,4-b]quinoline (72% yield).

mp: 241–243° C. (recrystallized from ethanol). NMR (CDCl$_3$) δ: 2.57 (3H, s), 2.75 (3H, s), 7.17–7.30 (2H, m), 7.49 (1H, d, J=7.3 Hz), 7.84–7.92 (1H, m), 8.00 (1H, d, J=8.4 Hz), 8.32 (1H, d, J=7.3 Hz), 8.46 (1H, d, J=4.0 Hz), 11.59 (1H, br s). Elementary Analysis: for C$_{17}$H$_{14}$N$_4$O Calcd.: C, 70.33; H, 4.86; N, 19.36. Found: C, 70.25; H, 4.65; N, 19.21.

EXAMPLE 1-48

8-Methoxy-3-methyl-1-(2-pyridinyl)-1H-pyrazolo[3,4-b]quinolin-4-ylamine hydrochloride Following the procedures described in Examples 1-35 and 1-36, the title compound was prepared from 4-chloro-8-methoxy-1-(2-pyridinyl)-1H-pyrazolo[3,4-b]quinoline and sodium azide (65% yield).

mp: 248–251° C. (recrystallized from ethanol). NMR (DMSO-d$_6$) δ: 2.73 (3H, s), 4.10 (3H, s), 7.53–7.60 (3H, m), 7.85 (1H, d. J=8.4 Hz), 8.03–8.20 (2H, m), 8.53 (1H, br d, J=5.1 Hz), hidden (2H). Elementary Analysis: for C$_{17}$H$_{15}$N$_5$O.HCl.1.5H$_2$O Calcd.: C, 55.36; H, 5.19; N, 18.99; Cl, 9.61. Found: C, 55.32; H, 4.95; N, 18.86; Cl, 9.54.

EXAMPLE 1-49

6,7-Dimethoxy-3-methyl-1-(2-pyridinyl)-1,9-dihydro-4H-pyrazolo[3,4-b]quinolin-4-one Following the procedure described in Example 1-39, the title compound was prepared from 4,5-dimethoxy-2-[[3-methyl-1-(2-pyridinyl)-1H-pyrazol-5-yl]amino]benzoic acid (35% yield).

mp: 238–239° C. (recrystallized from ethyl acetate/methanol). NMR (DMSO-d$_6$) δ: 2.60 (3H, s), 3.85 (3H, s), 3.93 (3H, s), 7.35–7.42 (1H, m), 7.56 (1H, s), 7.66 (1H, s), 7.88 (1H, d, J=8.4 Hz), 8.05 (1H, ddd, J=8.4 Hz, 7.4 Hz, 1.8 Hz), 8.59–8.61 (1H, m), 11.78 (1H, br s). Elementary Analysis: for C$_{18}$H$_{16}$N$_4$O$_3$.H$_2$O Calcd.: C, 61.01; H, 5.12; N, 15.81. Found: C, 60.81; H, 5.12; N, 15.86.

EXAMPLE 1-50

3-Methyl-6-(methylsulfanyl)-1-(2-pyridinyl)-1,9-dihydro-4H-pyrazolo[3,4-b]quinolin-4-one Following the procedure described in Example 1-39, the title compound was prepared from 6-(methylsulfanyl)-2-[[3-methyl-1-(2-pyridinyl)-1H-pyrazol-5-yl]amino]benzoic acid (50% yield).

mp: 182–185° C. (recrystallized from methanol/ethyl acetate). NMR (CDCl$_3$) δ: 2.58 (3H, s), 2.74 (3H, s), 7.17–7.25 (1H, m), 7.35 (1H, d, J=8.8 Hz), 7.54 (1H, dd, J=2.2 Hz, 8.8 Hz), 7.83–7.93 (1H, m), 7.99 (1H, d, J=8.8 Hz), 8.27 (1H, d, J=2.2 Hz), 8.43–8.49 (1H, m), 11.42 (1H, br s). Elementary Analysis: for C$_{17}$H$_{14}$N$_4$OS Calcd.: C, 63.33; H, 4.38; N, 17.38. Found: C, 62.92; H, 4.38; N, 17.09.

EXAMPLE 1-51

6-Chloro-3-methyl-1-(2-pyridinyl)-1,9-dihydro-4H-pyrazolo[3,4-b]quinolin-4-one

Following the procedure described in Example 1-40, the title compound was prepared from 4,6-dichloro-3-methyl-1-(2-pyridinyl)-1H-pyrazolo[3,4-b]quinoline (84% yield).

mp: 254–255° C. (recrystallized from ethanol). NMR (DMSO-d$_6$) δ: 2.59 (3H, s), 7.37–7.44 (1H, m), 7.74 (1H, dd, J=2.6 Hz, 9.2 Hz), 7.88 (1H, d, J=8.4 Hz), 8.02–8.13 (3H, m), 8.59–8.61 (1H, m), 12.05 (1H, br s). Elementary Analysis: for C$_{16}$H$_{11}$ClN$_4$O Calcd.: C, 61.84; H, 3.57; N, 18.03; Cl, 11.41. Found: C, 61.80; H, 3.61; N, 18.16; Cl, 11.36.

EXAMPLE 1-52

4-Chloro-6-fluoro-3-methyl-1-(2-pyridinyl)-1H-pyrazolo[3,4-b]quinoline

Following the procedures described in Reference Example 1-11 and Example 1-34, the title compound was prepared from 5-fluoro-2-iodobenzoic acid and 3-methyl-1-(2-pyridinyl)-1H-pyrazol-5-ylamine (57% yield).

mp: 185–187° C. (recrystallized from ethyl acetate). NMR (DMSO-d$_6$) δ: 3.00 (3H, s), 7.21–7.28 (1H, m), 7.62 (1H, ddd, J=3.0 Hz, 5.4 Hz, 9.4 Hz), 7.89–7.99 (2H, m), 8.19 (1H, dd, J=5.4 Hz, 9.4 Hz), 8.69 (1H, d, J=3.6 Hz), 8.77 (1H, d, J=8.2 Hz). Elementary Analysis: for C$_{16}$H$_{10}$ClFN$_4$O Calcd.: C, 61.45; H, 3.22; N, 17.92; Cl, 11.34; F, 6.08. Found: C, 61.60; H, 3.10; N, 17.62; Cl, 11.22; F, 5.80.

EXAMPLE 1-53

6-Fluoro-3-methyl-1-(2-pyridinyl)-1,9-dihydro-4H-pyrazolo[3,4-b]quinolin-4-one

Following the procedure described in Example 1-40, the title compound was prepared from 4-chloro-6-fluoro-3-methyl-1-(2-pyridinyl)-1H-pyrazolo[3,4-b]quinoline (51% yield).

mp: 278–280° C. (recrystallized from ethanol/tetrahydrofuran). NMR (CDCl$_3$) δ: 2.75 (3H, s), 7.16–7.27 (1H, m), 7.33–7.48 (2H, m), 7.87–8.14 (3H, m), 8.48 (1H, d, J=5.2 Hz), 11.51 (1H, s) Elementary Analysis: for C$_{16}$H$_{11}$FN$_4$O Calcd.: C, 65.30; H, 3.77; N, 19.04; F, 6.46. Found: C, 65.32; H, 3.83; N, 18.99; F, 6.17.

EXAMPLE 1-54

3-Methyl-1-(5-methyl-2-pyridinyl)-1H-pyrazolo[3,4-b]quinolin-4-ylamine

Following the procedure described in Example 1-35, the title compound was prepared from 4-chloro-3-methyl-1-(5-methyl-2-pyridinyl)-1H-pyrazolo[3,4-b]quinoline and sodium azide (52% yield).

mp: 229–232° C. (recrystallized from ethyl acetate/methanol). NMR (CDCl$_3$) δ: 2.38 (3H, s), 2.87 (3H, s), 5.60 (2H, br s), 7.25–7.38 (1H, m), 7.62–7.74 (2H, m), 7.84 (1H, d, J=8.8 Hz), 8.00 (1H, d, J=8.8 Hz), 8.44 (1H, s), 8.75 (1H, d, J=8.4 Hz). Elementary Analysis: for C$_{17}$H$_{15}$N$_5$ Calcd.: C, 70.57; H, 5.23; N, 24.21. Found: C, 70.37; H, 5.51; N, 23.97.

EXAMPLE 1-55

3-Methyl-1-(5-methyl-2-pyridinyl)-1,9-dihydro-4H-pyrazolo[3,4-b]quinolin-4-one hydrochloride Following the procedure described in Example 1-40, the title compound was prepared from 4-chloro-3-methyl-1-(5-methyl-2-pyridinyl)-1H-pyrazolo[3,4-b]quinoline (51% yield).

mp: 227–229° C. (recrystallized from ethanol). NMR (DMSO-d$_6$) δ: 2.38 (3H, s), 2.61 (3H, s), 7.33 (1H, t, J=7.5 Hz), 7.66–7.92 (3H, m), 8.03 (1H, d, J=8.4 Hz), 8.22 (1H, d, J=7.0 Hz), 8.43 (1H, s), 11.85 (1H, s). Elementary Analysis: for C$_{17}$H$_{14}$N$_4$.HCl.0.5H$_2$O Calcd.: C, 60.81; H, 4.80; N, 16.68. Found: C, 60.65; H, 5.25; N, 16.66.

EXAMPLE 1-56

4-Chloro-3-methyl-1-(3-methyl-2-pyridinyl)-1H-pyrazolo[3,4-b]quinoline

Following the procedures described in Reference Example 1-10 and Example 1-34, the title compound was prepared from 2-(2-oxopropyl)-4H-3,1-benzoxazin-4-one and 2-hydrazino-3-methylpyridine (21% yield).

mp: 160–161° C. (recrystallized from ethyl acetate/hexane). NMR (CDCl$_3$) δ: 2.37 (3H, s), 2.98 (3H, s), 7.37 (1H, dd, J=4.8 Hz, 7.6 Hz), 7.52–7.60 (1H, m), 7.72–7.83 (2H, m), 8.05 (1H, td, J=0.8 Hz, 8.8 Hz), 8.39–8.44 (1H, m), 8.54–8.57 (1H, m). Elementary Analysis: for C$_{17}$H$_{13}$ClN$_4$ Calcd.: C, 66.13; H, 4.24; N, 18.15; Cl, 11.48. Found: C, 66.13; H, 4.28; N, 18.12; Cl, 11.51.

EXAMPLE 1-57

4-Chloro-3,5-dimethyl-1-(6-ethoxy-2-pyridinyl)-1H-pyrazolo[3,4-b]quinoline

Following the procedure described in Example 1-43, the title compound was prepared from 2-amino-6-methylbenzoic acid and 6-ethoxy-2-hydrazinopyridine synthesized from 2-chloro-6-ethoxypyridine (32% yield).

mp: 146–148° C. (recrystallized from ethyl acetate). NMR (CDCl$_3$) δ: 1.48 (3H, t, J=7.0 Hz), 2.96 (3H, s), 3.13 (3H, s), 4.57 (2H, q, J=7.0 Hz), 6.69 (1H, d, J=8.1 Hz), 7.31 (1H, d, J=7.0 Hz), 7.63 (1H, t, J=7.0 Hz), 7.78 (1H, t, J=7.7 Hz), 7.96 (1H, d, J=7.7 Hz), 8.12 (1H, d, J=8.1 Hz). Elementary Analysis: for C$_{19}$H$_{17}$ClN$_4$O Calcd.: C, 64.68; H, 4.86; N, 15.88. Found: C, 64.62; H, 4.81; N, 16.10.

EXAMPLE 1-58

4-Chloro-3,8-dimethyl-1-(6-methoxy-2-pyridinyl)-1H-pyrazolo[3,4-b]quinoline

Following the procedures described in Reference Example 1-10 and Example 1-34, the title compound was prepared from 8-methyl-2-(2-oxopropyl)-4H-3,1-benzoxazin-4-one and 2-hydrazino-6-methoxypyridine which was prepared from 2-chloro-6-methoxypyridine following the procedure described in Reference Example 1-9 (75% yield).

mp: 148–151° C. (recrystallized from chloroform/hexane). NMR (CDCl$_3$) δ: 2.87 (3H, s), 2.97 (3H, s), 4.15 (3H, s), 6.69 (1H, d, J=8.1 Hz), 7.47 (1H, dd, J=6.8 Hz, 8.6 Hz), 7.64–7.71 (1H, m), 7.80 (1H, t, J=8.1 Hz), 8.20–8.30 (2H, m). Elementary Analysis: for C$_{18}$H$_{15}$ClN$_4$O Calcd.: C, 63.81; H, 4.46; N, 16.54. Found: C, 63.87; H, 4.44; N, 16.46.

EXAMPLE 1-59

3,8-Dimethyl-1-(6-methoxy-2-pyridinyl)-1H-pyrazolo[3,4-b]quinolin-4-ylamine

Following the procedure described in Example 1-35, the title compound was prepared from 4-chloro-3,8-dimethyl-1-(6-methoxy-2-pyridinyl)-1H-pyrazolo[3,4-b]quinoline and sodium azide (46% yield).

mp: 134–137° C. (recrystallized from ethyl acetate/hexane). NMR (CDCl$_3$) δ: 2.80 (3H, s), 2.86 (3H, s), 4.13 (3H, s), 5.50 (2H, br s), 6.63 (1H, d, J=8.1 Hz), 7.20–7.30 (1H, m), 7.56 (1H, d, J=6.6 Hz), 7.70 (1H, d, J=6.6 Hz), 7.78 (1H, t, J=8.1 Hz), 8.44 (1H, d, J=7.7 Hz). Elementary Analysis: for C$_{18}$H$_{17}$N$_5$O.H$_2$O Calcd.: C, 64.08; H, 5.68; N, 20.76. Found: C, 64.17; H, 5.43; N, 20.36.

EXAMPLE 1-60

3,8-Dimethyl-1-(6-ethoxy-2-pyridinyl-1H-pyrazolo[3,4-b]quinolin-4-ylamine

Following the procedure described in Example 1-35, the title compound was prepared from 4-chloro-3,8-dimethyl-1-(6-ethoxy-2-pyridinyl)-1H-pyrazolo[3,4-b]quinoline and sodium azide (82% yield).

mp: 184–187° C. (recrystallized from chloroform). NMR (CDCl$_3$) δ: 1.45 (3H, t, J=7.0 Hz), 2.81 (3H, s), 2.87 (3H, s), 4.56 (2H, q, J=7.0 Hz), 5.47 (2H, br s), 6.61 (1H, d, J=8.0 Hz), 7.25 (1H, q, J=7.0 Hz), 7.57 (1H, d, J=7.0 Hz), 7.70 (1H, d, J=8.0 Hz), 7.79 (1H, t, J=8.0 Hz), 8.43 (1H, d, J=8.0 Hz). Elementary Analysis: for C$_{19}$H$_{19}$N$_5$O Calcd.: C, 68.45; H, 5.74; N, 21.01. Found: C, 68.33; H, 6.00; N, 20.95.

EXAMPLE 1-61

3,8-Dimethyl-1-(6-ethoxy-2-pyridinyl)-1,9-dihydro-4H-pyrazolo[3,4-b]quinolin-4-one Following the procedure described in Example 1-40, the title compound was prepared from 4-chloro-3,8-dimethyl-1-(6-ethoxy-2-pyridinyl)-1H-pyrazolo[3,4-b]quinoline (73% yield).

mp: 239–241° C. (recrystallized from chloroform). NMR (CDCl$_3$) δ: 1.51 (3H, t, J=7.0 Hz), 2.52 (3H, s), 2.72 (3H, s), 4.40 (2H, q, J=7.0 Hz), 6.60 (1H, dd, J=0.74 Hz, 8.1 Hz), 7.18 (1H, t, J=8.1 Hz), 7.40–7.48 (1H, m), 7.53 (1H, dd, J=0.74 Hz, 8.1 Hz), 7.73 (1H, t, J=8.1 Hz), 8.30 (1H, d, J=7.3 Hz), 10.9 (1H, br s). Elementary Analysis: for C$_{19}$H$_{18}$N$_4$O$_2$ Calcd.: C, 68.25; H, 5.43; N, 16.76. Found: C, 68.08; H, 5.59; N, 16.60.

EXAMPLE 1-62

3,8-Dimethyl-1-(3-methyl-2-pyridinyl)-1H-pyrazolo[3,4-b]quinolin-4-ylamine

Following the procedure described in Example 1-35, the title compound was prepared from 4-chloro-3,8-dimethyl-1-(3-methyl-2-pyridinyl)-1H-pyrazolo[3,4-b]quinoline and sodium azide (68% yield).

mp: 199–202° C. (recrystallized from ethyl acetate). NMR (CDCl$_3$) δ: 2.43 (3H, s), 2.61 (3H, s), 2.76 (3H, s), 5.51 (2H, br s), 7.16 (1H, t, J=7.7 Hz), 7.30 (1H, dd, J=4.8 Hz, 7.7 Hz), 7.48 (1H, d, J=6.6 Hz), 7.67 (1H, d, J=8.1 Hz), 7.76 (1H, d, J=7.7 Hz), 8.52 (1H, dd, J=1.5 Hz, 4.8 Hz). Elementary Analysis: for C$_{18}$H$_{17}$N$_5$ Calcd.: C, 71.27; H, 5.65; N, 23.09. Found: C, 71.23; H, 5.60; N, 22.87.

EXAMPLE 1-63

3-Methyl-1-(3-pyridinyl)-1H-pyrazolo[3,4-b]quinolin-4-ylamine dihydrochloride

Following the procedures described in Examples 1-35 and 1-36, the title compound was prepared from 4-chloro-3-methyl-1-(3-pyridinyl)-1H-pyrazolo[3,4-b]quinoline and sodium azide (72% yield).

mp: 234–237° C. (recrystallized from methanol). NMR (DMSO-d$_6$) δ: 2.83 (3H, s), 7.53 (1H, t, J=8.1 Hz), 7.83–8.05 (3H, m), 8.58–8.85 (3H, m), 9.00 (2H, br s), 9.32 (1H, br s). Elementary Analysis: for C$_{16}$H$_{13}$N$_5$.2HCl.2H$_2$O Calcd.: C, 50.01; H, 4.98; N, 18.23; Cl, 18.45. Found: C, 49.98; H, 5.05; N, 18.18; Cl, 18.27.

EXAMPLE 1-64

3-Methyl-1-(3-pyridinyl)-1,9-dihydro-4H-pyrazolo[3,4-b]quinolin-4-one

Following the procedure described in Example 1-40, the title compound was prepared from 4-chloro-3-methyl-1-(3-pyridinyl)-1H-pyrazolo[3,4-b]quinoline (37% yield).

mp: 282–283° C. (recrystallized from ethanol). NMR (DMSO-d$_6$) δ: 2.60 (3H, s), 7.26–7.34 (1H, m), 7.66–7.72 (3H, m), 8.15 (1H, ddd, J=1.4 Hz, 2.6 Hz, 8.2 Hz), 8.22 (1H, d, J=8.2 Hz), 8.73 (1H, dd, J=1.4 Hz, 4.6 Hz), 8.96 (1H, d, J=2.6 Hz), 11.93 (1H, br s). Elementary Analysis: for C$_{16}$H$_{12}$N$_4$O.0.5H$_2$O Calcd.: C, 67.36; H, 4.59; N, 19.64. Found: C, 67.50; H, 4.83; N, 19.61.

EXAMPLE 1-65

3-Methyl-1-(2-pyrimidinyl)-1H-pyrazolo[3,4-b]quinolin-4-ylamine hydrochloride

Following the procedures described in Examples 1-35 and 1-36, the title compound was prepared from 4-chloro-3-methyl-1-(2-pyrimidinyl)-1H-pyrazolo[3,4-b]quinoline and sodium azide (53% yield).

mp: 287–290° C. (recrystallized from methanol). NMR (DMSO-d$_6$) δ: 2.84 (3H, s), 7.50–7.63 (2H, m), 7.87–7.98 (1H, m), 8.29 (1H, d, J=8.4 Hz), 8.73 (1H, d, J=8.1 Hz), 8.92 (2H, br s), 9.00 (2H, d, J=4.8 Hz). Elementary Analysis: for C$_{15}$H$_{12}$N$_6$.HCl.3H$_2$O Calcd.: C, 49.12; H, 5.22; N, 22.91. Found: C, 49.53; H, 4.94; N, 22.83.

EXAMPLE 1-66

3,8-Dimethyl-1-(2-quinolinyl)-1H-pyrazolo[3,4-b]quinolin-4-ylamine

Following the procedure described in Example 1-35, the title compound was prepared from 4-chloro-3,8-dimethyl-1-(2-quinolinyl)-1H-pyrazolo[3,4-b]quinoline and sodium azide (42% yield).

mp: 273–276° C. (recrystallized from ethyl acetate/methanol). NMR (CDCl$_3$) δ: 2.84 (3H, s), 2.93 (3H, s), 5.86 (2H, br s), 7.22–7.30 (1H, m), 7.48 (1H, t, J=7.0 Hz), 7.58 (1H, d, J=7.0 Hz), 7.70 (1H, t, J=1.5 Hz, 7.0 Hz), 7.83 (2H, d, J=8.1 Hz), 8.23 (1H, d, J=8.1 Hz), 8.34 (1H, d, J=8.8 Hz), 9.46 (1H, d, J=8.8 Hz) Elementary Analysis: for C$_{21}$H$_{17}$N$_5$ Calcd.: C, 74.32; H, 5.05; N, 20.63. Found: C, 73.83; H, 4.98; N, 20.31.

EXAMPLE 1-67

1-(2-Pyridinyl)-1H-pyrazolo[3,4-b]quinolin-4-ylamine hydrochloride

Following the procedures described in Examples 1-35 and 1-36, the title compound was prepared from 4-chloro-1-(2-pyridinyl)-1H-pyrazolo[3,4-b]quinoline and sodium azide (78% yield).

mp: 312–315° C. (recrystallized from methanol). NMR (DMSO-d$_6$) δ: 7.47–7.55 (1H, m), 7.63 (1H, t, J=7.7 Hz), 7.95–8.21 (3H, m), 8.45 (1H, d, J=8.4 Hz), 8.65–8.75 (2H, m), 9.11 (1H, s), 10.2 (2H, br s). Elementary Analysis: for C$_{15}$H$_{11}$N$_5$.HCl Calcd.: C, 60.51; H, 4.06; N, 23.52; Cl, 11.91. Found: C, 60.61; H, 4.06; N, 23.30; Cl, 11.83.

EXAMPLE 1-68

3-Methyl-1-(2-pyridinylmethyl)-1H-pyrazolo[3,4-b]quinolin-4-ylamine

Following the procedure described in Example 1-35, the title compound was prepared from 4-chloro-3-methyl-1-(2-pyridinylmethyl)-1H-pyrazolo[3,4-b]quinoline (81% yield).

mp: 262–265° C. (recrystallized from ethanol). NMR (DMSO-d$_6$) δ: 2.71 (3H, s), 6.00 (2H, s), 7.52–7.70 (3H, m), 7.95–8.01 (2H, m), 8.10–8.20 (1H, m), 8.65–8.73 (2H, m), hidden (1H). Elementary Analysis: for C$_{17}$H$_{15}$N$_5$.2HCl.0.5H$_2$O Calcd.: C, 55.00; H, 4.89; N, 18.86; Cl, 19.10. Found: C, 55.21; H, 4.89; N, 18.82; Cl, 19.21.

EXAMPLE 1-69

3-Methyl-1-(2-pyridinylmethyl)-1,9-dihydro-4H-pyrazolo[3,4-b]quinolin-4-one

Following the procedure described in Example 1-41, the title compound was prepared from 4-chloro-3-methyl-1-(2-pyridinylmethyl)-1H-pyrazolo[3,4-b]quinoline and methanol (23% yield).

mp: 269–272° C. (recrystallized from ethyl acetate/methanol). NMR (DMSO-d$_6$) δ: 2.51 (3H, s), 5.57 (2H, s), 7.14 (1H, d, J=8.1 Hz), 7.25–7.38 (2H, m), 7.55 (1H, d, J=8.1 Hz), 7.65–7.85 (2H, m), 8.23 (1H, d, J=8.1 Hz), 8.52 (1H, d, J=4.8 Hz). Elementary Analysis: for C$_{17}$H$_{14}$N$_4$O Calcd.: C, 70.33; H, 4.86; N, 19.30. Found: C, 70.14; H, 4.80; N, 19.17.

EXAMPLE 1-70

4-Chloro-3,8-dimethyl-1-(2-pyridinyl)-1H-pyrazolo[3,4-b]quinoline

Following the procedures described in Reference Examples 1-10 and Example 1-34, the title compound was prepared from 8-methyl-2-(2-oxopropyl)-4H-3,1-benzoxazin-4-one and 2-hydrazinopyridine (54% yield).

mp: 170–172° C. (recrystallized from ethyl acetate). NMR (CDCl$_3$) δ: 2.87 (3H, s), 3.00 (3H, s), 7.20–7.28 (1H, m), 7.48 (1H, dd, J=6.9 Hz, 8.4 Hz), 7.68 (1H, d, J=6.9 Hz), 7.90–8.00 (1H, m), 8.21–8.30 (1H, m), 8.65–8.73 (1H, m), 9.04 (1H, d, J=8.4 Hz). Elementary Analysis: for C$_{17}$H$_{13}$ClN$_4$ Calcd.: C, 66.13; H, 4.24; N, 18.15; Cl, 11.48. Found: C, 66.00; H, 4.08; N, 18.02; Cl, 11.43.

EXAMPLE 1-71

3,8-Dimethyl-1-(2-pyridinyl)-1H-pyrazolo[3,4-b]quinolin-4-ylamine

Following the procedure described in Example 1-35, the title compound was prepared from 4-chloro-3,8-dimethyl-1-(2-pyridinyl)-1H-pyrazolo[3,4-b]quinoline and sodium azide (67% yield).

mp: 208–211° C. (recrystallized from ethanol). NMR (DMSO-d$_6$) δ: 2.69 (3H, s), 2.82 (3H, s), 7.15–7.32 (2H, m), 7.39 (2H, br s), 7.56 (1H, d, J=6.6 Hz), 7.95–8.05 (1H, m), 8.29 (1H, d, J=8.1 Hz), 8.50–8.55 (1H, m), 8.90–9.10 (1H, m).

EXAMPLE 1-72

4-Chloro-8-methoxy-1-(2-pyridinyl)-1H-pyrazolo[3,4-b]quinoline

Following the procedures described in Reference Examples 1-10 and Example 1-34, the title compound was prepared from 8-methoxy-2-(2-oxopropyl)-4H-3,1-benzoxazin-4-one and 2-hydrazinopyridine (23% yield).

mp: 167–169° C. (recrystallized from ethyl acetate). NMR (CDCl$_3$) δ: 3.00 (3H, s), 4.13 (3H, s), 7.15 (1H, d, J=7.7 Hz), 7.20–7.28 (1H, m), 7.52 (1H, t, J=7.7 Hz), 7.91–8.03 (2H, m), 8.65–8.71 (1H, m), 8.83 (1H, d, J=7.7 Hz). Elementary Analysis: for C$_{17}$H$_{13}$ClN$_4$O Calcd.: C, 62.87; H, 4.03; N, 17.25; Cl, 10.92. Found: C, 62.88; H, 3.96; N, 17.16; Cl, 10.90.

EXAMPLE 1-73

4,6-Dichloro-3-methyl-1-(2-pyridinyl)-1H-pyrazolo[3,4-b]quinoline

Following the procedures described in Reference Examples 1-10 and Example 1-34, the title compound was prepared from 6-chloro-2-(2-oxypropyl)-4H-3,1-benzoxazin-4-one and 2-hydrazinopyridine (5% yield).

mp: 233–235° C. (recrystallized from ethyl acetate/methanol). NMR (CDCl$_3$) δ: 2.99 (3H, s), 7.22–7.29 (1H, m), 7.74 (1H, dd, J=2.6 Hz, 9.0 Hz), 7.89–7.98 (1H, m), 8.12 (1H, d, J=9.0 Hz), 8.37 (1H, d, J=2.2 Hz), 8.67–8.69 (1H, m), 8.75 (1H, d, J=8.0 Hz). Elementary Analysis: for C$_{16}$H$_{10}$Cl$_2$N$_4$ Calcd.: C, 58.38; H, 3.06; N, 17.02; Cl, 21.54. Found: C, 58.54; H, 3,06; N, 17.02; Cl, 21.48.

EXAMPLE 1-74

4-Chloro-3-methyl-1-(5-methyl-2-pyridinyl)-1H-pyrazolo[3,4-b]quinoline

Following the procedure described in Example 1-43, the title compound was prepared from anthranilic acid and 2-hydrazino-5-methylpyridine which was separately prepared from 2-bromo-5-methylpyridine following the method described in Reference Example 1-9 (22% yield).

mp: 197–200° C. (recrystallized from ethyl acetate/methanol). NMR (CDCl$_3$) δ: 2.42 (3H, s), 3.00 (3H, s), 7.53–7.64 (1H, m), 7.71–7.87 (2H, m), 8.16 (1H, d, J=8.8 Hz), 8.36–8.43 (1H, m), 8.46–8.52 (1H, m), 8.66 (1H, d, J=8.8 Hz). Elementary Analysis: for C$_{17}$H$_{13}$ClN$_4$ Calcd.: C, 66.13; H, 4.24; N, 18.15. Found: C, 66.16; H, 4.30; N, 18.10.

EXAMPLE 1-75

4-Chloro-3,8-dimethyl-1-(6-ethoxy-2-pyridinyl)-1H-pyrazolo[3,4-b]quinoline

Following the procedures described in Reference Example 1-10 and Example 1-34, the title compound was prepared from 8-methyl-2-(2-oxopropyl)-4H-3,1-benzoxazin-4-one and 6-ethoxy-2-hydrazinopyridine which was separately prepared from 2-chloro-6-ethoxypyridine following the method described in Reference Example 1-9 (62% yield).

mp: 151–153° C. (recrystallized from ethyl acetate). NMR (CDCl$_3$) δ: 1.46 (3H, t, J=7.1 Hz), 2.86 (3H, s), 2.96 (3H, s), 4.60 (2H, q, J=7.1 Hz), 6.66 (1H, dd, J=0.73 Hz, 8.1 Hz), 7.46 (1H, q, J=7.0 Hz), 7.63–7.70 (1H, m), 7.79 (1H, t, J=8.1 Hz), 8.15–8.28 (2H, m). Elementary Analysis: for C$_{19}$H$_{17}$ClN$_4$O Calcd,: C, 64.68; H, 4.86; N, 15.88; Cl, 10.05. Found: C, 64.54; H, 5.07; N, 15.69; Cl, 10.04.

EXAMPLE 1-76

4-Chloro-3,8-dimethyl-1-(3-methyl-2-pyridinyl)-1H-pyrazolo[3,4-b]quinoline

Following the procedures described in Reference Example 1-10 and Example 1-34, the title compound was prepared from 8-methyl-2-(2-oxopropyl)-4H-3,1-benzoxazin-4-one and 2-hydrazino-3-methylpyridine (57% yield).

mp: 182–185° C. (recrystallized from chloroform/methanol). NMR (CDCl$_3$) δ: 2.42 (3H, s), 2.70 (3H, s), 2.99 (3H, s), 7.32–7.50 (2H, m), 7.62 (1H, d, J=6.6 Hz), 7.77–7.85 (1H, m), 8.26 (1H, d, J=8.8 Hz), 8.54 (1H, dd, J=1.5 Hz, 4.4 Hz). Elementary Analysis: for C$_{18}$H$_{15}$ClN$_4$ Calcd.: C, 66.98; H, 4.68; N, 17.36. Found: C, 67.10; H, 4.61; N, 17.13.

EXAMPLE 1-77

4-Chloro-3-methyl-1-(3-pyridinyl)-1H-pyrazolo[3,4-b]quinoline

Following the procedure described in Example 1-34, the title compound was prepared from 2-[[3-methyl-1-(3-pyridinyl)-1H-pyrazol-5-yl]amino]benzoic acid (50% yield).

mp: 144–145° C. (recrystallized from ethyl acetate). NMR (CDCl$_3$) δ: 2.93 (3H, s), 7.46 (1H, dd, J=4.8 Hz, 8.2 Hz), 7.52–7.60 (1H, m), 7.76–7.84 (1H, m), 8.11 (1H, d, J=8.2 Hz), 8.33–8.38 (1H, m), 8.53 (1H, dd, J=1.4 Hz, 4.8 Hz), 8.81 (1H, ddd, J=1.4 Hz, 2.6 Hz, 8.4 Hz), 9.79–9.80 (1H, m). Elementary Analysis: for C$_{16}$H$_{11}$ClN$_4$ Calcd.: C, 65.20; H, 3.76; N, 19.01; Cl, 12.03. Found: C, 65.22; H, 3.73; N, 19.13; Cl, 11.91.

EXAMPLE 1-78

4-Chloro-3-methyl-1-(2-pyrimidinyl)-1H-pyrazolo[3,4-b]quinoline

Following the methods described in Reference Example 1-10 and Example 1-34, the title compound was prepared from 2-(2-oxopropyl)-4H-3,1-benzoxazin-4-one and 2-hydrazinopyrimidine (69% yield).

mp: 257–260° C. (recrystallized from ethyl acetate). NMR (CDCl$_3$) δ: 2.80 (3H, s), 7.24–7.36 (2H, m), 7.54–7.73 (2H, m), 8.43–8.50 (1H, m), 8.89 (2H, dd, J=1.5 Hz, 5.1 Hz). Elementary Analysis: for C$_{15}$H$_{10}$ClN$_5$ Calcd.: C, 60.92; H, 3.41; N, 23.68; Cl, 11.99. Found: C, 60.63; H, 3.49; N, 23.59; Cl, 11.79.

EXAMPLE 1-79

4-Chloro-3,8-dimethyl-1-(2-quinolinyl)-1H-pyrazolo[3,4-b]quinoline

Following the procedures described in Reference Example 1-10 and Example 1-34, the title compound was prepared from 8-methyl-2-(2-oxopropyl)-4H-3,1-benzoxazin-4-one and 2-hydrazinoquinoline which was separately prepared from 2-chloroquinoline following the method described in Reference Example 1-9 (42% yield).

mp: 165–168° C. (recrystallized from methanol/chloroform). NMR (CDCl$_3$) δ: 2.91 (3H, s), 3.04 (3H, s), 7.44–7.57 (2H, m), 7.65–7.80 (2H, m), 8.10 (1H, br d, J=8.4 Hz), 8.22–8.30 (2H, m), 8.38 (1H, d, J=8.8 Hz), 9.21 (1H, d, J=8.8 Hz).

EXAMPLE 1-80

4-Chloro-1-(2-pyridinyl)-1H-pyrazolo[3,4-b]quinoline

Following the procedure described in Example 1-34, the title compound was prepared from 2-[[1-(2-pyridinyl)-1H-pyrazol-5-yl]amino]benzoic acid (49% yield).

mp: 153–156° C. (recrystallized from ethyl acetate/methanol). NMR (CDCl$_3$) δ: 7.25–7.33 (1H, m), 7.58–7.67 (1H, m), 7.80–7.89 (1H, m), 7.93–8.01 (1H, m), 8.23 (1H, m), 8.39 (1H, m), 8.59 (1H, s), 8.70 (1H, br d, J=5.1 Hz), 8.78 (1H, d, J=8.4 Hz). Elementary Analysis: for C$_{15}$H$_9$ClN$_4$ Calcd.: C, 64.18; H, 3.23; N, 19.96. Found: C, 64.04; H, 3.01; N, 19.94.

EXAMPLE 1-81

4-Chloro-3-methyl-1-(2-pyridinylmethyl)-1H-pyrazolo[3,4-b]quinoline

Following the procedures described in Reference Example 1-10 and Example 1-34, the title compound was prepared from 2-(2-oxopropyl)-4H-3,1-benzoxazin-4-one and 2-hydrazinomethylpyridine which was separately prepared from 2-chloromethylpyridine following the method described in Reference Example 1-9 (75% yield).

mp: 113–115° C. (recrystallized from ethyl acetate). NMR (CDCl$_3$) δ: 2.89 (3H, s), 5.88 (2H, s), 6.44 (1H, d, J=7.7 Hz), 7.12–7.20 (1H, m), 7.46–7.62 (2H, m), 7.70–7.80 (1H, m), 8.06 (1H, d, J=8.8 Hz), 8.33–8.40 (1H, m), 8.55–8.61 (1H, m). Elementary Analysis: for $C_{17}H_{13}ClN_4$ Calcd.: C, 66.13; H, 4.24; N, 18.15; Cl, 11.48. Found: C, 66.27; H, 4.12; N, 18.11; Cl, 11.42.

TABLE 3

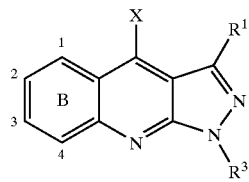

| Example Number | R$^1$ | R$^3$ | X | Substituent of Ring B |
|---|---|---|---|---|
| 1-34 | Me | 2-Py | Cl | |
| 1-35 | Me | 2-Py | NH$_2$ | |
| 1-36 | Me | 2-Py | NH$_2$ | |
| 1-37 | Me | 2-Py | MeNH | |
| 1-38 | Me | 2-Py | Me$_2$N | |
| 1-41 | Me | 2-Py | $^n$BuO | |
| 1-43 | Me | 2-Py | Cl | 1: Me |
| 1-44 | Me | 2-Py | NH$_2$ | 1: Me |
| 1-46 | Me | 2-Py | NH$_2$ | 4: Me |
| 1-48 | Me | 2-Py | NH$_2$ | 4: MeO |
| 1-52 | Me | 2-Py | Cl | 2: F |
| 1-54 | Me | 5-Me-2-Py | NH$_2$ | |
| 1-56 | Me | 3-Me-2-Py | Cl | |
| 1-57 | Me | 6-EtO-2-Py | Cl | 1: Me |
| 1-58 | Me | 6-MeO-2-Py | Cl | 4: Me |
| 1-59 | Me | 6-MeO-2-Py | NH$_2$ | 4: Me |
| 1-60 | Me | 6-EtO-2-Py | NH$_2$ | 4: Me |
| 1-62 | Me | 3-Me-2-Py | NH$_2$ | 4: Me |
| 1-63 | Me | 3-Py | NH$_2$ | |
| 1-65 | Me | 2-Pyrimidinyl | NH$_2$ | |
| 1-66 | Me | 2-quinolinyl | NH$_2$ | 4: Me |
| 1-67 | H | 2-Py | NH$_2$ | |
| 1-68 | Me | 2-Py-CH$_2$ | NH$_2$ | |
| 1-70 | Me | 2-Py | Cl | 4: Me |
| 1-71 | Me | 2-Py | NH$_2$ | 4: Me |
| 1-72 | Me | 2-Py | Cl | 4: MeO |
| 1-73 | Me | 2-Py | Cl | 2: Cl |
| 1-74 | Me | 5-Me-2-Py | Cl | |
| 1-75 | Me | 6-EtO-2-Py | Cl | 4: Me |
| 1-76 | Me | 3-Me-2-Py | Cl | 4: Me |
| 1-77 | Me | 3-Py | Cl | |
| 1-78 | Me | 2-Pyrimidinyl | Cl | |
| 1-79 | Me | 2-quinolinyl | Cl | 4: Me |
| 1-80 | H | 2-Py | Cl | |
| 1-81 | Me | 2-Py-CH$_2$ | Cl | |

TABLE 4

| Example Number | R$^1$ | R$^2$ | R$^3$ | X | Substituent of Ring B |
|---|---|---|---|---|---|
| 1-39 | Me | H | 2-Py | O | |
| 1-40 | Me | H | 2-Py | O | |
| 1-42 | Me | H | 2-Py | S | |
| 1-45 | Me | H | 2-Py | O | 1: Me |
| 1-47 | Me | H | 2-Py | O | 4: Me |
| 1-49 | Me | H | 2-Py | O | 2, 3: MeO |
| 1-50 | Me | H | 2-Py | O | 2: MeS |
| 1-51 | Me | H | 2-Py | O | 2: Cl |
| 1-53 | Me | H | 2-Py | O | 2: F |
| 1-55 | Me | H | 5-Me-2-Py | O | |
| 1-61 | Me | H | 6-EtO-2-Py | O | 4: Me |
| 1-64 | Me | H | 3-Py | O | |
| 1-69 | Me | H | 2-Py-CH$_2$ | O | |

FORMULATION EXAMPLE 1-1

| | |
|---|---|
| (1) The compound obtained in Example 1-1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound obtained in Example 1-1 (10.0 g), lactose (60.0 g) and cornstarch (35.0 g) was treated with 10 wt % aqueous gelatin solution (30 ml, 3.0 g as gelatin) and the resulting mixture was then granulated by sieving through a 1 mm mesh sieve, and the resulting granules were dried at 40° C. and sieved once again. The granules were mixed with magnesium stearate (2.0 g) and compressed. The core tablets thus obtained were subsequently sugarcoated by the use of an aqueous suspension of sucrose, titanium dioxide, talc and gum acacia. The coated tablets were glazed with beeswax to give 1000 coated tablets.

FORMULATION EXAMPLE 1-2

| | |
|---|---|
| (1) The compound obtained in Example 1-1 | 10.0 g |
| (2) Lactose | 70.0 g |
| (3) Cornstarch | 50.0 g |
| (4) Soluble starch | 7.0 g |
| (5) Magnesium stearate | 3.0 g |

A mixture of the compound obtained in Example 1-1 (10.0 g) and magnesium stearate (3.0 g) was granulated by the use of an aqueous solution of soluble starch (70 ml, 7.0 g as soluble starch), and the resulting granules were dried and mixed with lactose 70.0 g and cornstarch 50.0 g. The mixture was compressed to give 1000 tablets.

EXPERIMENTAL EXAMPLE 1-1

Effect on Cytokine Production of Mice Sensitized by Controlled-Release Ovalbumin An osmotic pump (Alza Co., USA) containing a solution (100 μL) containing 1.0 mg of ovalbumin (OVA; albumin chicken egg grade III, Sigma Chemical) was implanted in the back of a male BALB/c mouse (Charles River) of 8 weeks old under ether anesthesia, and the mouse is sensitized by the controlled-release ovalbumin. After 11 days from implantation of the pump, a sample of spleen was removed, and a splenic cell suspension was prepared by the use of the RPMI-1640 medium (Bio Whittaker Inc., USA) containing inactivated fetal bovine serum (10% V/V; Bio Whittaker Inc., USA), 2-mercaptoethanol (50 µM), and gentamicin (20 µg/ml). A sample compound (30 mg/kg b.w.) was suspended in 0.4 ml of methylcellulose (MC), and the suspension was orally administered, 5 days a week during the 9-day period from the initiation day of sensitization to the day before the day of blood sample collection (1 Group, n=10). The splenic cell suspension was adjusted to a concentration of $5.0 \times 10^6$ cells/ml, and the resulting suspension (100 µl) was pipetted onto a 96 well U-bottomed plate, each of the wells containing a solution (100 µl/well) of 400 µg/ml OVA, and the plate was incubated at 37° C. in a 5% carbon dioxide gas incubator for 3 days. The cultured media were centrifuged at 200×g for 5 minutes, and the supernatants were collected and the production of IL-4, IL-5 and IFN-γ in each of the supernatants was determined by the ELISA method [Mouse IL-4 Bulk Kit (PerSeptive Biosystems), Mouse IL-5 Bulk Kit (PerSeptive Biosystems), and Mouse IFN-γ Bulk Kit (PerSeptive Biosystems)]. The results are shown in Table 5.

TABLE 5

| Compound | Suppression Rate (%) | | |
|---|---|---|---|
| (Example No.) | IL-4 | IL-5 | IFN-γ |
| Example 1-49 | 13.9 | 11.8 | −9.0 |
| Example 1-51 | 31.9 | 53.7 | −11.2 |
| Example 1-47 | 49.9 | 61.1 | 31.8 |
| Example 1-50 | 45.5 | 60.2 | 11.1 |
| Example 1-61 | 16.0 | 26.1 | −8.7 |
| Example 1-64 | 49.1 | 39.9 | −6.8 |
| Example 1-69 | 19.4 | 50.0 | 8.3 |
| Example 1-56 | 23.7 | 12.2 | 12.2 |
| Example 1-57 | 43.2 | 53.9 | 36.7 |
| Example 1-36 | 99.8* | 61.5 | −130.6* |
| Example 1-46 | 80.4 | 5.2 | −132.4* |
| Example 1-48 | 31.6 | 16.2 | −7.6 |
| Example 1-44 | 68.2 | 3.1 | 36.3 |
| Example 1-59 | 66.5 | 27.8 | −124.0 |
| Example 1-60 | 56.7 | 59.3 | 23.4 |
| Example 1-62 | 19.4 | 4.8 | −13.8 |
| Example 1-66 | 27.1 | 34.3 | 50.0 |
| Example 1-65 | 8.1 | 16.5 | −15.7 |

**p < 0.05, *p < 0.01 vs control

EXPERIMENTAL EXAMPLE 1-2

Effect on Antibody Production of Mice Sensitized by Controlled-Release Ovalbumin A male BALB/c mouse (Charles River) of 7 weeks old was sensitized by intraabdominal administration, twice at an interval of a week, of a mixture of 10 µg/mouse of ovalbumin (OVA; albumin chicken egg grade III; Sigma Chemical) and 1 mg of aluminum hydroxide hydrate gel suspension (Alum; LSL Co. LTD.). After 11 days from the first sensitization, blood was collected from beneath eye under ether anesthesia, and the amount of OVA-specific IgE, IgG1 (Th2 type) and IgG2a (Th1 type) antibodies in the serum were determined by the ELISA method. A sample compound (30 mg/kg b.w.) was suspended in 0.4 ml of methylcellulose (MC), and the suspension was orally administered, 5 days a week during the 9-day period from the initiation day of sensitization to the day before the day of blood sample collection (1 Group, n=8 to 10). The results are shown in Table 6.

TABLE 6

| Compound | Suppression Rate (%) | |
|---|---|---|
| (Example No.) | IgE | IgG2a |
| Example 1-47 | 4.9 | −17.1 |
| Example 1-50 | 22.0 | 19.5 |
| Example 1-53 | 8.0 | 36.1 |
| Example 1-55 | 11.7 | 13.7 |
| Example 1-42 | 24.0 | 14.3 |
| Example 1-52 | 41.1* | 39.9 |
| Example 1-57 | 23.6 | −55.1 |
| Example 1-36 | 64.2** | 23.4 |
| Example 1-67 | 10.5 | −30.7 |
| Example 1-37 | 29.6 | 9.6 |
| Example 1-38 | 36.1 | −122.4 |
| Example 1-54 | 17.6 | −147.7 |
| Example 1-59 | 60.7* | 46.3 |
| Example 1-60 | 54.9** | 47.8 |
| Example 1-63 | 25.2 | −5.8 |
| Example 1-68 | 31.6 | 31.7 |
| Example 1-29 | 19.1 | −22.6 |
| Example 1-1 | 46.3* | 17.8 |
| Example 1-2 | 29.2 | −67.9 |
| Example 1-3 | 19.0 | −39.5 |
| Example 1-27 | 24.3 | 27.1 |
| Example 1-25 | 33.9 | 16.5 |
| Example 1-22 | 14.0 | −2.1 |

**p < 0.05, *p < 0.01 vs control

The results in Table 6 indicate that the compound (I) of the present invention has an excellent inhibitory activity to IgE antibody production.

REFERENCE EXAMPLE 2-1

2-(2-Oxopropyl)-4H-3,1-benzoxazin-4-one

To a solution of anthranilic acid (290 g, 2.1 mol) in acetone (1000 mL), diketene (460 mL, 6.0 mol) was added dropwise at room temperature. The solution was stirred at room temperature for 16 hours, and the resulting crystals were collected by filtration, washed with acetone and diethylether, and air dried (170 g yield). The crude crystals were suspended in a mixture of acetic anhydride (320 mL, 3.4 mol) and tetrahydrofuran (1000 mL), and the suspension was heated and stirred at 80° C. for 12 hours. The suspension was cooled to room temperature, and concentrated under reduced pressure, and the resulting crude crystals were collected by filtration. The crystals were washed with acetonitrile and air dried to give the title compound (244 g, 57% yield).

mp: 120–122° C. (recrystallized from acetonitrile).

REFERENCE EXAMPLE 2-2

2-Hydradinopyridine

According to the method described in J. Med. chem., vol. 28, p. 1394 (1985), the title compound was prepared. A mixture of 2-chloropyridine (200 mL, 2.1 mol) and hydrazine monohydrate (400 mL, 8.2 mol) was heated and refluxed for 20 hours. The solution was cooled to room temperature, excess hydrazine hydrate was evaporated under reduced pressure, and the residue was poured into water. The solution was made basic by the addition of a sodium hydroxide solution, and organic matter was extracted with chloroform. The extract was washed with saturated brine and water, and dried over anhydrous magnesium sulfate, and the solvent was evaporated under reduced pressure to give the title compound (157 g, 68% yield). The compound was used in the following process without further purification.

REFERENCE EXAMPLE 2-3

2-[[3-Methyl-1-(2-pyridinyl)-1H-pyrazol-5-yl]amino]benzoic acid

A solution of 2-(2-oxopropyl)-4H-3,1-benzoxazin-4-one (68.2 g, 0.34 mol) and 2-hydrazinopyridine (37.1 g, 0.34 mol) in ethanol (500 mL) was heated under reflux for 1 hour. After the solution was cooled to room temperature, the resulting crystals were collected by filtration. The crystals were washed with ethanol and air dried to give the title compound (50.2 g, 51% yield).

mp: 190–193° C. (recrystallized from methanol). NMR (DMSO-$d_6$) δ: 2.35 (3H, s), 6.15 (1H, s), 6.87–6.97 (1H, m), 7.05–7.15 (1H, m), 7.46–7.56 (1H, m), 7.69 (1H, d, J=8.4 Hz), 7.73–7.82 (1H, m), 7.92 (1H, d, J=8.4 Hz), 8.14 (1H, dd, J=1.5 Hz, 8.1 Hz), 8.45–8.50 (1H, m), 12.25 (1H, br s).

REFERENCE EXAMPLE 2-4

3-Methyl-1-(2-pyridinyl)-1H-pyrazol-5-ylamine

To an ice-cold solution of aminocrotononitrile (82 g, 1.0 mol) and 2-hydrazinopyridine (120 g, 1.1 mol) in ethanol (300 mL) was added acetic acid (132 g, 2.2 mol), and the solution was heated under reflux for 3.5 hours. The solution was cooled to room temperature, and the solution was concentrated under reduced pressure, and water was added to the residue. The solution was made basic by the addition of an aqueous sodium hydroxide solution, and organic matter was extracted with ethyl acetate. The extract was washed with saturated brine and water, and dried over anhydrous magnesium sulfate, and the solvent was evaporated under reduced pressure. The residue was purified by silica gel column chromatography (ethyl acetate) to give the title compound (156.3 g, 90% yield).

mp: 103–104° C. (recrystallized from ethyl acetate). NMR (CDCl$_3$) δ: 2.25 (3H, s), 5.37 (1H, s), 5.92 (2H, br s), 7.07 (1H, m), 7.76 (1H, m), 7.94 (1H, d, J=7.0 Hz), 8.32 (1H, d, J=6.0 Hz).

REFERENCE EXAMPLE 2-5

2-[[3-Methyl-1-(2-pyridinyl)-1H-pyrazol-5-yl]amino]benzoic acid

A solution of 3-methyl-1-(2-pyridinyl)-1H-pyrazol-5-ylamine (5.23 g, 30 mmol), o-iodobenzoic acid (8.93 g, 36 mmol), copper acetate (II) (0.654 g, 3.6 mmol) and potassium carbonate (4.98 g, 36 mmol) in N,N-dimethylformamide (30 mL) was heated under reflux for 1 hour under an argon atmosphere. After the solution was cooled to room temperature, the mixture was poured into water. The solution was made weakly acidic by the addition of acetic acid, and the resulting crude crystals were collected by filtration. The crystals were washed with water and air dried to give the title compound (8.64 g, 98% yield).

REFERENCE EXAMPLE 2-6

6-Methyl-2-(2-oxopropyl)-4H-3,1-benzoxazin-4-one

Following the procedure described in Reference Example 2–1, the title compound was prepared from 2-amino-5-methylbenzoic acid (79% yield).

mp: 137–140° C. (recrystallized from ethyl acetate/hexane). Elementary Analysis: for $C_{12}H_{11}NO_3$ Calcd.: C, 66.35; H, 5.10; N, 6.45. Found: C, 66.49; H, 5.06; N, 6.22.

REFERENCE EXAMPLE 2-7

5-Methyl-2-[[3-methyl-1-(2-pyridinyl)-1H-pyrazol-5-yl]amino]benzoic acid

Following the procedure described in Reference Example 2-3, the title compound was prepared from 6-methyl-2-(2-oxopropyl)-4H-3,1-benzoxazin-4-one and 2-hydrazinopyridine (61% yield).

mp: 229–232° C. (recrystallized from ethanol). NMR (DMSO-$d_6$) δ: 2.23 (3H, s), 2.28 (3H, s), 6.16 (1H, s), 7.25–7.38 (2H, m), 7.52 (1H, d, J=8.4 Hz), 7.75 (1H, s), 7.84 (1H, dd, J=1.1 Hz, 8.4 Hz), 7.91–8.02 (1H, m), 8.41–8.47 (1H, m), 12.11 (1H, s), hidden (1H). Elementary Analysis: for $C_{17}H_{16}N_4O_2$ Calcd.: C, 66.22; H, 5.23; N, 18.17. Found: C, 66.06; H, 5.10; N, 18.29.

REFERENCE EXAMPLE 2-8

8-Methyl-2-(2-oxopropyl)-4H-3,1-benzoxazin-4-one

Following the procedure described in Reference Example 2-1, the title compound was prepared from 2-amino-3-methylbenzoic acid (88% yield).

mp: 150–152° C. (recrystallized from ethanol). Elementary Analysis: for $C_{12}H_{11}N_4O_3$ Calcd.: C, 66.35; H, 5.10; N, 6.45. Found: C, 66.36; H, 5.12; N, 6.38.

REFERENCE EXAMPLE 2-9

2-Chloro-5-(trifluoromethyl)benzoic acid

The title compound was prepared according to the method described in Tetrahedron Lett., vol. 37, p. 2767 (1996). To a solution of 1-chloro-4-(trifluoromethyl)benzene (25.8 g, 143 mmol) and tetramethylethylene diamine (16.6 g, 143 mmol) in tetrahydrofuran (250 mL) cooled to –78° C., was added a solution of 1.6M butyllithium in hexane (89.4 mL, 143 mmol) was added dropwise under an argon atmosphere, and the mixture was stirred at the same temperature for 30 minutes. The solution was carefully poured onto crushed dry ice, and the resulting mixture was allowed to warm to room temperature. The solution was concentrated under reduced pressure, and the residue was poured into water. The solution was washed with diethylether, and subsequently made acidic by the addition of conc. hydrochloric acid, and organic matter was extracted with dichloromethane. The extract was washed with saturated brine and dried over anhydrous magnesium sulfate, and the solvent was evaporated under reduced pressure. The residue thus obtained was crystallized from hexane to give the title compound (20.6 g, 64% yield). NMR (CDCl$_3$) δ: 7.65. (1H, d, J=8.4 Hz), 7.75 (1H, dd, J=2.2 Hz. 8.4 Hz), 8.31 (1H, d, J=2.2 Hz), hidden (1H)

REFERENCE EXAMPLE 2-10

2-[[3-Methyl-1-(2-pyridinyl)-1H-pyrazol-5-yl]amino]-5-(trifluoromethyl)benzoic acid A solution of 3-methyl-1-(2-pyridinyl)-1H-pyrazol-5-ylamine (8.71 g, 50.0 mmol), 2-chloro-5-(trifluoromethyl)benzoic acid (12.4 g, 55.0 mmol), copper acetate (II) (1.00 g, 5.50 mmol) and potassium carbonate (7.60 g, 55.0 mmol) in N,N-dimethylformamide (50 mL) was heated under reflux for 1.5 hours under an argon atmosphere. The solution was cooled to room temperature, and poured into water. The solution was made acidic by the addition of acetic acid, and the resulting crude crystals were collected by filtration. The crystals were washed with water and air dried to give the title compound (17.7 g, 89% yield).

mp: 228–229° C. (recrystallized from ethyl acetate). NMR (CDCl$_3$) δ: 2.37 (3H, s), 6.19 (1H, s), 7.13 (1H, ddd, J=1.0 Hz, 4.8 Hz, 7.4 Hz), 7.70–7.85 (3H, m), 7.93 (1H, d, J=8.4 Hz), 8.39 (1H, d, J=1.8 Hz), 8.45 (1H, ddd, J=0.8 Hz, 1.8 Hz, 4.8 Hz), 12.46 (1H, br s), hidden (1H). Elementary Analysis: for $C_{17}H_{13}F_3N_4O_2$ Calcd.: C, 56.36; H, 3.62; N, 15.46. Found: C, 56.56; H, 3.52; N, 15.63.

REFERENCE EXAMPLE 2-11

2-Bromo-5-methoxybenzoic acid

The title compound was prepared according to the method described in JP 63-287756 A. To a solution of 3-methoxybenzoic acid (25.0 g, 164 mmol) in acetic acid (150 mL), a solution of bromine (26.5 g, 166 mmol) in acetic acid (75 mL) was added dropwise at room temperature, and the mixture was stirred at the same temperature for 8 hours. The mixture was poured into water, and the resulting crystals were collected by filtration, washed with water, and air dried to give the title compound (29.5 g, 78% yield).

NMR (CDCl$_3$) δ: 3.84 (3H, s), 6.95 (1H, dd, J=3.0 Hz, 8.8 Hz), 7.53 (1H, d, J=3.0 Hz), 7.58 (1H, d, J=8.8 Hz), hidden (1H).

REFERENCE EXAMPLE 2-12

5-Methoxy-2-[[3-methyl-1-(2-pyridinyl)-1H-pyrazol-5-yl]amino]benzoic acid

Following the procedure described in Reference Example 2-5, the title compound was prepared from 2-bromo-5-methoxybenzoic acid and 3-methyl-1-(2-pyridinyl)-1H-pyrazol-5-ylamine (48% yield).

mp: 195–196° C. (recrystallized from ethanol). NMR (DMSO-d$_6$) δ: 2.21 (3H, s), 3.77 (3H, s), 6.09 (1H, s), 7.17 (1H, dd, J=3.2 Hz, 9.2 Hz), 7.29 (1H, ddd, J=1.0 Hz, 5.2 Hz, 7.4 Hz), 7.44 (1H, d, J=3.2 Hz), 7.57 (1H, d, J=9.2 Hz), 7.83 (1H, d, J=8.4 Hz), 7.97 (1H, ddd, J=1.8 Hz, 7.4 Hz, 8.4 Hz), 8.43 (1H, ddd, J=1.0 Hz, 1.8 Hz, 5.2 Hz), 11.95 (1H, br s), hidden (1H). Elementary Analysis: for $C_{17}H_{16}N_4O_3$ Calcd.: C, 62.95; H, 4.97; N, 17.27. Found: C, 63.10; H, 5.17; N, 17.39.

REFERENCE EXAMPLE 2-13

8-Methoxy-2-(2-oxopropyl)-4H-3,1-benzoxazin-4-one

Following the procedure described in Reference Example 2-1, the title compound was prepared from 2-amino-3-methoxybenzoic acid (92% yield).

mp: 177–180° C. (recrystallized from methanol/ethyl acetate). Elementary Analysis: for $C_{12}H_{11}NO_4$ Calcd.: C, 61.80; H, 4.75; N, 6.01. Found: C, 61.81; H, 4.72; N, 6.01.

REFERENCE EXAMPLE 2-14

6,7-Dimethoxy-2-(2-oxopropyl)-4H-3,1-benzoxazin-4-one

Following the procedure described in Reference Example 2-1, the title compound was prepared from 2-amino-4,5-dimethoxybenzoic acid (65% yield).

mp: 200–202° C. (recrystallized from acetonitrile). Elementary Analysis: for $C_{13}H_{13}NO_5$ Calcd.: C, 59.31; H, 4.98; N, 5.32. Found: C, 59.28; H, 4.91; N, 5.56.

REFERENCE EXAMPLE 2-15

4,5-Dimethoxy-2-[[3-methyl-1-(2-pyridinyl)-1H-pyrazol-5-yl]amino]benzoic acid

Following the procedure described in Reference Example 2-3, the title compound was prepared from 6,7-dimethoxy-2-(2-oxopropyl)-4H-3,1-benzoxazin-4-one and 2-hydrazinopyridine (64% yield).

NMR (DMSO-d$_6$) δ: 2.24 (3H, s), 3.75 (3H, s), 3.86 (3H, s), 6.27 (1H, s), 7.14 (1H, s), 7.26–7.33 (1H, m), 7.41 (1H, s), 7.83 (1H, d, J=8.0 Hz), 7.97 (1H, dt, J=1.8 Hz, 8.4 Hz), 8.41–8.45 (1H, m), hidden (2H).

REFERENCE EXAMPLE 2-16

6-(Methylsulfanyl)-2-(2-oxopropyl)-4H-3,1-benzoxazin-4-one

Following the procedure described in Reference Example 2-1, the title compound was prepared from 2-amino-5-(methylsulfanyl)benzoic acid (68% yield).

mp: 137–140° C. (recrystallized from ethyl acetate/hexane). Elementary Analysis: for $C_{12}H_{11}NO_3S$ Calcd.: C, 57.82; H, 4.45; N, 5.62. Found: C, 57.80; H, 4.61; N, 5.48.

REFERENCE EXAMPLE 2-17

5-(Methylsulfanyl)-2-[[3-methyl-1-(2-pyridinyl)-1H-pyrazol-5-yl]amino]benzoic acid Following the procedure described in Reference Example 2-3, the title compound was prepared from 6-(methylsulfanyl)-2-(2-oxopropyl)-4H-3,1-benzoxazin-4-one and 2-hydrazinopyridine (67% yield).

NMR (DMSO-d$_6$) δ: 2.24 (3H, s), 2.47 (3H, s), 6.21 (1H, s), 7.31 (1H, ddd, J=1.0 Hz, 4.8 Hz, 7.4 Hz), 7.48 (1H, dd, J=2.2 Hz, 8.8 Hz), 7.60 (1H, d, J=8.8 Hz), 7.81–7.86 (2H, m), 7.98 (1H, ddd, J=1.8 Hz, 7.4 Hz, 8.4 Hz), 8.44 (1H, ddd, J=0.8 Hz, 1.8 Hz, 4.8 Hz), 12.18 (1H, s), hidden (1H).

REFERENCE EXAMPLE 2-18

2-[[3-Methyl1-(2-pyridinyl)-1H-pyrazol-5-yl]amino]-5-nitrobenzoic acid

Following the procedure described in Reference Example 2-5, the title compound was prepared from 2-bromo-5-nitrobenzoic acid and 3-methyl-1-(2-pyridinyl)-1H-pyrazol-5-ylamine (96% yield).

mp: 270° C. NMR (DMSO-d$_6$) δ: 2.28 (3H, s), 6.42 (1H, s), 7.32 (1H, ddd, J=0.8 Hz, 4.8 Hz, 7.4 Hz), 7.63 (1H, d, J=9.4 Hz), 7.81 (1H, d, J=8.4 Hz), 7.94–8.03 (1H, m), 8.22 (1H, dd, J=2.8 Hz, 9.4 Hz), 8.46–8.49 (1H, m), 8.78 (1H, d, J=2.8 Hz), 13.20 (1H, br s), hidden (1H). Elementary Analysis: for $C_{16}H_{13}N_5O_4 \cdot 0.75H_2O$ Calcd.: C, 54.47; H, 4.14; N, 19.85. Found: C, 54.49; H, 3.77; N, 19.79.

REFERENCE EXAMPLE 2-19

2-[[3-Methyl-1-(2-pyridinyl)-1H-pyrazol-5-yl]amino]-4-nitrobenzoic acid

Following the procedure described in Reference Example 2-5, the title compound was prepared from 2-chloro-4-nitrobenzoic acid and 3-methyl-1-(2-pyridinyl)-1H-pyrazol-5-ylamine (86% yield).

mp: 270–271° C. NMR (DMSO-$d_6$) δ: 2.28 (3H, s), 6.35 (1H, s), 7.30–7.35 (1H, m), 7.66 (1H, dd, J=1.8 Hz, 8.4 Hz), 7.84 (1H, d, J=8.4 Hz), 7.95–8.04 (1H, m), 8.17 (1H, d, J=8.4 Hz), 8.28 (1H, d, J=1.8 Hz), 8.42–8.46 (1H, m), 13.20 (1H, br s), hidden (1H). Elementary Analysis: for $C_{16}H_{13}N_5O_4 \cdot 0.25H_2O$ Calcd.: C, 55.90; H, 3.96; N, 20.37. Found: C, 55.88; H, 4.00; N, 20.23.

REFERENCE EXAMPLE 2-20

Methyl 4-oxo-2-(2-oxopropyl)-4H-3,1-benzoxazine-5-carboxylate

To a solution of 2-methoxycarbonyl-6-nitrobenzoic acid (22.5 g, 0.1 mol) in methanol (100 mL) was added 10% palladium-carbon (2.0 g, 50% hydrate), and the mixture was stirred at room temperature under hydrogen atmosphere for 1 hour. The catalyst was removed by filtration, and the filtrate was concentrated under reduced pressure, and the residue was dissolved in acetone (100 mL). To the solution was added dropwise diketene (23 mL, 0.30 mol) at room temperature. After the mixture was stirred at room temperature for 16 hours, the solution was concentrated under reduced pressure. The resulting crude crystals were collected by filtration, washed with acetone and diethylether, and air dried (15.4 g). The crude crystals were suspended in a mixture of acetic anhydride (10.4 mL, 0.11 mol) and tetrahydrofuran (60 mL), and the suspension was heated under reflux for 12 hours. The suspension was allowed to cool to room temperature, and the solvents were evaporated under reduced pressure to give crude crystals. The crystals were collected by filtration, washed with diethylether, and air dried to give the title compound (8.03 g, 31% yield).

NMR (CDCl$_3$) δ: 2.14 (2.25H, s), 2.35 (0.75H, s), 3.84 (0.5H, s), 3.98 (2.25H, s), 4.00 (0.75H, s), 5.26 (0.75H, s), 7.32 (0.75H, dd, J=1.0 Hz, 7.4 Hz), 7.40 (0.75H, dd, J=1.0 Hz, 8.0 Hz), 7.53 (0.25H, dd, J=1.0 Hz, 7.4 Hz), 7.66 (0.25H, dd, J=1.0 Hz, 8.0 Hz), 7.69–7.88 (1H, m).

REFERENCE EXAMPLE 2-21

2-Chloro-6-iodobenzoic acid

The title compound was prepared according to the method described in Collection Czechoslov. Chem. Commn., vol. 40, p. 719 (1975). To an ice-cold mixture of 2-amino-6-chlorobenzoic acid (10.0 g, 58.3 mmol) and conc. hydrochloric acid (50 mL), was added dropwise a solution of sodium nitrite (4.42 g, 64.1 mmol) in water (10 mL). Furthermore, a solution of potassium iodide (14.5 g, 87.5 mmol) and conc. sulfuric acid (4 mL) in water (30 mL) was added thereto at the same temperature, and the mixture was heated to 100° C. and stirred for 2 hours. The reaction mixture was allowed to cool to room temperature, poured into an aqueous sodium thiosulfate solution, and organic matter was extracted with ethyl acetate. The extract was washed with saturated brine and water and dried over anhydrous sulfuric acid, and the solvent was evaporated under reduced pressure. The resulting crude crystals were collected by filtration, washed with hexane/diethylether, and air dried to give the title compound (12.1 g, 73% yield).

NMR (CDCl$_3$) δ: 7.20 (1H, dd, J=2.6 Hz, 8.8 Hz), 7.97 (1H, d, J=8.8 Hz), 7.99 (1H, d, J=2.6 Hz), hidden (1H).

REFERENCE EXAMPLE 2-22

6-Chloro-2-[[3-methyl-1-(2-pyridinyl)-1H-pyrazol-5-yl]amino]benzoic acid

Following the procedure described in Reference Example 2-5, the title compound was prepared from 2-chloro-6-iodobenzoic acid and 3-methyl-1-(2-pyridinyl)-1H-pyrazol-5-ylamine (28% yield).

mp: 201–202° C. (recrystallized from ethanol). NMR (DMSO-$d_6$) δ: 2.22 (3H, s), 6.12 (1H, s), 7.10 (1H, dd, J=1.0 Hz, 7.8 Hz), 7.32 (1H, ddd, J=1.0 Hz, 5.0 Hz, 7.0 Hz), 7.41 (1H, dd, J=7.4 Hz, 7.8 Hz), 7.52 (1H, dd, J=1.0 Hz, 8.4 Hz), 7.88 (1H, dd, J=1.0 Hz, 7.4 Hz), 8.01 (1H, ddd, J=1.8 Hz, 7.0 Hz, 8.4 Hz), 8.42 (1H, ddd, J=0.8 Hz, 1.8 Hz, 5.0 Hz), 11.35 (1H, br s), hidden (1H). Elementary Analysis: for $C_{16}H_{13}ClN_4O_2$ Calcd.: C, 58.45; H, 3.99; N, 17.04. Found: C, 58.29; H, 4.07; N, 17.03.

REFERENCE EXAMPLE 2-23

6-Chloro-2-(2-oxopropyl)-4H-3,1-benzoxazin-4-one

Following the procedure described in Reference Example 2-1, the title compound was prepared from 2-amino-5-chlorobenzoic acid (46% yield).

mp: 159–160° C. (recrystallized from acetonitrile). Elementary Analysis: for $C_{11}H_8ClNO_3$ Calcd.: C, 57.82; H, 4.45; N, 5.62. Found: C, 57.80; H, 4.61; N, 5.48.

REFERENCE EXAMPLE 2-24

4-Chloro-2-iodobenzoic acid

Following the procedure described in Reference Example 2-21, the title compound was prepared from 2-amino-4-chlorobenzoic acid (28% yield).

NMR (CDCl$_3$) δ: 7.44 (1H, dd, J=2.2 Hz, 8.4 Hz), 7.98 (1H, d, J=8.4 Hz), 8.08 (1H, d, J=2.2 Hz), hidden (1H).

REFERENCE EXAMPLE 2-25

2,4,5-Trichlorobenzoic acid

The title compound was prepared according to the method described in JP 7-165638 A. Aluminum chloride (53.3 g, 0.4 mol) was suspended in carbon tetrachloride (194 g, 2 mol) at 0° C., and the suspension was gradually heated. 1,3,4-Trichlorobenzene (36.4 g, 0.2 mol) was added dropwise over 2 hours under reflux, and the mixture was heated under reflux further for 0.5 hour. After the solution was allowed to cool to room temperature, the mixture was carefully poured into iced water. The organic layer was washed with water, an aqueous 5% sodium bicarbonate solution and water, dried over anhydrous magnesium sulfate, and concentrated under reduced pressure to give crude crystals of 1,2,4-trichloro-5-(trichloromethyl)benzene (41.0 g, 69% yield) which were collected by filtration. The crude crystals (27.6 g, 92.4 mmol) were suspended in 95% sulfuric acid (90 mL), and the suspension was stirred at 50° C. for 7 hours. The solution was poured into iced water, and the resulting crude crystals were collected by filtration. The crystals were dissolved in 1N sodium hydroxide, and the solution was washed with ethyl acetate. The aqueous layer was neutralized with 6N hydrochloric acid, and the organic matter was extracted with ethyl acetate. The extract was washed with saturated brine, dried over anhydrous magnesium sulfate, and concentrated under reduced pressure. The crude crystals thus obtained were collected by filtration, washed with hexane, and air dried to give the title compound (17.6 g, 85% yield). NMR (CDCl$_3$) δ: 7.20 (1H, dd, J=2.6 Hz, 8.8 Hz), 7.97 (1H, d, J=8.8 Hz), 7.99 (1H, d, J=2.6 Hz), hidden (1H).

REFERENCE EXAMPLE 2-26

4,5-Dichloro-2-[[3-methyl-1-(2-pyridinyl)-1H-pyrazol-5-yl]amino]benzoic acid

Following the procedure described in Reference Example 2-5, the title compound was prepared from 2,4,5- trichlorobenzoic acid and 3-methyl-1-(2-pyridinyl)-1H-pyrazol-5-ylamine (92% yield).

mp: 288–289° C. (recrystallized from ethanol). NMR (DMSO-$d_6$) δ: 2.26 (3H, s), 6.32 (1H, s), 7.29–7.35 (1H, m), 7.69 (1H, s), 7.83 (1H, d, J=8.4 Hz), 7,94–8.03 (2H, m), 8.41–8.44 (1H, m), 12.34 (1H, br s), hidden (1H). Elementary Analysis: for $C_{16}H_{12}Cl_2N_4O_2$ Calcd.: C, 52.91; H, 3.33; N, 15.43. Found: C, 52.64; H, 3.20; N, 15.30.

REFERENCE EXAMPLE 2-27

3,5-Dichloro-2-iodobenzoic acid

Following the procedure described in Reference Example 2-21, the title compound was prepared from 2-amino-3,5-dichlorobenzoic acid (88% yield).

NMR (CDCl$_3$) δ: 7.44 (1H, dd, J=2.2 Hz, 8.4 Hz), 7.98 (1H, d, J=8.4 Hz), 8.08 (1H, d, J=2.2 Hz), hidden (1H).

REFERENCE EXAMPLE 2-28

3,5-Dichloro-2-[[3-methyl-1-(2-pyridinyl)-1H-pyrazol-5-yl]amino]benzoic acid

Following the procedure described in Reference Example 2-5, the title compound was prepared from 3,5-dichloro-2-iodobenzoic acid and 3-methyl-1-(2-pyridinyl)-1H-pyrazol-5-ylamine (16% yield).

mp: 288–289° C. NMR (DMSO-$d_6$) δ: 2.12 (3H, s), 5.21 (1H, s), 7.28 (1H, t, J=5.4 Hz), 7.83–7.94 (4H, m), 8.43 (1H, d, J=4.4 Hz), 10.66 (1H, br s), hidden (1H). Elementary Analysis: for $C_{16}H_{21}Cl_2N_4O_2$ Calcd.: C, 52.91; H, 3.33; N, 15.43. Found: C, 52.67; H, 3.25; N, 15.31.

REFERENCE EXAMPLE 2-29

2-Amino-5-fluorobenzoic acid

Following the procedures described below in Reference Examples 2-31 and 2-32, the title compound was prepared from 5-fluoro-2-nitrotoluene (25% yield).

NMR (CDCl$_3$) δ: 5.94 (3H, br s), 6.64 (1H, dd, J=4.6 Hz, 9.0 Hz), 7.04–7.15 (1H, m), 7.60 (1H, dd, J=3.0 Hz, 9.6 Hz).

REFERENCE EXAMPLE 2-30

5-Fluoro-2-iodobenzoic acid

Following the procedure described in Reference Example 2-21, the title compound was prepared from 2-amino-5-fluorobenzoic acid (41% yield).

NMR (CDCl$_3$) δ: 6.99 (1H, ddd, J=3.0 Hz, 5.4 Hz, 8.8 Hz), 7.76 (1H, dd, J=3.0 Hz, 8.8 Hz), 8.02 (1H, dd, J=5.4 Hz, 8.8 Hz), hidden (1H).

REFERENCE EXAMPLE 2-31

4-Fluoro-2-nitrobenzoic acid

A mixture of 4-fluoro-2-nitrotoluene (25.0 g, 161 mmol), potassium permanganate (102 g, 645 mmol) and water (500 mL) was heated and stirred at 100° C. for 3 hours. The solution was allowed to cool to room temperature, filtered through Celite to remove the insoluble derived from potassium permanganate. The filtrate was washed with diethylether and made acidic by the addition of conc. hydrochloric acid, and organic matter was extracted with diethylether. The extract was washed with saturated brine and dried over anhydrous magnesium sulfate, and the solvent was evaporated under reduced pressure to give the title compound (10.1 g, 34% yield).

NMR (CDCl$_3$) δ: 7.40 (1H, ddd, J=2.6 Hz, 7.4 Hz, 8.8 Hz), 7.53 (1H, dd, J=2.6 Hz, 7.6 Hz), 8.00 (1H, dd, J=5.6 Hz, 8.8 Hz), 8.52 (1H, br s).

REFERENCE EXAMPLE 2-32

2-Amino-4-fluorobenzoic acid

To a solution of 4-fluoro-2-nitrobenzoic acid (22.5 g, 0.1 mol) in ethanol (200 mL), 10% palladium-carbon (1.0 g, 50% hydrate) was added, and the mixture was stirred at room temperature under hydrogen atmosphere for 4 hours. The solution was filtered to remove the catalyst, and the filtrate was concentrated under reduced pressure to give the title compound (8.38 g, 100% yield).

NMR (CDCl$_3$) δ: 5.95 (2H, br s), 6.31–6.44 (2H, m), 7.93 (1H, dd, J=6.4 Hz, 8.6 Hz), hidden (1H).

REFERENCE EXAMPLE 2-33

4-Fluoro-2-iodobenzoic acid

Following the procedure described in Reference Example 2-21, the title compound was prepared from 2-amino-4-fluorobenzoic acid (60% yield).

NMR (CDCl$_3$) δ: 7.17 (1H, ddd, J=2.6 Hz, 7.8 Hz, 8.8 Hz), 7.80 (1H, dd, J=2.6 Hz, 8.4 Hz), 8.08 (1H, dd, J=5.8 Hz, 8.8 Hz), hidden (1H).

REFERENCE EXAMPLE 2-34

4-Fluoro-2-[[3-methyl-1-(2-pyridinyl)-1H-pyrazol-5-yl]amino]benzoic acid

Following the procedure described in Reference Example 2-5, the title compound was prepared from 4-fluoro-2-iodobenzoic acid and 3-methyl-1-(2-pyridinyl)-1H-pyrazol-5-ylamine (86% yield).

mp: 242–243° C. (recrystallized from ethanol). NMR (DMSO-$d_6$) δ: 2.26 (3H, s), 6.35 (1H, s), 6.74 (1H, ddd, J=2.2 Hz, 8.0 Hz, 8.8 Hz), 7.27–7.36 (2H, m), 7.83 (1H, ddd, J=0.6 Hz, 1.2 Hz, 8.4 Hz), 7.95–8.06 (2H, m), 8.44 (1H, ddd, J=0.6 Hz, 1.8 Hz, 4.8 Hz), 12.37 (1H, br s), hidden (1H). Elementary Analysis: for $C_{16}H_{13}FN_4O_2$ Calcd.: C, 61.53; H, 4.20; N, 17.94. Found: C, 61.42; H, 4.32; N, 17.98.

REFERENCE EXAMPLE 2-35

N-(2-Fluorophenyl)-2-(hydroxyimino)acetamide

The title compound was prepared according to the method described in J. Heterocyclic Chem., vol. 27, p. 2151 (1990). To a solution of chloral hydrate (44.2 g, 267 mmol) and sodium sulfate (304 g, 2.14 mol) in water (700 mL), was added a solution of 2-fluoroaniline (27.0 g, 243 mmol) and conc. hydrochloric acid (70 mL) in water (140 mL) dropwise at room temperature, and furthermore hydroxylamine hydrochloride (74.4 g, 1.07 mol), and the resulting solution was heated under reflux for 10 minutes. The solution was ice cooled and the resulting crystals were collected by filtration and air dried to give the title compound (38.0 g, 86% yield).

mp: 120° C. (recrystallized from ethyl acetate/hexane). NMR (CDCl$_3$) δ: 7.06–7.21 (3H, m), 7.61 (1H, s), 8.30–8.39 (1H, m), 8.57 (2H, br s). Elementary Analysis: for $C_8H_7FN_2O_2$ Calcd.: C, 52.75; H, 3.87; N, 15.38. Found: C, 52.76; H, 3.81; N, 15.32.

REFERENCE EXAMPLE 2-36

7-Fluoro-1H-indol-2,3-dione

A solution of N-(2-fluorophenyl)-2-(hydroxyimino)acetamide (35.0 g, 192 mmol) in sulfuric acid (150 mL) was heated and stirred at 70° C. for 45 minutes. The solution was allowed to cool to room temperature and poured into iced water, and organic matter was extracted with ethyl acetate. The extract was washed with saturated brine, dried over anhydrous magnesium sulfate, and the solvent was evaporated under reduced pressure. The resulting crystals were collected by filtration to give the title compound (14.6 g, 46% yield).

mp: 195–196° C. (recrystallized from ethyl acetate/hexane). NMR (CDCl$_3$) δ: 7.12 (1H, ddd, J=4.4 Hz, 7.4 Hz, 8.4 Hz), 7.38 (1H, ddd, J=1.0 Hz, 8.4 Hz, 9.6 Hz), 7.47 (1H, ddd, J=1.0 Hz, 1.2 Hz, 7.4 Hz), 8.33 (1H, br s). Elementary Analysis: for C$_8$H$_4$FNO$_2$ Calcd.: C, 58.19; H, 2.44; N, 8.48; F, 11.51. Found: C, 58.10; H, 2.56; N, 8.37; F, 11.35.

REFERENCE EXAMPLE 2-37

2-Amino-3-fluorobenzoic acid

A solution of 7-fluoro-1H-indol-2,3-dione (13.0 g, 78.7 mmol) in 10N sodium hydroxide (125 mL) was heated and stirred at 70° C. for 1 hour. 30% Hydrogen peroxide (25 mL) was added dropwise over 20 minutes at the same temperature, and the mixture was heated and stirred at the same temperature further for 1 hour. The solution was ice cooled, and conc. hydrochloric acid was added to the solution carefully until the pH of the solution became 4. Organic matter was extracted with ethyl acetate, and the extract was washed with saturated brine and dried over anhydrous magnesium sulfate, and the solvent was evaporated under reduced pressure. The crystals thus obtained were collected by filtration to give the title compound (7.15 g, 59% yield).

NMR (CDCl$_3$) δ: 6.00 (2H, br s), 6.60 (1H, dt, J=5.2 Hz, 8.0 Hz), 7.16 (1H, ddd, J=1.4 Hz, 8.0 Hz, 11.2 Hz), 7.72 (1H, td, J=1.4 Hz, 8.0 Hz), hidden (1H).

REFERENCE EXAMPLE 2-38

3-Fluoro-2-iodobenzoic acid

Following the procedure described in Reference Example 2-21, the title compound was prepared from 2-amino-3-fluorobenzoic acid (19% yield).

NMR (CDCl$_3$) δ: 7.26 (1H, ddd, J=1.6 Hz, 7.6 Hz, 8.2 Hz), 7.42 (1H, ddd, J=5.6 Hz, 7.6 Hz. 8.2 Hz), 7.79 (1H, ddd, J=0.8 Hz, 1.6 Hz, 7.6 Hz), hidden (1H).

REFERENCE EXAMPLE 2-39

6-Bromo-2,3-difluorobenzoic acid

A solution of 1.6M butyllithium in hexane (60 mL, 96 mmol) was diluted with tetrahydrofuran (180 mL) under an argon atmosphere, and cooled to −78° C. To the solution, were added dropwise 2,2,6,6-tetramethylpiperidine (16.2 g, 116 mmol) and subsequently 4-bromo-1,2-difluorobenzene (15.4 g, 80 mmol), and the mixture was stirred at the same temperature for 2 hours. The solution was carefully poured onto crushed dry ice, and the mixture was allowed to warm to room temperature. The solution was concentrated under reduced pressure, and the residue was poured into water. After the solution was washed with diethylether, the aqueous layer was made acidic by the addition of 6N hydrochloric acid, and organic matter was extracted with dichloromethane. The extract was washed with saturated brine, dried over anhydrous magnesium sulfate, and concentrated under reduced pressure to give the title compound (10.8 g, 57% yield).

NMR (CDCl$_3$) δ: 7.18 (1H, td, J=8.6 Hz, 9.2 Hz), 7.40 (1H, ddd, J=2.0 Hz, 4.2 Hz, 8.6 Hz), hidden (1H).

REFERENCE EXAMPLE 2-40

Methyl 6-bromo-2,3-difluorobenzoate

A solution of 6-bromo-2,3-difluorobenzoic acid (7.66 g, 32.3 mmol), methyl iodide (10 mL, 160 mmol) and potassium carbonate (5.36 g, 38.8 mmol) in N,N-dimethylformamide (30 mL) was stirred at room temperature for 1 hour. The solution was poured into water, and organic matter was extracted with ethyl acetate. The extract was washed with water and saturated brine, dried over anhydrous magnesium sulfate, and concentrated under reduced pressure to give the title compound (8.11 g, 100% yield).

NMR (CDCl$_3$) δ: 3.99 (3H, s), 7.07–7.21 (1H, m), 7.35 (1H, ddd, J=2.0 Hz, 4.2 Hz, 8.8 Hz), hidden (1H).

REFERENCE EXAMPLE 2-41

Methyl 2,3-difluoro-6-[[3-methyl-1-(2-pyridinyl)-1H-pyrazol-5-yl]amino]benzoate

A solution of 3-methyl-1-(2-pyridinyl)-1H-pyrazol-5-ylamine (6.16 g, 35.4 mmol), methyl 6-bromo-2,3-difluorobenzoate (8.11 g, 32.3 mmol), copper acetate (II) (0.49 g, 2.7 mmol) and potassium carbonate (4.46 g, 323 mmol) in N,N-dimethylformamide (30 mL) was heated under reflux for 1 hour under an argon atmosphere, and the solution was allowed to cool to room temperature and poured into water. The solution was made weakly acidic by the addition of acetic acid, and organic matter was extracted with ethyl acetate. The extract was washed with water and saturated brine, dried over anhydrous magnesium sulfate, and concentrated under reduced pressure. The residue thus obtained was purified by silica gel column chromatography (hexane:ethyl acetate=10:1 to 5:1) to give the title compound (0.86 g, 8% yield).

NMR (CDCl$_3$) δ: 2.30 (3H, s), 4.00 (3H, s), 5.94 (1H, s), 7.11–7.27 (2H, m), 7.23 (1H, dd, J=8.2 Hz, 9.2 Hz), 7.80 (1H, ddd, J=1.8 Hz, 7.4 Hz, 8.4 Hz), 7.94 (1H, ddd, J=1.0 Hz, 1.2 Hz, 8.4 Hz), 8.50 (1H, ddd, J=1.0 Hz, 1.8 Hz, 5.0 Hz), 11.60 (1H, br s). Elementary Analysis: for C$_{17}$H$_{14}$F$_2$N$_4$O$_2$ Calcd.: C, 59.30; H, 4.10; N, 16.27; F, 11.04. Found: C, 59.23; H, 4.22; N, 16.01; F, 10.86.

REFERENCE EXAMPLE 2-42

2,3-Difluoro-6-[[3-methyl-1-(2-pyridinyl)-1H-pyrazol-5-yl]amino]benzoic acid

To a solution of methyl 2,3-difluoro-6-[[3-methyl1-1-(2-pyridinyl)-1H-pyrazol-5-yl]amino]benzoate (0.80 g, 2.3 mmol) in methanol (40 mL) was added 1N sodium hydroxide (5 mL), and the mixture was heated under reflux for 2 hours. The solution was allowed to cool to room temperature, and concentrated under reduced pressure, and the residue was poured into water. The solution was made weakly acidic by the addition of acetic acid, and the resulting crude crystals were collected by filtration, washed with water, and air dried to give the title compound (0.64 g, 84% yield).

NMR (DMSO-d$_6$) δ: 2.22 (3H, s), 6.12 (1H, s), 7.32 (1H, ddd, J=1.2 Hz, 4.8 Hz, 7.2 Hz), 7.37 (1H, ddd, J=1.8 Hz, 4.2 Hz, 9.6 Hz), 7.53 (1H, dd, J=9.6 Hz, 18.4 Hz), 7.86 (1H, br d, J=8.4 Hz), 7.99 (1H, ddd, J=1.8 Hz, 7.2 Hz, 8.4 Hz), 8.43 (1H, ddd, J=0.8 Hz, 1.8 Hz, 4.8 Hz), 11.64 (1H, br s), hidden (1H).

REFERENCE EXAMPLE 2-43

4,5-Difluoro-2-[[3-methyl-1-(2-pyridinyl)-1H-pyrazol-5-yl]amino]benzoic acid Under an argon atmosphere, a solution of 3-methyl-1-(2-pyridinyl)-1H-pyrazol-5-ylamine (6.01 g, 34.5 mmol), 2-chloro-4,5-difluorobenzoic acid (6.64 g, 34.5 mmol), copper acetate (II) (0.718 g, 3.95 mmol) and potassium carbonate (4.77 g, 34.5 mmol) in N,N-dimethylformamide (30 mL) was heated under reflux for 2 hours. The solution was cooled to room temperature, and poured into water. The solution was made weakly acidic by the addition of acetic acid, and the resulting crude crystals were collected by filtration. The crystals were washed with water and air dried to give the title compound (9.21 g, 81% yield).

mp: 247–248° C. (recrystallized from methanol). NMR (DMSO-$d_6$) δ: 2.25 (3H, s), 6.33 (1H, s), 7.28–7.34 (1H, m), 7.46–7.56 (1H, m), 7.80–8.02 (3H, m), 8.30–8.44 (1H, m), 12.30 (1H, br s), hidden (1H). Elementary Analysis: for $C_{16}H_{12}F_2N_4O_2$ Calcd.: C, 58.18; H, 3.66; N, 16.96. Found: C, 58.0.9; H, 3.48; N, 16.88.

REFERENCE EXAMPLE 2-44

2,4-Dichloro-5-fluorobenzoic acid

Following the procedure described in Reference Example 2-25, the title compound was prepared from 2,4-dichloro-1-fluorobenzene (66% yield).

NMR (CDCl$_3$) δ: 7.59 (1H, d, J=6.2 Hz), 7.85 (1H, d, J=8.8 Hz), 8.28 (1H, br s).

REFERENCE EXAMPLE 2-45

4-Chloro-5-fluoro-2-[[3-methyl-1-(2-pyridinyl)-1H-pyrazol-5-yl]amino]benzoic acid Following the procedure described in Reference Example 2-5, the title compound was prepared from 2,4-dichloro-5-fluorobenzoic acid and 3-methyl-1-(2-pyridinyl)-1H-pyrazol-5-ylamine (24% yield).

mp: 245–246° C. (recrystallized from ethyl acetate). NMR (DMSO-$d_6$) δ: 2.25 (3H, s), 6.28 (1H, s), 7.28–7.35 (1H, m), 7.64 (1H, d, J=6.6 Hz), 7.80–7.85 (2H, m), 7.95–8.03 (1H, m), 8.42 (1H, dd, J=1.2 Hz, 4.8 Hz), 12.21 (1H, br s), hidden (1H). Elementary Analysis: for $C_{16}H_{12}ClFN_4O_2$ Calcd.: C, 55.42; H, 3.49; N, 16.16. Found: C, 55.39; H, 3.43; N, 16.09.

REFERENCE EXAMPLE 2-46

2,5-Dichloro-4-fluorobenzoic acid

Following the procedure described in Reference Example 2-25, the title compound was prepared from 1,4-dichloro-2-fluorobenzene (68% yield).

NMR (CDCl$_3$) δ: 7.33 (1H, d, J=8.8 Hz), 7.45 (1H, br s), 8.15 (1H, d, J=7.6 Hz).

REFERENCE EXAMPLE 2-47

5-Chloro-4-fluoro-2-[[3-methyl-1-(2-pyridinyl)-1H-pyrazol-5-yl]amino]benzoic acid Following the procedure described in Reference Example 2-5, the title compound was prepared from 2,5-dichloro-4-fluorobenzoic acid and 3-methyl-1-(2-pyridinyl)-1H-pyrazol-5-ylamine (95% yield).

mp: 250–252 ° C. (recrystallized from ethanol). NMR (DMSO-$d_6$) δ: 2.26 (3H, s), 6.38 (1H, s), 7.32 (1H, ddd, J=1.2 Hz, 4.8 Hz, 7.4 Hz), 7.49 (1H, d, J=12.4 Hz), 7.83 (1H, ddd, J=0.8 Hz, 1.2 Hz, 8.4 Hz), 7.99 (1H, ddd, J=1.8 Hz, 7.4 Hz, 8.4 Hz), 8.03 (1H, d, J=8.8 Hz), 8.42 (1H, ddd, J=0.8 Hz, 1.8 Hz, 4.8 Hz), 12.41 (1H, br s), hidden (1H). Elementary Analysis: for $C_{16}H_{12}ClFN_4O_2$ Calcd.: C, 55.42; H, 3.49; N, 16.16. Found: C, 55.37; H, 3.44; N, 16.20.

REFERENCE EXAMPLE 2-48

2-Chloro-6-hydrazinopyridine

The title compound was prepared according to the method described in U.S. Pat. No. 4,260,767 (1981). A mixture of 2,6-dichloropyridine (25.0 g, 169 mmol) and hydrazine monohydrate (60 mL, 1.24 mol) was heated and stirred at 100° C. for 4 hours. The solution was ice cooled, and the resulting crude crystals were collected by filtration. The crystals were washed with cold water and air dried. The crystals thus obtained were recrystallized from chloroform/hexane to give the title compound (15.8 g, 65% yield).

NMR (CDCl$_3$) δ: 4.17 (2H, br s), 6.52 (1H, d, J=7.4 Hz), 6.65 (1H, d, J=8.0 Hz), 7.45 (1H, dd, J=7.4 Hz, 8.0 Hz), 7.82 (1H, br s).

REFERENCE EXAMPLE 2-49

2-[[1-(6-Chloropyridine-2-yl)-3-methyl-1H-pyrazol-5-yl]amino]benzoic acid

Following the procedure described in Reference Example 2-3, the title compound was prepared from 2-(2-oxypropyl)-4H-3,1-benzoxazin-4-one and 2-chloro-6-hydrazinopyridine (79% yield).

NMR (DMSO-$d_6$) δ: 2.23 (3H, s), 6.21 (1H, s), 6.92–7.00 (1H, m), 7.35–7.38 (1H, m), 7.42–7.59 (2H, m), 7.80–7.88 (1H, m), 7.94–7.98 (1H, m), 8.03 (1H, d, J=8.0 Hz), 11.26 (1H, br s), hidden (1H).

REFERENCE EXAMPLE 2-50

5-Chloro-2-hydrazinopyridine

Following the procedure described in Reference Example 2-48, the title compound was prepared from 2,5-dichloropyridine and hydrazine hydrate (51% yield).

NMR (CDCl$_3$) δ: 4.13 (2H, br s), 6.73 (1H, d, J=8.8 Hz), 7.49 (1H, dd, J=2.6 Hz, 8.8 Hz), 7.61 (1H, br s), 7.96 (1H, d, J=2.6 Hz).

REFERENCE EXAMPLE 2-51

2-[[1-(5-Chloropyridin-2-yl)-3-methyl-1H-pyrazol-5-yl]amino]benzoic acid

Following the procedure described in Reference Example 2-3, the title compound was prepared from 2-(2-oxypropyl)-4H-3,1-benzoxazin-4-one and 5-chloro-2-hydrazinopyridine (63% yield).

NMR (DMSO-$d_6$) δ: 2.24 (3H, s), 6.26 (1H, s), 6.92–7.00 (1H, m), 7.49–7.63 (2H, m), 7.87 (1H, d, J=8.8 Hz), 7.96 (1H, d, J=7.6 Hz), 8.09 (1H, dd, J=2.4 Hz, 8.8 Hz), 8.42 (1H, d, J=2.4 Hz), 12.03 (1H, br s), hidden (1H).

REFERENCE EXAMPLE 2-52

2-Hydrazino-3-methylpyridine

Following the procedure described in Reference Example 2-48, the title compound was prepared from 2-bromo-3-methylpyridine and hydrazine monohydrate (60% yield).

NMR (DMSO-$d_6$) δ: 2.03 (3H, s), 4.10 (2H, br s), 6.53 (1H, dd, J=5.2 Hz, 7.4 Hz), 7.09 (1H, br s), 7.23 (1H, dd, J=1.0 Hz, 7.4 Hz), 7.94 (1H, dd, J=1.0 Hz, 5.2 Hz).

REFERENCE EXAMPLE 2-53

3-Hydrazinopyridine dihydrochloride

To a mixture of 3-aminopyridine (9.41 g, 100 mmol) and conc. hydrochloric acid (100 mL) which was cooled to a temperature of lower than −5° C., a solution of sodium nitrite (7.20 g, 105 mmol) in water (60 mL) was added dropwise. Subsequently, a solution of tin chloride (II) (56.9 g, 300 mmol) in conc. hydrochloric acid (50 mL) was added dropwise thereto carefully so that the temperature of the solution did not exceed −5° C. The solution was stirred at a temperature of lower than −5° C. for additional 3 hours, and the resulting crystals were collected by filtration. The crystals were washed with diethylether/methanol and air dried to give the title compound (15.6 g, 85% yield). The compound was used in the following process without further purification.

REFERENCE EXAMPLE 2-54

2-[[3-Methyl-1-(3-pyridinyl)-1H-pyrazol-5-yl]amino]benzoic acid

A solution of 2-(2-oxopropyl)-4H-3,1-benzoxazin-4-one (10.2 g, 50.0 mmol), 3-hydrazinopyridine dihydrochloride (9.10 g, 50.0 mmol) and sodium acetate (9.84 g, 120 mmol) in ethanol (100 mL) was heated under reflux for 1 hour. The solution was cooled to room temperature and concentrated under reduced pressure. The residue was poured into water, and organic matter was extracted with a mixture of chloroform/methanol. The extract was washed with saturated brine and dried over anhydrous magnesium sulfate, and the solvents were evaporated under reduced pressure. The residue thus obtained was crystallized from ethyl acetate/diethylether/hexane to give the title compound (10.1 g, 69% yield).

NMR (DMSO-$d_6$) δ: 2.27 (3H, s), 6.27 (1H, s), 6.77–6.84 (1H, m), 6.91 (1H, d, J=8.2 Hz), 7.38 (1H, t, J=7.6 Hz), 7.45–7.52 (1H, m), 7.88 (1H, d, J=7.6 Hz), 7.97 (1H, d, J=7.6 Hz), 8.50–8.53 (1H, m), 8.79 (1H, br s), 9.94 (1H, br s), hidden (1H).

REFERENCE EXAMPLE 2-55

4-Hydrazinopyridine hydrochloride

The title compound was prepared according to the method described in J. Chem. Soc., p. 3830 (1959). A solution of 4-chloropyridine (16.5 g, 145 mmol) and hydrazine monohydrate (7.76 mL, 160 mmol) in 1-propanol (50 mL) was heated under reflux for 18 hours. The solution was cooled to 0° C., and the resulting crystals were collected by filtration. The crystals were washed with cold 1-propanol and air dried to give the title compound (15.2 g, 72% yield). The compound was used in the following process without further purification.

REFERENCE EXAMPLE 2-56

2-[[3-Methyl-1-(4-pyridinyl)-1H-pyrazol-5-yl]amino]benzoic acid

A solution of 2-(2-oxopropyl)-4H-3,1-benzoxazin-4-one (16.7 g, 82.4 mmol), 4-hydrazinopyridine hydrochloride (12.0 g, 82.4 mmol) and sodium acetate (8.10 g, 98.9 mmol) in ethanol (300 mL) was heated under reflux for 30 minutes. The solution was cooled to room temperature and concentrated under reduced pressure. The residue was poured into water and the resulting crude crystals were collected by filtration. The crystals were washed with ethanol and air dried to give the title compound (11.9 g, 49% yield).

NMR (DMSO-$d_6$) δ: 2.27 (3H, s), 6.31 (1H, s), 6.80–6.91 (2H, m), 7.35–7.39 (1H, m), 7.65 (2H, d, J=6.2 Hz), 7.91 (1H, d, J=8.2 Hz), 8.58 (2H, d, J=6.2 Hz), 10.28 (1H, br s), hidden (1H).

REFERENCE EXAMPLE 2-57

2-Hydrazinopyrimidine

The title compound was prepared according to the method described in Yakugaku Zasshi, vol. 73, p. 598 (1953). A mixture of 2-chloropyrimidine (25.0 g, 218 mmol), potassium carbonate (25.0 g, 181 mmol), and hydrazine monohydrate (50 mL, 1.01 mol) was heated and stirred at 100° C. for 20 minutes. The mixture was ice cooled and the resulting crude crystals were collected by filtration. The crystals were washed with cold water, air dried, and recrystallized from benzene to give the title compound (19.7 g, 82% yield).

NMR (DMSO-$d_6$) δ: 4.12 (2H, br s), 6.60 (1H, t, J=4.8 Hz), 8.10 (1H, br s), 8.31 (2H, d, J=4.8 Hz).

REFERENCE EXAMPLE 2-58

2-[[3-Methyl-1-(4,6-dimethyl-2-pyrimidinyl)-1H-pyrazol-5-yl]amino]benzoic acid

Following the procedure described in Reference Example 2-3, the title compound was prepared from 2-(2-oxypropyl)-4H-3,1-benzoxazin-4-one and 2-hydrazino-4,6-dimethylpyrimidine (91% yield).

mp: 142–143° C. (recrystallized from ethyl acetate/methanol). NMR (CDCl$_3$) δ: 2.37 (3H, s), 2.54 (6H, s), 6.12 (1H, s), 6.81 (1H, s), 6.93 (1H, dd, J=1.0 Hz, 8.0 Hz), 7.49 (1H, ddd, J=1.6 Hz, 8.0 Hz, 8.6 Hz), 7.67 (1H, dd, J=1.0 Hz, 8.6 Hz), 8.09 (1H, dd, J=1.6 Hz, 8.0 Hz), 11.54 (1H, dd, J=1.0 Hz, 8.6 Hz), hidden (1H).

REFERENCE EXAMPLE 2-59

2-Hydrazinothiazole hydrochloride

The title compound was prepared according to the method described in Can. J. Chem., vol. 48, p. 3554 (1970). To a mixture of 2-aminothiazole (10.0 g, 100 mmol) and conc. hydrochloric acid (80 mL) cooled to a temperature of below −10° C., a solution of sodium nitrite (6.90 g, 100 mmol) in water (50 mL) was added dropwise. Furthermore, a solution of tin chloride (II) (37.9 g, 200 mmol) in conc. hydrochloric acid (20 mL) was added dropwise carefully so that the temperature of the solution did not exceed −10° C. After the addition, the resulting crystals were collected by filtration. The crystals were recrystallized from diethylether/methanol to give the title compound (9.22 g, 61% yield)

NMR (DMSO-$d_6$) δ: 3.49 (3H, br s), 7.02 (1H, d, J=4.0 Hz), 7.29 (1H, d, J=4.0 Hz).

REFERENCE EXAMPLE 2-60

2-[[3-Methyl-1-(1,3-thiazol-2-yl)-1H-pyrazol-5-yl]amino]benzoic acid

Following the procedure described in Reference Example 2-3, the title compound was prepared from 2-(2-oxopropyl)-

4H-3,1-benzoxazin-4-one and 2-hydrazinothiazole hydrochloride (46% yield)

NMR (DMSO-$d_6$) δ: 2.22 (3H, s), 6.24 (1H, s), 6.97–7.05 (1H, m), 7.47 (1H, d, J=3.8 Hz), 7.57–7.64 (3H, m), 7.97 (1H, dd, J=1.4 Hz, 7.6 Hz), 11.59 (1H, br s), hidden (1H).

REFERENCE EXAMPLE 2-61

Methyl 3-[[3-methyl-1-(2-pyridinyl)-1H-pyrazol-5-yl]amino]-2-thiphenecarboxylate Following the procedure described in Reference Example 2-5, the title compound was prepared from methyl 3-iodo-2-thiphenecarboxylate and 3-methyl-1-(2-pyridinyl)-1H-pyrazol-5-ylamine (40% yield).

mp: 140–141° C. NMR (CDCl$_3$) δ: 2.32 (3H, s), 3.93 (3H, s), 5.95 (1H, s), 7.11–7.18 (1H, m), 7.30 (1H, d, J=5.6 Hz), 7.45 (1H, d, J=5.6 Hz), 7.75–7.83 (1H, m), 7.93 (1H, dd, J=1.2 Hz, 8.4 Hz), 8.53–8.57 (1H, m), hidden (1H). Elementary Analysis: for $C_{15}H_{14}N_4O_2S$ Calcd.: C, 57.31; H, 4.49; N, 17.82. Found: C, 57.40; H, 4.61; N, 17.85.

REFERENCE EXAMPLE 2-62

3-[[3-Methyl-1-(2-pyridinyl)-1H-pyrazol-5-yl]amino]-2-thiophenecarboxylic acid

Following the procedure described in Reference Example 2-42, the title compound was prepared from methyl 3-[[3-methyl-1-(2-pyridinyl)-1H-pyrazole-5-yl]amino]-2-thiophenecarboxylic acid (47% yield).

mp: 169–170° C. (recrystallized from methanol). NMR (DMSO-$d_6$) δ: 2.24 (3H, s), 6.18 (1H, s), 7.27–7.33 (1H, m), 7.41 (1H, d, J=5.4 Hz), 7.82–7.87 (2H, m), 7.94–8.02 (1H, m), 8.43 (1H, dd, J=1.0 Hz, 5.1 Hz), 12.31 (1H, br s), hidden (1H). Elementary Analysis: for $C_{14}H_{12}N_4O_2S$ Calcd.: C, 55.99; H, 4.03; N, 18.65. Found: C, 55.92; H, 4.03; N, 18.62.

REFERENCE EXAMPLE 2-63

Ethyl 5-amino-1-(2-pyridinyl)-1H-pyrazole-4-carboxylate

A solution of ethyl 2-(ethoxymethylene)-2-cyanoacetate (33.8 g, 200 mmol) and 2-hydrazinopyridine (21.8 g, 200 mmol) in ethanol (100 mL) was heated under reflux for 20 minutes. The solution was cooled to room temperature, and the resulting crystals were collected by filtration. The crystals were washed with ethanol and air dried to give the title compound (33.8 g, 73% yield).

mp: 103–104° C. (recrystallized from ethyl acetate). NMR (CDCl$_3$) δ: 1.37 (3H, t, J=7.0 Hz), 4.31 (2H, q, J=7.0 Hz), 7.12–7.18 (1H, m), 7.48 (2H, br s), 7.76 (1H, s), 7.77–7.87 (1H, m), 7.95 (1H, d, J=8.4 Hz), 8.35–8.38 (1H, m).

REFERENCE EXAMPLE 2-64

1-(2-Pyridinyl)-1H-pyrazol-5-ylamine

A suspension of ethyl 5-amino-1-(2-pyridinyl)-1H-pyrazole-4-carboxylate (27.9 g, 120 mmol) in 4N sodium hydroxide (300 mL) was heated under reflux for 1 hour. The suspension was allowed to cool to room temperature, neutralized by the addition of conc. hydrochloric acid, and further made acidic by the addition of acetic acid. The resulting crystals were collected by filtration, washed with ethanol, and air dried. The crystals thus obtained were subjected to heat at 200° C., and washed with diethylether to give the title compound (6.02 g, 31% yield). NMR (CDCl$_3$) δ: 5.51 (1H, d, J=1.8 Hz), 5.95 (2H, br s), 7.07–7.13 (1H, m), 7.42 (1H, d, J=1.8 Hz), 7.75–7.84 (1H, m), 7.98 (1H, d, J=8.4 Hz), 8.33 (1H, dd, J=1.6 Hz, 4.6 Hz).

REFERENCE EXAMPLE 2-65

2-[[1-(2-Pyridinyl)-1H-pyrazol-5-yl]amino]benzoic acid

A solution of 1-(2-pyridinyl)-1H-pyrazol-5-ylamine (6.02 g, 37.6 mmol), 2-iodobenzoic acid (9.32 g, 37.6 mmol), copper acetate (II) (0.683 g, 3.76 mmol) and potassium carbonate (5.72 g, 41.4 mmol) in N,N-dimethylformamide (20 mL) was heated under reflux for 1 hour under an argon atmosphere. The solution was allowed to cool to room temperature, and poured into water. The solution was made weakly acidic by the addition of acetic acid, and the resulting crude crystals were collected by filtration. The crystals were washed with water and air dried to give the title compound (9.45 g, 90% yield).

mp: 216–218° C. (recrystallized from ethanol). NMR (DMSO-$d_6$) δ: 6.40 (1H, d, J=2.2 Hz), 6.90–6.98 (1H, m), 7.37 (1H, ddd, J=1.2 Hz, 5.0 Hz, 7.2 Hz), 7.48–7.57 (1H, m), 7.61 (1H, dd, J=1.0 Hz, 8.4 Hz), 7.69 (1H, d, J=2.2 Hz), 7.88–8.08 (3H, m), 8.49 (1H, dd, J=1.0 Hz, 5.0 Hz), 12.20 (1H, br s), hidden (1H).

Elementary Analysis: for $C_{15}H_{12}N_4O_2$ Calcd.: C, 64.28; H, 4.32; N, 19.99. Found: C, 64.44; H, 4.26; N, 20.11.

REFERENCE EXAMPLE 2-66

5-Chloro-2-[[1-(2-pyridinyl)-1H-pyrazol-5-yl]amino]benzoic acid

Following the procedure described in Reference Example 2-5, the title compound was prepared from 5-chloro-2-iodobenzoic acid and 1-(2-pyridinyl)-1H-pyrazol-5-ylamine (88% yield).

mp: 233–234° C. (recrystallized from ethanol). NMR (DMSO-$d_6$) δ: 6.42 (1H, d, J=2.0 Hz), 7.38 (1H, ddd, J=1.2 Hz, 4.8 Hz, 7.4 Hz), 7.54 (1H, dd, J=2.6 Hz, 8.8 Hz), 7.63 (1H, d, J=8.8 Hz), 7.71 (1H, d, J=2.0 Hz), 7.88–7.92 (2H, m), 7.99–8.08 (1H, m), 8.47 (1H, dd, J=0.8 Hz, 1.8 Hz, 4.8 Hz), 12.24 (1H, br s), hidden (1H). Elementary Analysis: for $C_{15}H_{11}ClN_4O_2$ Calcd.: C, 57.24; H, 3.52; N, 17.80. Found: C, 57.13; H, 3.46; N, 17.72.

REFERENCE EXAMPLE 2-67

1-(2-Pyridinyl)-3-(trifluoromethyl)-1H-pyrazol-5-ylamine

To diisopropylamine (32 mL, 0.23 mol), a solution of 1.6 M butyllithium in hexane (148 mL, 0.23 mol) was added dropwise at −78° C. under a dry nitrogen atmosphere. Furthermore, a solution of acetonitrile (8.2 g, 0.20 mol) and methyl trifluoroacetate (12.8 g, 0.10 mol) in tetrahydrofuran (100 mL) was added dropwise thereto. After addition, the solution was stirred while the solution was allowed to warm gradually to 0° C. Iced water was added to the reaction solution, and the reaction solution was concentrated under reduced pressure. After the residue (an aqueous solution) was extracted with diethylether, pH of the solution was adjusted to about 1 to 2 by the addition of conc. hydrochloric acid. The solution was washed with dichloromethane, and subsequently extracted with diethylether. The extract was dried over magnesium sulfate, and the solvent was evaporated under reduced pressure to give an oil. A solution of the oil thus obtained (5.04 g, 32.5 mmol) and 2-hydrazinopyridine (3.91 g, 35.8 mmol) in dichloroethane (100 mL) was heated under reflux for 8 hours. The solution was cooled to room temperature, and the solvent was evaporated under reduced pressure. The residue thus obtained was dissolved in methanol (100 mL). To the mixture was added 28% sodium methoxide (0.65 mL, 3.2 mmol) and the mixture was stirred at room temperature for 20 hours. The solution was concentrated under reduced pressure, water was added to the residue, and the organic matter was extracted with chloroform. The extract was washed with saturated brine and dried over anhydrous magnesium sulfate, and the solvent was evaporated under reduced pressure. The residue thus obtained was purified by silica gel column chromatography (hexane:ethyl acetate=3:1 to 2:1) to give the title compound (0.40 g, 7% yield).

NMR (CDCl$_3$) δ: 5.75 (1H, s), 6.09 (2H, br s), 7.16–7.22 (1H, m), 8.01–8.05 (1H, m), 8.35–8.39 (1H, m). Elementary Analysis: for $C_9H_7F_3N_4$ Calcd.: C, 47.37; H, 3.09; N, 24.55; F, 24.98. Found: C, 47.35; H, 2.90; N, 24.63; F, 25.09.

REFERENCE EXAMPLE 2-68

2-(2-Oxobutyl)-4H-3,1-benzoxazin-4-one

To a solution in a mixture of benzene (100 mL)/acetone (100 mL) of the crude 5-(2-hydroxybutylidene)-2,2-dimethyl-1,3-dioxane-4,6-dione which was previously prepared from Meldrum's acid (57.7 g, 0.40 mol) and propionyl chloride(37.0 g, 0.40 mol) according to the methods described in Synthesis, p. 1213 (1992) and Org. Synth., vol. 63, p. 198 (1985), anthranilic acid (45.8 g, 0.33 mol) was added and the mixture was heated under reflux for 3 hours. The solution was cooled to room temperature and concentrated under reduced pressure. The residue was suspended in a mixture of acetic anhydride (68.1 g, 0.667 mol) and tetrahydrofuran (150 mL), and the suspension was heated under reflux for 30 minutes. The solution was cooled to room temperature and concentrated under reduced pressure, and the residue thus obtained was purified by silica gel column chromatography (ethyl acetate:hexane=2:8) to give the title compound (28.4 g, 33% yield).

mp: 70–72° C. (recrystallized from hexane). Elementary Analysis: for $C_{12}H_{11}NO_3$ Calcd.: C, 66.35; H, 5.10; N, 6.45. Found: C, 66.24; H, 5.16; N, 6.49.

REFERENCE EXAMPLE 2-69

5-Amino-3-(cyanomethyl)-1-(2-pyridinyl)-1H-pyrazole-4-carbonitrile

A solution of malononitrile (19.8 g, 300 mmol) and 2-hydrazinopyridine (16.4 g, 150 mmol) in ethanol (300 mL) was heated under reflux for 12 hours. The solution was cooled to room temperature, and the resulting crystals were collected by filtration. The crystals were purified by silica gel column chromatography (chloroform to 2% methanol/chloroform) to give the title compound (12.5 g, 37% yield).

mp: 178–179° C. (recrystallized from ethanol). NMR (CDCl$_3$) δ: 3.78 (2H, s), 7.00 (2H, br s), 7.20–7.27 (1H, m), 7.83–7.92 (1H, m), 7.96–8.00 (1H, m), 8.36–8.39 (1H, m). Elementary Analysis: for $C_{11}H_8N_6 \cdot 0.1H_2O$ Calcd.: C, 58.45; H, 3.66; N, 37.18. Found: C, 58.58; H, 3.53; N, 36.90.

REFERENCE EXAMPLE 2-70

Methyl 2-[5-amino-1-(2-pyridinyl)-1H-pyrazol-3-yl]acetate

A solution of 5-amino-3-(cyanomethyl)-1-(2-pyridinyl)-1H-pyrazole-4-carbonitrile (2.24 g, 10 mmol) in 7.5N sodium hydroxide (20 mL) was heated under reflux for 12 hours. The solution was cooled to room temperature, and diluted with water. The solution was made acidic by the addition of 6N hydrochloric acid, and the resulting crystals were collected by filtration. To a suspension of the crystals in methanol (60 mL), conc. sulfuric acid (1 mL) was added carefully, and the mixture was heated under reflux for 16 hours. The solution was cooled to room temperature and diluted with water. The solution was made basic by the addition of an aqueous saturated sodium bicarbonate solution, and extracted with chloroform. The extract was washed with saturated brine and dried over anhydrous magnesium sulfate, and the solvent was evaporated under reduced pressure to give the title compound (1.73 g, 75% yield).

mp: 84–85° C. (recrystallized from ethanol). NMR (CDCl$_3$) δ: 3.63 (3H, s), 3.73 (3H, s), 5.52 (1H, s), 5.94 (2H, br s), 7.08 (1H, ddd, J=1.2 Hz, 5.2 Hz, 7.4 Hz), 7.77 (1H, ddd, J=1.8 Hz, 7.4 Hz, 8.4 Hz), 7.94 (1H, td, J=1.2 Hz, 8.4 Hz), 8.31 (1H, ddd, J=1.0 Hz, 1.8 Hz, 5.2 Hz). Elementary Analysis: for $C_{11}H_8N_6 \cdot 0.1H_2O$ Calcd.: C, 56.89; H, 5.21; N, 24.12. Found: C, 56.94; H, 5.22; N, 24.05.

REFERENCE EXAMPLE 2-71

Ethyl 5-amino-1-(2-pyridinyl)-1H-pyrazole-3-carboxylate

To diethyl ether (200 mL), was added a 20% sodium ethoxide ethanol solution (280 g, 820 mmol) at 0° C., and subsequently was added dropwise diethyl oxalate (19.8 g, 400 mmol), and the mixture was stirred at the same temperature for 30 minutes. To the solution, was added dropwise a solution of acetonitrile (21 mL, 400 mmol) in diethylether (20 mL), and the mixture was allowed to warm to room temperature and stirred at the same temperature for 24 hours. The resulting crystals were collected by filtration. The crystals were suspended in chloroform (400 mL), to which a solution of 2-hydrazinopyridine (34.3 g, 314 mmol) and conc. sulfuric acid (16.7 mL, 314 mmol) in water (300 mL) was added dropwise at room temperature, and the mixture was stirred at the same temperature for 72 hours. The organic layer was separated and the aqueous layer was extracted with chloroform. The organic layers were combined, washed with saturated brine and dried over anhydrous magnesium sulfate, and the solvent was evaporated under reduced pressure. The residue thus obtained was purified by silica gel column chromatography (hexane:ethyl acetate=3:1 to 1:1) to give the title compound (30.0 g, 45% yield).

NMR (CDCl$_3$) δ: 1.41 (3H, t, J=7.0 Hz), 4.41 (2H, q, J=7.0 Hz), 7.18 (1H, ddd, J=1.0 Hz, 5.2 Hz, 7.4 Hz), 7.84 (1H, ddd, J=1.8 Hz, 7.4 Hz, 8.4 Hz), 8.13 (1H, ddd, J=0.8 Hz, 1.0 Hz, 8.4 Hz), 8.37 (1H, ddd, J=0.8 Hz, 1.8 Hz, 5.2 Hz). Elementary Analysis: for $C_{11}H_{12}N_4O_2$ Calcd.: C, 56.89; H, 5.21; N, 24.12. Found: C, 56.80; H, 5.17; N, 23.94.

REFERENCE EXAMPLE 2-72

3-(4-Methoxyphenyl)-1-(2-pyridinyl)-1H-pyrazol-5-ylamine

Following the procedure described in Reference Example 2-4, the title compound was prepared from 2-hydrazinopyridine and 3-(4-methoxyphenyl)-3-oxypropanenitrile prepared from tert-butyl cyanoacetate and 4-methoxybenzoyl chloride according to the method described in Synthesis, p. 337 (1997) (3.48 g, 95% yield).

NMR (CDCl$_3$) δ; 3.85 (3H, s), 5.80 (1H, s), 5.99 (2H, br s), 6,94 (2H, ddd, J=1.2 Hz, 3.0 Hz, 8.8 Hz), 7.08 (1H, ddd, J=1.0 Hz, 5.0 Hz, 7.2 Hz), 7.75–7.84 (3H, m), 8.11 (1H, td, J=1.0 Hz, 8.4 Hz), 8.33 (1H, ddd, J=1.0 Hz, 1.8 Hz, 5.0 Hz).

REFERENCE EXAMPLE 2-73

2-[[3-Methyl-1-(3-pyridinylmethyl)-1H-pyrazol-5-yl]amino]benzoic acid

A solution in ethanol (50 mL) of 2-(2-oxopropyl)-4H-3,1-benzoxazin-4-one (11.2 g, 55.1 mmol) and 3-hydrazinomethylpyridine (7.44 g, 60.4 mmol) which was prepared from 3-chloromethylpyridine following the method described in Reference Example 2-2, was heated under reflux for 1 hour. The solution was cooled to room temperature, and the resulting crude crystals were collected by filtration. The crystals were washed with ethanol and air dried to give the title compound (11.3 g, 67% yield). mp: 180–183° C. (recrystallized from ethanol).

NMR (DMSO-d$_6$) δ: 2.18 (3H, s), 5.18 (2H, s), 6.05 (1H, s), 6.75–6.92 (2H, m), 7.28–7.44 (2H, m), 7.49–7.58 (1H, m), 7.89 (1H, dd, J=1.5 Hz, 8.1 Hz), 8.40 (1H, s), 8.46 (1H, dd, J=1.5 Hz, 4.8 Hz), 9.66 (1H, br s). Elementary Analysis: for C$_{17}$H$_{16}$N$_4$O$_2$ Calcd.: C, 66.22; H, 5.23; N, 18.17. Found: C, 66.02; H, 5,09; N, 18.30.

REFERENCE EXAMPLE 2-74

2-[[3-Methyl-1-(4-pyridinylmethyl)-1H-pyrazol-5-yl]amino]benzoic acid

An ethanol (50 mL) solution of 2-(2-oxypropyl)-4H-3,1-benzoxazin-4-one (9.04 g, 44.5 mmol) and 4-hydrazinomethylpyridine (6.03 g, 49 mmol) which was previously prepared from 4-chloromethylpyridine following the method described in Reference Example 2-2, was heated under reflux for 1 hour. The solution was cooled to room temperature, and the resulting crude crystals were collected by filtration. The crystals were washed with ethanol and air dried to give the title compound (7.66 g, 56% yield).

mp: 235–238° C. (recrystallized from ethanol). Elementary Analysis: for C$_{17}$H$_{16}$N$_4$O$_2$ Calcd.: C, 66.22; H, 5.23; N, 18.17. Found: C, 66.24; H, 4.98; N, 18.37.

REFERENCE EXAMPLE 2-75

2-[[3-Methyl-1-(2-pyridinyl)-1H-pyrazol-5-yl]amino]nicotinic acid

Following the procedure described in Reference Example 2-5, the title compound was prepared from 2-chloronicotinic acid and 3-methyl-1-(2-pyridinyl)-1H-pyrazol-5-ylamine (72% yield).

mp: 252–254° C. (recrystallized from ethanol). NMR (DMSO-d$_6$) δ: 2.26 (3H, s), 7.00 (1H, dd, J=4.6 Hz, 7.6 Hz), 7.07 (1H, s), 7.32 (1H, ddd, J=1.4 Hz, 5.0 Hz, 7.0 Hz), 7.89 (1H, d, J=8.4 Hz), 7.95–8.04 (1H, m), 8.32 (1H, dd, J=2.0 Hz, 7.6 Hz), 8.48–8.54 (2H, m), 13.28 (1H, br s), hidden (1H). Elementary Analysis: for C$_{15}$H$_{13}$N$_5$O$_2$ Calcd.: C, 57.24; H, 3.52; N, 17.80. Found: C, 57.13; H, 3.46; N, 17.72.

EXAMPLE 2-1

4-Chloro-3-methyl-1-(2-pyridinyl)-1H-pyrazolo[3,4-b]quinoline

A solution of 2-[[3-methyl-1-(2-pyridinyl)-1H-pyrazol-5-yl]amino]benzoic acid (50.2 g, 0.17 mol) in phosphorous oxychloride (120 mL, 1.27 mol) was heated under reflux for 1 hour. The solution was cooled to room temperature and concentrated under reduced pressure, and the residue was poured into iced water. The solution was made basic by the addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform:methanol=98:2) to give the title compound (21.5 g, 43% yield).

mp: 157–159° C. (recrystallized from ethyl acetate/hexane). NMR (CDCl$_3$) δ: 3.00 (3H, s), 7.21–7.25 (1H, m), 7.60–7.64 (1H, m), 7.78–7.87 (1H, m), 7.90–7.99 (1H, m), 8.18 (1H, dd, J=0.8 Hz, 8.4 Hz), 8.41 (1H, dt, J=0.8 Hz, 7.6 Hz), 8.68 (1H, d, J=4.8 Hz), 8.85 (1H, d, J=8.4 Hz). Elementary Analysis: for C$_{16}$H$_{11}$ClN$_4$ Calcd.: C, 65.20; H, 3.76; N, 19.01; Cl, 12.03. Found: C, 65.22; H, 3.73; N, 19.13; Cl, 11.76.

EXAMPLE 2-2

3-Methyl-1-(2-pyridinyl)-1H-pyrazolo[3,4-b]quinolin-4-ylamine

A solution of 4-chloro-3-methyl-1-(2-pyridinyl)-1H-pyrazolo[3,4-b]quinoline (1.44 g, 4.89 mmol) and sodium azide (0.35 g, 5.37 mmol) in N,N-dimethylformamide (10 mL) was heated under reflux at 100° C. for 30 minutes. The solution was cooled to room temperature, poured into water, and the organic matter was extracted with chloroform. The extract was washed with saturated brine and water and dried over anhydrous magnesium sulfate and the solvent was evaporated under reduced pressure. To a solution of the residue thus obtained in ethanol (70 mL), 10% palladium-carbon (2 g, 50% hydrate) was added and the mixture was stirred at room temperature under hydrogen atmosphere for 1 hour. The solution was filtered to remove the catalyst, and the filtrate was concentrated under reduced pressure. The residue thus obtained was purified by basic silica gel column chromatography (ethyl acetate:methanol=95:5) to give the title compound (760 mg, 57% yield).

mp: 210–213° C. (recrystallized from methanol/ethyl acetate/hexane).

NMR (CDCl$_3$) δ: 2.80 (3H, s), 5.60 (2H, br s), 7.13–7.22 (1H, m), 7.29–7.40 (1H, m), 7.63–7.75 (1H, m), 7.80–7.95 (2H, m), 7.98–8.05 (1H, m), 8.60–8.67 (1H, m), 8.90–8.98 (1H, m). Elementary Analysis: for C$_{16}$H$_{13}$N$_5$ Calcd.: C, 69.80; H, 4.76; N. 25.44. Found: C, 69.61; H, 4.70; N, 25.30.

EXAMPLE 2-3

3-Methyl-1-(2-pyridinyl)-1H-pyrazolo[3,4-b]quinolin-4-ylamine hydrochloride

To a solution of 3-methyl-1-(2-pyridinyl)-1H-pyrazolo[3,4-b]quinolin-4-ylamine (1.56 g, 5.65 mmol) in ethanol (5 mL), a solution of 4N hydrochloric acid/ethyl acetate (10 mL) was added, and the solution was concentrated under reduced pressure. The residue thus obtained was recrystallized from ethanol to give the title compound (1.41 g, 80% yield).

mp: 268–271° C. (recrystallized from ethanol). NMR (DMSO-d$_6$) δ: 2.85 (3H, s), 7.46–7.52 (1H, m), 7.59–7.67 (1H, m), 7.92–8.04 (2H, m), 8.09–8.18 (1H, m), 8.44 (1H, d, J=8.4 Hz), 8.68–8.70 (1H, m), 8.82–8.87 (2H, m), 9.85 (2H, br s). Elementary Analysis: for C$_{16}$H$_{13}$N$_5$.HCl.1.6H$_2$O Calcd.: C, 56.42; H, 5.09; N, 20.56; Cl, 10.41. Found: C, 56.20; H, 5.01; N, 20.60; Cl, 10.39.

EXAMPLE 2-4

N-Methyl-N-[3-methyl-1-(2-pyridinyl)-1H-pyrazolo[3,4-b]quinolin-4-yl]amine hydrochloride A solution of 4-chloro-3-methyl-1-(2-pyridinyl)-1H-pyrazolo[3,4-b]quinoline (0.8 g, 2.71 mmol) in 40% methylamine in methanol (21 mL, 0.27 mol) was heated under reflux at 100° C. for 4 hours in a sealed stainless tube. The solution was allowed to cool to room temperature, and concentrated under reduced pressure. The residue thus obtained was purified by silica gel column chromatography (chloroform:methanol=98:2) to give an oil of N-methyl-N-[3-methyl-1-(2-pyridinyl)-1H-pyrazolo[3,4-b]quinolin-4-yl]amine. To a solution of the oil in ethanol (10 mL), was added a saturated hydrochloric acid/ethanol solution (10 mL), and the solvent was evaporated under reduced pressure. The residue thus obtained was recrystallized from methanol/ethyl acetate to give the title compound (0.63 g, 64% yield).

mp: 229–232° C. (recrystallized from ethyl acetate/methanol). NMR (DMSO-$d_6$) δ: 2.84 (3H, s), 3.57 (3H, s), 7.45–7.62 (2H, m), 7.87–8.00 (2H, m), 8.14 (1H, d, J=1.8 Hz, 7.3 Hz), 8.34 (1H, d, J=8.1 Hz), 8.55–8.71 (1H, m), 8.72–8.82 (1H, m), 10.40 (1H, br s). Elementary Analysis: for $C_{17}H_{15}N_5 \cdot 1.5HCl \cdot H_2O$ Calcd.: C, 56.40; H, 5.15; N, 19.34. Found: C, 56.29; H, 5.10; N, 19.08.

EXAMPLE 2-5

N-Cyclopropyl-N-[3-methyl-1-(2-pyridinyl)-1H-pyrazolo[3,4-b]quinolin-4-yl]amine hydrochloride A solution of 4-chloro-3-methyl-1-(2-pyridinyl)-1H-pyrazolo[3,4-b]quinoline (0.7 g, 2.37 mmol) and cyclopropylamine (0.7 g, 73.6 mmol) in tetrahydrofuran (20 mL) was heated under reflux at 100° C. overnight in a sealed stainless tube. The solution was cooled to room temperature, and concentrated under reduced pressure. The residue thus obtained was purified by silica gel column chromatography (chloroform:methanol=93:7) to give N-cyclopropyl-N-[3-methyl-1-(2-pyridinyl)-1H-pyrazolo[3,4-b]quinolin-4-yl]amine. To a solution of the compound above in ethanol (10 mL), a saturated hydrochloric acid/ethanol solution (10 mL) was added and the solvent was evaporated under reduced pressure. The residue thus obtained was recrystallized from methanol/ethyl acetate to give the title compound (0.52 g, 56% yield).

mp: 208–211° C. (recrystallized from ethyl acetate/methanol). NMR (DMSO-$d_6$) δ: 0.95–1.20 (4H, m), 2.88 (3H, s), 3.55 (1H, m), 7.45–7.65 (2H, m), 7.92–8.03 (2H, m), 8.15 (1H, t, J=7.7 Hz), 8.40 (1H, d, J=9.2 Hz), 8.67–8.75 (1H, m), 8.80–8.91 (1H, m), 9.80 (1H, br s). Elementary Analysis: for $C_{19}H_{17}N_5 \cdot HCl \cdot 2H_2O$ Calcd.: C, 58.84; H, 5.72; N, 18.06. Found: C, 59.14; H, 5.44; N, 17.83.

EXAMPLE 2-6

N-[3-Methyl-1-(2-pyridinyl)-1H-pyrazolo[3,4-b]quinolin-4-yl]-N-propylamine

A mixture of 4-chloro-3-methyl-1-(2-pyridinyl)-1H-pyrazolo[3,4-b]quinoline (1.47 g, 5.00 mmol) and propylamine (2.96 g, 50.0 mmol) was heated and stirred at 100° C. for 6 hours in a sealed stainless tube. The solution was allowed to cool to room temperature and poured into water, and the organic matter was extracted with ethyl acetate. The extract was washed with saturated brine, dried over anhydrous sodium sulfate, and evaporated under reduced pressure. The residue thus obtained was purified by basic silica gel column chromatography (hexane:ethyl acetate=1:1), and the resulting crystals were recrystallized from ethyl acetate/hexane to give the title compound (1.14 g, 72% yield).

mp: 121–122° C. (recrystallized from ethyl acetate/hexane). NMR (CDCl$_3$) δ: 1.08 (3H, t, J=7.4 Hz), 1.73–1.92 (2H, m), 2.91 (3H, s), 3.81 (2H, dt, J=5.4 Hz, 7.0 Hz), 5.17 (1H, br t), 7.17 (1H, ddd, J=0.8 Hz, 4.8 Hz, 7.4 Hz), 7.26–7.34 (1H, m), 7.65 (1H, ddd, J=1.4 Hz, 6.6 Hz, 8.8 Hz), 7.89 (1H, ddd, J=2.2 Hz, 7.4 Hz, 8.4 Hz), 8.00 (1H, dd, J=1.4 Hz, 8.8 Hz), 8.15 (1H, d, J=8.8 Hz), 8.63 (1H, ddd, J=0.8 Hz, 2.2 Hz, 4.8 Hz), 8.97 (1H, d, J=8.4 Hz). Elementary Analysis: for $C_{19}H_{19}N_5$ Calcd.: C, 71.90; H, 6.03; N, 22.07. Found: C, 71.79; H, 6.17; N, 22.12.

EXAMPLE 2-7

N-Butyl-N-[3-methyl-1-(2-pyridinyl)-1H-pyrazolo[3,4-b]quinolin-4-yl]amine

Following the procedure described in Example 2-6, the title compound was prepared from 4-chloro-3-methyl-1-(2-pyridinyl)-1H-pyrazolo[3,4-b]quinoline and butylamine (68% yield).

mp: 97–99° C. (recrystallized from ethyl acetate/hexane). NMR (CDCl$_3$) δ: 0.99 (3H, t, J=7.0 Hz), 1.41–1.59 (2H, m), 1.71–1.85 (2H, m), 2.90 (3H, s), 3.84 (2H, dt, J=5.2 Hz, 7.0 Hz), 5.15 (1H, br t), 7.17 (1H, ddd, J=1.2 Hz, 4.8 Hz, 7.4 Hz), 7.26–7.34 (1H, m), 7.65 (1H, ddd, J=1.4 Hz, 6.8 Hz, 8.6 Hz), 7.89 (1H, ddd, J=2.2 Hz, 7.4 Hz, 8.4 Hz), 8.01 (1H, dd, J=1.4 Hz, 8.6 Hz), 8.14 (1H, dd, J=1.4 Hz, 8.8 Hz), 8.63 (1H, ddd, J=0.8 Hz, 2.2 Hz, 4.8 Hz), 8.97 (1H, dd, J=1.2 Hz, 8.4 Hz). Elementary Analysis: for $C_{20}H_{21}N_5$ Calcd.: C, 72.48; H, 6.39; N, 21.13. Found: C, 72.28; H, 6.37; N, 21.09.

EXAMPLE 2-8

N,N-Dimethyl-N-[3-methyl-1-(2-pyridinyl)-1H-pyrazolo[3,4-b]quinolin-4-yl]amine 4-chloro-3-methyl-1-(2-pyridinyl)-1H-pyrazolo[3,4-b]quinoline (1.00 g, 3.39 mmol) was added to a 2M dimethylamine in tetrahydrofuran solution (5.00 mL, 10.0 mmol), and the solution was heated under reflux overnight at 100° C. in a sealed tube. The solution was cooled to room temperature and poured into water, and the organic matter was extracted with ethyl acetate. The extract was washed with saturated brine, dried over anhydrous magnesium sulfate, and evaporated under reduced pressure. The residue thus obtained was purified by silica gel column chromatography (ethyl acetate to ethyl acetate:methanol=9:1) to give the title compound (1.00 g, 97% yield).

mp: 98–101° C. (recrystallized from ethyl acetate/hexane). NMR (CDCl$_3$) δ: 2.89 (3H, s), 3.39 (6H, s), 7.16–7.22 (1H, m), 7.37–7.45 (1H, m), 7.66–7.74 (1H, m), 7.87–7.96 (1H, m), 8.12 (1H, d, J=9.0 Hz), 8.22 (1H, d, J=7.3 Hz), 8.64–8.67 (1H, m), 8.94 (1H, d, J=8.4 Hz). Elementary Analysis: for $C_{18}H_{17}N_5$ Calcd.: C, 71.27; H, 5.65, N, 23.09. Found: C, 71.25; H, 5.64; N, 23.02.

EXAMPLE 2-9

N-Methyl-N-[3-methyl-1-(2-pyridinyl)-1H-pyrazolo[3,4-b]quinolin-4-yl]-N-propylamine Following the procedure described in Example 2-6, the title compound was prepared from 4-chloro-3-methyl-1-(2- pyridinyl)-1H-pyrazolo[3,4-b]quinoline and N-methyl-N-propylamine (64% yield).

mp: 110–112° C. (recrystallized from ethyl acetate/hexane). NMR (CDCl$_3$) δ: 0.89 (3H, t, J=7.4 Hz), 1.60–1.82 (2H, m), 2.89 (3H, s), 3.34 (3H, s), 3.57 (2H, t, J=7.4 Hz), 7.19 (1H, ddd, J=1.0 Hz, 4.8 Hz, 7.4 Hz), 7.41 (1H, ddd, J=1.4 Hz, 6.6 Hz, 8.8 Hz), 7.70 (1H, ddd, J=1.4 Hz, 6.6 Hz, 8.6 Hz), 7.91 (1H, ddd, J=1.8 Hz, 7.4 Hz, 8.4 Hz), 8.10–8.21 (2H, m), 8.65 (1H, ddd, J=1.0 Hz, 1.8 Hz, 4.8 Hz), 8.94 (1H, td, J=1.0 Hz, 8.4 Hz). Elementary Analysis: for C$_{20}$H$_{21}$N$_5$ Calcd.: C, 72.48; H, 6.39; N, 21.13. Found: C, 72.47; H, 6.50; N, 21.15.

EXAMPLE 2-10

N-Butyl-N-methyl-[3-methyl-1-(2-pyridinyl)-1H-pyrazolo[3,4-b]quinolin-4-yl]amine Following the procedure described in Example 2-6, the title compound was prepared from 4-chloro-3-methyl-1-(2-pyridinyl)-1H-pyrazolo[3,4-b]quinoline and N-butyl-N-methylamine (55% yield).

mp: 85–87° C. (recrystallized from ethyl acetate/hexane). NMR (CDCl$_3$) δ: 0.87 (3H, t, J=7.4 Hz), 1.22–1.40 (2H, m), 1.60–1.75 (2H, m), 2.89 (3H, s), 3.34 (3H, s), 3.60 (2H, t, J=7.6 Hz), 7.19 (1H, ddd, J=1.2 Hz, 5.0 Hz, 7.4 Hz), 7.41 (1H, ddd, J=1.4 Hz, 6.6 Hz, 8.8 Hz), 7.70 (1H, ddd, J=1.4 Hz, 6.6 Hz, 8.4 Hz), 7.91 (1H, ddd, J=1.8 Hz, 7.4 Hz, 8.4 Hz), 8.10–8.20 (2H, m), 8.65 (1H, ddd, J=0.6 Hz, 1.8 Hz, 5.0 Hz), 8.94 (1H, ddd, J=0.6 Hz, 1.2 Hz, 8.4 Hz). Elementary Analysis: for C$_{21}$H$_{23}$N$_5$ Calcd.: C, 73.02; H, 6.71; N, 20.27. Found: C, 72.87; H, 6.68; N, 20.22.

EXAMPLE 2-11

3-Methyl-4-(4-morpholinyl)-1-(2-pyridinyl)-1H-pyrazolo[3,4-b]quinoline

A solution of 4-chloro-3-methyl-1-(2-pyridinyl)-1H-pyrazolo[3,4-b]quinoline (1.47 g, 5.00 mmol), morpholine (0.87 g, 10.0 mmol) and potassium carbonate (1.38 g, 10.0 mmol) in N,N-dimethylformamide (20 mL) was heated under reflux at 100° C. for 12 hours. The solution was cooled to room temperature, and concentrated under reduced pressure. The residue was poured into water and organic matter was extracted with chloroform. The extract was washed with saturated brine, dried over anhydrous sodium sulfate, and evaporated under reduced pressure. The residue thus obtained was purified by basic silica gel column chromatography (hexane:chloroform=3:1) to give the title compound (0.63 g, 36% yield).

mp: 203–205° C. (recrystallized from ethyl acetate). NMR (CDCl$_3$) δ: 2.99 (3H, s), 3.61 (4H, t, J=4.5 Hz), 4.04 (4H, t, J=4.5 Hz), 7.21 (1H, ddd, J=0.8 Hz, 4.8 Hz, 7.4 Hz), 7.47 (1H, ddd, J=0.8 Hz, 6.6 Hz, 8.8 Hz), 7.83 (1H, ddd, J=0.8 Hz, 6.6 Hz, 8.8 Hz), 7.92 (1H, ddd, J=1.8 Hz, 7.4 Hz, 8.4 Hz), 8.17 (1H, dd, J=0.8 Hz, 8.8 Hz), 8.38 (1H, ddd, J=0.6 Hz, 0.8 Hz, 8.8 Hz), 8.66 (1H, ddd, J=0.6 Hz, 1.8 Hz, 4.8 Hz), 8.92 (1H, dd, J=0.8 Hz, 8.4 Hz). Elementary Analysis: for C$_{20}$H$_{19}$N$_5$O Calcd.: C, 69.55; H, 5.54; N, 20.28. Found: C, 69.47; H, 5.43; N, 20.26.

EXAMPLE 2-12

3-Methyl-1-(2-pyridinyl)-1,9-dihydro-4H-pyrazolo[3,4-b]quinolin-4-one

A mixture of methanesulfonic acid (120 mL, 1.85 mmol) and phosphorus pentoxide (24.0 g, 0.17 mol) was heated to 100° C. To the mixture stirred at the same temperature, powdery 2-[[3-methyl-1-(2-pyridinyl)-1H-pyrazole-5-yl]amino]benzoic acid (24.0 g, 82 mmol) was added gradually in small portions. The mixture was heated and stirred at the same temperature for 15 minutes. After the solution was allowed to cool to room temperature, iced water was added to the solution. The solution was made basic by the addition of an aqueous sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by basic silica gel column chromatography (chloroform). The crystals thus obtained we dissolved in a hot mixture of ethyl acetate (300 mL) and methanol (300 mL), and the solution was heated under reflux for 30 minutes in the presence of activated carbon (2.5 g). The hot solution was filtered and the solvents were evaporated under reduced pressure. The residue was recrystallized from ethyl acetate to give the title compound (15.1 g, 67% yield).

mp: 199–200° C. (recrystallized from ethyl acetate). NMR (CDCl$_3$) δ: 2.77 (3H, s), 7.19–7.26 (1H, m), 7.33 (1H, td, J=1.2 Hz, 8.0 Hz), 7.44 (1H, d, J=8.0 Hz), 7.61–7.70 (1H, m), 7.90 (1H, td, J=1.6 Hz, 8.4 Hz), 8.02 (1H, d, J=8.4 Hz), 8.46–8.50 (2H, m), 11.45 (1H, br s). Elementary Analysis: for C$_{16}$H$_{12}$N$_4$O Calcd.: C, 69.55; H, 4.38; N, 20.28. Found: C, 69.47; H, 4.26; N, 20.33.

EXAMPLE 2-13

3-Methyl-1-(2-pyridinyl)-1,9-dihydro-4H-pyrazolo[3,4-b]quinolin-4-one

To a solution of 4-chloro-3-methyl-1-(2-pyridinyl)-1H-pyrazolo[3,4-b]quinoline (34.9 g, 0.12 mol) in ethanol (500 mL) was added 6N hydrochloric acid (50 mL, 0.30 mol), and the mixture was heated under reflux for 2 hours. The solution was cooled to room temperature, and concentrated under reduced pressure. The residue was made basic by the addition of an aqueous sodium hydroxide solution, and the organic matter was extracted with chloroform. The extract was washed with saturated brine and water, and dried over anhydrous magnesium sulfate, and the solvent was evaporated under reduced pressure. The residue was purified by silica gel column chromatography (chloroform:methanol= 95:5) to give the title compound (25.8 g, 79% yield).

EXAMPLE 2-14

3,9-Dimethyl-1-(2-pyridinyl)-1,9-dihydro-4H-pyrazolo[3,4-b]quinolin-4-one

To an ice-cold solution of 3-methyl-1-(2-pyridinyl)-1,9-dihydro-4H-pyrazolo[3,4-b]quinolin-4-one (1.11 g, 4.0 mmol) in N,N-dimethylformamide (16 mL), sodium hydride (oiliness, content 60%, 0.19 g, 4.8 mmol) was added and the mixture was stirred at room temperature for 1 hour. Subsequently, iodomethane (2.5 mL, 40.2 mmol) was added thereto at 0° C., and the mixture was stirred at room temperature for additional 16 hours. To the mixture was added iced water, and the mixture was made basic by the addition of an aqueous sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by basic silica gel column chromatography (hexane:ethyl acetate:chloroform=3:1:1) to give the title compound (0.47 g, 40% yield).

mp: 192–193° C. (recrystallized from ethyl acetate/ diethylether). NMR (CDCl$_3$) δ: 2.75 (3H, s), 3.57 (3H, s), 7.30–7.48 (3H, m), 7.55–7.66 (1H, m), 7.83–8.00 (2H, m), 8.50–8.56 (2H, m). Elementary Analysis: for C$_{17}$H$_{14}$N$_4$O Calcd.: C, 70.33; H, 4.86; N, 19.30. Found: C, 70.34; H, 4.87; N, 19.41.

EXAMPLE 2-15

4-Methoxy-3-methyl-1-(2-pyridinyl)-1H-pyrazolo[3, 4-b]quinoline

4-Chloro-3-methyl-1-(2-pyridinyl)-1H-pyrazolo[3,4-b] quinoline (1.00 g, 3.39 mmol) and 28% sodium methoxide in methanol (9.69 g, 50.2 mmol) were added to a mixture of methanol (30 mL) and tetrahydrofuran (30 mL), and the solution was heated under reflux for 2.5 hours. After the solution was cooled to room temperature, the solvents were evaporated under reduced pressure. The residue was poured into water, and the organic matter was extracted with ethyl acetate. The extract was washed with saturated brine and dried over anhydrous magnesium sulfate, and the solvent was evaporated under reduced pressure. The residue thus obtained was purified by silica gel column chromatography (hexane:ethyl acetate=1:1 to ethyl acetate) to give the title compound (0.73 g, 50% yield).

mp: 44–47° C. (recrystallized from ethyl acetate/hexane/ petroleum ether). NMR (CDCl$_3$) δ: 2.99 (3H, s), 4.28 (3H, s), 7.21 (1H, ddd, J=1.1 Hz, 4.8 Hz, 7.4 Hz), 7.46–7.54 (1H, m), 7.74–7.82 (1H, m), 7.93 (1H, ddd, J=1.8 Hz, 7.4 Hz, 8.6 Hz), 8.17 (1H, d, J=8.0 Hz), 8.28 (1H, ddd, J=0.8 Hz, 1.4 Hz, 8.6 Hz), 8.67 (1H, ddd, J=0.8 Hz, 1.8 Hz, 4.8 Hz), 8.91 (1H, d, J=8.4 Hz).

EXAMPLE 2-16

4-Ethoxy-3-methyl-1-(2-pyridinyl)-1H-pyrazolo[3,4-b]quinoline

To an ice-cold solution of 3-methyl-1-(2-pyridinyl)-1,9-dihydro-4H-pyrazolo[3,4-b]quinolin-4-one (2.76 g, 10 mmol) in N,N-dimethylformamide (30 mL) was added sodium hydride (oiliness, content 60%, 0.48 g, 12 mmol), and the mixture was stirred at room temperature for 1 hour. Subsequently, iodoethane (1.96 mL, 24.5 mmol) was added to the mixture and the mixture was stirred at room temperature further for 16 hours. Ice water was added to the mixture, and the organic matter was extracted with ethyl acetate. The extract was washed with saturated brine and water, and dried over anhydrous magnesium sulfate, and the solvent was evaporated under reduced pressure. The residue thus obtained was purified by basic silica gel column chromatography (hexane:ethyl acetate:chloroform=3:1:1) to give the title compound (1.02 g, 34% yield).

mp: 121–123° C. (recrystallized from ethyl acetate/ hexane). NMR (CDCl$_3$) δ: 1.64 (3H, t, J=7.0 Hz), 2.92 (3H, s), 4.47 (2H, q, J=7.0 Hz), 7.16–7.23 (1H, m), 7.43–7.53 (1H, m), 7.73–7.82 (1H, m), 7.88–7.98 (1H, m), 8.13–8.30 (2H, m), 8.64–8.69 (1H, m), 8.93 (1H, d, J=8.4 Hz). Elementary Analysis: for C$_{18}$H$_{16}$N$_4$O Calcd.: C, 71.04; H. 5.30; N. 18.41. Found: C, 70.84; H, 5.25; N, 18.28.

EXAMPLE 2-17

3-Methyl-4-propoxy-1-(2-pyridinyl)-1H-pyrazolo[3, 4-b]quinoline

Following the procedure described in Example 2-16, the title compound was prepared from 3-methyl-1-(2-pyridinyl)-1,9-dihydro-4H-pyrazolo[3,4-b]quinolin-4-one and 1-iodopropane (62% yield).

mp: 103–105° C. (recrystallized from ethyl acetate/ hexane). NMR (CDCl$_3$) δ: 1.20 (3H, t, J=7.3 Hz), 1.97–2.17 (2H, m), 2.92 (3H, s), 4.34 (2H, t, J=6.6 Hz), 7.17–7.25 (1H, m), 7.43–7.53 (1H, m), 7.72–7.82 (1H, m), 7.88–7.98 (1H, m), 8.13–8.19 (1H, m), 8.23–8.31 (1H, m), 8.64–8.69 (1H, m), 8.92 (1H, d, J=8.4 Hz).

EXAMPLE 2-18

4-Isopropoxy-3-methyl-1-(2-pyridinyl)-1H-pyrazolo [3,4-b]quinoline

Following the procedure described in Example 2-16, the title compound was prepared from 3-methyl-1-(2-pyridinyl)-1,9-dihydro-4H-pyrazolo[3,4-b]quinolin-4-one and 2-iodopropane (37% yield).

mp: 93–96° C. (recrystallized from ethyl acetate/hexane). NMR (CDCl$_3$) δ: 1.48 (6H, d, J=6.4 Hz), 2.92 (3H, s), 4.89 (1H, m), 7.17–7.25 (1H, m), 7.42–7.51 (1H, m), 7.72–7.80 (1H, m), 7.88–7.98 (1H, m), 8.12–8.27 (2H, m), 8.64–8.69 (1H, m), 8.93 (1H, d, J=8.4 Hz). Elementary Analysis: for C$_{19}$H$_{18}$N$_4$O.H$_2$O Calcd.: C, 67.84; H, 5.99; N, 16.66. Found: C, 67.55; H, 6.26; N, 16.66.

EXAMPLE 2-19

4-Butoxy-3-methyl-1-(2-pyridinyl)-1H-pyrazolo[3, 4-b]quinoline

To an ice-cold solution of 1-butanol (5.0 g, 68 mmol) in tetrahydrofuran (15 mL), sodium hydride (oiliness, content 60%, 0.41 g, 17 mmol) was added at room temperature and the mixture was stirred for 15 minutes. Subsequently, 4-chloro-3-methyl-1-(2-pyridinyl)-1H-pyrazolo[3,4-b] quinoline (1.0 g, 3.39 mmol) was added to the mixture at 0° C., and the mixture was heated under reflux for another 1 hour. After the reaction solution was cooled to room temperature, the reaction solvent was concentrated and evaporated under reduced pressure. To the reaction mixture was added iced water and the mixture was neutralized by the addition of dilute hydrochloric acid, and the organic matter was extracted with ethyl acetate. The extract was washed with saturated brine and water and dried over anhydrous magnesium sulfate, and the solvent was evaporated under reduced pressure. The residue thus obtained was purified by silica gel column chromatography (ethyl acetate) to give the title compound (0.29 g, 26% yield).

mp: 59–61° C. (recrystallized from petroleum ether/ hexane). NMR (CDCl$_3$) δ: 1.06 (3H, t, J=7.3 Hz), 1.56–1.75 (2H, m), 1.95–2.10 (2H, m), 2.91 (3H, s), 4.37 (2H, t, J=6.6 Hz), 7.16–7.26 (1H, m), 7.43–7.54 (1H, m), 7.72–7.84 (1H, m), 7.88–7.98 (1H, m), 8.15 (1H, d, J=8.4 Hz), 8.31 (1H, d, J=8.4 Hz), 8.64–8.70 (1H, m), 8.92 (1H, d, J=8.4 Hz).

EXAMPLE 2-20

4-Isobutoxy-3-methyl-1-(2-pyridinyl)-1H-pyrazolo [3,4-b]quinoline

To an ice-cold solution of 3-methyl-1-(2-pyridinyl)-1,9-dihydro-4H-pyrazolo[3,4-b]quinolin-4-one (1.93 g, 7.0 mmol) in N,N-dimethylformamide (30 mL), sodium hydride (oiliness, content 60%, 0.42 g, 10.5 mmol) was added and the mixture was stirred at room temperature for 1 hour. Subsequently, isobutyl iodide (2.0 mL, 17.4 mmol) was added to the mixture, and the mixture was stirred at room temperature for 16 hours, and heated under reflux at 70° C.

for 8 hours. The reaction solution was allowed to cool and iced water was added to the mixture, and the organic matter was extracted with ethyl acetate. The extract was washed with saturated brine and water and dried over anhydrous magnesium sulfate, and the solvent was evaporated under reduced pressure. The residue thus obtained was purified by basic silica gel column chromatography (hexane:ethyl acetate:chloroform=3:1:1) to give the title compound (0.54 g, 23% yield).

mp: 117–120° C. (recrystallized from ethyl acetate/hexane). NMR (CDCl$_3$) δ: 1.22 (6H, d, J=6.8 Hz), 2.30 (1H, m), 2.91 (3H, s), 4.14 (2H, d, J=6.2 Hz), 7.17–7.27 (1H, m), 7.44–7.52 (1H, m), 7.72–7.81 (1H, m), 7.88–7.98 (1H, m), 8.16 (1H, d, J=8.4 Hz), 8.23–8.29 (1H, m), 8.64–8.68 (1H, m), 8.93 (1H, d, J=8.4 Hz). Elementary Analysis: for $C_{20}H_{20}N_4O$ Calcd.: C, 72.27; H, 6.06; N, 16.86. Found: C, 72.24; H, 6.21; N, 17.11.

EXAMPLE 2-21

4-Cyclopentyloxy-3-methyl-1-(2-pyridinyl)-1H-pyrazolo[3,4-b]quinoline

Following the procedure described in Example 2-20, the title compound was prepared from 3-methyl-1-(2-pyridinyl)-1,9-dihydro-4H-pyrazolo[3,4-b]quinolin-4-one and bromocyclopentane (19% yield).

mp: 102–105° C. (recrystallized from ethyl acetate/hexane). NMR (CDCl$_3$) δ: 1.60–2.20 (8H, m), 2.92 (3H, s), 5.10–5.22 (1H, m), 7.17–7.25 (1H, m), 7.41–7.50 (1H, m), 7.70–7.80 (1H, m), 7.88–7.98 (1H, m), 8.14 (1H, d, J=8.8 Hz), 8.25 (1H, dd, J=1.1 Hz, 8.8 Hz), 8.63–8.69 (1H, m), 8.93 (1H, d, J=8.4 Hz).

EXAMPLE 2-22

4-Cyclohexyloxy-3-methyl-1-(2-pyridinyl)-1H-pyrazolo[3,4-b]quinoline

Following the procedure described in Example 2-20, the title compound was prepared from 3-methyl-1-(2-pyridinyl)-1,9-dihydro-4H-pyrazolo[3,4-b]quinolin-4-one and bromocyclohexane (11% yield).

mp: 88–91° C. (recrystallized from ethyl acetate/hexane). NMR (CDCl$_3$) δ: 1.20–2.20 (10H, m), 2.92 (3H, s), 4.40–4.60 (1H, m), 7.15–7.28 (1H, m), 7.46 (1H, t, J=7.6 Hz), 7.65–7.81 (1H, m), 7.87–7.98 (1H, m), 8.14 (1H, d, J=8.8 Hz), 8.26 (1H, d, J=8.8 Hz), 8.63–8.70 (1H, m), 8.91 (1H, d, J=8.6 Hz). Elementary Analysis: for $C_{22}H_{22}N_4O \cdot 1.5H_2O$ Calcd.: C, 68.55; H, 6.54; N, 14.53. Found: C, 68.57; H, 6.62; N, 14.40.

EXAMPLE 2-23

4-Benzyloxy-3-methyl-6-nitro-1-(2-pyridinyl)-1H-pyrazolo[3,4-b]quinoline

Following the procedure described in Example 2-19, the title compound was prepared from 4-chloro-3-methyl-6-nitro-1-(2-pyridinyl)-1H-pyrazolo[3,4-b]quinoline and benzyl alcohol (6% yield).

mp: 178–180° C. (recrystallized from ethyl acetate/methanol). NMR (CDCl$_3$) δ: 2.82 (3H, s), 5.51 (2H, s), 7.28 (1H, ddd, J=1.0 Hz, 4.8 Hz, 7.4 Hz), 7.42 (5H, s), 7.96 (1H, ddd, J=1.8 Hz, 7.4 Hz, 8.4 Hz), 8.21 (1H, dd, J=0.8 Hz, 9.6 Hz), 8.47 (1H, dd, J=2.6 Hz, 9.6 Hz), 8.70 (1H, ddd, J=0.8 Hz, 1.8 Hz, 4.8 Hz), 8.76 (1H, ddd, J=0.8 Hz, 1.0 Hz, 8.4 Hz), 9.10 (1H, dd, J=0.8 Hz, 2.6 Hz). Elementary Analysis: for $C_{23}H_{17}N_5O_3$ Calcd.: C, 67.15; H, 4.16; N, 17.02. Found: C, 67.02; H, 4.05; N, 17.08.

EXAMPLE 2-24

3-Methyl-1-(2-pyridinyl)-1,9-dihydro-4H-pyrazolo[3,4-b]quinolin-4-thione

A solution of 3-methyl-1-(2-pyridinyl)-1,9-dihydro-4H-pyrazolo[3,4-b]quinolin-4-one (13.94 g, 50.5 mmol) and Lawesson's Reagent (12.5 g, 30.9 mmol) in toluene (750 mL) was heated under reflux for 1 hour. The reaction solution was cooled to room temperature, and the resulting crude crystals were collected by filtration. The crystals were recrystallized from ethyl acetate to give the title compound (13.11 g, 89% yield).

mp: 252–253° C. (recrystallized from ethyl acetate). NMR (CDCl$_3$) δ: 2.96 (3H, s), 7.23–7.28 (1H, m), 7.37–7.50 (2H, m), 7.65–7.73 (1H, m), 7.88–7.97 (1H, m), 8.05 (1H, d, J=7.6 Hz), 8.51 (1H, d, J=4.2 Hz), 9.08 (1H, d, J=8.6 Hz), 12.01 (1H, br s). Elementary Analysis: for $C_{16}H_{12}N_4S$ Calcd.: C, 65.73; H, 4.14; N, 19.16. Found: C, 65.53; H, 4.10; N, 19.04.

EXAMPLE 2-25

4-(Isopropylsulfanyl)-3-methyl-1-(2-pyridinyl)-1H-pyrazolo[3,4-b]quinoline

Following the procedure described in Example 2-27 described below, the title compound was prepared from 3-methyl-1-(2-pyridinyl)-1,9-dihydro-4H-pyrazolo[3,4-b]quinolin-4-thione and 2-iodopropane (72% yield).

mp: 113–114° C. (recrystallized from isopropylether/hexane). NMR (CDCl$_3$) δ: 1.29 (6H, d, J=7.0 Hz), 3.08 (3H, s), 3.42–3.55 (1H, m), 7.19–7.27 (1H, m), 7.55–7.63 (1H, m), 7.76–7.85 (1H, m), 7.90–7.99 (1H, m), 8.20 (1H, dd, J=0.8 Hz, 8.4 Hz), 8.66–8.70 (1H, m), 8.75 (1H, dd, J=0.8 Hz, 8.5 Hz), 8.89 (1H, d, J=8.4 Hz). Elementary Analysis: for $C_{19}H_{18}N_4S$ Calcd.: C, 68.24; H, 5.42; N, 16.75. Found: C, 68.36; H, 5.59; N. 16.54.

EXAMPLE 2-26

4-(Isopropylsulfinyl)-3-methyl-1-(2-pyridinyl)-1H-pyrazolo[3,4-b]quinoline

Following the procedure described in Example 2-28 described below, the title compound was prepared from 4-(isopropylsulfanyl)-3-methyl-1-(2-pyridinyl)-1H-pyrazolo[3,4-b]quinoline and m-chloroperbenzoic acid (82% yield).

mp: 125–126° C. (recrystallized from ethyl acetate). NMR (CDCl$_3$) δ: 1.06 (3H, d, J=7.0 Hz), 1.62 (3H, d, J=7.0 Hz), 2.97 (3H, s), 3.71–3.85 (1H, m), 7.25–7.31 (1H, m), 7.56–7.65 (1H, m), 7.83–7.91 (1H, m), 7.93–8.02 (1H, m), 8.27 (1H, dd, J=0.6 Hz, 8.2 Hz), 8.68–8.71 (1H, m), 8.82 (1H, d, J=8.4 Hz), 9.27–9.34 (1H, m).

EXAMPLE 2-27

3-Methyl-4-(propylsulfanyl)-1-(2-pyridinyl)-1H-pyrazolo[3,4-b]quinoline

A solution of 3-methyl-1-(2-pyridinyl)-1,9-dihydro-4H-pyrazolo[3,4-b]quinolin-4-thione (4.04 g, 13.8 mmol), 1-iodopropane (6.80 mL, 69.7 mmol) and potassium carbonate (3.79 g, 27.5 mmol) in N,N-dimethylformamide (25 mL) was stirred at room temperature for 8 hours. The reaction solvent was evaporated under reduced pressure. Water was added to the residue, and the organic matter was extracted with ethyl acetate. The extract was washed with saturated brine and dried over anhydrous sodium sulfate, and the solvent was evaporated under reduced pressure. The residue thus obtained was recrystallized from ethyl acetate/hexane to give the title compound (3.83 g, 83% yield).

mp: 91–93° C. (recrystallized from ethyl acetate/hexane). NMR (CDCl$_3$) δ: 0.93 (3H, t, J=7.4 Hz), 1.53–1.64 (2H, m), 2.99 (2H, t, J=7.2 Hz), 3.09 (3H, s), 7.19–7.25 (1H, m), 7.55–7.64 (1H, m), 7.76–7.85 (1H, m), 7.89–7.98 (1H, m), 8.20 (1H, d, J=8.4 Hz), 8.66–8.69 (1H, m), 8.73 (1H, dd, J=0.8 Hz, 8.8 Hz), 8.89 (1H, d, J=8.2 Hz). Elementary Analysis: for $C_{19}H_{18}N_4S \cdot H_2O$ Calcd.: C, 64.75; H, 5.72; N, 15.90. Found: C, 64.48; H, 5.79; N, 15.90.

EXAMPLE 2-28

3-Methyl-4-(propylsulfinyl)-1-(2-pyridinyl)-1H-pyrazolo[3,4-b]quinoline

A solution of m-chloroperbenzoic acid (0.96 g, 5.6 mmol) in chloroform (55 mL) was added dropwise to a solution of 3-methyl-4-propylsulfanyl-1-(2-pyridinyl)-1H-pyrazolo[3,4-b]quinoline (1.54 g, 4.6 mmol) in chloroform (55 mL) at a temperature of lower than 0° C., and the mixture was stirred at the same temperature for another 2.5 hours. The reaction solution was washed with an aqueous saturated sodium bicarbonate solution and saturated brine, and dried over anhydrous sodium sulfate, and the solvent was evaporated under reduced pressure. The residue thus obtained was purified by silica gel column chromatography (hexane:chloroform:ethyl acetate=2:1:1 to 1:1:1) to give the title compound (0.84 g, 52% yield).

mp: 125–127° C. (recrystallized from ethyl acetate). NMR (CDCl$_3$) δ: 1.30 (3H, t, J=7.2 Hz), 1.75–2.05 (2H, m), 2.96 (3H, s), 3.02–3.16 (1H, m), 3.58–3.71 (1H, m), 7.24–7.31 (1H, m), 7.57–7.66 (1H, m), 7.83–7.91 (1H, m), 7.93–8.01 (1H, m), 8.27 (1H, d, J=8.4 Hz), 8.68–8.71 (1H, m), 8.82 (1H, dd, J=0.8 Hz, 7.8 Hz), 9.36 (1H, d, J=8.4 Hz).

EXAMPLE 2-29

4-Chloro-3,5-dimethyl-1-(2-pyridinyl)-1H-pyrazolo[3,4-b]quinoline

To a solution of 2-amino-6-methylbenzoic acid (20 g, 0.132 mol) in acetone (100 mL), diketene (15.3 mL, 0.198 mol) was added dropwise at room temperature, and the mixture was stirred overnight at room temperature. The reaction solvent and excess diketene were concentrated and evaporated under reduced pressure, and tetrachloride (80 mL) were added to the residue, and subsequently acetic anhydride (27 g, 0.265 mol) was added thereto, and the mixture was heated under reflux for 3 hours. The reaction solvent and excess acetic anhydride were concentrated and evaporated under reduced pressure, and the resulting powder was collected, and washed with diethylether to give crude 5-methyl-2-(2-oxopropyl)-4H-3,1-benzoxazin-4-one (13.75 g, 48% yield). A solution of the compound (12.99 g, 0.06 mol) and 2-hydrazinopyridine (7.18 g, 0.066 mol) in ethanol (100 mL) was heated under reflux for 1 hour. The reaction solution was allowed to cool to room temperature, the reaction solvent was concentrated and evaporated under reduced pressure. A solution of the residue in phosphorous oxychloride (45.8 g, 0.3 mol) was heated and stirred at 100° C. for 1 hour. The reaction solution was allowed to cool to room temperature, and the solvent was concentrated and evaporated under reduced pressure, and the residue was poured into iced water. A sodium hydroxide solution was added to the mixture to become basic, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (ethyl acetate:methanol= 98:2) to give the title compound (4.4 g, 24% yield)

mp: 167–169° C. (recrystallized from ethyl acetate/methanol). NMR (CDCl$_3$) δ: 2.98 (3H, s), 3.08 (3H, s), 7.18–7.33 (2H, m), 7.60 (1H, q, J=7.1 Hz), 7.87–7.97 (1H, m), 8.01 (1H, d, J=8.1 Hz), 8.64–8.70 (1H, m), 8.83 (1H, d, J=8.4 Hz). Elementary Analysis: for $C_{17}H_{13}ClN_4$ Calcd.: C, 66.13; H, 4.24; N, 18.15; Cl, 11.48. Found: C, 66.18; H, 4.22; N, 18.17; Cl, 11.54.

EXAMPLE 2-30

3,5-Dimethyl-1-(2-pyridinyl)-1H-pyrazolo[3,4-b]quinolin-4-ylamine

Following the procedure described in Example 2-2, the title compound was prepared from 4-chloro-3,5-dimethyl-1-(2-pyridinyl)-1H-pyrazolo[3,4-b]quinoline and sodium azide (58% yield).

mp: 252–255° C. (recrystallized from methanol). NMR (DMSO-d$_6$) δ: 2.82 (3H, s), 2.99 (3H, s), 6.73 (2H, br s), 7.04 (1H, d, J=6.2 Hz), 7.22–7.31 (1H, m), 7.47 (1H, t, J=7.3 Hz), 7.63 (1H, d, J=8.8 Hz), 7.93–8.07 (1H, m), 8.50–8.56 (1H, m), 8.71 (1H, d, J=8.4 Hz). Elementary Analysis: for $C_{17}H_{15}N$. Calcd.: C, 70.57; H, 5.23; N, 24.21. Found: C, 70.79; H, 5.17; N, 23.81.

EXAMPLE 2-31

3,5-Dimethyl-1-(2-pyridinyl)-1,9-dihydro-4H-pyrazolo[3,4-b]quinolin-4-one

A solution of 4-chloro-3,5-dimethyl-1-(2-pyridinyl)-1H-pyrazolo[3,4-b]quinoline (1.65 g, 5.34 mmol), sodium iodide (0.96 g, 6.41 mmol) and conc. hydrochloric acid (1 mL) in dimethylsulfoxide (20 mL) was heated and stirred at 100° C. for 2 hours. The solution was allowed to cool to room temperature, and the residue was poured into water. The solution was made basic by the addition of an aqueous sodium hydroxide solution, and the organic matter was extracted with 10% methanol/chloroform. The extract was washed with saturated brine and water and dried over anhydrous magnesium sulfate, and the solvents were evaporated under reduced pressure. The residue thus obtained was purified by silica gel column chromatography (ethyl acetate:hexane=90:10) to give the title compound (1.13 g, 73% yield).

mp: 183–186° C. (recrystallized from ethyl acetate). NMR (CDCl$_3$) δ: 2.73 (3H, s), 2.99 (3H, s), 7.01 (1H, d, J=7.3 Hz), 7.15–7.28 (2H, m), 7.44 (1H, t, J=7.9 Hz), 7.82–8.02 (2H, m), 8.43–8.49 (1H, m), 11.18 (1H, br s). Elementary Analysis: for $C_{17}H_{14}N_4O$ Calcd.: C, 70.33; H, 4.86; N, 19.36. Found: C, 70.46; H, 4.87; N, 19.27.

EXAMPLE 2-32

4-Chloro-3,6-dimethyl-1-(2-pyridinyl)-1H-pyrazolo[3,4-b]quinoline

Following the procedure described in Example 2-1, the title compound was prepared from 5-methyl-2-[[3-methyl-1-(2-pyridinyl)-1H-pyrazol-5-yl]amino]benzoic acid (56% yield).

mp: 158–160° C. (recrystallized from ethyl acetate). NMR (CDCl$_3$) δ: 2.61 (3H, s), 2.99 (3H, s), 7.19–7.28 (1H, m), 7.65 (1H, dd, J=1.8 Hz, 8.8 Hz), 7.88–7.98 (1H, m), 8.07 (1H, d, J=8.8 Hz), 8.13 (1H, br s), 8.64–8.70 (1H, m), 8.82 (1H, d, J=8.4 Hz). Elementary Analysis: for C$_{17}$H$_{13}$ClN$_4$.1.5H$_2$O Calcd.: C, 60.81; H, 4.80; N, 16.69. Found: C, 60.90; H, 4.88; N, 16.81.

EXAMPLE 2-33

3,6-Dimethyl-1-(2-pyridinyl)-1H-pyrazolo[3,4-b] quinolin-4-ylamine hydrochloride Following the procedures described in Examples 2-2 and 2-3, the title compound was prepared from 4-chloro-3,6-dimethyl-1-(2-pyridinyl)-1H-pyrazolo[3,4-b]quinoline and sodium azide (62% yield).

mp: 287–290° C. (recrystallized from ethanol). NMR (DMSO-d$_6$) δ: 2.50 (3H, s), 2.82 (3H, s), 7.42–7.50 (1H, m), 7.73–7.81 (1H, m), 7.89 (1H, d, J=8.1 Hz), 8.05–8.15 (1H, m), 8.29 (1H, d, J=8.4 Hz), 8.60–8.68 (2H, m), 9.80 (2H, br s). Elementary Analysis: for C$_{17}$H$_{15}$N$_5$.HCl.H$_2$O Calcd.: C, 59.39; H, 5.28; N, 20.37. Found: C, 59.01; H, 5.29; N, 20.25.

EXAMPLE 2-34

3,6-Dimethyl-1-(2-pyridinyl)-1,9-dihydro-4H-pyrazolo[3,4-b]quinolin-4-one

Following the procedure described in Example 2-12, the title compound was prepared from 5-methyl-2-[[3-methyl-1-(2-pyridinyl)-1H-pyrazol-5-yl]amino]benzoic acid (57% yield).

mp: 198–200° C. (recrystallized from ethanol). NMR (CDCl$_3$) δ: 2.47 (3H, s), 2.76 (3H, s), 7.17–7.25 (1H, m), 7.34 (1H, d, J=8.4 Hz), 7.46 (1H, dd, J=1.8 Hz, 8.4 Hz), 7.78–8.12 (2H, m), 8.25 (1H, s), 8.45–8.50 (1H, m), 11.38 (1H, br s).

EXAMPLE 2-35

4-Chloro-3,8-dimethyl-1-(2-pyridinyl)-1H-pyrazolo[3,4-b]quinoline

Following the procedures described in Reference Example 2-3 and Example 2-1, the title compound was prepared from 8-methyl-2-(2-oxypropyl)-4H-3,1-benzoxazin-4-one and 2-hydrazinopyridine (54% yield).

mp: 170–172° C. (recrystallized from ethyl acetate). NMR (CDCl$_3$) δ: 2.87 (3H, s), 3.00 (3H, s), 7.20–7.28 (1H, m), 7.48 (1H, dd, J=6.9 Hz, 8.4 Hz), 7.68 (1H, d, J=6.9 Hz), 7.90–8.00 (1H, m), 8.21–8.30 (1H, m), 8.65–8.73 (1H, m), 9.04 (1H, d, J=8.4 Hz). Elementary Analysis: for C$_{17}$H$_{13}$ClN$_4$ Calcd.: C, 66.13; H, 4.24; N, 18.15; Cl, 11.48. Found: C, 66.00; H, 4.08; N, 18.02; Cl, 11.43.

EXAMPLE 2-36

3,8-Dimethyl-1-(2-pyridinyl)-1H-pyrazolo[3,4-b] quinolin-4-ylamine

Following the procedure described in Example 2-2, the title compound was prepared from 4-chloro-3,8-dimethyl-1-(2-pyridinyl)-1H-pyrazolo[3,4-b]quinoline and sodium azide (67% yield).

mp: 208–211° C. (recrystallized from ethanol). NMR (DMSO-d$_6$) δ: 2.69 (3H, s), 2.82 (3H, s), 7.15–7.32 (2H, m), 7.39 (2H, br s), 7.56 (1H, d, J=6.6 Hz), 7.95–8.05 (1H, m), 8.29 (1H, d, J=8.1 Hz), 8.50–8.55 (1H, m), 8.90–9.10 (1H, m).

EXAMPLE 2-37

3,8-Dimethyl-1-(2-pyridinyl)-1H-pyrazolo[3,4-b] quinolin-4-ylamine hydrochloride Following the procedure described in Example 2-3, the title compound was prepared from 3,8-dimethyl-1-(2-pyridinyl)-1H-pyrazolo[3,4-b]quinolin-4-ylamine (57% yield).

mp: 283–286° C. (recrystallized from ethanol). NMR (DMSO-d$_6$) δ: 2.59 (3H, s), 2.77 (3H, s), 3.36 (2H, br s), 7.30–7.55 (2H, m), 7.62–7.82 (1H, m), 8.00–8.20 (2H, m), 8.50–8.70 (2H, m). Elementary Analysis: for C$_{17}$H$_{15}$N$_5$.HCl.0.5H$_2$O Calcd.: C, 60.99; H, 5.12; N, 20.92; Cl, 10.59. Found: C, 61.38; H, 4.96; N, 20.71; Cl, 10.64.

EXAMPLE 2-38

3,8-Dimethyl-1-(2-pyridinyl)-1,9-dihydro-4H-pyrazolo[3,4-b]quinolin-4-one

Following the procedure described in Example 2-13, the title compound was prepared from 4-chloro-3,8-dimethyl-1-(2-pyridinyl)-1H-pyrazolo[3,4-b]quinoline (72% yield).

mp: 241–243° C. (recrystallized from ethanol). NMR (CDCl$_3$) δ: 2.57 (3H, s), 2.75 (3H, s), 7.17–7.30 (2H, m), 7.49 (1H, d, J=7.3 Hz), 7.84–7.92 (1H, m), 8.00 (1H, d, J=8.4 Hz), 8.32 (1H, d, J=7.3 Hz), 8.46 (1H, d, J=4.0 Hz), 11.59 (1H, br s). Elementary Analysis: for C$_{17}$H$_{14}$N$_4$O Calcd.: C, 70.33; H, 4.86; N, 19.36. Found: C, 70.25; H, 4.65; N, 19.21.

EXAMPLE 2-39

4-Chloro-3-methyl-1-(2-pyridinyl)-6-(trifluoromethyl)-1H-pyrazolo[3,4-b]quinoline A solution of 2-[[3-methyl-1-(2-pyridinyl)-1H-pyrazol-5-yl]amino]-5-(trifluoromethyl)benzoic acid (14.0 g, 38.6 mmol) in phosphorous oxychloride (27.4 mL, 294 mmol) was heated under reflux for 1 hour. The solution was allowed to cool to room temperature, and the reaction solvent was evaporated under reduced pressure, and the residue was poured into iced water. The solution was neutralized by the addition of a sodium hydroxide solution, and the organic matter was extracted with chloroform. The extract was washed with saturated brine and water and dried over anhydrous magnesium sulfate, and the solvent was evaporated under reduced pressure. The residue was purified by silica gel column chromatography (hexane:chloroform=1:1 to chloroform) to give the title compound (7.07 g, 50% yield).

mp: 206° C. (recrystallized from ethyl acetate/methanol). NMR (CDCl$_3$) δ: 3.01 (3H, s), 7.28 (1H, ddd, J=1.0 Hz, 4.8 Hz, 7.4 Hz), 7.91–7.99 (2H, m), 8.27 (1H, d, J=9.2 Hz), 8.68–8.77 (3H, m). Elementary Analysis: for C$_{17}$H$_{10}$ClF$_3$N$_4$ Calcd.: C, 56.29; H, 2.78; N, 15.45; Cl, 9.77; F, 15.71. Found: C, 56.23; H, 3.00; N, 15.23; Cl, 9.62; F, 15.70.

EXAMPLE 2-40

3-Methyl-1-(2-pyridinyl)-6-(trifluoromethyl)-1,9-dihydro-4H-pyrazolo[3,4-b]quinolin-4-one To a solution of 4-chloro-3-methyl-1-(2-pyridinyl)-6-(trifluoromethyl)-1H-pyrazolo[3,4-b]quinoline (6.50 g, 17.9 mmol) in ethanol (300 mL), 6N hydrochloric acid (10 mL, 60 mmol) was added and the mixture was heated under reflux for 5 hours. The solution was allowed to cool to room temperature, and the resulting crystals were collected by filtration. The crystals were washed with ethanol and air dried, and recrystallized from ethanol to give the title compound (4.69 g, 76% yield).

mp: 250–251° C. (recrystallized from ethanol). NMR (CDCl$_3$) δ: 2.74 (3H, s), 7.26 (1H, ddd, J=1.2 Hz, 5.0 Hz, 7.2 Hz), 7.53 (1H, d, J=8.8 Hz), 7.84 (1H, dd, J=2.0 Hz, 8.8 Hz), 7.92 (1H, ddd, J=1.8 Hz, 7.2 Hz, 8.4 Hz), 8.03 (1H, ddd, J=1.0 Hz, 1.2 Hz, 8.4 Hz), 8.49 (1H, ddd, J=1.0 Hz, 1.8 Hz, 5.0 Hz), 8.75 (1H, d, J=2.0 Hz), 11.65 (1H, br s). Elementary Analysis: for $C_{17}H_{11}F_3N_4O$ Calcd.: C, 59.31; H, 3.22; N, 16.27; F, 16.55. Found: C, 59.23; H, 3.40; N, 16.00; F, 16.59.

EXAMPLE 2-41

4-Chloro-6-methoxy-3-methyl-1-(2-pyridinyl)-1H-pyrazolo[3,4-b]quinoline

Following the procedure described in Example 2-1, the title compound was prepared from 5-methoxy-2-[[3-methyl-1-(2-pyridinyl)-1H-pyrazol-5-yl]amino]benzoic acid (75% yield).

mp: 186–187° C. (recrystallized from ethyl acetate/methanol). NMR (CDCl$_3$) δ: 2.98 (3H, s), 4.01 (3H, s), 7.22 (1H, ddd, J=1.0 Hz, 4.8 Hz, 7.2 Hz), 7.48 (1H, dd, J=2.8 Hz, 9.2 Hz), 7.53 (1H, d, J=2.8 Hz), 7.92 (1H, ddd, J=1.8 Hz, 7.2 Hz, 8.4 Hz), 8.06 (1H, dd, J=1.0 Hz, 8.4 Hz), 8.67 (1H, dd, J=1.0 Hz, 4.8 Hz), 8.80 (1H, dd, J=1.0 Hz, 9.2 Hz). Elementary Analysis: for $C_{17}H_{13}ClN_4O$ Calcd.: C, 62.87; H, 4.03; N, 17.25; Cl, 10.92. Found: C, 62.84; H, 4.14; N, 17.32; Cl, 10.88.

EXAMPLE 2-42

6-Methoxy-3-methyl-1-(2-pyridinyl)-1H-pyrazolo[3,4-b]quinolin-4-ylamine

Following the procedure described in Example 2-2, the title compound was prepared from 4-chloro-6-methoxy-3-methyl-1-(2-pyridinyl)-1H-pyrazolo[3,4-b]quinoline and sodium azide (61% yield).

mp: 267–268° C. (recrystallized from ethanol). NMR (DMSO-d$_6$) δ: 2.82 (3H, s), 3.91 (3H, s), 7.25 (1H, ddd, J=0.8 Hz, 4.8 Hz, 7.4 Hz), 7.28 (2H, br s), 7.35 (1H, dd, J=2.8 Hz, 9.4 Hz), 7.73 (1H, d, J=9.4 Hz), 7.77 (1H, d, J=2.8 Hz), 7.98 (1H, ddd, J=2.0 Hz, 7.4 Hz, 8.4 Hz), 8.52 (1H, ddd, J=0.8 Hz, 2.0 Hz, 4.8 Hz), 8.71 (1H, d, J=8.4 Hz). Elementary Analysis: for $C_{17}H_{15}N_5O$ Calcd.: C, 66.87; H, 4.95; N, 22.94. Found: C, 66.84; H, 4.91; N, 22.85.

EXAMPLE 2-43

6-Methoxy-3-methyl-1-(2-pyridinyl)-1,9-dihydro-4H-pyrazolo[3,4-b]quinolin-4-one

Following the procedure described in Example 2-12, the title compound was prepared from 5-methoxy-2-[[3-methyl-1-(2-pyridinyl)-1H-pyrazol-5-yl]amino]benzoic acid (55% yield).

mp: 227–229° C. (recrystallized from ethyl acetate). NMR (CDCl$_3$) δ: 2.76 (3H, s), 3.92 (3H, s), 7.19 (1H, ddd, J=1.0 Hz, 5.0 Hz, 7.4 Hz), 7.27 (1H, dd, J=3.0 Hz, 9.2 Hz), 7.38 (1H, d, J=9.2 Hz), 7.83–7.92 (2H, m), 7.99 (1H, dd, J=1.0 Hz, 8.4 Hz), 8.46 (1H, ddd, J=1.0 Hz, 1.8 Hz, 5.0 Hz), 11.38 (1H, br s). Elementary Analysis: for $C_{17}H_{14}N_4O_2$ Calcd.: C, 66.66; H, 4.61; N, 18.29. Found: C, 66.68; H, 4.62; N, 18.31.

EXAMPLE 2-44

4-Chloro-8-methoxy-1-(2-pyridinyl)-1H-pyrazolo[3,4-b]quinoline

Following the procedures described in Reference Example 2-3 and Example 2-1, the title compound was prepared from 8-methoxy-2-(2-oxypropyl)-4H-3,1-benzoxazin-4-one and 2-hydrazinopyridine (23% yield).

mp: 167–169° C. (recrystallized from ethyl acetate). NMR (CDCl$_3$) δ: 3.00 (3H, s), 4.13 (3H, s), 7.15 (1H, d, J=7.7 Hz), 7.20–7.28 (1H, m), 7.52 (1H, t, J=7.7 Hz), 7.91–8.03 (2H, m), 8.65–8.71 (1H, m), 8.83 (1H, d, J=7.7 Hz). Elementary Analysis: for $C_{17}H_{13}ClN_4O$ Calcd.: C, 62.87; H, 4.03; N, 17.25; Cl, 10.92. Found: C, 62.88; H, 3.96; N, 17.16; Cl, 10.90.

EXAMPLE 2-45

8-Methoxy-3-methyl-1-(2-pyridinyl)-1H-pyrazolo[3,4-b]quinolin-4-ylamine hydrochloride Following the procedures described in Examples 2-2 and 2-3, the title compound was prepared from 4-chloro-8-methoxy-1-(2-pyridinyl)-1H-pyrazolo[3,4-b]quinoline and sodium azide (65% yield).

mp: 248–251° C. (recrystallized from ethanol). NMR (DMSO-d$_6$) δ: 2.73 (3H, s), 4.10 (3H, s), 7.53–7.60 (3H, m), 7.85 (1H, d, J=8.4 Hz), 8.03–8.20 (2H, m), 8.53 (1H, br d, J=5.1 Hz), hidden (2H). Elementary Analysis: for $C_{17}H_{15}N_5O \cdot HCl \cdot 1.5H_2O$ Calcd.: C, 55.36; H, 5.19; N, 18.99; Cl, 9.61. Found: C, 55.32; H, 4.95; N, 18.86; Cl, 9.54.

EXAMPLE 2-46

4-Chloro-6,7-dimethoxy-1-(2-pyridinyl)-1H-pyrazolo[3,4-b]quinoline

Following the procedure described in Example 2-1, the title compound was prepared from 4,5-dimethoxy-2-[[3-methyl-1-(2-pyridinyl)-1H-pyrazol-5-yl]amino]benzoic acid (32% yield).

mp: 248–251° C. (recrystallized from ethyl acetate/methanol/chloroform). NMR (CDCl$_3$) δ: 4.10 (6H, s), 2.96 (3H, s), 7.18–7.27 (1H, m), 7.44 (1H, s), 7.51 (1H, s), 7.86–7.97 (1H, m), 8.65–8.76 (2H, m).

EXAMPLE 2-47

6,7-Dimethoxy-3-methyl-1-(2-pyridinyl)-1H-pyrazolo[3,4-b]quinolin-4-ylamine hydrochloride Following the procedures described in Examples 2-2 and 2-3, the title compound was prepared from 4-chloro-6,7-dimethoxy-1-(2-pyridinyl)-1H-pyrazolo[3,4-b]quinoline and sodium azide (71% yield).

mp: 277–280° C. (recrystallized from methanol). NMR (DMSO-d$_6$) δ: 2.71 (3H, s), 3.85 (3H, s), 3.91 (3H, s), 7.40 (1H, br t, J=6.1 Hz), 7.56 (1H, s), 7.67 (1H, s), 7.74 (1H, br d, J=8.4 Hz), 8.04 (1H, br t, J=8.4 Hz), 8.59 (1H, br d, J=6.1 Hz), hidden (2H). Elementary Analysis: for $C_{18}H_{17}N_5O_2 \cdot HCl \cdot 1.5H_2O$ Calcd.: C, 54.20; H, 5.31; N, 17.56; Cl, 8.89. Found: C, 53.95; H, 5.26; N, 17.49; Cl, 8.80.

EXAMPLE 2-48

6,7-Dimethoxy-3-methyl-1-(2-pyridinyl)-1,9-dihydro-4H-pyrazolo[3,4-b]quinolin-4-one Following the procedure described in Example 2-12, the title compound was prepared from 4,5-dimethoxy-2-[[3-methyl-1-(2-pyridinyl)-1H-pyrazol-5-yl]amino]benzoic acid (35% yield).

mp: 238–239° C. (recrystallized from ethyl acetate/methanol). NMR (DMSO-d$_6$) δ: 2.60 (3H, s), 3.85 (3H, s), 3.93 (3H, s), 7.35–7.42 (1H, m), 7.56 (1H, s), 7.66 (1H, s), 7.88 (1H, d, J=8.4 Hz), 8.05 (1H, ddd, J=1.8 Hz, 7.4 Hz, 8.4 Hz), 8.59–8.61 (1H, m), 11.78 (1H, br s). Elementary Analysis: for $C_{18}H_{16}N_4O_3 \cdot H_2O$ Calcd.: C, 61.01; H, 5.12; N, 15.81. Found: C, 60.81; H, 5.12; N, 15.86.

EXAMPLE 2-49

4-Chloro-3-methyl-6-(methylsulfanyl)-1-(2-pyridinyl)-1H-pyrazolo[3,4-b]quinoline Following the procedure described in Example 2-1, the title compound was prepared from 6-(methylsulfanyl)-2-[[3-methyl-1-(2-pyridinyl)-1H-pyrazol-5-yl]amino]benzoic acid (29% yield).

mp: 182° C. (recrystallized from ethyl acetate/methanol). NMR (CDCl$_3$) δ: 2.66 (3H, s), 2.98 (3H, s), 7.23 (1H, ddd, J=1.2 Hz, 4.8 Hz, 7.4 Hz), 7.67 (1H, dd, J=2.2 Hz, 8.8 Hz), 7.92 (1H, ddd, J=1.8 Hz, 7.4 Hz, 8.4 Hz), 8.01–8.06 (2H, m), 8.67 (1H, ddd, J=0.6 Hz, 1.8 Hz, 4.8 Hz), 8.78 (1H, ddd, J=0.6 Hz, 1.2 Hz, 8.4 Hz). Elementary Analysis: for $C_{17}H_{13}ClN_4S$ Calcd.: C, 59.91; H, 3.84; N, 16.44; Cl, 10.40; S, 9.41. Found: C, 59.86; H, 3.75; N, 16.59; Cl, 10.42; S, 9.39.

EXAMPLE 2-50

3-Methyl-6-(methylsulfanyl)-1-(2-pyridinyl)-1,9-dihydro-4H-parazolo[3,4-b]quinolin-4-one Following the procedure described in Example 2-12, the title compound was prepared from 6-(methylsulfanyl)-2-[[3-methyl-1-(2-pyridinyl)-1H-pyrazol-5-yl]amino]benzoic acid (50% yield).

mp: 182–185° C. (recrystallized from methanol/ethyl acetate). NMR (CDCl$_3$) δ: 2.58 (3H, s), 2.74 (3H, s), 7.17–7.25 (1H, m), 7.35 (1H, d, J=8.8 Hz), 7.54 (1H, dd, J=2.2 Hz, 8.8 Hz), 7.83–7.93 (1H, m), 7.99 (1H, d, J=8.8 Hz), 8.27 (1H, d, J=2.2 Hz), 8.43–8.49 (1H, m), 11.42 (1H, br s). Elementary Analysis: for $C_{17}H_{14}N_4OS$ Calcd.: C, 63.33; H, 4.38; N, 17.38. Found: C, 62.92; H, 4.38; N, 17.09.

EXAMPLE 2-51

3-Methyl-6-(methylsulfinyl)-1-(2-pyridinyl)-1,9-dihydro-4H-pyrazolo[3,4-b]quinolin-4-one A solution in a mixed solvent of methanol (40 mL), tetrahydrofuran (10 mL) and water (10 mL) of 3-methyl-6-(methylsulfanyl)-1-(2-pyridinyl)-1,9-dihydro-4H-pyrazolo[3,4-b]quinolin-4-one (1.00 g, 3.10 mmol) and sodium periodate (0.66 g, 3.10 mmol) was heated under reflux for 2 hours. The solution was allowed to cool to room temperature, and concentrated under reduced pressure. The residue was poured into water, and the organic matter was extracted with chloroform. The extract was washed with saturated brine and dried over anhydrous sodium sulfate, and the solvent was evaporated under reduced pressure. The residue thus obtained was purified by silica gel column chromatography (chloroform to chloroform:methanol=98:2) to give the title compound (0.63 g, 61% yield).

mp: 268–269° C. (recrystallized from ethanol). NMR (DMSO-d$_6$) δ: 2.63 (3H, s), 2.81 (3H, s), 7.39–7.45 (1H, m), 7.91 (1H, d, J=8.4 Hz), 8.00 (1H, dd, J=2.2 Hz, 8.8 Hz), 8.03–8.12 (1H, m), 8.26 (1H d, J=8.8 Hz), 8.50 (1H, d, J=2.2 Hz), 8.61–8.64 (1H, m), 12.16 (1H, br s). Elementary Analysis: for $C_{17}H_{14}N_4O_2S \cdot 0.2H_2O$ Calcd.: C, 59.71; H, 4.24; N, 16.38; S, 9.38. Found: C, 59.59; H, 3.95; N, 16.42; S, 9.48.

EXAMPLE 2-52

3-Methyl-6-(methylsulfonyl)-1-(2-pyridinyl)-1,9-dihydro-4H-pyrazolo[3,4-b]quinolin-4-one A solution in a mixed solvent of methanol (40 mL), tetrahydrofuran (10 mL) and water (10 mL), of 3-methyl-6-(methylsulfanyl)-1-(2-pyridinyl)-1,9-dihydro-4H-pyrazolo[3,4-b]quinolin-4-one (1.00 g, 3.10 mmol), and sodium periodate (1.99 g, 9.30 mmol) was heated under reflux for 5 days. The solution was allowed to cool to room temperature, and concentrated under reduced pressure. The residue was poured into water, and the organic matter was extracted with chloroform. The extract was washed with saturated brine and dried over anhydrous sodium sulfate, and the solvent was evaporated under reduced pressure. The residue thus obtained was purified by silica gel column chromatography (chloroform to chloroform:methanol=99:1) to give the title compound (0.17 g, 15% yield).

mp: >300° C. (recrystallized from chloroform/methanol). NMR (DMSO-d$_6$) δ: 2.63 (3H, s), 3.29 (3H, s), 7.43 (1H, ddd, J=1.2 Hz, 4.8 Hz, 7.2 Hz), 7.91 (1H, d, J=8.4 Hz), 8.08 (1H, ddd, J=1.8 Hz, 7.2 Hz, 8.4 Hz), 8.20 (1H, dd, J=2.2 Hz, 8.6 Hz), 8.31 (1H, d, J=8.8 Hz), 8.63 (1H, ddd, J=0.8 Hz, 1.8 Hz, 4.8 Hz), 8.70 (1H, d, J=2.2 Hz), 12.31 (1H, br s). Elementary Analysis: for $C_{17}H_{14}N_4O_3S \cdot 0.25H_2O$ Calcd.: C, 56.89; H, 4.07; N, 15.61; S, 8.93. Found: C, 56.84; H, 3.86; N, 15.63; S, 8.93.

EXAMPLE 2-53

4-Chloro-3-methyl-6-nitro-1-(2-pyridinyl)-1H-pyrazolo[3,4-b]quinoline

Following the procedure described in Example 2-1, the title compound was prepared from 2-[[3-methyl-1-(2-pyridinyl)-1H-pyrazol-5-yl]amino]-5-nitrobenzoic acid (58% yield).

mp: 282° C. (recrystallized from chloroform). NMR (CDCl$_3$) δ: 3.02 (3H, s), 7.31 (1H, ddd, J=1.0 Hz, 4.8 Hz, 7.4 Hz), 7.97 (1H, ddd, J=1.8 Hz, 7.4 Hz, 8.0 Hz), 8.28 (1H, d, J=9.6 Hz), 8.56 (1H, dd, J=2.4 Hz, 9.6 Hz), 8.66–8.72 (2H, m), 9.38 (1H, d, J=2.4 Hz). Elementary Analysis: for $C_{16}H_{10}ClN_5O_2$ Calcd.: C, 56.56; H, 2.97; N, 20.61; Cl, 10.44. Found: C, 56.49; H, 2.70; N, 20.64; Cl, 10.39.

EXAMPLE 2-54

3-Methyl-6-nitro-1-(2-pyridinyl)-1,9-dihydro-4H-pyrazolo[3,4-b]quinolin-4-one

Following the procedure described in Example 2-13, the title compound was prepared from 4-chloro-3-methyl-6-nitro-1-(2-pyridinyl)-1H-pyrazolo[3,4-b]quinoline (98% yield).

mp: >300° C. NMR (DMSO-d$_6$) δ: 2.60 (3H, s), 7.40–7.46 (1H, m), 7.89 (1H, d, J=8.4 Hz), 8.03–8.12 (1H, m), 8.26 (1H, d, J=9.2 Hz), 8.47 (1H, dd, J=2.4 Hz, 9.2 Hz), 8.60–8.63 (1H, m), 8.91 (1H, d, J=2.4 Hz), 12.37 (1H, br s). Elementary Analysis: for $C_{16}H_{11}N_5O_3 \cdot 0.25H_2O$ Calcd.: C, 58.99; H, 3.56; N, 21.50. Found: C, 58.71; H, 3.47; N, 21.55.

EXAMPLE 2-55

6-Amino-3-methyl-1-(2-pyridinyl)-1,9-dihydro-4H-pyrazolo[3,4-b]quinolin-4-one

A solution of 3-methyl-6-nitro-1-(2-pyridinyl)-1,9-dihydro-4H-pyrazolo[3,4-b]quinolin-4-one (4.64 g, 14.4 mmol) and 5% palladium-carbon (4.64 g, 50% hydrate) in N,N-dimethylformamide (400 mL) was stirred at room temperature under hydrogen atmosphere for 4 hours. The reaction solution was filtered to remove the catalyst, and the filtrate was evaporated under reduced pressure. The residue thus obtained was purified by silica gel column chromatography (chloroform:methanol=99:1 to chloroform:methanol=95:5) to give the title compound (2.86 g, 69% yield).

mp: 260–262° C. (recrystallized from chloroform/methanol). NMR (DMSO-d$_6$) δ: 2.61 (3H, s), 5.24 (2H, br s), 7.05 (1H, dd, J=2.6 Hz, 8.8 Hz), 7.33–7.39 (2H, m), 7.76 (1H, d, J=8.8 Hz), 7.87 (1H, d, J=8.4 Hz), 8.04 (1H, ddd, J=1.8 Hz, 7.2 Hz, 8.4 Hz), 8.57–8.61 (1H, m), 11.64 (1H, br s). Elementary Analysis: for C$_{16}$H$_{13}$N$_5$O.0.1H$_2$O Calcd.: C, 65.56; H, 4.54; N, 23.89. Found: C, 65.41; H, 4.74; N, 23.86.

EXAMPLE 2-56

6-Dimethylamino-3-methyl-1-(2-pyridinyl)-1,9-dihydro-4H-pyrazolo[3,4-b]quinolin-4-one A solution of 6-amino-3-methyl-1-(2-pyridinyl)-1,9-dihydro-4H-pyrazolo[3,4-b]quinolin-4-one (1.00 g, 3.43 mmol), sodium cyanotrihydroborate (1.08 g, 17.2 mmol) and paraformaldehyde (1.00 g) in acetic acid (20 mL) was stirred at room temperature for 18 hours under an argon atmosphere. The reaction solvent was evaporated under reduced pressure, and the residue was poured into iced water. After the solution was made basic by the addition of a sodium hydroxide solution, the organic matter was extracted with chloroform. The extract was washed with saturated brine and water and dried over anhydrous magnesium sulfate, and the solvent was evaporated under reduced pressure. The residue thus obtained was purified by silica gel column chromatography (chloroform to chloroform:methanol=99:1) to give the title compound (0.56 g, 51% yield).

mp: 171–173° C. (recrystallized from ethyl acetate/hexane). NMR (CDCl$_3$) (: 2.76 (3H, s), 3.02 (6H, s), 7.14–7.21 (2H, m), 7.35 (1H, d, J=8.8 Hz), 7.69 (1H, d, J=2.6 Hz), 7.85 (1H, ddd, J=1.8 Hz, 7.0 Hz, 8.4 Hz), 7.98 (1H, ddd, J=0.8 Hz, 1.2 Hz, 8.4 Hz), 8.46 (1H, ddd, J=0.8 Hz, 1.8 Hz, 5.0 Hz), 11.24 (1H, br s). Elementary Analysis: for C$_{18}$H$_{17}$N$_5$O.H$_2$O Calcd.: C, 64.08; H, 5.63; N, 20.76. Found: C, 64.15; H, 5.78; N, 21.02.

EXAMPLE 2-57

4-Chloro-3-methyl-7-nitro-1-(2-pyridinyl)-1H-pyrazolo[3,4-b]quinoline

Following the procedure described in Example 2-1, the title compound was prepared from 2-[[3-methyl-1-(2-pyridinyl)-1H-pyrazol-5-yl]amino]-4-nitrobenzoic acid (36% yield).

mp: 226–227° C. (recrystallized from ethyl acetate). NMR (CDCl$_3$) δ: 3.03 (3H, s), 7.31 (1H, ddd, J=0.8 Hz, 4.8 Hz, 7.4 Hz), 7.98 (1H, ddd, J=1.8 Hz, 7.4 Hz, 8.4 Hz), 8.32 (1H, dd, J=2.2 Hz, 9.2 Hz), 8.57 (1H, d, J=9.2 Hz), 8.69–8.76 (2H, m), 9.10 (1H, d, J=2.2 Hz). Elementary Analysis: for C$_{16}$H$_{10}$ClN$_5$O$_2$ Calcd.: C, 56.56; H, 2.97; N, 20.61; Cl, 10.44. Found: C, 56.42; H, 2.74; N, 20.54; Cl, 10.32.

EXAMPLE 2-58

3-Methyl-7-nitro-1-(2-pyridinyl)-1,9-dihydro-4H-pyrazolo[3,4-b]quinolin-4-one

Following the procedure described in Example 2-13, the title compound was prepared from 4-chloro-3-methyl-7-nitro-1-(2-pyridinyl)-1H-pyrazolo[3,4-b]quinoline (96% yield).

mp: >300° C. (recrystallized from chloroform/methanol). NMR (DMSO-d$_6$) δ: 2.62 (3H, s), 7.42 (1H, ddd, J=0.8 Hz, 4.8 Hz, 7.4 Hz), 7.90 (1H, d, J=8.4 Hz), 8.01–8.12 (2H, m), 8.39 (1H, d, J=8.8 Hz), 8.61 (1H, ddd, J=0.8 Hz, 1.8 Hz, 4.8 Hz), 9.18 (1H, d, J=2.2 Hz), 12.41 (1H, br s). Elementary Analysis: for C$_{16}$H$_{11}$N$_5$O$_3$.0.25H$_2$O Calcd.: C, 58.99; H, 3.56; N, 21.50. Found: C, 58.90; H, 3.67; N, 21.72.

EXAMPLE 2-59

7-Amino-3-methyl-1-(2-pyridinyl)-1,9-dihydro-4H-pyrazolo[3,4-b]quinolin-4-one

Following the procedure described in Example 2-55, the title compound was prepared from 3-methyl-7-nitro-1-(2-pyridinyl)-1,9-dihydro-4H-pyrazolo[3,4-b]quinolin-4-one (58% yield).

mp: 284–286° C. (recrystallized from chloroform/methanol). NMR (DMSO-d$_6$) δ: 2.57 (3H, s), 5.98 (2H, br s), 6.58 (1H, dd, J=2.2 Hz, 8.8 Hz), 6.87 (1H, d, J=2.2 Hz), 7.36 (1H, ddd, J=1.0 Hz, 4.8 Hz, 7.4 Hz), 7.85–7.90 (2H, m), 8.04 (1H, ddd, J=1.8 Hz, 7.4 Hz, 8.4 Hz), 8.59 (1H, ddd, J=1.0 Hz, 1.8 Hz, 4.8 Hz), 11.43 (1H, br s). Elementary Analysis: for C$_{16}$H$_{13}$N$_5$O.0.6H$_2$O Calcd.: C, 63.61; H, 4.74; N, 23.18. Found: C, 63.90; H, 4.70; N, 22.79.

EXAMPLE 2-60

Methyl 4-chloro-3-methyl-1-(2-pyridinyl)-1H-pyrazolo[3,4-b]quinoline-5-carboxylate Following the procedures described in Reference Example 2-3 and Example 2-1, the title compound was prepared from methyl 4-oxo-2-(2-oxopropyl)-4H-3,1-benzoxazine-5-carboxylate and 2-hydrazinopyridine (38% yield).

mp: 168–171° C. (recrystallized from ethyl acetate). NMR (CDCl$_3$) δ: 3.00 (3H, s), 4.04 (3H, s), 7.23–7.30 (1H, m), 7.65 (1H, dd, J=1.6 Hz, 7.0 Hz), 7.79 (1H, dd, J=7.0 Hz, 8.8 Hz), 7.91–8.00 (1H, m), 8.28 (1H, dd, J=1.6 Hz, 8.8 Hz), 8.67–8.72 (1H, m), 8.76–8.81 (1H, m). Elementary Analysis: for C$_{18}$H$_{13}$ClN$_4$O Calcd.: C, 61.28; H, 3.71; N, 15.88; Cl, 10.05. Found: C, 61.48; H, 3.74; N, 16.07; Cl, 9.90.

EXAMPLE 2-61

Methyl 3-methyl-4-oxo-1-(2-pyridinyl)-4,9-dihydro-1H-pyrazolo[3,4-b]quinoline-5-carboxylate Following the procedure described in Example 2-13, the title compound was prepared from methyl 4-chloro-3-methyl-1-(2-pyridinyl)-1H-pyrazolo[3,4-b]quinoline-5-carboxylate (30% yield).

mp: 241–244° C. (recrystallized from ethyl acetate). NMR (CDCl$_3$) δ: 2.73 (3H, s), 4.08 (3H, s), 7.20–7.25 (2H, m), 7.47–7.53 (1H, m), 7.65 (1H, dd, J=6.8 Hz, 8.4 Hz), 7.86–7.95 (1H, m), 8.01 (1H, d, J=8.4 Hz), 8.46–8.50 (1H, m), 11.58 (1H, s). Elementary Analysis: for C$_{18}$H$_{14}$N$_4$O$_3$ Calcd.: C, 64.66; H, 4.22; N, 16.76. Found: C, 61.90; H, 4.45; N, 16.78.

EXAMPLE 2-62

3-Methyl-4-oxo-1-(2-pyridinyl)-4,9-dihydro-1H-pyrazolo[3,4-b]quinoline-5-carboxylic acid The basic aqueous layer described in Example 2-61 was made acidic by the addition of an aqueous hydrochloric acid solution, and the resulting precipitate was collected by filtration. The crude crystals were washed with water and ethanol and dried to give the title compound (32% yield).

mp: 303–306° C. (recrystallized from chloroform/methanol). NMR (DMSO-d$_6$) δ: 2.61 (3H, s), 7.22 (1H, d, J=7.0 Hz), 7.37–7.44 (1H, m), 7.69–7.78 (1H, m), 7.91 (1H, d, J=8.2 Hz), 8.02–8.08 (1H, m), 8.12 (1H, d, J=7.8 Hz), 8.63 (1H, d, J=4.4 Hz), 12.05 (1H, s), 12.85 (1H, br s). Elementary Analysis: for $C_{17}H_{12}N_4O_3 \cdot 0.2H_2O$ Calcd.: C, 63.04; H, 3.86; N, 17.30. Found: C, 63.13; H, 3.72; N, 17.44.

EXAMPLE 2-63

Methyl 4-chloro-3-methyl-1-(2-pyridinyl)-1H-pyrazolo[3,4-b]quinoline-6-carboxylate Following the procedure described in Reference Example 2-5, 4-[[3-methyl-1-(2-pyridinyl)-1H-pyrazol-5-yl]amino]isophthalic acid was prepared from bromoisophthalic acid and 3-methyl-1-(2-pyridinyl)-1H-pyrazol-5-ylamine (99% yield). A solution of the compound (23.0 g, 68.0 mmol) in phosphorus oxychloride (108 g, 704 mmol) was heated under reflux for 1 hour. The reaction solution was allowed to cool to room temperature, and the solvent was evaporated under reduced pressure. To a stirred mixture of the residue in tetrahydrofuran (100 mL), methanol (10 mL) was added dropwise carefully, and the precipitate was collected by filtration. The precipitate was dissolved in a sodium hydroxide solution, and organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform) to give the title compound (3.40 g, 14% yield).

mp: 199–200° C. (recrystallized from ethyl acetate). NMR (CDCl$_3$) δ: 3.01 (3H, s), 4.04 (3H, s), 7.27 (1H, ddd, J=1.0 Hz, 4.8 Hz, 7.4 Hz), 7.95 (1H, ddd, J=1.8 Hz, 7.4 Hz, 8.4 Hz), 8.19 (1H, d, J=9.0 Hz), 8.38 (1H, dd, J=1.8 Hz, 9.0 Hz), 8.69 (1H, ddd, J=0.8 Hz, 1.8 Hz, 4.8 Hz), 8.78 (1H, ddd, J=0.8 Hz, 1.0 Hz, 8.4 Hz), 9.15 (1H, d, J=1.8 Hz). Elementary Analysis: for $C_{18}H_{13}ClN_4O_2$ Calcd.: C, 61.28; H, 3.71; N, 15.88; Cl, 10.05. Found: C, 61.19; H, 3.53; N, 15.71; Cl, 9,95.

EXAMPLE 2-64

Methyl 3-methyl-4-oxo-1-(2-pyridinyl)-4,9-dihydro-1H-pyrazolo[3,4-b]quinoline-6-carboxylate Following the procedure described in Example 2-13, the title compound was prepared from methyl 4-chloro-3-methyl-1-(2-pyridinyl)-1H-pyrazolo[3,4-b]quinoline-6-carboxylate (58% yield).

mp: 265–266° C. (recrystallized from ethyl acetate/methanol). NMR (CDCl$_3$) δ: 2.74 (3H, s), 3.96 (3H, s), 7.25 (1H, ddd, J=1.2 Hz, 5.2 Hz, 7.0 Hz), 7.46 (1H, d, J=8.4 Hz), 7.91 (1H, ddd, J=1.2 Hz, 7.0 Hz, 8.4 Hz), 8.01 (1H, ddd, J=0.8 Hz, 1.2 Hz, 8.4 Hz), 8.27 (1H, dd, J=2.2 Hz, 8.4 Hz), 8.48 (1H, ddd, J=0.8 Hz, 2.0 Hz, 5.2 Hz), 9.11 (1H, d, J=2.2 Hz), 11.61 (1H, br s). Elementary Analysis: for $C_{18}H_{14}N_4O_3$ Calcd.: C, 64.66; H, 4.22; N, 16.76. Found: C, 64.56; H, 4.28; N, 16.72.

EXAMPLE 2-65

3-Methyl-4-oxo-1-(2-pyridinyl)-4,9-dihydro-1H-pyrazolo[3,4-b]quinoline-6-carboxylic acid To a solution of methyl 3-methyl-4-oxo-1-(2-pyridinyl)-4,9-dihydro-1H-pyrazolo[3,4-b]quinoline-6-carboxylate (0.96 g, 2.87 mmol) in ethanol (20 mL), was added 2N sodium hydroxide (20 mL), and the mixture was heated under reflux for 1 hour. The solution was allowed to cool to room temperature, and made acidic by the addition of 1N hydrochloric acid, and the resulting precipitate was collected by filtration. The crude crystals were recrystallized from chloroform/methanol to give the title compound (0.87 g, 93% yield).

mp: >300° C. (recrystallized from chloroform/methanol). NMR (DMSO-d$_6$) δ: 2.62 (3H, s), 4.10 (1H, br s), 7.42 (1H, ddd, J=1.0 Hz, 4.8 Hz, 7.2 Hz), 7.90 (1H, ddd, J=0.8 Hz, 1.0 Hz, 8.4 Hz), 8.07 (1H, ddd, J=1.8 Hz, 7.2 Hz, 8.4 Hz), 8.12 (1H, d, J=8.8 Hz), 8.20 (1H, dd, J=1.8 Hz, 8.8 Hz), 8.62 (1H, ddd, J=0.8 Hz, 1.8 Hz, 4.8 Hz), 8.80 (1H, d, J=1.8 Hz), 12.16 (1H, br s). Elementary Analysis: for $C_{17}H_{12}N_4O_3 \cdot 0.8H_2O$ Calcd.: C, 61.00; H, 4.10; N, 16.74. Found: C, 60.84; H, 4.00; N, 16.60.

EXAMPLE 2-66

Methyl 4-chloro-3-methyl-1-(2-pyridinyl)-1H-pyrazolo[3,4-b]quinoline-7-carboxylate Following the procedure described in Example 2-63, the title compound was prepared from bromoterephthalic acid and 3-methyl-1-(2-pyridinyl)-1H-pyrazol-5-ylamine (24% yield).

mp: 239–240° C. (recrystallized from chloroform/hexane). NMR (CDCl$_3$) δ: 3.00 (3H, s), 4.04 (3H, s), 7.23–7.30 (1H, m), 7.95 (1H, ddd, J=1.8 Hz, 7.4 Hz, 8.4 Hz), 8.13 (1H, dd, J=1.6 Hz, 8.8 Hz), 8.43 (1H, d, J=8.8 Hz), 8.68 (1H, ddd, J=0.6 Hz, 1.8 Hz, 4.8 Hz), 8.83 (1H, d, J=8.4 Hz), 8.87 (1H, d, J=1.6 Hz). Elementary Analysis: for $C_{18}H_{13}ClN_4O_2$ Calcd.: C, 61.28; H, 3.71; N, 15.88; Cl, 10.05. Found: C, 61.24; H, 3.83; N, 16.04; Cl, 9.98.

EXAMPLE 2-67

Methyl 3-methyl-4-oxo-1-(2-pyridinyl)-4,9-dihydro-1H-pyrazolo[3,4-b]quinoline-7-carboxylate Following the procedure described in Example 2-13, the title compound was prepared from methyl 4-chloro-3-methyl-1-(2-pyridinyl)-1H-pyrazolo[3,4-b]quinoline-7-carboxylate (34% yield).

mp: 251–252° C. (recrystallized from chloroform/methanol). NMR (DMSO-d$_6$) δ: 2.61 (3H, s), 3.94 (3H, s), 7.40 (1H, ddd, J=1.2 Hz, 5.2 Hz, 7.4 Hz), 7.79 (1H, dd, J=1.6 Hz, 8.4 Hz), 7.87 (1H, dd, J=1.2 Hz, 8.4 Hz), 8.05 (1H, ddd, J=11.8 Hz, 7.4 Hz, 8.4 Hz), 8.28 (1H, d, J=8.4 Hz), 8.60 (1H, ddd, J=1.0 Hz, 1.8 Hz, 5.2 Hz), 8.80 (1H, d, J=1.6 Hz), 12.18 (1H, br s). Elementary Analysis: for $C_{18}H_{14}N_4O_3 \cdot H_2O$ Calcd.: C, 61.36; H, 4.58; N, 15.90. Found: C, 61.36; H, 4.51; N, 16.09.

EXAMPLE 2-68

3-Methyl-4-oxo-1-(2-pyridinyl)-4,9-dihydro-1H-pyrazolo[3,4-b]quinoline-7-carboxylic acid Following the procedure described in Example 2-65, the title compound was prepared from methyl 3-methyl-4-oxo-1-(2-pyridinyl)-4,9-dihydro-1H-pyrazolo[3,4-b]quinoline-7-carboxylate (74% yield).

mp: >300° C. (recrystallized from chloroform/methanol). NMR (DMSO-d$_6$) δ: 2.62 (3H, s), 7.40 (1H, ddd, J=1.0 Hz, 4.8 Hz, 7.4 Hz), 7.81 (1H, dd, J=1.4 Hz, 8.4 Hz), 7.88 (1H, d, J=8.4 Hz), 8.05 (1H, ddd, J=1.8 Hz, 7.4 Hz, 8.4 Hz), 8.28 (1H, d, J=8.4 Hz), 8.61 (1H, ddd, J=0.8 Hz, 1.8 Hz, 4.8 Hz), 8.79 (1H, d, J=1.4 Hz), 12.19 (1H, br s), hidden (1H). Elementary Analysis: for $C_{17}H_{12}N_4O_3 \cdot 0.1H_2O$ Calcd.: C, 63.39; H, 3.82; N, 17.39. Found: C, 63.33; H, 3.89; N, 17.41.

EXAMPLE 2-69

5-Chloro-3-methyl-1-(2-pyridinyl)-1,9-dihydro-4H-pyrazolo[3,4-b]quinolin-4-one Following the procedure described in Example 2-12, the title compound was prepared from 6-chloro-2-[[3-methyl-1-(2-pyridinyl)-1H-pyrazol-5-yl]amino]benzoic acid (44% yield).

mp: 212–213° C. (recrystallized from ethanol). NMR (DMSO-$d_6$) δ: 2.58 (3H, s), 7.28 (1H, dd, J=1.0 Hz, 7.8 Hz), 7.40 (1H, ddd, J=1.0 Hz, 4.8 Hz, 7.2 Hz), 7.60 (1H, dd, J=7.8 Hz, 8.4 Hz), 7.87 (1H, dd, J=1.0 Hz, 8.4 Hz), 8.02 (1H, dd, J=1.0 Hz, 8.4 Hz), 8.02–8.10 (1H, m), 8.60 (1H, ddd, J=0.8 Hz, 1.8 Hz, 4.8 Hz), 11.84 (1H, br s). Elementary Analysis: for $C_{16}H_{11}ClN_4 \cdot 0.5H_2O$ Calcd.: C, 60.10; H, 3.78; N, 17.52; Cl, 11.09. Found: C, 59.91; H, 3.77; N, 17.47; Cl, 10.91.

EXAMPLE 2-70

4,6-Dichloro-3-methyl-1-(2-pyridinyl)-1H-pyrazolo[3,4-b]quinoline

Following the procedures described in Reference Example 2-3 and Example 2-1, the title compound was prepared from 6-chloro-2-(2-oxypropyl)-4H-3,1-benzoxazin-4-one and 2-hydrazinopyridine (5% yield).

mp: 233–235° C. (recrystallized from ethyl acetate/methanol). NMR (CDCl$_3$) δ: 2.99 (3H, s), 7.22–7.29 (1H, m), 7.74 (1H, dd, J=2.6 Hz, 9.0 Hz), 7.89–7.98 (1H, m), 8.12 (1H, d, J=9.0 Hz), 8.37 (1H, d, J=2.2 Hz), 8.67–8.69 (1H, m), 8.75 (1H, d, J=8.0 Hz). Elementary Analysis: for $C_{16}H_{10}Cl_2N_4$ Calcd.: C, 58.38; H, 3.06; N, 17.02; Cl, 21.54. Found: C, 58.54; H, 3.06; N, 17.02; Cl, 21.48.

EXAMPLE 2-71

6-Chloro-3-methyl-1-(2-pyridinyl)-1H-pyrazolo[3,4-b]quinolin-4-ylamine

Following the procedure described in Example 2-2, the title compound was prepared from 4,6-dichloro-3-methyl-1-(2-pyridinyl)-1H-pyrazolo[3,4-b]quinoline and sodium azide (61% yield).

mp: 289–292° C. (recrystallized from ethyl acetate/methanol). NMR (DMSO-$d_6$) δ: 2.80 (3H, s), 7.38 (1H, dd, J=5.2 Hz, 6.6 Hz), 7.80 (1H, dd, J=2.4 Hz, 8.8 Hz), 8.00–8.11 (2H, m), 8.29 (1H, d, J=8.0 Hz), 8.40 (2H, s), 8.58 (1H, d, J=6.6 Hz), 8.73 (1H, d, J=2.4 Hz). Elementary Analysis: for $C_{16}H_{12}ClN_5 \cdot 1.5H_2O$ Calcd.: C, 57,06; H, 4.49; N, 20.80. Found: C, 57.03; H, 4.11; N, 20.73.

EXAMPLE 2-72

6-Chloro-3-methyl-1-(2-pyridinyl)-1,9-dihydro-4H-pyrazolo[3,4-b]quinolin-4-one Following the procedure described in Example 2-13, the title compound was prepared from 4,6-dichloro-3-methyl-1-(2-pyridinyl)-1H-pyrazolo[3,4-b]quinoline (84% yield).

mp: 254–255° C. (recrystallized from ethanol). NMR (DMSO-$d_6$) δ: 2.59 (3H, s), 7.37–7.44 (1H, m), 7.74 (1H, dd, J=2.6 Hz, 9.2 Hz), 7.88 (1H, d, J=8.4 Hz), 8.02–8.13 (3H, m), 8.59–8.61 (1H, m), 12.05 (1H, br s). Elementary Analysis: for $C_{16}H_{11}ClN_4O$ Calcd.: C, 61.84; H, 3.57; N, 18.03; Cl, 11.41. Found: C, 61.80; H, 3.61; N, 18.16; Cl, 11.36.

EXAMPLE 2-73

4,7-Dichloro-3-methyl-1-(2-pyridinyl)-1H-pyrazolo[3,4-b]quinoline

Following the procedures described in Reference Example 2-5 and Example 2-1, the title compound was prepared from 4-chloro-2-iodobenzoic acid and 3-methyl-1-(2-pyridinyl)-1H-pyrazol-5-ylamine (23% yield).

mp: 203–204° C. (recrystallized from ethyl acetate). NMR (CDCl$_3$) δ: 2.99 (3H, s), 7.26 (1H, ddd, J=1.0 Hz, 4.8 Hz, 7.4 Hz), 7.53 (1H, dd, J=1.8 Hz, 9.2 Hz), 7.94 (1H, ddd, J=1.8 Hz, 7.4 Hz, 8.4 Hz), 8.18 (1H, d, J=1.8 Hz), 8.32 (1H, d, J=9.2 Hz), 8.68 (1H, ddd, J=0.8 Hz, 1.8 Hz, 4.8 Hz), 8.77 (1H, ddd, J=0.8 Hz, 1.0 Hz, 8.4 Hz). Elementary Analysis: for $C_{16}H_{10}Cl_2N_4$ Calcd.: C, 58.38; H, 3.06; N, 17.02; Cl, 21.54. Found: C, 58.32; H, 3.22; N, 16.99; Cl, 21.54.

EXAMPLE 2-74

7-Chloro-3-methyl-1-(2-pyridinyl)-1,9-dihydro-4H-pyrazolo[3,4-b]quinolin-4-one Following the procedure described in Example 2-13, the title compound was prepared from 4,7-dichloro-3-methyl-1-(2-pyridinyl)-1H-pyrazolo[3,4-b]quinoline (92% yield).

mp: 274–275° C. (recrystallized from ethanol). NMR (DMSO-$d_6$) δ: 2.60 (3H, s), 7.34 (1H, dd, J=1.8 Hz, 8.4 Hz), 7.37–7.44 (1H, m), 7.89 (1H, d, J=8.4 Hz), 8.02–8.11 (1H, m), 8.19 (1H, d, J=8.4 Hz), 8.25 (1H, d, J=1.8 Hz), 8.58–8.61 (1H, m), 12.04 (1H, br s). Elementary Analysis: for $C_{16}H_{11}ClN_4O$ Calcd.: C, 61.84; H, 3.57; N, 18.03; Cl, 11.41. Found: C, 61.69; H, 3.76; N, 17.95; Cl, 11.31.

EXAMPLE 2-75

4,6,7-Trichloro-3-methyl-1-(2-pyridinyl)-1H-pyrazolo[3,4-b]quinoline

Following the procedure described in Example 2-1, the title compound was prepared from 4,5-dichloro-2-[[3-methyl-1-(2-pyridinyl)-1H-pyrazol-5-yl]amino]benzoic acid (45% yield).

mp: 213–214° C. (recrystallized from ethyl acetate). NMR (CDCl$_3$) δ: 2.98 (3H, s), 7.23–7.30 (1H, m), 7.93 (1H, ddd, J=1.8 Hz, 7.6 Hz, 8.4 Hz), 8.30 (1H, s), 8.47 (1H, s), 8.67–8.72 (2H, m). Elementary Analysis: for $C_{16}H_9Cl_3N_4$ Calcd.: C, 52.85; H, 2.49; N, 15.41; Cl, 29.25. Found: C, 52.92; H, 2.44; N, 15.39; Cl, 29.10.

EXAMPLE 2-76

6,7-Dichloro-3-methyl-1-(2-pyridinyl)-1,9-dihydro-4H-pyrazolo[3,4-b]quinolin-4-one Following the procedure described in Example 2-13, the title compound was prepared from 4,6,7-trichloro-3-methyl-1-(2-pyridinyl)-1H-pyrazolo[3,4-b]quinoline (99% yield).

mp: 303–304° C. (recrystallized from ethanol). NMR (DMSO-$d_6$) δ: 2.56 (3H, s), 7.40, (1H, ddd, J=0.8 Hz, 4.8 Hz, 7.4 Hz), 7.86 (1H, d, J=8.4 Hz), 8.06 (1H, ddd, J=1.8 Hz, 7.4 Hz, 8.4 Hz), 8.18 (1H, s), 8.44 (1H, s), 8.56 (1H, ddd, J=0.6 Hz, 1.8 Hz, 4.8 Hz), 12.06 (1H, br s). Elementary Analysis: for $C_{16}H_{10}Cl_2N_4O$ Calcd.: C, 55.67; H, 2.92; N, 16.23; Cl, 20.54. Found: C, 55.55; H, 2.74; N, 16.18; Cl, 20.54.

EXAMPLE 2-77

6,8-Dichloro-3-methyl-1-(2-pyridinyl)-1,9-dihydro-4H-pyrazolo[3,4-b]quinolin-4-one Following the procedure described in Example 2-12, the title compound was prepared from 3,5-dichloro-2-[3-methyl-1-(2-pyridinyl)-1H-pyrazol-5-yl]amino]benzoic acid (65% yield).

mp: 288–289° C. (recrystallized from DMSO). NMR (CDCl$_3$:CF$_3$CO$_2$D=50:1) δ: 2.75 (3H, s), 7.31–7.37 (1H, m), 7.81 (1H, d, J=2.2 Hz), 7.97–8.00 (2H, m), 8.35 (1H, d, J=2.2 Hz), 8.53–8.57 (1H, m), 11.32 (1H, br s). Elementary Analysis: for C$_{16}$H$_{10}$Cl$_2$N$_4$O Calcd.: C, 55.62; H, 2.92; N, 16.23. Found: C, 55.48; H, 2.81; N, 16.18.

EXAMPLE 2-78

4-Chloro-5-fluoro-3-methyl-1-(2-pyridinyl)-1H-pyrazolo[3,4-b]quinoline

Following the procedures described in Reference Example 2-5 and Example 2-1, the title compound was prepared from 2-fluoro-6-iodobenzoic acid and 3-methyl-1-(2-pyridinyl)-1H-pyrazol-5-ylamine (51% yield).

mp: 160–161° C. (recrystallized from ethyl acetate). NMR (CDCl$_3$) δ: 3.01 (3H, s), 7.14–7.29 (2H, m), 7.63–7.76 (1H, m), 7.88–8.01 (2H, m), 8.65–8.78 (2H, m). Elementary Analysis: for C$_{16}$H$_{10}$ClFN$_4$ Calcd.: C, 61.45; H, 3.22; N, 17.92; Cl, 11.34; F, 6.08. Found: C, 61.19; H, 3.43; N, 17.94; Cl, 11.23; F, 6.05.

EXAMPLE 2-79

5-Fluoro-3-methyl-1-(2-pyridinyl)-1,9-dihydro-4H-pyrazolo[3,4-b]quinolin-4-one hydrochloride Following the procedure described in Example 2-13, the title compound was prepared from 4-chloro-5-fluoro-3-methyl-1-(2-pyridinyl)-1H-pyrazolo[3,4-b]quinoline (80% yield).

mp: >380° C. NMR (DMSO-d$_6$) δ: 2.58 (3H, s), 6.42–6.54 (1H, m), 7.09–7.29 (3H, m), 7.84–7.95 (1H, m), 8.44 (1H, dd, J=1.2 Hz, 4.8 Hz), 8.95 (1H, d, J=8.4 Hz), hidden (1H). Elementary Analysis: for C$_{16}$H$_{11}$FN$_4$O.HCl Calcd.: C, 58.10; H, 3.66; N, 16.94; F, 5.74. Found: C, 58.44; H, 3.32; N, 16.83; F, 5.75.

EXAMPLE 2-80

4-Chloro-6-fluoro-3-methyl-1-(2-pyridinyl)-1H-pyrazolo[3,4-b]quinoline

Following the procedures described in Reference Example 2-5 and Example 2-1, the title compound was prepared from 5-fluoro-2-iodobenzoic acid and 3-methyl-1-(2-pyridinyl)-1H-pyrazol-5-ylamine (57% yield).

mp: 185–187° C. (recrystallized from ethyl acetate). NMR (DMSO-d$_6$) δ: 3.00 (3H, s), 7.21–7.28 (1H, m), 7.62 (1H, ddd, J=3.0 Hz, 5.4 Hz, 9.4 Hz), 7.89–7.99 (2H, m), 8.19 (1H, dd, J=5.4 Hz, 9.4 Hz), 8.69 (1H, d, J=3.6 Hz), 8.77 (1H, d, J=8.2 Hz). Elementary Analysis: for C$_{16}$H$_{10}$ClFN$_4$O Calcd.: C, 61.45; H, 3.22; N, 17.92; Cl, 11.34; F, 6.08. Found: C, 61.60; H, 3.10; N, 17.62; Cl, 11.22; F, 5.80.

EXAMPLE 2-81

6-Fluoro-3-methyl-1-(2-pyridinyl)-1,9-dihydro-4H-pyrazolo[3,4-b]quinolin-4-one Following the procedure described in Example 2-13, the title compound was prepared from 4-chloro-6-fluoro-3-methyl-1-(2-pyridinyl)-1H-pyrazolo[3,4-b]quinoline (51% yield).

mp: 278–280° C. (recrystallized from ethanol/tetrahydrofuran). NMR (CDCl$_3$) δ: 2.75 (3H, s), 7.16–7.27 (1H, m), 7.33–7.48 (2H, m), 7.87–8.14 (3H, m), 8.48 (1H, d, J=5.2 Hz), 11.51 (1H, s). Elementary Analysis: for C$_{16}$H$_{11}$FN$_4$O Calcd.: C, 65.30; H, 3.77; N, 19.04; F, 6.46. Found: C, 65.32; H, 3.83; N, 18.99; F, 6.17.

EXAMPLE 2-82

4-Chloro-7-fluoro-3-methyl-1-(2-pyridinyl)-1H-pyrazolo[3,4-b]quinoline

Following the procedure described in Example 2-1, the title compound was prepared from 4-fluoro-2-[[3-methyl-1-(2-pyridinyl)-1H-pyrazol-5-yl]amino]benzoic acid (45% yield).

mp: 192–193° C. (recrystallized from ethyl acetate). NMR (CDCl$_3$) δ: 2.98 (3H, s), 7.22–7.29 (1H, m), 7.34–7.43 (1H, m), 7.78 (1H, dd, J=2.2 Hz, 10.4 Hz), 7.89–7.98 (1H, m), 8.41 (1H, dd, J=6.0 Hz, 9.2 Hz), 8.67–8.70 (1H, m), 8.77 (1H, d, J=8.4 Hz). Elementary Analysis: for C$_{16}$H$_{10}$ClFN$_4$ Calcd. : C, 61.45; H, 3.22; N, 17.92; Cl, 11.34; F, 6.08. Found: C, 61.48; H, 3.20; N, 18.13; Cl, 11.14; F, 6.10.

EXAMPLE 2-83

7-Fluoro-3-methyl-1-(2-pyridinyl)-1,9-dihydro-4H-pyrazolo[3,4-b]quinolin-4-one Following the procedure described in Example 2-13, the title compound was prepared from 4-chloro-7-fluoro-3-methyl-1-(2-pyridinyl)-1H-pyrazolo[3,4-b]quinoline (73% yield).

mp: 260–261° C. (recrystallized from ethanol). NMR (DMSO-d$_6$) δ: 2.60 (3H, s), 7.12–7.22 (1H, m), 7.41 (1H, ddd, J=1.2 Hz, 4.8 Hz, 7.4 Hz), 7.87–7.96 (2H, m), 8.06 (1H, ddd, J=1.8 Hz, 7.4 Hz, 8.4 Hz), 8.24 (1H, dd, J=6.6 Hz, 8.8 Hz), 8.60 (1H, ddd, J=1.2 Hz, 1.8 Hz, 4.8 Hz), 12.01 (1H, br s). Elementary Analysis: for C$_{16}$H$_{11}$FN$_4$O Calcd.: C, 65.30; H, 3.77; N, 19.04; F, 6.46. Found: C, 65.34; H, 3.71; N, 19.15; F, 6.44.

EXAMPLE 2-84

4-Chloro-8-fluoro-3-methyl-1-(2-pyridinyl)-1H-pyrazolo[3,4-b]quinoline

Following the procedures described in Reference Example 2-5 and Example 2-1, the title compound was prepared from 3-fluoro-2-iodobenzoic acid and 3-methyl-1-(2-pyridinyl)-1H-pyrazol-5-ylamine (36% yield).

mp: 191° C. (recrystallized from ethyl acetate). NMR (CDCl$_3$) δ: 3.01 (3H, s), 7.26 (1H, ddd, J=1.2 Hz, 4.8 Hz, 7.4 Hz), 7.45–7.59 (2H, m), 7.97 (1H, ddd, J=1.2 Hz, 7.4 Hz, 8.4 Hz), 8.15–8.23 (1H, m), 8.68 (1H, ddd, J=0.8 Hz, 1.8 Hz, 4.8 Hz), 8.92 (1H, ddd, J=0.8 Hz, 1.2 Hz, 8.4 Hz). Elementary Analysis: for C$_{16}$H$_{10}$ClFN$_4$ Calcd.: C, 61.45; H, 3.22; N, 17.92; Cl, 11.34; F, 6.08. Found: C, 61.23; H, 3.33; N, 17.85; Cl, 11.21; F, 6.10.

EXAMPLE 2-85

8-Fluoro-3-methyl-1-(2-pyridinyl)-1,9-dihydro-4H-pyrazolo[3,4-b]quinolin-4-one Following the procedure described in Example 2-13, the title compound was prepared from 4-chloro-8-fluoro-3-methyl-1-(2-pyridinyl)-1H-pyrazolo[3,4-b]quinoline (82% yield).

mp: 241° C. (recrystallized from ethanol). NMR (DMSO-d$_6$) δ: 2.56 (3H, s), 7.24–7.42 (2H, m), 7.67 (1H, ddd, J=1.4 Hz, 8.0 Hz, 11.0 Hz), 7.87 (1H, d, J=8.0 Hz), 7.97 (1H, d, J=8.0 Hz), 8.07 (1H, ddd, J=1.8 Hz, 7.2 Hz, 8.4 Hz), 8.56–8.59 (1H, m), 11.45 (1H, br s). Elementary Analysis: for $C_{16}H_{11}FN_4O$ Calcd. : C, 65.30; H, 3.77; N, 19.04; F, 6.46. Found: C, 65.10; H, 3.74; N, 18.95; F, 6.43.

EXAMPLE 2-86

6-Bromo-4-chloro-3-methyl-1-(2-pyridinyl)-1H-pyrazolo[3,4-b]quinoline

Following the procedures described in Reference Examples 2-1 and 2-3 and Example 2-1, the title compound was prepared from 2-amino-5-bromobenzoic acid and 2-hydrazinopyridine (24% yield).

mp: 234–235° C. (recrystallized from ethyl acetate/methanol). NMR ($CDCl_3$) δ: 2.98 (3H, s), 7.22–7.29 (1H, m), 7.83–7.99 (3H, m), 8.05 (1H, d, J=9.2 Hz), 8.67–8.70 (1H, m), 8.75 (1H, d, J=8.4 Hz). Elementary Analysis: for $C_{16}H_{10}BrClN_4$ Calcd.: C, 51.43; H, 2.70; N, 15.00; Br, 21.39; Cl, 9.49. Found: C, 51.20; H, 2.85; N, 15.12; Br, 21.22; Cl, 9.37.

EXAMPLE 2-87

6-Bromo-3-methyl-1-(2-pyridinyl)-1,9-dihydro-4H-pyrazolo[3,4-b]quinolin-4-one

Following the procedure described in Example 2-13, the title compound was prepared from 6-bromo-4-chloro-3-methyl-1-(2-pyridinyl)-1H-pyrazolo[3,4-b]quinoline (92% yield).

mp: 240–242° C. (recrystallized from ethanol/tetrahydrofuran). NMR ($CDCl_3$) δ: 2.74 (3H, s), 7.20–7.24 (1H, m), 7.33 (1H, d, J=8.8 Hz), 7.71 (1H, dd, J=1.8 Hz, 8.4 Hz), 7.86–7.95 (1H, m), 8.01 (1H, d, J=8.4 Hz), 8.48 (1H, d, J=5.8 Hz), 8.56 (1H, d, J=1.8 Hz), 11.51 (1H, br s). Elementary Analysis: for $C_{16}H_{11}BrN_4O.0.5H_2O$ Calcd.: C, 52.77; H, 3.32; N, 15.38; Br, 21.94. Found: C, 52.81; H, 3.36; N, 15.09; Br, 21.92.

EXAMPLE 2-88

4-Chloro-5,6-difluoro-3-methyl-1-(2-pyridinyl)-1H-pyrazolo[3,4-b]quinoline

Following the procedure described in Example 2-1, the title compound was prepared from 5,6-difluoro-2-[[3-methyl-1-(2-pyridinyl)-1H-pyrazol-5-yl]amino]benzoic acid (78% yield).

mp: 240–242° C. (recrystallized from ethyl acetate). NMR ($CDCl_3$) δ: 3.01 (3H, s), 7.22–7.31 (1H, m), 7.60–7.76 (1H, m), 7.88–8.03 (2H, m), 8.67–8.72 (2H, m). Elementary Analysis: for $C_{16}H_9ClF_2N_4$ Calcd.: C, 58.11; H, 2.74; N, 16.94; Cl, 10.72; F, 11.49. Found: C, 58.17; H, 2.93; N, 17.11; Cl, 10.56; F, 11.56.

EXAMPLE 2-89

5,6-Difluoro-3-methyl-1-(2-pyridinyl)-1,9-dihydro-4H-pyrazolo[3,4-b]quinolin-4-one Following the procedure described in Example 2-13, the title compound was prepared from 4-chloro-5,6-difluoro-3-methyl-1-(2-pyridinyl)-1H-pyrazolo[3,4-b]quinoline (86% yield).

mp: 300–303° C. (recrystallized from ethanol). NMR (DMSO-$d_6$) δ: 3.34 (3H, s), 7.36–7.43 (1H, m), 7.71–7.94 (3H, m), 8.00–8.10 (1H, m), 8.56–8.60 (1H, m), 11.91 (1H, s). Elementary Analysis: for $C_{16}H_{10}F_2N_4O$ Calcd.: C, 61.54; H, 3.23; N, 17.94; F, 12.17. Found: C, 61.60; H, 3.33; N, 18.24; F, 12.24.

EXAMPLE 2-90

4-Chloro-6,7-difluoro-3-methyl-1-(2-pyridinyl)-1H-pyrazolo[3,4-b]quinoline

A solution of 4,5-difluoro-2-[[3-methyl-1-(2-pyridinyl)-1H-pyrazol-5-yl]amino]benzoic acid (8.14 g, 24.6 mmol) in phosphorous oxychloride (13 mL, 138 mmol) was heated under reflux for 1.5 hours. The solution was cooled to room temperature and concentrated under reduced pressure, and the residue was poured into iced water. The solution was neutralized by the addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform) to give the title compound (4.42 g, 54% yield).

mp: 175–176° C. (recrystallized from ethyl acetate). NMR ($CDCl_3$) δ: 2.98 (3H, s), 7.23–7.30 (1H, m), 7.87–7.98 (2H, m), 8.13 (1H, dd, J=8.6 Hz, 10.8 Hz), 8.67–8.72 (2H, m). Elementary Analysis: for $C_{16}H_9ClF_2N_4$ Calcd.: C, 58.11; H, 2.74; N, 16.94; Cl, 10.72; F, 11.49. Found: C, 57.71; H, 2.77; N, 16.90; Cl, 10.50; F, 11.17.

EXAMPLE 2-91

6,7-Difluoro-3-methyl-1-(2-pyridinyl)-1,9-dihydro-4H-pyrazolo[3,4-b]quinolin-4-one To a solution of 4-chloro-6,7-difluoro-3-methyl-1-(2-pyridinyl)-1H-pyrazolo[3,4-b]quinoline (2.21 g, 6.68 mmol) in ethanol (120 mL), 6N hydrochloric acid (6 mL, 36.0 mmol) was added and the mixture was heated under reflux for 3 hours. The solution was allowed to cool to room temperature, and the resulting crystals were collected by filtration. The crystals were washed with ethanol and air dried to give the title compound (2.08 g, 99% yield).

mp: 274–277° C. (recrystallized from ethanol). NMR (DMSO-$d_6$) δ: 2.57 (3H, s), 7.40 (1H, ddd, J=1.0 Hz, 5.2 Hz, 7.4 Hz), 7.84–8.11 (3H, m), 8.17 (1H, dd, J=7.0 Hz, 12.4 Hz), 8.57–8.60 (1H, m), 12.04 (1H, s). Elementary Analysis: for $C_{16}H_{10}F_2N_4O$ Calcd.: C, 61.54; H, 3.23; N, 17.94; F, 12.17. Found: C, 61.45; H, 3.00; N, 17.77; F, 12.20.

EXAMPLE 2-92

6,7-Difluoro-3-methyl-1-(2-pyridinyl)-1,9-dihydro-4H-pyrazolo[3,4-b]quinolin-4-one monohydrate A suspension of 6,7-difluoro-3-methyl-1-(2-pyridinyl)-1,9-dihydro-4H-pyrazolo[3,4-b]quinolin-4-one (20.00 g, 64 mmol) in ethanol (200 mL) and water (200 mL) was heated under reflux for 6 hours. The suspension was allowed to cool to room temperature, and the resulting crystals were collected by filtration. The crystals were washed with water and air dried to give the title compound (20.77 g, 98% yield).

mp: 273–275° C. NMR (DMSO-$d_6$) δ: 2.57 (3H, s), 7.40 (1H, ddd, J=1.0 Hz, 5.2 Hz, 7.4 Hz), 7.84–8.11 (3H, m), 8.17 (1H, dd, J=7.0 Hz, 12.4 Hz), 8.57–8.60 (1H, m), 12.04 (1H, s). Elementary Analysis: for $C_{16}H_{10}F_2N_4O.H_2O$ Calcd.: C, 58.18; H, 3.66; N, 16.96; F, 11.50. Found: C, 58.40; H, 3.74; N, 17.09; F, 11.49.

EXAMPLE 2-93

6,7-Difluoro-3-methyl-9-propyl-1-(2-pyridinyl)-1,9-dihydro-4H-pyrazolo[3,4-b]quinolin-4-one Following the procedure described in Example 2-16, the title compound was prepared from 6,7-difluoro-3-methyl-1-

(2-pyridinyl)-1,9-dihydro-4H-pyrazolo[3,4-b]quinolin-4-one and 1-iodopropane (11% yield).

mp: 198–200° C. (recrystallized from ethyl acetate/hexane). NMR (CDCl$_3$) δ: 0.55 (3H, t, J=7.6 Hz), 1.52–1.70 (2H, m), 2.72 (3H, s), 3.95 (2H, t, J=7.6 Hz), 7.26 (1H, dd, J=6.0 Hz, 12.2 Hz), 7.45 (1H, ddd, J=1.2 Hz, 4.8 Hz, 7.4 Hz), 7.78 (1H, ddd, J=0.8 Hz, 1.2 Hz, 8.0 Hz), 8.00 (1H, ddd, J=1.8 Hz, 7.4 Hz, 8.0 Hz), 8.31 (1H, dd, J=9.2 Hz, 10.8 Hz), 8.58 (1H, ddd, J=0.8 Hz, 1.8 Hz, 4.8 Hz). Elementary Analysis: for C$_{19}$H$_{16}$F$_2$N$_4$O Calcd.: C, 64.40; H, 4.55; N, 15.81; F, 10.72. Found: C, 64.34; H, 4.35; N, 15.67; F, 10.75.

EXAMPLE 2-94

6,7-Difluoro-3-methyl-4-propoxy-1-(2-pyridinyl)-1H-pyrazolo[3,4-b]quinoline

Following the procedure described in Example 2-16, from 6,7-difluoro-3-methyl-1-(2-pyridinyl)-1,9-dihydro-4H-pyrazolo[3,4-b]quinolin-4-one and 1-iodopropane was prepared the title compound (27% yield).

mp: 162–163° C. (recrystallized from ethyl acetate/hexane). NMR (CDCl$_3$) δ: 1.20 (3H, t, J=7.4 Hz), 1.97–2.14 (2H, m), 2.90 (3H, s), 4.31 (2H, t, J=6.8 Hz), 7.23 (1H, ddd, J=1.0 Hz, 4.8 Hz, 7.4 Hz), 7.82–8.00 (3H, m), 8.67 (1H, ddd, J=0.8 Hz, 1.8 Hz, 4.8 Hz), 8.78 (1H, ddd, J=0.8 Hz, 1.0 Hz, 8.2 Hz). Elementary Analysis: for C$_{19}$H$_{16}$F$_2$N$_4$O Calcd.: C, 64.40; H, 4.55; N, 15.81; F, 10.72. Found: C, 64.49; H, 4.51; N, 15.80; F, 10.58.

EXAMPLE 2-95

6,7-Difluoro-4-isopropoxy-3-methyl-1-(2-pyridinyl)-1H-pyrazolo[3,4-b]quinoline

Following the procedure described in Example 2-16, the title compound was prepared from 6,7-difluoro-3-methyl-1-(2-pyridinyl)-1,9-dihydro-4H-pyrazolo[3,4-b]quinolin-4-one and 2-iodopropane (42% yield).

mp: 159–160° C. (recrystallized from ethyl acetate). NMR (CDCl$_3$) δ: 1.48 (6H, d, J=6.2 Hz), 2.90 (3H, s), 4.76–4.89 (1H, m), 7.20–7.27 (1H, m), 7.82–8.00 (3H, m), 8.67 (1H, dd, J=1.0 Hz, 4.8 Hz), 8.79 (1H, d, J=8.6 Hz). Elementary Analysis: for C$_{19}$H$_{16}$F$_2$N$_4$O Calcd.: C, 64.40; H, 4.55; N, 15.81. Found: C, 64.33; H, 4.39; N, 15.75.

EXAMPLE 2-96

4,7-Dichloro-6-fluoro-3-methyl-1-(2-pyridinyl)-1H-pyrazolo[3,4-b]quinoline

Following the procedure described in Example 2-1, the title compound was prepared from 4-chloro-5-fluoro-2-[[3-methyl-1-(2-pyridinyl)-1H-pyrazol-5-yl]amino]benzoic acid (22% yield).

mp: 214–215° C. (recrystallized from ethyl acetate). NMR (CDCl$_3$) δ: 2.97 (3H, s), 7.22–7.29 (1H, m), 7.89–7.98 (1H, m), 8.07 (1H, d, J=10.0 Hz), 8.26 (1H, d, J=6.8 Hz), 8.66–8.73 (2H, m). Elementary Analysis: for C$_{16}$H$_9$Cl$_2$FN$_4$ Calcd.: C, 55.35; H, 2.61; N, 16.14. Found: C, 55.37; H, 2.60; N, 15.86.

EXAMPLE 2-97

7-Chloro-6-fluoro-3-methyl-1-(2-pyridinyl)-1,9-dihydro-4H-pyrazolo[3,4-b]quinolin-4-one Following the procedure described in Example 2-13, the title compound was prepared from 4,7-dichloro-6-fluoro-3-methyl-1-(2-pyridinyl)-1H-pyrazolo[3,4-b]quinoline (61% yield).

mp: 264–265° C. (recrystallized from ethanol). NMR (DMSO-d$_6$) δ: 2.56 (3H, s), 7.37–7.43 (1H, m), 7.83–7.94 (2H, m), 8.06 (1H, dt, J=1.0 Hz, 7.9 Hz), 8.41 (1H, d, J=6.6 Hz), 8.57 (1H, d, J=4.8 Hz), 12.03 (1H, br s). Elementary Analysis: for C$_{16}$H$_{10}$ClFN$_4$O.0.25H$_2$O Calcd.: C, 57.67; H, 3.18; N, 16.81. Found: C, 57.66; H, 3.23; N, 16.86.

EXAMPLE 2-98

4,6-Dichloro-7-fluoro-3-methyl-1-(2-pyridinyl)-1H-pyrazolo[3,4-b]quinoline

Following the procedure described in Example 2-1, the title compound was prepared from 5-chloro-4-fluoro-2-[[3-methyl-1-(2-pyridinyl)-1H-pyrazol-5-yl]amino]benzoic acid (58% yield).

mp: 211° C. (recrystallized from ethyl acetate). NMR (CDCl$_3$) δ: 2.98 (3H, s), 7.23–7.30 (1H, m), 7.88 (1H, d, J=10.2 Hz), 7.94 (1H, ddd, J=1.8 Hz, 7.4 Hz, 8.4 Hz), 8.46 (1H, d, J=7.6 Hz), 8.67–8.72 (2H, m). Elementary Analysis: for C$_{16}$H$_9$Cl$_2$FN$_4$ Calcd.: C, 55.35; H, 2.61; N, 16.14; Cl, 20.42; F, 5.47. Found: C, 55.33; H, 2.35; N, 16.15; Cl, 20.31; F, 5.35.

EXAMPLE 2-99

6-Chloro-7-fluoro-3-methyl-1-(2-pyridinyl)-1,9-dihydro-4H-pyrazolo[3,4-b]quinolin-4-one Following the procedure described in Example 2-13, the title compound was prepared from 4,6-dichloro-7-fluoro-3-methyl-1-(2-pyridinyl)-1H-pyrazolo[3,4-b]quinoline (79% yield).

mp: 284° C. (recrystallized from ethanol). NMR (DMSO-d$_6$) δ: 2.54 (3H, s), 7.40 (1H, ddd, J=1.0 Hz, 4.8 Hz, 7.4 Hz), 7.84 (1H, d, J=8.4 Hz), 8.05 (1H, ddd, J=1.8 Hz, 7.4 Hz, 8.4 Hz), 8.09 (1H, d, J=9.0 Hz), 8.14 (1H, d, J=6.6 Hz), 8.56 (1H, ddd, J=0.8 Hz, 1.8 Hz, 4.8 Hz), 12.02 (1H, br s). Elementary Analysis: for C$_{16}$H$_{10}$ClFN$_4$O Calcd.: C, 58.46; H, 3.07; N, 17.04; Cl, 10.78; F, 5.78. Found: C, 58.38; H, 2.97; N, 17.14; Cl, 10.76; F, 5.76.

EXAMPLE 2-100

3-Methyl-1-(2-pyridinyl)-1H-pyrazolo[3,4-b]quinoline

To a solution of 4-chloro-3-methyl-1-(2-pyridinyl)-1H-pyrazolo[3,4-b]quinoline (1.0 g, 3.39 mmol) in ethanol (30 mL), 5% palladium-carbon (0.8 g, 50% hydrate) was added and the mixture was stirred at room temperature under hydrogen atmosphere for 1 hour. The solution was filtered to remove the catalyst, and the filtrate was concentrated under reduced pressure, and the residue thus obtained was purified by silica gel column chromatography (ethyl acetate:hexane=6:4) to give the title compound (380 mg, 43% yield).

mp: 153–154° C. (recrystallized from ethyl acetate/hexane). NMR (CDCl$_3$) δ: 2.82 (3H, s), 7.18–7.25 (1H, m), 7.48–7.56 (1H, m), 7.76–7.85 (1H, m), 7.89–8.05 (2H, m), 8.21 (1H, d, J=8.4 Hz), 8.59 (1H, s), 8.65–8.70 (1H, m), 8.94 (1H, d, J=8.4 Hz).

EXAMPLE 2-101

3,4-Dimethyl-1-(2-pyridinyl)-1H-pyrazolo[3,4-b]quinoline

A solution of o-bromoacetophenone (1.09 g, 5.5 mmol), 3-methyl-1-phenyl-1H-pyrazol-5-ylamine (0.87 g, 5.0 mmol), copper acetate (II) (91 mg, 0.5 mmol) and potassium carbonate (0.76 g, 5.5 mmol) in N,N-dimethylformamide (5 mL) was heated under reflux under an argon atmosphere for 1 hour. The solution was cooled to room temperature, and poured into water. The solution was made basic by the addition of a sodium bicarbonate solution, and the organic matter was extracted with ethyl acetate. The extract was washed with saturated brine and water, and dried over anhydrous magnesium sulfate, and the solvent was evaporated under reduced pressure. The residue thus obtained was purified by silica gel column chromatography (hexane:ethyl acetate=1:1) to give the title compound (0.21 g, 15% yield).

mp: 157–159° C. (recrystallized from ethyl acetate/ diethyl ether).

NMR (CDCl$_3$) δ: 2.97 (3H, s), 3.13 (3H, s), 7.17–7.24 (1H, m), 7.48–7.57 (1H, m), 7.73–7.82 (1H, m), 7.88–7.98 (1H, m), 8.14–8.24 (2H, m), 8.65–8.69 (1H, m), 8.96 (1H, d, J=8.6 Hz). Elementary Analysis: for $C_{17}H_{14}N_4$ Calcd.: C, 74.43; H, 5.14; N, 20.42. Found: C, 74.28; H, 5.13; N, 20.56.

EXAMPLE 2-102

4-Ethyl-3-methyl-1-(2-pyridinyl)-1H-pyrazolo[3,4-b]quinoline

To an ice-cold solution of 4-chloro-3-methyl-1-(2-pyridinyl)-1H-pyrazolo[3,4-b]quinoline (2.95 g, 10.0 mmol) in tetrahydrofuran (100 mL), a solution of 3M ethylmagnesium bromide in diethyl ether (4.00 mL, 12.0 mmol) was added dropwise under an argon atmosphere, and the solution was stirred at the same temperature for 1 hour. The reaction mixture was poured into iced water, and the organic matter was extracted with ethyl acetate. The extract was washed with saturated brine and dried over anhydrous magnesium sulfate, and the solvents were evaporated under reduced pressure. The residue thus obtained was purified by basic silica gel column chromatography (hexane:ethyl acetate= 2:1) to give the title compound (0.33 g, 11% yield).

mp: 112–114° C. (recrystallized from ethyl acetate/ hexane).

NMR (CDCl$_3$) δ: 1.49 (3H, t, J=7.6 Hz), 2.96 (3H, s), 3.59 (2H, q, J=7.6 Hz), 7.20 (1H, ddd, J=1.0 Hz, 4.8 Hz, 7.4 Hz), 7.52 (1H, ddd, J=1.4 Hz, 6.6 Hz, 8.8 Hz), 7.77 (1H, ddd, J=1.4 Hz, 6.6 Hz, 8.8 Hz), 7.93 (1H, ddd, J=1.8 Hz, 7.4 Hz, 8.4 Hz), 8.18 (1H, dd, J=1.4 Hz, 8.8 Hz), 8.23 (1H, dd, J=1.4 Hz, 8.8 Hz), 8.67 (1H, ddd, J=0.8 Hz, 1.8 Hz, 4.8 Hz), 8.97 (1H, ddd, J=0.8 Hz, 1.0 Hz, 8.4 Hz). Elementary Analysis: for $C_{18}H_{16}N_4 \cdot 0.25H_2O$ Calcd.: C, 73.82; H, 5.68; N, 19.13. Found: C, 73.67; H, 5.74; N, 19.24.

EXAMPLE 2-103

3-Methyl-4-propyl-1-(2-pyridinyl)-1H-pyrazolo[3,4-b]quinoline

Following the procedure described in Example 2-102, the title compound was prepared from 4-chloro-3-methyl-1-(2-pyridinyl)-1H-pyrazolo[3,4-b]quinoline and a solution of 2M propylmagnesium chloride in diethylether (16% yield).

mp: 108–109° C. (recrystallized from ethyl acetate/ hexane). NMR (CDCl$_3$) δ: 1.16 (3H, t, J=7.4 Hz), 1.78–1.97 (2H, m), 2.95 (3H, s), 3.50–3.58 (2H, m), 7.20 (1H, ddd, J=0.8 Hz, 4.8 Hz, 7.4 Hz), 7.51 (1H, ddd, J=1.2 Hz, 6.6 Hz, 8.8 Hz), 7.77 (1H, ddd, J=1.2 Hz, 6.6 Hz, 8.6 Hz), 7.93 (1H, ddd, J=1.8 Hz, 7.4 Hz, 8.4 Hz), 8.15 (2H, m), 8.67 (1H, ddd, J=0.8 Hz, 1.8 Hz, 4.8 Hz), 8.97 (1H, td, J=0.8 Hz, 8.4 Hz). Elementary Analysis: for $C_{19}H_{18}N_4$ Calcd.: C, 75.47; H, 6.00; N, 18.53. Found: C, 75.18; H, 5.84; N, 18.59.

EXAMPLE 2-104

4-Butyl-3-methyl-1-(2-pyridinyl)-1H-pyrazolo[3,4-b]quinoline

Following the procedure described in Example 2-102, the title compound was prepared from 4-chloro-3-methyl-1-(2-pyridinyl)-1H-pyrazolo[3,4-b]quinoline and a solution of 2M butylmagnesium chloride in tetrahydrofuran (15% yield).

mp: 102–103° C. (recrystallized from ethyl acetate/ hexane). NMR (CDCl$_3$) δ: 1.04 (3H, t, J=7.2 Hz), 1.52–1.66 (2H, m), 1.70–1.89 (2H, m), 2.95 (3H, s), 3.51–3.59 (2H, m), 7.20 (1H, ddd, J=1.2 Hz, 4.8 Hz, 7.4 Hz), 7.51 (1H, ddd, J=1.4 Hz, 6.6 Hz, 8.8 Hz), 7.76 (1H, ddd, J=1.4 Hz, 6.6 Hz, 8.8 Hz), 7.93 (1H, ddd, J=1.8 Hz, 7.4 Hz, 8.4 Hz), 8.14–8.24 (2H, m), 8.66 (1H, ddd, J=0.8 Hz, 1.8 Hz, 4.8 Hz), 8.97 (1H, ddd, J=0.8 Hz, 1.2 Hz, 8.4 Hz). Elementary Analysis: for $C_{20}H_{20}N_4$ Calcd.: C, 75.92; H, 6.37; N, 17.71. Found: C, 75.74; H, 6.15; N, 17.82.

EXAMPLE 2-105

4-Isobutyl-3-methyl-1-(2-pyridinyl)-1H-pyrazolo[3,4-b]quinoline

Following the procedure described in Example 2-102, the title compound was prepared from 4-chloro-3-methyl-1-(2-pyridinyl)-1H-pyrazolo[3,4-b]quinoline and a solution of 1M isobutylmagnesium bromide in tetrahydrofuran (11% yield).

mp: 87–88° C. (recrystallized from ethyl acetate/hexane). NMR (CDCl$_3$) δ: 1.04 (6H, d, J=6.6 Hz), 2.13–2.27 (1H, m), 2.96 (3H, s), 3.46 (2H, d, J=7.4 Hz), 7.21 (1H, ddd, J=1.0 Hz, 4.8 Hz, 7.4 Hz), 7.50 (1H, ddd, J=1.4 Hz, 6.6 Hz, 8.6 Hz), 7.77 (1H, ddd, J=1.4 Hz, 6.6 Hz, 8.6 Hz), 7.93 (1H, ddd, J=1.8 Hz, 7.4 Hz, 8.4 Hz), 8.15–8.24 (2H, m), 8.67 (1H, ddd, J=0.8 Hz, 1.8 Hz, 4.8 Hz), 8.97 (1H, ddd, J=0.8 Hz, 1.0 Hz, 8.4 Hz). Elementary Analysis: for $C_{20}H_{20}N_4 \cdot H_2O$ Calcd.: C, 71.83; H, 6.63; N, 16.75. Found: C, 71.92; H, 6.66; N, 16.80.

EXAMPLE 2-106

3-Methyl-4-pentyl-1-(2-pyridinyl)-1H-pyrazolo[3,4-b]quinoline

Following the procedure described in Example 2-102, the title compound was prepared from 4-chloro-3-methyl-1(2-pyridinyl)-1H-pyrazolo[3,4-b]quinoline and a solution of 1M pentylmagnesium bromide in tetrahydrofuran (24% yield).

mp: 121–122° C. (recrystallized from ethyl acetate/ hexane). NMR (CDCl$_3$) δ: 0.95 (3H, t, J=7.0 Hz), 1.33–1.92 (6H, m), 2.95 (3H, s), 3.50–3.59 (2H, m), 7.17–7.27 (1H, m), 7.48–7.57 (1H, m), 7.72–7.82 (1H, m), 7.88–7.98 (1H, m), 8.14–8.24 (2H, m), 8.64–8.69 (1H, m), 8.95–9.00 (1H, m) Elementary Analysis: for $C_{21}H_{22}N_4$ Calcd.: C, 76.33; H, 6.71; N, 16.96. Found: C, 76.16; H, 6.89; N, 17.23.

EXAMPLE 2-107

3-Methyl-1-(2-pyridinyl)-1H-pyrazolo[3,4-b] quinoline-4-carbonitrile

A solution of 4-chloro-3-methyl-1-(2-pyridinyl)-1H-pyrazolo[3,4-b]quinoline (5.89 g, 20.0 mmol), potassium cyanide (2.04 g, 31.3 mmol) and 18-crown-6 (6.96 g, 26.3 mmol) in tetrahydrofuran (90 mL) and acetonitrile (90 mL)

was heated under reflux for 8 hours. The solution was allowed to cool to room temperature, and poured into water. The solution was made weakly basic by the addition of a sodium hydroxide solution, and extracted with chloroform. The extract was washed with saturated brine and dried over anhydrous sodium sulfate, and the solvents were evaporated under reduced pressure. The residue thus obtained was purified by silica gel column chromatography (chloroform) to give crude crystals. The crude crystals were recrystallized from ethyl acetate to give the title compound (2.86 g, 50% yield).

mp: 210–211° C. (recrystallized from ethyl acetate). NMR (CDCl$_3$) δ: 3.04 (3H, s), 7.28–7.33 (1H, m), 7.70–7.78 (1H, m), 7.88–8.02 (2H, m), 8.29 (1H, d, J=8.8 Hz), 8.38 (1H, dd, J=0.8 Hz, 7.6 Hz), 8.69–8.77 (2H, m). Elementary Analysis: for C$_{17}$H$_{11}$N$_5$ Calcd.: C, 71.57; H, 3.89; N, 24.55. Found: C, 71.44; H, 3.68; N, 24.49.

EXAMPLE 2-108

3-Methyl-1-(2-pyridinyl)-1H-pyrazolo[3,4-b] quinoline-4-carboxamide

A solution of 3-methyl-1-(2-pyridinyl)-1H-pyrazolo[3,4-b]quinoline-4-carbonitrile (0.30 g, 1.1 mmol) and conc. sulfuric acid (1.0 mL) in acetic acid (6.0 mL) was heated under reflux for 31.5 hours. The solution was allowed to cool to room temperature, and poured into iced water. The resulting solution was neutralized with an aqueous sodium hydroxide solution, and extracted with chloroform. The extract was washed with saturated brine and dried over anhydrous sodium sulfate, and the solvent was evaporated under reduced pressure. The residue thus obtained was recrystallized from methanol/isopropylether to give the title compound (0.14 g, 44% yield).

mp: >300° C. (recrystallized from methanol/isopropylether). NMR (CDCl$_3$: CF$_3$CO$_2$D=50:1) δ: 2.80 (3H, s), 7.56–7.66 (1H, m), 7.75–7.84 (1H, m), 8.00–8.09 (1H, m), 8.23 (2H, d, J=9.8 Hz), 8.42–8.51 (1H, m), 8.63–8.72 (2H, m), hidden (2H). Elementary Analysis: for C$_{17}$H$_{13}$N$_5$O Calcd.: C, 67.32; H, 4.32; N, 23.09. Found: C, 67.15; H, 4.34; N, 22.97.

EXAMPLE 2-109

4-Chloro-1-(6-chloro-2-pyridinyl)-3-methyl-1H-pyrazolo[3,4-b]quinoline

Following the procedure described in Example 2-1, the title compound was prepared from 2-[[3-methyl-1-(6-chloro-2-pyridinyl)-1H-pyrazole-5-yl]amino]benzoic acid (35% yield).

mp: 191–193° C. (recrystallized from ethyl acetate/methanol). NMR (CDCl$_3$) δ: 2.99 (3H, s), 7.25–7.29 (1H, m), 7.58–7.66 (1H, m), 7.80–7.88 (1H, m), 7.91 (1H, d, J=8.0 Hz), 8.17 (1H, d, J=8.8 Hz), 8.39–8.44 (1H, m), 8.83 (1H, dd, J=0.8 Hz, 8.0 Hz). Elementary Analysis: for C$_{16}$H$_{10}$Cl$_2$N$_4$ Calcd.: C, 58.38; H, 3.06; N, 17.02; Cl, 21.54. Found: C, 58.43; H, 3.07; N, 17.03; Cl, 21.54.

EXAMPLE 2-110

1-(6-Chloro-2-pyridinyl)-3-methyl-1,9-dihydro-4H-pyrazolo[3,4-b]quinolin-4-one

Following the procedure described in Example 2-31, the title compound was prepared from 4-chloro-1-(6-chloro-2-pyridinyl)-3-methyl-1H-pyrazolo[3,4-b]quinoline (18% yield).

mp: 251–253° C. (recrystallized from methanol). NMR (DMSO-d$_6$) δ: 2.61 (3H, s), 7.35 (1H, t, J=7.4 Hz), 7.52 (1H, d, J=7.4 Hz), 7.69–7.82 (2H, m), 7.89 (1H, d, J=8.0 Hz), 8.11 (1H, t, J=8,0 Hz), 8.22 (1H, d, J=8.6 Hz), 11.44 (1H, br s). Elementary Analysis: for C$_{16}$H$_{11}$ClN$_4$O Calcd.: C, 61.84; H, 3.57; N, 18.03; Cl, 11.41. Found: C, 61.64; H, 3.62; N, 17.78; Cl, 11.18.

EXAMPLE 2-111

4-Chloro-1-(6-ethoxy-2-pyridinyl)-3-methyl-1H-pyrazolo[3,4-b]quinoline

Following the procedure described in Reference Example 2-4, 1-(6-ethoxy-2-pyridinyl)-3-methyl-1H-pyrazol-5-ylamine was prepared from 6-ethoxy-2-hydrazinopyridine which was prepared from 2-chloro-6-ethoxypyridine following the method described in Reference Example 2-2. Subsequently, following the methods described in Reference Example 2-5 and Example 2-1, the title compound was prepared from o-iodobenzoic acid and 1-(6-ethoxy-2-pyridinyl)-3-methyl-1H-pyrazol-5-ylamine (36% yield).

mp: 212–215° C. (recrystallized from ethyl acetate/methanol). NMR (DMSO-d$_6$) δ: 1.62 (3H, t, J=7.1 Hz), 2.75 (3H, s), 4.49 (2H, q, J=7.1 Hz), 6.66 (1H, dd, J=0.74 Hz, 8.1 Hz), 7.23 (1H, d, J=8.4 Hz), 7.29–7.38 (1H, m), 7.52 (1H, d, J=7.0 Hz), 7.60–7.71 (1H, m), 7.77 (1H, t, J=8.1 Hz), 8.54 (1H, d, J=8.4 Hz).

EXAMPLE 2-112

1-(6-Ethoxy-2-pyridinyl)-3-methyl-1,9-dihydro-4H-pyrazolo[3,4-b]quinolin-4-one

Following the procedure described in Example 2-13, the title compound was prepared from 4-chloro-1-(6-ethoxy-2-pyridinyl)-3-methyl-1H-pyrazolo[3,4-b]quinoline (92% yield).

mp: 231–234° C. (recrystallized from ethanol/diethylether). NMR (DMSO-d$_6$) δ: 1.62 (3H, t, J=7.0 Hz), 2.73 (3H, s), 4.47 (2H, q, J=7.0 Hz), 6.63 (1H, dd, J=0.73 Hz, 8.1 Hz), 7.16 (1H, d, J=7.7 Hz), 7.25–7.34 (1H, m), 7.49 (1H, d, J=7.7 Hz), 7.57–7.66 (1H, m), 7.74 (1H, t, J=8.1 Hz), 8.43 (1H, d, J=8.1 Hz), 11.15 (1H, br s).

EXAMPLE 2-113

4-Chloro-1-(5-chloro-2-pyridinyl)-3-methyl-1H-pyrazolo[3,4-b]quinoline

Following the procedure described in Example 2-1, the title compound was prepared from 2-[[3-methyl-1-(5-chloro-2-pyridinyl)-1H-pyrazol-5-yl]amino]benzoic acid (22% yield).

mp: 216–217° C. (recrystallized from ethyl acetate/methanol). NMR (CDCl$_3$) δ: 2.97 (3H, s), 7.56–7.64 (1H, m), 7.78–7.91 (2H, m), 8.14 (1H, td, J=0.8 Hz, 8.0 Hz), 8.38 (1H, td, J=0.8 Hz, 8.8 Hz), 8.60 (1H, dd, J=0.8 Hz, 2.4 Hz), 8.87 (1H, dd, J=0.8 Hz, 8.8 Hz). Elementary Analysis: for C$_{16}$H$_{10}$Cl$_2$N$_4$ Calcd.: C, 58.38; H, 3.06; N, 17.02; Cl, 21.54. Found: C, 58.28; H, 3.10; N, 16.94; Cl, 21.83.

EXAMPLE 2-114

1-(5-Chloro-2-pyridinyl)-3-methyl-1,9-dihydro-4H-pyrazolo[3,4-b]quinolin-4-one

Following the procedure described in Example 2-31, the title compound was prepared from 4-chloro-1-(5-chloro-2-pyridinyl)-3-methyl-1H-pyrazolo[3,4-b]quinoline (60% yield).

mp: 262–263° C. (recrystallized from methanol). NMR (DMSO-$d_6$) δ: 2.60 (3H, s), 7.34 (1H, t, J=7.6 Hz), 7.68–7.76 (1H, m), 7.88 (1H, d, J=8.8 Hz), 8.00 (1H, t, J=8.4 Hz), 8.14 (1H, dd, J=2.6 Hz, 8.8 Hz), 8.21 (1H, d, J=7.0 Hz), 8.57 (1H, d, J=2.6 Hz), 11.74 (1H, br s). Elementary Analysis: for $C_{16}H_{11}ClN_4O \cdot 0.3H_2O$ Calcd.: C, 60.79; H, 3.70; N, 17.72; Cl, 11.21. Found: C, 60.91; H, 3.82; N, 17.71; Cl, 11.04.

EXAMPLE 2-115

4-Chloro-3-methyl-1-(5-methyl-2-pyridinyl)-1H-pyrazolo[3,4-b]quinoline

Following the procedure described in Example 2-29, the title compound was prepared from anthranilic acid and 2-hydrazino-5-methylpyridine which was previously prepared from 2-bromo-5-methylpyridine (22% yield).

mp: 197–200° C. (recrystallized from ethyl acetate/methanol). NMR (CDCl$_3$) δ: 2.42 (3H, s), 3.00 (3H, s), 7.53–7.64 (1H, m), 7.71–7.87 (2H, m), 8.16 (1H, d, J=8.8 Hz), 8.36–8.43 (1H, m) , 8.46–8.52 (1H, m), 8.66 (1H, d, J=8.8 Hz). Elementary Analysis: for $C_{17}H_{13}ClN_4$ Calcd.: C, 66.13; H, 4.24; N, 18.15. Found: C, 66.16; H, 4.30; N, 18.10.

EXAMPLE 2-116

3-Methyl-1-(5-methyl-2-pyridinyl)-1H-pyrazolo[3,4-b]quinolin-4-ylamine

Following the procedure described in Example 2-2, the title compound was prepared from 4-chloro-3-methyl-1-(5-methyl-2-pyridinyl)-1H-pyrazolo[3,4-b]quinoline and sodium azide (52% yield).

mp: 229–232° C. (recrystallized from ethyl acetate/methanol). NMR (CDCl$_3$) δ: 2.38 (3H, s), 2.87 (3H, s), 5.60 (2H, br s), 7.25–7.38 (1H, m), 7.62–7.74 (2H, m), 7.84 (1H, d, J=8.8 Hz), 8.00 (1H, d, J=8.8 Hz), 8.44 (1H, s), 8.75 (1H, d, J=8.4 Hz). Elementary Analysis: for $C_{17}H_{15}N_5$ Calcd.: C, 70.57; H, 5.23; N, 24.21. Found: C, 70.37; H, 5.51; N, 23.97.

EXAMPLE 2-117

3-Methyl-1-(5-methyl-2-pyridinyl)-1,9-dihydro-4H-pyrazolo[3,4-b]quinolin-4-one hydrochloride Following the procedure described in Example 2-13, the title compound was prepared from 4-chloro-3-methyl-1-(5-methyl-2-pyridinyl)-1H-pyrazolo[3,4-b]quinoline (51% yield).

mp: 227–229° C. (recrystallized from ethanol). NMR (DMSO-$d_6$) δ: 2.38 (3H, s), 2.61 (3H, s), 7.33 (1H, t, J=7.5 Hz), 7.66–7.92 (3H, m), 8.03 (1H, d, J=8.4 Hz), 8.22 (1H, d, J=7.0 Hz), 8.43 (1H, s), 11.85 (1H, s). Elementary Analysis: for $C_{17}H_{14}N_4 \cdot HCl \cdot 0.5H_2O$ Calcd.: C, 60.81; H, 4.80; N, 16.68. Found: C, 60.65; H, 5.25; N, 16.66.

EXAMPLE 2-118

4-Chloro-3-methyl-1-(3-methyl-2-pyridinyl)-1H-pyrazolo[3,4-b]quinoline

Following the procedures described in Reference Example 2-3 and Example 2-1, the title compound was prepared from 2-(2-oxopropyl)-4H-3,1-benzoxazin-4-one and 2-hydrazino-3-methylpyridine (21% yield).

mp: 160–161° C. (recrystallized from ethyl acetate/hexane). NMR (CDCl$_3$) δ: 2.37 (3H, s), 2.98 (3H, s), 7.37 (1H, dd, J=4.8 Hz, 7.6 Hz), 7.52–7.60 (1H, m), 7.72–7.83 (2H, m), 8.05 (1H, td, J=0.8 Hz, 8.8 Hz), 8.39–8.44 (1H, m), 8.54–8.57 (1H, m). Elementary Analysis: for $C_{17}H_{13}ClN_4$ Calcd.: C, 66.13; H, 4.24; N, 18.15; Cl, 11.48. Found: C, 66.13; H, 4.28; N, 18.12; Cl, 11.51.

EXAMPLE 2-119

3-Methyl-1-(3-methyl-2-pyridinyl)-1H-pyrazolo[3,4-b]quinolin-4-ylamine

Following the procedure described in Example 2-2, the title compound was prepared from 4-chloro-3-methyl-1-(3-methyl-2-pyridinyl)-1H-pyrazolo[3,4-b]quinoline and sodium azide (63% yield).

mp: 202–205° C. (recrystallized from ethanol). NMR (CDCl$_3$) δ: 2.35 (3H, s), 2.72 (3H, s), 5.67 (2H, br s), 7.20–7.33 (2H, m), 7.53–7.63 (1H, m), 7.69–7.76 (1H, m), 7.79–7.89 (2H, m), 8.51 (1H, dd, J=1.5 Hz, 4.8 Hz). Elementary Analysis: for $C_{17}H_{15}N_5$ Calcd.: C, 70.57; H, 5.23; N, 24.21. Found: C, 70.53; H, 5.35; N, 23.96.

EXAMPLE 2-120

3-Methyl-1-(3-methyl-2-pyridinyl)-1,9-dihydro-4H-pyrazolo[3,4-b]quinolin-4-one Following the procedure described in Example 2-13, the title compound was prepared from 4-chloro-3-methyl-1-(3-methyl-2-pyridinyl)-1H-pyrazolo[3,4-b]quinoline (49% yield).

mp: 184–185° C. (recrystallized from ethanol). NMR (DMSO-$d_6$) δ: 2.43 (3H, s), 2.60 (3H, s), 7.26–7.34 (1H, m), 7.51 (1H, dd, J=4.8 Hz, 7.6 Hz), 7.62–7.76 (2H, m), 7.96–8.01 (1H, m), 8.21–8.25 (1H, m), 8.51 (1H, dd, J=1.6 Hz, 4.8 Hz), 11.78 (1H, br s). Elementary Analysis: for $C_{17}H_{14}N_4O \cdot 0.2H_2O$ Calcd.: C, 65.46; H, 5.30; N, 17.96. Found: C, 65.47; H, 5.07; N, 17.81.

EXAMPLE 2-121

4-Chloro-3,5-dimethyl-1-(6-ethoxy-2-pyridinyl)-1H-pyrazolo[3,4-b]quinoline

Following the procedure described in Example 2-29, the title compound was prepared from 2-amino-6-methylbenzoic acid and 6-ethoxy-2-hydrazinopyridine which was previously prepared from 2-chloro-6-ethoxypyridine (32% yield).

mp: 146–148° C. (recrystallized from ethyl acetate). NMR (CDCl$_3$) δ: 1.48 (3H, t, J=7.0 Hz), 2.96 (3H, s), 3.13 (3H, s), 4.57 (2H, q, J=7.0 Hz), 6.69 (1H, d, J=8.1 Hz), 7.31 (1H, d, J=7.0 Hz), 7.63 (1H, t, J=7.0 Hz), 7.78 (1H, t, J=7.7 Hz), 7.96 (1H, d, J=7.7 Hz), 8.12 (1H, d, J=8.1 Hz). Elementary Analysis: for $C_{19}H_{17}ClN_4O$ Calcd.: C, 64.68; H, 4.86; N, 15.88. Found: C, 64.62; H, 4.81; N, 16.10.

EXAMPLE 2-122

3,5-Dimethyl-1-(6-ethoxy-2-pyridinyl)-1,9-dihydro-4H-pyrazolo[3,4-b]quinolin-4-one Following the procedure described in Example 2-13, the title compound was prepared from 4-chloro-3,5-dimethyl-1-(6-ethoxy-2-pyridinyl)-1H-pyrazolo[3,4-b]quinoline (90% yield).

mp: 213–215° C. (recrystallized from chloroform). NMR (CDCl$_3$) δ: 1.61 (3H, t, J=7.0 Hz), 2.70 (3H, s), 2.97 (3H, s), 4.45 (2H, q, J=7.0 Hz), 6.62 (1H, dd, J=0.7 Hz, 8.1 Hz), 6.98 (2H, t, J=7.7 Hz), 7.39 (1H, d, J=7.7 Hz), 7.47 (1H, d, J=8.1

Hz), 7.74 (1H, t, J=8.1 Hz), 10.93 (1H, s). Elementary Analysis: for $C_{19}H_{18}N_4O_2 \cdot 0.5H_2O$ Calcd.: C, 66.46; H, 5.58; N, 16.32. Found: C, 67.06; H, 5.43; N, 16.32.

EXAMPLE 2-123

4-Chloro-3,5-dimethyl-1-(3-methyl-2-pyridinyl)-1H-pyrazolo[3,4-b]quinoline

Following the procedure described in Example 2-29, the title compound was prepared from 2-amino-6-methylbenzoic acid and 2-hydrazino-3-methylpyridine (38% yield).

mp: 176–178° C. (recrystallized from methanol/ethyl acetate). NMR (CDCl$_3$) δ: 2.37 (3H, s), 2.97 (3H, s), 3.14 (3H, s), 7.23–7.30 (1H, m), 7.35 (1H, dd, J=4.8 Hz, 7.7 Hz), 7.54 (1H, dd, J=7.0 Hz, 8.8 Hz), 7.75–7.83 (1H, m), 7.85–7.93 (1H, m), 8.51–8.58 (1H, m). Elementary Analysis: for $C_{18}H_{15}ClN_4$ Calcd.: C, 66.98; H, 4.68; N, 17.36. Found: C, 66.94; H, 4.52; N, 17.51.

EXAMPLE 2-124

3,5-Dimethyl-1-(3-methyl-2-pyridinyl)-1H-pyrazolo[3,4-b]quinolin-4-ylamine

Following the procedure described in Example 2-2, the title compound was prepared from 4-chloro-3,5-dimethyl-1-(3-methyl-2-pyridinyl)-1H-pyrazolo[3,4-b]quinoline and sodium azide (65% yield).

mp: 271–274° C. (recrystallized from methanol/chloroform). NMR (CDCl$_3$) δ: 2.36 (3H, s), 2.77 (3H, s), 2.99 (3H, s), 5.83 (2H, br s), 6.95 (1H, d, J=7.0 Hz), 7.25–7.44 (2H, m), 7.64–7.78 (2H, m), 8.48–8.55 (1H, m). Elementary Analysis: for $C_{18}H_{17}N_5$ Calcd.: C, 71.27; H, 5.65; N, 23.09. Found: C, 70.89;. H, 5.56; N, 22.96.

EXAMPLE 2-125

3,5-Dimethyl-1-(3-methyl-2-pyridinyl)-1,9-dihydro-4H-pyrazolo[3,4-b]quinolin-4-one Following the procedure described in Example 2-13, the title compound was prepared from 4-chloro-3,5-dimethyl-1-(3-methyl-2-pyridinyl)-1H-pyrazolo[3,4-b]quinoline (73% yield).

mp: 195–197° C. (recrystallized from ethanol). NMR (CDCl$_3$) δ: 2.71 (3H, s), 2.72 (3H, s), 2.99 (3H, s), 6.98–7.05 (1H, m), 7.28–7.49 (3H, m), 7.80–7.88 (1H, m), 8.39–8.45 (1H, m), 11.50 (1H, br s). Elementary Analysis: for $C_{18}H_{16}N_4O \cdot 2H_2O$ Calcd.: C, 63.52; H, 5.92; N, 16.46. Found: C, 63.77; H, 5.11; N, 16.50.

EXAMPLE 2-126

4-Chloro-3,8-dimethyl-1-(6-methoxy-2-pyridinyl)-1H-pyrazolo[3,4-b]quinoline

Following the procedures described in Reference Example 2-3 and Example 2-1, the title compound was prepared from 8-methyl-2-(2-oxypropyl)-4H-3,1-benzoxazin-4-one and 2-hydrazino-6-methoxypyridine which was previously prepared from and 2-chloro-6-methoxypyridine following the method described in Reference Example 2-2 (75% yield).

mp: 148–151° C. (recrystallized from chloroform/hexane). NMR (CDCl$_3$) δ: 2.87 (3H, s), 2.97 (3H, s), 4.15 (3H, s), 6.69 (1H, d, J=8.1 Hz), 7.47 (1H, dd, J=6.8 Hz, 8.6 Hz), 7.64–7.71 (1H, m), 7.80 (1H, t, J=8.1 Hz), 8.20–8.30 (2H, m). Elementary Analysis: for $C_{18}H_{15}ClN_4O$ Calcd.: C, 63.81; H, 4.46; N, 16.54. Found: C, 63.87; H, 4.44; N, 16.46.

EXAMPLE 2-127

3,8-Dimethyl-1-(6-methoxy-2-pyridinyl)-1H-pyrazolo[3,4-b]quinolin-4-ylamine

Following the procedure described in Example 2-2, the title compound was prepared from 4-chloro-3,8-dimethyl-1-(6-methoxy-2-pyridinyl)-1H-pyrazolo[3,4-b]quinoline and sodium azide (46% yield).

mp: 134–137° C. (recrystallized from ethyl acetate/hexane). NMR (CDCl$_3$) δ: 2.80 (3H, s), 2.86 (3H, s), 4.13 (3H, s), 5.50 (2H, br s), 6.63 (1H, d, J=8.1 Hz), 7.20–7.30 (1H, m), 7.56 (1H, d, J=6.6 Hz), 7.70 (1H, d, J=6.6 Hz), 7.78 (1H, t, J=8.1 Hz), 8.44 (1H, d, J=7.7 Hz). Elementary Analysis: for $C_{18}H_{17}N_5O \cdot H_2O$ Calcd.: C, 64.08; H, 5.68; N, 20.76. Found: C, 64.17; H, 5.43; N, 20.36.

EXAMPLE 2-128

4-Chloro-3,8-dimethyl-1-(6-ethoxy-2-pyridinyl)-1H-pyrazolo[3,4-b]quinoline

Following the procedures described in Reference Example 2-3 and Example 2-1, the title compound was prepared from 8-methyl-2-(2-oxopropyl)-4H-3,1-benzoxazin-4-one and 6-ethoxy-2-hydrazinopyridine which was previously prepared from 2-chloro-6-ethoxypyridine following the method described in Reference Example 2-2 (62% yield).

mp: 151–153° C. (recrystallized from ethyl acetate). NMR (CDCl$_3$) δ: 1.46 (3H, t, J=7.1 Hz), 2.86 (3H, s), 2.96 (3H, s), 4.60 (2H, q, J=7.1 Hz), 6.66 (1H, dd, J=0.73 Hz, 8.1 Hz), 7.46 (1H, q, J=7.0 Hz), 7.63–7.70 (1H, m), 7.79 (1H, t, J=8.1 Hz), 8.15–8.28 (2H, m). Elementary Analysis: for $C_{19}H_{17}ClN_4O$ Calcd.: C, 64.68; H, 4.86; N, 15.88; Cl, 10.05. Found: C, 64.54; H, 5.07; N, 15.69; Cl, 10.04.

EXAMPLE 2-129

3,8-Dimethyl-1-(6-ethoxy-2-pyridinyl)-1H-pyrazolo[3,4-b]quinolin-4-ylamine

Following the procedure described in Example 2-2, the title compound was prepared from 4-chloro-3,8-dimethyl-1-(6-ethoxy-2-pyridinyl)-1H-pyrazolo[3,4-b]quinoline and sodium azide (82% yield).

mp: 184–187° C. (recrystallized from chloroform). NMR (CDCl$_3$) δ: 1.45 (3H, t, J=7.0 Hz), 2.81 (3H, s), 2.87 (3H, s), 4.56 (2H, q, J=7.0 Hz), 5.47 (2H, br s), 6.61 (1H, d, J=8.0 Hz), 7.25 (1H, q, J=7.0 Hz), 7.57 (1H, d, J=7.0 Hz), 7.70 (1H, d, J=8.0 Hz), 7.79 (1H, t, J=8.0 Hz), 8.43 (1H, d, J=8.0 Hz). Elementary Analysis: for $C_{19}H_{19}N_5O$ Calcd.: C, 68.45; H, 5.74; N, 21.01. Found: C, 68.33; H, 6.00; N, 20.95.

EXAMPLE 2-130

3,8-Dimethyl-1-(6-ethoxy-2-pyridinyl)-1,9-dihydro-4H-pyrazolo[3,4-b]quinolin-4-one Following the procedure described in Example 2-13, the title compound was prepared from 4-chloro-3,8-dimethyl-1-(6-ethoxy-2-pyridinyl)-1H-pyrazolo[3,4-b]quinoline (73% yield).

mp: 239–241° C. (recrystallized from chloroform). NMR (CDCl$_3$) δ: 1.51 (3H, t, J=7.0 Hz), 2.52 (3H, s), 2.72 (3H, s), 4.40 (2H, q, J=7.0 Hz), 6.60 (1H, dd, J=0.74 Hz, 8.1 Hz), 7.18 (1H, t, J=8.1 Hz), 7.40–7.48 (1H, m), 7.53 (1H, dd, J=0.74 Hz, 8.1 Hz), 7.73 (1H, t, J=8.1 Hz), 8.30 (1H, d, J=7.3 Hz), 10.9 (1H, br s). Elementary Analysis: for $C_{19}H_{18}N_4O_2$ Calcd.: C, 68.25; H, 5.43; N, 16.76. Found: C, 68.08; H, 5.59; N, 16.60.

EXAMPLE 2-131

4-Chloro-3,8-dimethyl-1-(5-methyl-2-pyridinyl)-1H-pyrazolo[3,4-b]quinoline

Following the procedures described in Reference Example 2-3 and Example 2-1, the title compound was prepared from 8-methyl-2-(2-oxopropyl)-4H-3,1-benzoxazin-4-one and 2-hydrazino-5-methylpyridine which was previously prepared from 2-bromo-5-methylpyridine following the method described in Reference Example 2-2 (62% yield).

mp: 165–168° C. (recrystallized from methanol/ethyl acetate). NMR (CDCl$_3$) δ: 2.42 (3H, s), 2.85 (3H, s), 2.99 (3H, s), 7.46 (1H, dd, J=7.7 Hz, 8.4 Hz), 7.62–7.72 (1H, m), 7.75 (1H, m), 8.23 (1H, m), 8.48 (1H, m), 8.88 (1H, d, J=8.4 Hz). Elementary Analysis: for $C_{18}H_{15}ClN_4$ Calcd.: C, 66.98; H, 4.68; N, 17.36. Found: C, 66.93; H, 4.59; N, 17.23.

EXAMPLE 2-132

3,8-Dimethyl-1-(5-methyl-2-pyridinyl)-1H-pyrazolo[3,4-b]quinolin-4-ylamine

Following the procedure described in Example 2-2, the title compound was prepared from 4-chloro-3,8-dimethyl-1-(5-methyl-2-pyridinyl)-1H-pyrazolo[3,4-b]quinoline and sodium azide (43% yield).

mp: 257–260° C. (recrystallized from ethyl acetate). NMR (CDCl$_3$) δ: 2.39 (3H, s), 2.78 (3H, s), 2.87 (3H, s), 5.48 (2H, br s), 7.18–7.30 (1H, m), 7.55 (1H, d, J=6.6 Hz), 7.65–7.75 (2H, m), 8.43 (1H, s), 9.02 (1H, d, J=8.1 Hz). Elementary Analysis: for $C_{18}H_{17}N_5$ Calcd.: C, 71.27; H, 5.65; N, 23.09. Found: C, 70.87; H, 5.57; N, 22.78.

EXAMPLE 2-133

4-Chloro-3,8-dimethyl-1-(3-methyl-2-pyridinyl)-1H-pyrazolo[3,4-b]quinoline

Following the procedures described in Reference Example 2-3 and Example 2-1, the title compound was prepared from 8-methyl-2-(2-oxopropyl)-4H-3,1-benzoxazin-4-one and 2-hydrazino-3-methylpyridine (57% yield).

mp: 182–185° C. (recrystallized from chloroform/methanol). NMR (CDCl$_3$) δ: 2.42 (3H, s), 2.70 (3H, s), 2.99 (3H, s), 7.32–7.50 (2H, m), 7.62 (1H, d, J=6.6 Hz), 7.77–7.85 (1H, m), 8.26 (1H, d, J=8.8 Hz), 8.54 (1H, dd, J=1.5 Hz, 4.4 Hz). Elementary Analysis: for $C_{18}H_{15}ClN_4$ Calcd.: C, 66.98; H, 4.68; N, 17.36. Found: C, 67.10; H, 4.61; N, 17.13.

EXAMPLE 2-134

3,8-Dimethyl-1-(3-methyl-2-pyridinyl)-1H-pyrazolo[3,4-b]quinolin-4-ylamine

Following the procedure described in Example 2-2, the title compound was prepared from 4-chloro-3,8-dimethyl-1-(3-methyl-2-pyridinyl)-1H-pyrazolo[3,4-b]quinoline and sodium azide (68% yield).

mp: 199–202° C. (recrystallized from ethyl acetate). NMR (CDCl$_3$) δ: 2.43 (3H, s), 2.61 (3H, s), 2.76 (3H, s), 5.51 (2H, br s), 7.16 (1H, t, J=7.7 Hz), 7.30 (1H, dd, J=4.8 Hz, 7.7 Hz), 7.48 (1H, d, J=6.6 Hz), 7.67 (1H, d, J=8.1 Hz), 7.76 (1H, d, J=7.7 Hz), 8.52 (1H, dd, J=1.5 Hz, 4.8 Hz). Elementary Analysis: for $C_{18}H_{17}N_5$ Calcd.: C, 71.27; H, 5.65; N, 23.09. Found: C, 71.23; H, 5.60; N, 22.87.

EXAMPLE 2-135

3,8-Dimethyl-1-(3-methyl-2-pyridinyl)-1,9-dihydro-4H-pyrazolo[3,4-b]quinolin-4-one Following the procedure described in Example 2-13, the title compound was prepared from 4-chloro-3,8-dimethyl-1-(3-methyl-2-pyridinyl)-1H-pyrazolo[3,4-b]quinoline (72% yield).

mp: 193–195° C. (recrystallized from ethanol). NMR (CDCl$_3$) δ: 2.56 (3H, s), 2.73 (3H, s), 2.80 (3H, s), 4.23 (1H, br s), 7.18 (1H, d, J=7.7 Hz), 7.23 (1H, t, J=8.1 Hz), 7.47–7.54 (1H, m), 7.71–7.78 (1H, m), 8.32–8.41 (2H, m). Elementary Analysis: for $C_{18}H_{16}N_4O\cdot HCl\cdot 0.7H_2O$ Calcd.: C, 61.17; H, 5.25; N, 15.85. Found: C, 61.22; H, 5.53; N, 15.76.

EXAMPLE 2-136

4-Chloro-3-methyl-1-(3-pyridinyl)-1H-pyrazolo[3,4-b]quinoline

Following the procedure described in Example 2-1, the title compound was prepared from 2-[[3-methyl-1-(3-pyridinyl)-1H-pyrazol-5-yl]amino]benzoic acid (50% yield).

mp: 144–145° C. (recrystallized from ethyl acetate). NMR (CDCl$_3$) δ: 2.93 (3H, s), 7.46 (1H, dd, J=4.8 Hz, 8.2 Hz), 7.52–7.60 (1H, m), 7.76–7.84 (1H, m), 8.11 (1H, d, J=8.2 Hz), 8.33–8.38 (1H, m), 8.53 (1H, dd, J=1.4 Hz, 4.8 Hz), 8.81 (1H, ddd, J=1.4 Hz, 2.6 Hz, 8.4 Hz), 9.79–9.80 (1H, m). Elementary Analysis: for $C_{16}H_{11}ClN_4$ Calcd.: C, 65.20; H, 3.76; N, 19.01; Cl, 12.03. Found: C, 65.22; H, 3.73; N, 19.13; Cl, 11.91.

EXAMPLE 2-137

3-Methyl-1-(3-pyridinyl)-1H-pyrazolo[3,4-b]quinolin-4-ylamine dihydrochloride

Following the procedures described in Examples 2-2 and 2-3, the title compound was prepared from 4-chloro-3-methyl-1-(3-pyridinyl)-1H-pyrazolo[3,4-b]quinoline and sodium azide (72% yield).

mp: 234–237° C. (recrystallized from methanol). NMR (DMSO-d$_6$) δ: 2.83 (3H, s), 7.53 (1H, t, J=8.1 Hz), 7.83–8.05 (3H, m), 8.58–8.85 (3H, m), 9.00 (2H, br s), 9.32 (1H, br s). Elementary Analysis: for $C_{16}H_{13}N_5\cdot 2HCl\cdot 2H_2O$ Calcd.: C, 50.01; H, 4.98; N, 18.23; Cl, 18.45. Found: C, 49.98; H, 5.05; N, 18.18; Cl, 18.27.

EXAMPLE 2-138

3-Methyl-1-(3-pyridinyl)-1,9-dihydro-4H-pyrazolo[3,4-b]quinolin-4-one

Following the procedure described in Example 2-31, the title compound was prepared from 4-chloro-3-methyl-1-(3-pyridinyl)-1H-pyrazolo[3,4-b]quinoline (37% yield).

mp: 282–283° C. (recrystallized from ethanol). NMR (DMSO-d$_6$) δ: 2.60 (3H, s), 7.26–7.34 (1H, m), 7.66–7.72 (3H, m), 8.15 (1H, ddd, J=1.4 Hz, 2.6 Hz, 8.2 Hz), 8.22 (1H, d, J=8.2 Hz), 8.73 (1H, dd, J=1.4 Hz, 4.6 Hz), 8.96 (1H, d, J=2.6 Hz), 11.93 (1H, br s). Elementary Analysis: for $C_{16}H_{12}N_4O.0.5H_2O$ Calcd.: C, 67.36; H, 4.59; N, 19.64. Found: C, 67.50; H, 4.83; N, 19.61.

EXAMPLE 2-139

4-Methoxy-3-methyl-1-(3-pyridinyl)-1H-pyrazolo[3,4-b]quinoline

Following the procedure described in Example 2-19, the title compound was prepared from 4-chloro-3-methyl-1-(3-pyridinyl)-1H-pyrazolo[3,4-b]quinoline and methanol (83% yield).

mp: 126–128° C. (recrystallized from ethyl acetate/hexane). NMR (CDCl$_3$) δ: 2.88 (3H, s), 4.28 (3H, s), 7.43–7.53 (2H, m), 7.73–7.82 (1H, m), 8.13 (1H, d, J=8.4 Hz), 8.27 (1H, dd, J=1.2 Hz, 8.4 Hz), 8.52 (1H, dd, J=1.4 Hz, 4.6 Hz), 8.87 (1H, ddd, J=1.4 Hz, 2.6 Hz, 8.4 Hz), 9.82 (1H, d, J=2.6 Hz). Elementary Analysis: for $C_{17}H_{14}N_4O$ Calcd.: C, 70.33; H, 4.86; N, 19.30. Found: C, 70.11; H, 4.86; N, 19.12.

EXAMPLE 2-140

4-Chloro-3-methyl-1-(4-pyridinyl)-1H-pyrazolo[3,4-b]quinoline

Following the procedure described in Example 2-1, the title compound was prepared from 2-[[3-methyl-1-(4-pyridinyl)-1H-pyrazol-5-yl]amino]benzoic acid (73% yield).

mp: 165–168° C. (recrystallized from ethyl acetate). NMR (CDCl$_3$) δ: 2.91 (3H, s), 7.56–7.64 (1H, m), 7.79–7.88 (1H, m), 8.15 (1H, d, J=8.4 Hz), 8.36 (1H, dd, J=0.7 Hz, 8.8 Hz), 8.56 (2H, dd, J=1.5 Hz, 5.0 Hz), 8.71 (2H, dd, J=1.5 Hz, 4.8 Hz). Elementary Analysis: for $C_{16}H_{11}ClN_4$ Calcd.: C, 65.20; H, 3.76; N, 19.01; Cl, 12.03. Found: C, 65.25; H, 3.79; N, 18.98; Cl, 12.05.

EXAMPLE 2-141

3-Methyl-1-(4-pyridinyl)-1H-pyrazolo[3,4-b]quinolin-4-ylamine dihydrochloride

Following the procedures described in Examples 2-2 and 2-3, the title compound was prepared from 4-chloro-3-methyl-1-(4-pyridinyl)-1H-pyrazolo[3,4-b]quinoline and sodium azide (36% yield).

mp: 259–266° C. (recrystallized from ethanol). NMR (DMSO-d$_6$) δ: 2.82 (3H, s), 4.34 (2H, br s), 7.40–7.49 (1H, m), 7.73–7.90 (2H, m), 8.55 (1H, d, J=8.4 Hz), 8.86 (2H, d, J=7.2 Hz), 9.04 (2H, d, J=6.6 Hz). Elementary Analysis: for $C_{16}H_{13}N_5.2HCl$ Calcd.: C, 55.19; H, 4.34; N, 20.11; Cl, 20.36. Found: C, 54.93; H, 4.39; N, 19.84; Cl, 20.01.

EXAMPLE 2-142

N,N-Dimethyl-N-[3-methyl-1-(4-pyridinyl)-1H-pyrazolo[3,4-b]quinolin-4-yl]amine

Following the procedure described in Example 2-8, the title compound was prepared from 4-chloro-3-methyl-1-(4-pyridinyl)-1H-pyrazolo[3,4-b]quinoline and a solution of 2M dimethylamine in tetrahydrofuran (51% yield).

mp: 155–156° C. (recrystallized from ethyl acetate). NMR (CDCl$_3$) δ: 2.82 (3H, s), 3.37 (6H, s), 7.37–7.46 (1H, m), 7.68–7.76 (1H, m), 8.12 (1H, d, J=8.6 Hz), 8.18 (1H, d, J=8.8 Hz), 8.61 (2H, dd, J=1.6 Hz, 5.0 Hz), 8.68 (2H, dd, J=1.4 Hz, 5.2 Hz). Elementary Analysis: for $C_{18}H_{17}N_5$ Calcd.: C, 71.21; H, 5.65; N, 23.09. Found: C, 71.24; H, 5.52; N, 23.12.

EXAMPLE 2-143

3-Methyl-1-(4-pyridinyl)-1,9-dihydro-4H-pyrazolo[3,4-b]quinolin-4-one

Following the procedure described in Example 2-12, the title compound was prepared from 2-[[3-methyl-1-(4-pyridinyl)-1H-pyrazol-5-yl]amino]benzoic acid (61% yield).

mp: >300° C. (recrystallized from ethyl acetate/methanol). NMR (DMSO-d$_6$) δ: 2.60 (3H, s), 7.32 (1H, ddd, J=1.6 Hz, 6.6 Hz, 8.0 Hz), 7.65–7.78 (2H, m), 7.83 (2H, d, J=6.2 Hz), 8.21 (1H, dd, J=1.4 Hz, 8.0 Hz), 8.79 (2H, d, J=6.2 Hz), 11.94 (1H, br s). Elementary Analysis: for $C_{16}H_{12}N_4O.0.5H_2O$ Calcd.: C, 67.36; H, 4.59; N, 19.64. Found: C, 67.62; H, 4.44; N, 19.69.

EXAMPLE 2-144

4-Chloro-3-methyl-1-(2-pyrimidinyl)-1H-pyrazolo[3,4-b]quinoline

Following the methods described in Reference Example 2-3 and Example 2-1, the title compound was prepared from 2-(2-oxopropyl)-4H-3,1-benzoxazin-4-one and 2-hydrazinopyrimidine (69% yield).

mp: 257–260° C. (recrystallized from ethyl acetate). NMR (CDCl$_3$) δ: 2.80 (3H, s), 7.24–7.36 (2H, m), 7.54–7.73 (2H, m), 8.43–8.50 (1H, m), 8.89 (2H, dd, J=1.5 Hz, 5.1 Hz). Elementary Analysis: for $C_{15}H_{10}ClN_5$ Calcd.: C, 60.92; H, 3.41; N, 23.68; Cl, 11.99. Found: C, 60.63; H, 3.49; N, 23.59; Cl, 11.79.

EXAMPLE 2-145

3-Methyl-1-(2-pyrimidinyl)-1H-pyrazolo[3,4-b]quinolin-4-ylamine hydrochloride

Following the procedures described in Examples 2-2 and 2-3, the title compound was prepared from 4-chloro-3-methyl-1-(2-pyrimidinyl)-1H-pyrazolo[3,4-b]quinoline and sodium azide (53% yield).

mp: 287–290° C. (recrystallized from methanol). NMR (DMSO-d$_6$) δ: 2.84 (3H, s), 7.50–7.63 (2H, m), 7.87–7.98 (1H, m), 8.29 (1H, d, J=8.4 Hz), 8.73 (1H, d, J=8.1 Hz), 8.92 (2H, br s), 9.00 (2H, d, J=4.8 Hz). Elementary Analysis: for $C_{15}H_{12}N_6.HCl.3H_2O$ Calcd.: C, 49.12; H, 5.22; N, 22.91. Found: C, 49.53; H, 4.94; N, 22.83.

EXAMPLE 2-146

3-Methyl-1-(2-pyrimidinyl)-1,9-dihydro-4H-pyrazolo[3,4-b]quinolin-4-one

Following the procedure described in Example 2-13, the title compound was prepared from 4-chloro-3-methyl-1-(2-pyrimidinyl)-1H-pyrazolo[3,4-b]quinoline (69% yield).

mp: 263–264° C. (recrystallized from ethanol). NMR (DMSO-d$_6$) δ: 2.62 (3H, s), 7.32–7.41 (1H, m), 7.53 (1H, t, J=4.8 Hz), 7.70–7.79 (1H, m), 8.06 (1H, d, J=7.6 Hz), 8.24 (1H, dd, J=1.4 Hz, 8.2 Hz), 8.97 (2H, d, J=4.8 Hz), 11.88 (1H, br s). Elementary Analysis: for $C_{15}H_{11}N_5O.0.2H_2O$ Calcd.: C, 64.14; H, 4.09; N, 24.93. Found: C, 64.20; H, 4.29; N, 25.07.

EXAMPLE 2-147

4-Chloro-1-(4,6-dimethyl-2-pyrimidinyl)-3-methyl-1H-pyrazolo[3,4-b]quinoline

Following the procedures described in Reference Example 2-3 and Example 2-1, the title compound was prepared from 2-(2-oxopropyl)-4H-3,1-benzoxazin-4-one and 2-hydrazino-4,6-dimethylpyrimidine (67% yield).

mp: 191–192° C. (recrystallized from ethyl acetate). NMR (CDCl$_3$) δ: 2.69 (6H, s), 3.01 (3H, s), 7.02 (1H, s), 7.61 (1H, ddd, J=1.2 Hz, 8.4 Hz, 8.6 Hz), 7.83 (1H, ddd, J=1.6 Hz, 8.4 Hz, 8.6 Hz), 8.24 (1H, d, J=8.4 Hz), 8.41 (1H, dd, J=1.2 Hz, 8.6 Hz). Elementary Analysis: for C$_{17}$H$_{14}$ClN$_5$ Calcd.: C, 63.06; H, 4.36; N, 21.63; Cl, 10.95. Found: C, 63.12; H, 4.29; N, 21.63; Cl, 10.91.

EXAMPLE 2-148

1-(4,6-Dimethyl-2-pyrimidinyl)-3-methyl-1,9-dihydro-4H-pyrazolo[3,4-b]quinolin-4-one Following the procedure described in Example 2-12, the title compound was prepared from 2-[[3-methyl-1-(4,6-dimethyl-2-pyrimidinyl)-1H-pyrazol-5-yl]amino]benzoic acid (49% yield).

mp: 312–315° C. (recrystallized from ethanol). NMR (DMSO-d$_6$) δ: 2.61 (9H, s), 7.26 (1H, s), 7.31–7.40 (1H, m), 7.69–7.78 (1H, m), 7.92 (1H, d, J=8.0 Hz), 8.23 (1H, dd, J=1.2 Hz, 8.2 Hz), 11.66 (1H, br s). Elementary Analysis: for C$_{11}$H$_{15}$N$_5$O Calcd.: C, 66.87; H, 4.95; N, 22.94. Found: C, 66.80; H, 4.84; N, 22.95.

EXAMPLE 2-149

4-Chloro-3-methyl-1-(1,3-thiazol-2-yl)-1H-pyrazolo[3,4-b]quinoline

Following the procedure described in Example 2-1, the title compound was prepared from 2-[[3-methyl-1-(1,3-thiazol-2-yl)-1H-pyrazol-5-yl]amino]benzoic acid (68% yield).

mp: 208–209° C. (recrystallized from ethyl acetate/methanol). NMR (CDCl$_3$) δ: 2.96 (3H, s), 7.19 (1H, d, J=3.4 Hz), 7.58–7.66 (1H, m), 7.73 (1H, d, J=3.4 Hz), 7.81–7.89 (1H, m), 8.25 (1H, d, J=8.8 Hz), 8.39 (1H, dd, J=1.4 Hz, 8.8 Hz). Elementary Analysis: for C$_{14}$H$_9$ClN$_4$S Calcd.: C, 55.91; H, 3.02; N, 18.63; Cl, 11.79; S, 10.66. Found: C, 56.00; H, 2.93; N, 18.51; Cl, 11.66; S, 10.83.

EXAMPLE 2-150

3-Methyl-1-(1,3-thiazol-2-yl)-1H-pyrazolo[3,4-b]quinolin-4-ylamine

Following the procedure described in Example 2-2, the title compound was prepared from 4-chloro-3-methyl-1-(1,3-thiazol-2-yl)-1H-pyrazolo[3,4-b]quinoline and sodium azide (48% yield).

mp: 261–263° C. (recrystallized from methanol). NMR (DMSO-d$_6$) δ: 2.81 (3H, s), 7.31–7.40 (1H, m), 7.44 (1H, d, J=3.7 Hz), 7.58 (2H, br s), 7.61 (1H, d, J=3.7 Hz), 7.66–7.75 (1H, m), 7.83 (1H, dd, J=1.1 Hz, 8.4 Hz), 8.46 (1H, dd, J=1.1 Hz, 8.4 Hz). Elementary Analysis: for C$_{14}$H$_{11}$N$_5$S Calcd.: C, 59.77; H, 3.94; N, 24.89. Found: C, 59.42; H, 3.93; N, 24.53.

EXAMPLE 2-151

3-Methyl-1-(1,3-thiazol-2-yl)-1,9-dihydro-4H-pyrazolo[3,4-b]quinolin-4-one

Following the procedure described in Example 2-13, the title compound was prepared from 4-chloro-3-methyl-1-(1,3-thiazol-2-yl)-1H-pyrazolo[3,4-b]quinoline (61% yield).

mp: 226–227° C. (recrystallized from ethyl acetate). NMR (DMSO-d$_6$) δ: 2.60 (3H, s), 7.35 (1H, t, J=7.6 Hz), 7.60 (1H, d, J=3.6 Hz), 7.67–7.76 (1H, m), 7.80 (1H, d, J=3.6 Hz), 8.12 (1H, d, J=8.4 Hz), 8.22 (1H, dd, J=1.0 Hz, 7.6 Hz), 11.72 (1H, br s). Elementary Analysis: for C$_{14}$H$_{10}$N$_4$OS Calcd.: C, 59.56; H, 3.57; N, 19.85; S, 11.36. Found: C, 59.63; H, 3.53; N, 19.85; S, 11.36.

EXAMPLE 2-152

4-Chloro-3,8-dimethyl-1-(2-quinolinyl)-1H-pyrazolo[3,4-b]quinoline

Following the procedure described in Reference Example 2-3 and Example 2-1, the title compound was prepared from 8-methyl-2-(2-oxopropyl)-4H-3,1-benzoxazin-4-one and 2-hydrazinoquinoline which was previously prepared form 2-chloroquinoline following the method described in Reference Example 2-2 (42% yield).

mp: 165–168° C. (recrystallized from methanol/chloroform). NMR (CDCl$_3$) δ: 2.91 (3H, s), 3.04 (3H, s), 7.44–7.57 (2H, m), 7.65–7.80 (2H, m), 8.10 (1H, br d, J=8.4 Hz), 8.22–8.30 (2H, m), 8.38 (1H, d, J=8.8 Hz), 9.21 (1H, d, J=8.8 Hz).

EXAMPLE 2-153

3,8-Dimethyl-1-(2-quinolinyl)-1H-pyrazolo[3,4-b]quinolin-4-ylamine

Following the procedure described in Example 2-2, the title compound was prepared from 4-chloro-3,8-dimethyl-1-(2-quinolinyl)-1H-pyrazolo[3,4-b]quinoline and sodium azide (42% yield).

mp: 273–276° C. (recrystallized from ethyl acetate/methanol). NMR (CDCl$_3$) δ: 2.84 (3H, s), 2.93 (3H, s), 5.86 (2H, br s), 7.22–7.30 (1H, m), 7.48 (1H, t, J=7,0 Hz), 7.58 (1H, d, J=7.0 Hz), 7.70 (1H, t, J=1.5 Hz, 7.0 Hz), 7.83 (2H, d, J=8.1 Hz), 8.23 (1H, d, J=8.1 Hz), 8.34 (1H, d, J=8.8 Hz), 9.46 (1H, d, J=8.8 Hz). Elementary Analysis: for C$_{21}$H$_{17}$N$_5$ Calcd.: C, 74.32; H, 5.05; N, 20.63. Found: C, 73.83; H, 4.98; N, 20.31.

EXAMPLE 2-154

3,8-Dimethyl-1-(2-quinolinyl)-1,9-dihydro-4H-pyrazolo[3,4-b]quinolin-4-one

Following the procedure described in Example 2-13, the title compound was prepared from 4-chloro-3,8-dimethyl-1-(2-quinolinyl)-1H-pyrazolo[3,4-b]quinoline (63% yield).

mp: 255–257° C. (recrystallized from ethanol). NMR (DMSO-d$_6$) δ: 2.45 (3H, s), 2.51 (3H, s), 7.12 (1H, t, J=7.0 Hz), 7.43–7.58 (2H, m), 7.66–8.00 (5H, m), 8.39 (1H, d, J=8.4 Hz). Elementary Analysis: for C$_{21}$H$_{16}$N$_4$O Calcd.: C, 74.10; H, 4.74; N, 16.46. Found: C, 74.10; H, 4.76; N, 16.49.

EXAMPLE 2-155

4-Chloro-3-methyl-1-(2-pyridinyl)-1H-pyrazolo[3,4-b]thieno[2,3-e]pyridine

Following the procedure described in Example 2-1, the title compound was prepared from 3-[[3-methyl-1-(2-pyridinyl-1H-pyrazol-5-yl)amino]-2-thiphenecarboxylic acid (49% yield).

mp: 230–231° C. (recrystallized from ethyl acetate/acetonitrile). NMR (CDCl$_3$) δ: 2.93 (3H, s), 7.22–7.27 (1H, m), 7.62 (1H, d, J=5.6 Hz), 7.88–7.97 (2H, m), 8.61 (1H, d, J=8.0 Hz), 8.69 (1H, d, J=4.4 Hz). Elementary Analysis: for C$_{14}$H$_9$ClN$_4$S Calcd.: C, 55.91; H, 3.02; N, 18.63. Found: C, 55.96; H, 3.12; N, 18.72.

EXAMPLE 2-156

3-Methyl-1-(2-pyridinyl)-1,8-dihydro-4H-pyrazolo[3,4-b]thieno[2,3-e]pyridin-4-one Following the procedure described in Example 2-12, the title compound was prepared from 3-[[3-methyl-1-(2-pyridinyl)-1H-pyrazol-5-yl]amino]-2-thiphenecarboxylic acid (28% yield).

mp: 228–229° C. (recrystallized from ethyl acetate). NMR (DMSO-$d_6$) δ: 2.61 (3H, s), 7.36–7.42 (1H, m), 7.63 (1H, d, J=5.2 Hz), 7.91 (1H, d, J=8.0 Hz), 8.02–8.10 (2H, m), 8.59–8.62 (1H, m), 12.60 (1H, br s). Elementary Analysis: for $C_{14}H_{10}N_4OS \cdot 0.5H_2O$ Calcd.: C, 57.72; H, 3.81; N, 19.23. Found: C, 57.32; H, 3.88; N, 19.19.

EXAMPLE 2-157

4-Chloro-1-(2-pyridinyl)-1H-pyrazolo[3,4-b]quinoline

A solution of 2-[[1-(2-pyridinyl)-1H-pyrazol-5-yl]amino]benzoic acid (62.0 g, 0.221 mol) in phosphorous oxychloride (166 g, 1.08 mol) was heated under reflux for 1 hour. The solution was allowed to cool to room temperature and poured into water. The solution was neutralized by addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform) to give the title compound (47.4 g, 76% yield).

mp: 153–156° C. (recrystallized from ethyl acetate/methanol). NMR (CDCl$_3$) δ: 7.25–7.33 (1H, m), 7.58–7.67 (1H, m), 7.80–7.89 (1H, m), 7.93–8.01 (1H, m), 8.23 (1H, m), 8.39 (1H, m), 8.59 (1H, s), 8.70 (1H, br d, J=5.1 Hz), 8.78 (1H, d, J=8.4 Hz). Elementary Analysis: for $C_{15}H_9ClN_4$ Calcd.: C, 64.18; H, 3.23; N, 19.96. Found: C, 64.04; H, 3.01; N, 19.94.

EXAMPLE 2-158

1-(2-Pyridinyl)-1H-pyrazolo[3,4-b]quinolin-4-ylamine hydrochloride

Following the procedures described in Examples 2-2 and 2-3, the title compound was prepared from 4-chloro-1-(2-pyridinyl)-1H-pyrazolo[3,4-b]quinoline and sodium azide (78% yield).

mp: 312–315° C. (recrystallized from methanol). NMR (DMSO-$d_6$) δ: 7.47–7.55 (1H, m), 7.63 (1H, t, J=7.7 Hz), 7.95–8.21 (3H, m), 8.45 (1H, d, J=8.4 Hz), 8.65–8.75 (2H, m), 9.11 (1H, s), 10.2 (2H, br s).

Elementary Analysis: for $C_{15}H_{11}N_5 \cdot HCl$ Calcd.: C, 60.51; H, 4.06; N, 23.52; Cl, 11.91. Found: C, 60.61; H, 4.06; N, 23.30; Cl, 11.83.

EXAMPLE 2-159

1-(2-Pyridinyl)-1,9-dihydro-4H-pyrazolo[3,4-b]quinolin-4-one

A solution of methanesulfonic acid (20 mL, 0.31 mol) in phosphorus pentoxide (5.00 g, 35.2 mmol) was heated at 100° C. The mixture was stirred at the same temperature, while powdery 2-[[1-(2-pyridinyl)-1H-pyrazol-5-yl]amino]benzoic acid (1.94 g, 6.92 mmol) was added in small portions. The reaction mixture was heated and stirred at the same temperature for 10 minutes. The mixture was allowed to cool to room temperature, and iced water was added thereto. The solution was made basic by the addition of an aqueous sodium hydroxide solution, and the organic matter was extracted with ethyl acetate. The extract was washed with saturated brine and water, and dried over anhydrous magnesium sulfate, and the solvent was evaporated under reduced pressure. The residue thus obtained was purified by silica gel column chromatography (chloroform:methanol= 99:1) to give the title compound (1.35 g, 74% yield).

mp: 240–242° C. (recrystallized from ethanol). NMR (DMSO-$d_6$) δ: 7.32–7.40 (1H, m), 7.42–7.49 (1H, m), 7.71–7.80 (1H, m), 7.96–8.01 (1H, m), 8.07–8.15 (2H, m), 8.24–8.29 (1H, m), 8.39 (1H, s), 8.64–8.68 (1H, m), 12.03 (1H, br s). Elementary Analysis: for $C_{15}H_{10}N_4O$ Calcd.: C, 68.69; H, 3.84; N, 21.36. Found: C, 68.68; H, 3.89; N, 21.36.

EXAMPLE 2-160

4,6-Dichloro-1-(2-pyridinyl)-1H-pyrazolo[3,4-b]quinoline

Following the procedure described in Example 2-1, the title compound was prepared from 5-chloro-2-[[1-(2-pyridinyl)-1H-pyrazol-5-yl]amino]benzoic acid (25% yield).

mp: 175–176° C. (recrystallized from ethyl acetate). NMR (CDCl$_3$) δ: 7.28–7.34 (1H, m), 7.77 (1H, dd, J=2.4 Hz, 9.0 Hz), 7.93–8.01 (1H, m), 8.18 (1H, d, J=9.0 Hz), 8.37 (1H, d, J=2.4 Hz), 8.59 (1H, s), 8.66–8.71 (2H, m). Elementary Analysis: for $C_{15}H_8Cl_2N_4 \cdot 0.5H_2O$ Calcd.: C, 55.58; H, 2.80; N, 17.28; Cl, 21.87. Found: C, 55.42; H, 2.74; N, 17.25; Cl, 21.80.

EXAMPLE 2-161

6-Chloro-1-(2-pyridinyl)-1,9-dihydro-4H-pyrazolo[3,4-b]quinolin-4-one

Following the procedure described in Example 2-13, the title compound was prepared from 4,6-dichloro-1-(2-pyridinyl)-1H-pyrazolo[3,4-b]quinoline (76% yield).

mp: 297–298° C. (recrystallized from ethanol). NMR (DMSO-$d_6$) δ: 7.46 (1Hm, ddd, J=1.0 Hz, 5.0 Hz, 7.4 Hz), 7.79 (1H, dd, J=2.6 Hz, 8.8 Hz), 7.97 (1H, d, J=8.0 Hz), 8.07–8.20 (3H, m), 8.40 (1H, s), 8.63–8.66 (1H, m), 11.89 (1H, br s). Elementary Analysis: for $C_{15}H_9ClN_4O$ Calcd.: C, 60.72; H, 3.06; N, 18.88; Cl, 11.95. Found: C, 60.52; H, 3.04; N, 18.79; Cl, 11.89.

EXAMPLE 2-162

4-Chloro-5-fluoro-1-(2-pyridinyl)-1H-pyrazolo[3,4-b]quinoline

Following the procedures described in Reference Example 2-5 and Example 2-1, the title compound was prepared from 2-fluoro-6-iodobenzoic acid and 1-(2-pyridinyl)-1H-pyrazol-5-ylamine (64% yield).

mp: 173–176° C. (recrystallized from ethyl acetate). NMR (CDCl$_3$) δ: 7.18–7.34 (2H, m), 7.66–7.79 (1H, m), 7.92–8.07 (2H, m), 8.62 (1H, s), 8.66–8.73 (2H, m). Elementary Analysis: for $C_{15}H_8ClFN_4$ Calcd.: C, 60.31; H, 2.70; N, 18.76; Cl, 11.87; F, 6.36. Found: C, 60.14; H, 2.57; N, 18.79; Cl, 11.81; F, 6.33.

EXAMPLE 2-163

5-Fluoro-1-(2-pyridinyl)-1,9-dihydro-4H-pyrazolo[3,4-b]quinolin-4-one

Following the procedure described in Example 2-13, the title compound was prepared from 4-chloro-5-fluoro-1-(2-pyridinyl)-1H-pyrazolo[3,4-b]quinoline (92% yield).

mp: 278–281° C. (recrystallized from ethanol). NMR (DMSO-$d_6$) δ: 7.04 (1H, dq, J=1.0 Hz, 8.0 Hz), 7.46 (1H, dq, J=1.0 Hz, 4.8 Hz), 7.63–8.16 (4H, m), 8.34 (1H, s), 8.62–8.67 (1H, m), 12.00 (1H, br s). Elementary Analysis: for $C_{15}H_9FN_4O \cdot 0.2H_2O$ Calcd.: C, 63.47; H, 3.34; N, 19.74; F, 6.69. Found: C, 63.25; H, 3.42; N, 19.79; F, 6.62.

EXAMPLE 2-164

4-Chloro-6-fluoro-1-(2-pyridinyl)-1H-pyrazolo[3,4-b]quinoline

Following the procedures described in Reference Example 2-5 and Example 2-1, the title compound was prepared from 2-fluoro-5-iodobenzoic acid and 1-(2-pyridinyl)-1H-pyrazol-5-ylamine (40% yield).

mp: 176–179° C. (recrystallized from ethyl acetate/hexane). NMR (CDCl$_3$) δ: 7.26–7.35 (1H, m), 7.59–7.70 (1H, m), 7.93–8.02 (2H, m), 8.26.(1H, dd, J=5.4 Hz, 9.4 Hz), 8.59 (1H, s), 8.63–8.73 (2H, m). Elementary Analysis: for $C_{15}H_8ClFN_4 \cdot 0.2H_2O$ Calcd.: C, 59.60; H, 2.80; N, 18.53; Cl, 11.73; F, 6.28. Found: C, 59.58; H, 2.79; N, 18.62; Cl, 11.56; F, 6.02.

EXAMPLE 2-165

6-Fluoro-1-(2-pyridinyl)-1,9-dihydro-4H-pyrazolo[3,4-b]quinolin-4-one

Following the procedure described in Example 2-13, the title compound was prepared from 4-chloro-6-fluoro-1-(2-pyridinyl)-1H-pyrazolo[3,4-b]quinoline (56% yield).

mp: 263–266° C. (recrystallized from ethanol/tetrahydrofuran). NMR (DMSO-$d_6$) δ: 7.18–7.35 (2H, m), 7.61 (1H, dd, J=5.0 Hz, 9.0 Hz), 7.81 (1H, dd, J=3.3 Hz, 10.2 Hz), 7.91–8.01 (1H, m), 8.11 (1H, s), 8.47–8.51 (1H, m), 8.92 (1H, d, J=8.4 Hz), hidden (1H). Elementary Analysis: for $C_{15}H_9FN_4O \cdot 0.8HCl$ Calcd.: C, 58.22; H, 3.19; N, 18.11; F, 6.14. Found: C, 58.09; H, 2.90; N, 17.71; F, 5.84.

EXAMPLE 2-166

4-Chloro-1-(2-pyridinyl)-3-trifluoromethyl-1H-pyrazolo[3,4-b]quinoline

Following the procedures described in Reference Example 2-5 and Example 2-1, the title compound was prepared from o-iodobenzoic acid and 1-(2-pyridinyl)-3-trifluoromethyl-1H-pyrazol-5-ylamine (53% yield).

mp: 166–168° C. (recrystallized from ethyl acetate/hexane). NMR (CDCl$_3$) δ: 7.36–7.43 (1H, m), 7.65–7.74 (1H, m), 7.86–8.07 (2H, m), 8.23 (1H, d, J=8.6 Hz), 8.48–8.54 (1H, m), 8.62 (1H, d, J=8.4 Hz), 8.74–8.79 (1H, m). Elementary Analysis: for $C_{16}H_8ClF_3N_4$ Calcd.: C, 55.11; H, 2.31; N, 16.07. Found: C, 55.12; H, 2.19; N, 16.26.

EXAMPLE 2-167

1-(2-Pyridinyl)-3-trifluoromethyl-1,9-dihydro-4H-pyrazolo[3,4-b]quinolin-4-one

Following the procedure described in Example 2-13, the title compound was prepared from 4-chloro-1-(2-pyridinyl)-3-trifluoromethyl-1H-pyrazolo[3,4-b]quinoline (78% yield).

mp: 231–233° C. (recrystallized from ethanol). NMR (DMSO-$d_6$) δ: 7.36–7.44 (1H, m), 7.51–7.57 (1H, m), 7.76–7.83 (1H, m), 7.99–8.28 (4H, m), 8.69–8.71 (1H, m), 12.19 (1H, br s). Elementary Analysis: for $C_{16}H_9F_3N_4O \cdot 0.25H_2O$ Calcd.: C, 57.40; H, 2.86; N, 16.74; F, 17.03. Found: C, 57.45; H, 2.84; N, 16.89; F, 16.96.

EXAMPLE 2-168

3-Bromomethyl-4-chloro-1-(2-pyridinyl)-1H-pyrazolo[3,4-b]quinoline

A solution of 4-chloro-3-methyl-1-(2-pyridinyl)-1H-pyrazolo[3,4-b]quinoline (1.22 g, 4.1 mmol), N-bromosuccinimide (0.87 g, 4.9 mmol) and 2,2'-azobis(isobutyronitrile) (66 mg, 0.4 mmol) in carbon tetrachloride (40 mL) was heated under reflux under an argon atmosphere for 3 hours. The solution was allowed to cool to room temperature, the insoluble solid was removed and the solution was concentrated under reduced pressure. The residue thus obtained was purified by silica gel column chromatography (hexane:chloroform:ethyl acetate=2:1:1) to give the title compound (0.82 g, 53% yield).

mp: 203–205° C. (recrystallized from ethyl acetate/methanol). NMR (CDCl$_3$) δ: 5.17 (2H, s), 7.26–7.34 (1H, m), 7.60–7.70 (1H, m), 7.82–8.03 (2H, m), 8.18–8.24 (1H, m), 8.43–8.49 (1H, m), 8.68–8.73 (1H, m), 8.82–8.87 (1H, m). Elementary Analysis: for $C_{16}H_{10}BrClN_4$ Calcd.: C, 51.43; H, 2.70; N, 15.00; Br, 21.39; Cl, 9.49. Found: C, 51.40; H, 2.72; N, 15.13; Br, 21.29; Cl, 9.73.

EXAMPLE 2-169

4-Chloro-3-ethyl-1-(2-pyridinyl)-1H-pyrazolo[3,4-b]quinoline

Following the procedures described in Reference Example 2-3 and Example 2-1, the title compound was prepared from 2-(2-oxobutyl)-4H-3,1-benzoxazin-4-one and 2-hydrazinopyridine (43% yield).

mp: 132–135° C. (recrystallized from ethyl acetate/hexane). NMR (DMSO-$d_6$) δ: 1.57 (3H, t, J=7.3 Hz), 3.41 (2H, q, J=7.3 Hz), 7.30–7.38 (1H, m), 7.59–7.70 (1H, m), 7.81–7.95 (1H, m), 8.02–8.15 (1H, m), 8.34 (1H, d, J=8.1 Hz), 8.40–8.47 (1H, m), 8.86–8.95 (2H, m).

EXAMPLE 2-170

3-Ethyl-1-(2-pyridinyl)-1H-pyrazolo[3,4-b]quinolin-4-ylamine hydrochloride

Following the procedures described in Examples 2-2 and 2-3, the title compound was prepared from 4-chloro-3-ethyl-1-(2-pyridinyl)-1H-pyrazolo[3,4-b]quinoline and sodium azide (62% yield).

mp: 249–252° C. (recrystallized from methanol). NMR (DMSO-$d_6$) δ: 1.40 (3H, t, J=7.3 Hz), 3.30 (2H, q, J=7.3 Hz), 7.44–7.68 (2H, m), 7.92–8.20 (3H, m), 8.43 (1H, d, J=8.4 Hz), 8.65–8.72 (1H, m), 8.84 (1H, d, J=8.4 Hz), hidden (2H). Elementary Analysis: for $C_{17}H_{15}N_5 \cdot HCl \cdot 2.2H_2O$ Calcd.: C, 55.88; H, 5.63; N, 19.16; Cl, 9.70. Found: C, 55.81; H, 5.48; N, 19.18; Cl, 9.70.

EXAMPLE 2-171

3-Ethyl-1-(2-pyridinyl)-1,9-dihydro-4H-pyrazolo[3,4-b]quinolin-4-one

Following the procedures described in Reference Example 2-3 and Example 2-12, the title compound was prepared from 2-(2-oxobutyl)-4H-3,1-benzoxazin-4-one and 2-hydrazinopyridine (43% yield).

mp: 191–193° C. (recrystallized from ethyl acetate). NMR (DMSO-$d_6$) δ: 1.46 (3H, t, J=7.3 Hz), 3.17 (2H, q, J=7.3 Hz), 7.20–7.25 (1H, m), 7.33 (1H, t, J=8.1 Hz), 7.43 (1H, d, J=8.4 Hz), 7.60–7.70 (1H, m), 7.85–7.94 (1H, m), 8.04 (1H, d, J=8.4 Hz), 8.40–8.48 (2H, m), 11.48 (1H, br s).

EXAMPLE 2-172

4-Chloro-3-isopropyl-1-(2-pyridinyl)-1H-pyrazolo[3,4-b]quinoline

Following the procedures described in Reference Examples 2-68 and 2-3, and Example 2-1, the title compound was prepared from Meldrum's acid, isobutyryl chloride and 2-hydrazinopyridine (5% yield).

mp: 146–148° C. (recrystallized from ethyl acetate/hexane). NMR (CDCl$_3$) δ: 1.61 (6H, d, J=6.8 Hz), 3.94–4.08 (1H, m), 7.21–7.25 (1H, m), 7.56–7.63 (1H, m), 7.77–7.86 (1H, m), 7.88–7.97 (1H, m), 8.20 (1H, d, J=8.4 Hz), 8.43 (1H, dd, J=1.2 Hz, 8.8 Hz), 8.60 (1H, d, J=8.4 Hz), 8.72 (1H, d, J=4.0 Hz). Elementary Analysis: for $C_{18}H_{15}ClN_4$ Calcd.: C, 66.98; H, 4.68; N, 17.36; Cl, 10.98. Found: C, 67.19; H, 4.64; N, 17.58; Cl, 10.92.

EXAMPLE 2-173

3-Isopropyl-1-(2-pyridinyl)-1,9-dihydro-4H-pyrazolo[3,4-b]quinolin-4-one

Following the procedures described in Reference Examples 2-68 and 2-3, and Example 2-12, the title compound was prepared from Meldrum's acid, isobutyryl chloride and 2-hydrazinopyridine (16% yield).

mp: 143–144° C. (recrystallized from ethyl acetate/hexane). NMR (CDCl$_3$) δ: 1.50 (6H, d, J=6.8 Hz), 3.63–3.76 (1H, m), 7.18–7.24 (1H, m), 7.29–7.37 (1H, m), 7.44 (1H, d, J=8.0 Hz), 7.61–7.69 (1H, m), 7.90 (1H, dt, J=1.2 Hz, 8.4 Hz), 8.07 (1H, dd, J=0.8 Hz, 8.4 Hz), 8.47–8.50 (2H, m), 11.55 (1H, br s). Elementary Analysis: for $C_{18}H_{16}N_4O$ Calcd.: C, 71.04; H, 5.30; N, 18.41. Found: C, 70.99; H, 5.30; N, 18.49.

EXAMPLE 2-174

3-Isobutyl-1-(2-pyridinyl)-1,9-dihydro-4H-pyrazolo[3,4-b]quinolin-4-one

Following the procedures described in Reference Examples 2-11 and 2-3, and Example 2-12, the title compound was prepared from Meldrum's acid, isovaleryl chloride and 2-hydrazinopyridine (16% yield).

mp: 167–169° C. (recrystallized from ethyl acetate/hexane). NMR (DMSO-d$_6$) δ: 0.99 (6H, d, J=6.6 Hz), 2.24–2.37 (1H, m), 2.91 (2H, d, J=7.0 Hz), 7.32–7.45 (2H, m), 7.69–7.78 (1H, m), 7.94 (1H, d, J=8.0 Hz), 8.04–8.12 (2H, m), 8.24 (1H, dd, J=1.4 Hz, 8.0 Hz), 8.63–8.67 (1H, m), 11.95 (1H, br s). Elementary Analysis: for $C_{19}H_{18}N_4O \cdot 0.2H_2O$ Calcd.: C, 70.88; H, 5.76; N, 17.40. Found: C, 70.93; H, 5.62; N, 17.45.

EXAMPLE 2-175

Methyl 2-[4-chloro-1-(2-pyridinyl)-1H-pyrazolo[3,4-b]quinolin-3-yl]acetate

Following the procedures described in Reference Example 2-5 and Example 2-1, the title compound was prepared from o-iodobenzoic acid and methyl 2-[5-amino-1-(2-pyridinyl)-1H-pyrazol-3-yl]acetate (24% yield).

mp: 152–153° C. (recrystallized from ethyl acetate/diethylether). NMR (CDCl$_3$) δ: 3.75 (3H, s), 4.47 (2H, s), 7.24–7.31 (1H, m), 7.58–7.82 (1H, m), 7.84–8.01 (2H, m), 8.21 (1H, d, J=8.6 Hz), 8.40 (1H, dd, J=1.2 Hz, 8.6 Hz), 8.67–8.72 (1H, m), 8.87 (1H, d, J=8.4 Hz). Elementary Analysis: for $C_{18}H_{13}ClN_4O_2$ Calcd.: C, 61.28; H, 3.71; N, 15.88. Found: C, 61.06; H, 3.78; N, 15.97.

EXAMPLE 2-176

Methyl 2-[4-oxo-1-(2-pyridinyl)-4,9-dihydro-1H-pyrazolo[3,4-b]quinolin-3-yl]acetate Following the procedure described in Example 2-13, the title compound was prepared from methyl 2-[4-chloro-1-(2-pyridinyl)-1H-pyrazolo[3,4-b]quinolin-3-yl]acetate (84% yield).

mp: 240–241° C. (recrystallized from ethyl acetate). NMR (CDCl$_3$) δ: 3.81 (3H, s), 4.21 (2H, s), 7.20–7.36 (2H, m), 7.45 (1H, d, J=7.6 Hz), 7.65 (1H, ddd, J=1.6 Hz, 7.0 Hz, 8.4 Hz), 7.88 (1H, ddd, J=1.6 Hz, 7.0 Hz, 8.4 Hz), 7.99 (1H, d, J=8.4 Hz), 8.41 (1H, d, J=8.0 Hz), 8.48–8.50 (1H, m), 11.41 (1H, s). Elementary Analysis: for $C_{18}H_{14}N_4O_3$ Calcd.: C, 64.66; H, 4.22; N, 16.76. Found: C, 64.56; H, 4.20; N, 16.88.

EXAMPLE 2-177

2-[4-Oxo-1-(2-pyridinyl)-4,9-dihydro-1H-pyrazolo[3,4-b]quinolin-3-yl]acetic acid To a solution of methyl 2-[4-oxo-1-(2-pyridinyl)-4,9-dihydro-1H-pyrazolo[3,4-b]quinolin-3-yl]acetate (5.47 g, 16.4 mmol) in methanol (150 mL), an aqueous 2N sodium hydroxide solution (15 mL) was added at 0° C., and the mixture was stirred at room temperature for 2 hours, and refluxed further for 3 hours. The solution was allowed to cool to room temperature, made acidic by the addition of an aqueous 2N hydrochloric acid solution, and the resulting precipitate was collected by filtration. The collected crude crystals were washed with water and dried to give the title compound (4.96 g, 95% yield).

mp: 229–231° C. (recrystallized from chloroform/methanol). NMR (DMSO-d$_6$) δ: 4.02 (2H, s), 7.30–7.47 (2H, m), 7.68–7.80 (1H, m), 7.91 (1H, d, J=8.4 Hz), 8.02–8.25 (3H, m), 8.61–8.68 (1H, m), 11.99 (1H, s), 12.6 (1H, br s). Elementary Analysis: for $C_{17}H_{12}N_4O_3 \cdot 0.8H_2O$ Calcd.: C, 61.00; H, 4.10; N, 16.74. Found: C, 61.22; H, 4.09; N, 16.45.

EXAMPLE 2-178

2-[4-Oxo-1-(2-pyridinyl)-4,9-dihydro-1H-pyrazolo[3,4-b]quinolin-3-yl]acetamide

To a solution of 2-[4-oxo-1-(2-pyridinyl)-4,9-dihydro-1H-pyrazolo[3,4-b]quinolin-3-yl]acetic acid (1.60 g, 5.0 mmol) in a mixed solvent of tetrahydrofuran (100 mL) and N,N-dimethylformamide (20 mL), 1,1'-carbonyldiimidazole (0.89 g, 5.5 mmol) was added and the mixture was stirred at room temperature for 30 minutes. Subsequently, 25% aqueous ammonia solution was added to the mixture and the resulting solution was stirred at room temperature for 1 hour. The solution was poured into water, and the resulting precipitate was collected by filtration. The collected crude crystals were washed with water, and dried to give the title compound (0.94 g, 59% yield).

mp: 302–305° C. NMR (DMSO-d$_6$) δ: 3.87 (2H, s), 7.02 (1H, br s), 7.30–7.45 (2H, m), 7.70–7.79 (1H, m), 7.94 (1H, d, J=8.4 Hz), 8.03–8.13 (2H, m), 8.24 (1H, dd, J=1.0 Hz, 8.0 Hz), 8.62–8.65 (1H, m), 11.60 (2H, br s). Elementary Analysis: for $C_{17}H_{13}N_5O_2 \cdot 0.2H_2O$ Calcd.: C, 63.23; H, 4.18; N, 21.69. Found: C, 63.27; H, 4.09; N, 21.44.

EXAMPLE 2-179

Ethyl 4-chloro-1-(2-pyridinyl)-1H-pyrazolo[3,4-b]quinoline-3-carboxylate

Following the procedures described in Reference Example 2-5 and Example 2-1, the title compound was prepared from o-iodobenzoic acid and ethyl 5-amino-1-(2-pyridinyl)-1H-pyrazole-3-carboxylate (52% yield).

mp: 164–166° C. (recrystallized from ethyl acetate). NMR (CDCl$_3$) δ: 1.53 (3H, t, J=7.4 Hz), 4.60 (2H, q, J=7.4 Hz), 7.37 (1H, dq, J=1.0 Hz, 5.0 Hz), 7.62–7.72 (1H, m), 7.84–8.05 (2H, m), 8.17–8.25 (1H, m), 8.50–8.80 (3H, m). Elementary Analysis: for C$_{18}$H$_{13}$ClN$_4$O$_2$ Calcd.: C, 61.28; H, 3.71; N, 15.88; Cl, 10.05.
Found: C, 61.27; H, 3.80; N, 16.01; Cl, 9.82.

EXAMPLE 2-180

Ethyl 4-oxo-1-(2-pyridinyl)-4,9-dihydro-1H-pyrazolo[3,4-b]quinoline-3-carboxylate Following the procedures described in Reference Example 2-5 and Example 2-12, the title compound was prepared from o-iodobenzoic acid and ethyl 5-amino-1-(2-pyridinyl)-1H-pyrazole-3-carboxylate (63% yield).

mp: 183–186° C. (recrystallized from ethyl acetate). NMR (CDCl$_3$) δ: 1.53 (3H, t, J=7.0 Hz), 4.59 (2H, q, J=7.0 Hz), 7.25–7.48 (3H, m), 7.63–7.72 (1H, m), 7.91–8.01 (1H, m), 8.19 (1H, d, J=8.4 Hz), 8.48–8.60 (2H, m), 11.62 (1H, br s). Elementary Analysis: for C$_{18}$H$_{14}$N$_4$O$_3$ Calcd.: C, 64.66; H, 4.22; N, 16.76. Found: C, 64.63; H, 4.16; N, 16.76.

EXAMPLE 2-181

4-Oxo-1-(2-pyridinyl)-4,9-dihydro-1H-pyrazolo[3,4-b]quinoline-3-carboxylic acid

Following the procedure described in Example 2-177, the title compound was prepared from methyl 4-oxo-1-(2-pyridinyl)-4,9-dihydro-1H-pyrazolo[3,4-b]quinoline-3-carboxylate (92% yield).

mp: 306–309° C. NMR (DMSO-d$_6$) δ: 7.48–7.59 (2H, m), 7.92 (1H, ddd, J=1.4 Hz, 7.0 Hz, 8.4 Hz), 8.03–8.07 (1H, m), 8.18 (1H, dd, J=1.8 Hz, 8.4 Hz), 8.26–8.38 (2H, m), 8.71 (1H, d, J=4.4 Hz), 12.40 (1H, br s), hidden (1H). Elementary Analysis: for C$_{16}$H$_{10}$N$_4$O$_3$ Calcd.: C, 62.74; H, 3.29; N, 18.29. Found: C, 62.36; H, 3.21; N, 18.07.

EXAMPLE 2-182

3-Phenyl-1-(2-pyridinyl)-1,9-dihydro-4H-pyrazolo[3,4-b]quinolin-4-one

Following the procedures described in Reference Example 2-5 and Example 2-12, the title compound was prepared from o-iodobenzoic acid and 3-phenyl-1-(2-pyridinyl)-1H-pyrazol-5-ylamine which was previously prepared from benzoylacetonitrile and 2-hydrazinopyridine following the method described in Reference Example 2-72 (58% yield).

mp: 237–240° C. (recrystallized from ethyl acetate). NMR (DMSO-d$_6$) δ: 7.34–7.57 (5H, m), 7.73–7.81 (1H, m), 7.81–8.15 (3H, m), 8.31 (1H, dd, J=1.4 Hz, 8.2 Hz), 8.46–8.50 (2H, m), 8.67–8.70 (1H, m), 12.21 (1H, br s). Elementary Analysis: for C$_{21}$H$_{14}$N$_4$O Calcd.: C, 74.54; H, 4.17; N, 16.56. Found: C, 74.59; H, 4.20; N, 16.56.

EXAMPLE 2-183

4-Chloro-3-(4-methoxyphenyl)-1-(2-pyridinyl)-1H-pyrazolo[3,4-b]quinoline

Following the procedures described in Reference Example 2-5 and Example 2-1, the title compound was prepared from o-iodobenzoic acid and 3-(4-methoxyphenyl)-1-(2-pyridinyl)-1H-pyrazol-5-ylamine (86% yield).

mp: 205–207° C. (recrystallized from chloroform/methanol). NMR (CDCl$_3$) δ: 3.92 (3H, s), 7.06 (2H, d, J=8.8 Hz), 7.25–7.35 (1H, m), 7.56–7.67 (1H, m), 7.81 (2H, d, J=8.8 Hz), 7.85–8.03 (2H, m), 8.24 (1H, d, J=8.8 Hz), 8.44 (1H, d, J=8.4 Hz), 8.70–8.80 (2H, m). Elementary Analysis: for C$_{12}$H$_{15}$ClN$_4$O.H$_2$O Calcd.: C, 65.27; H, 4.23; N, 13.84. Found: C, 65.13; H, 4.48; N, 13.66.

EXAMPLE 2-184

3-(4-Methoxyphenyl-1-(2-pyridinyl)-1H-pyrazolo[3,4-b]quinolin-4-ylamine hydrochloride Following the procedures described in Examples 2-2 and 2-3, the title compound was prepared from 4-chloro-3-(4-methoxyphenyl)-1-(2-pyridinyl)-1H-pyrazolo[3,4-b]quinoline (37% yield).

mp: 248–251° C. (recrystallized from ethanol). NMR (DMSO-d$_6$) δ: 3.90 (3H, s), 7.22 (2H, d, J=8.8 Hz), 7.48–7.70 (2H, m), 7.77 (2H, d, J=8.8 Hz), 7.99–8.20 (3H, m), 8.49 (1H, d, J=8.8 Hz), 8.70–8.75 (1H, m), 8.79 (1H, d, J=8.4 Hz), 10.20 (2H, br s). Elementary Analysis: for C$_{22}$H$_{17}$N$_5$O.HCl.3H$_2$O Calcd.: C, 57.70; H, 5.28; N, 15.29; Cl, 7.74. Found: C, 57.45; H, 5.20; N, 14.99; Cl, 8.05.

EXAMPLE 2-185

3-(4-Methoxyphenyl)-1-(2-pyridinyl)-1,9-dihydro-4H-pyrazolo[3,4-b]quinolin-4-one Following the procedures described in Reference Example 2-5 and Example 2-12, the title compound was prepared from o-iodobenzoic acid and 3-(4-methoxyphenyl)-1-(2-pyridinyl)-1H-pyrazol-5-ylamine (73% yield).

mp: 197–199° C. (recrystallized from ethyl acetate). NMR (DMSO-d$_6$) δ: 3.86 (3H, s), 7.08 (2H, td, J=2.4 Hz, 9.0 Hz), 7.37 (1H, t, J=7.5 Hz), 7.42–7.49 (1H, m), 7.72–7.80 (1H, m), 8.05–8.13 (3H, m), 8.31 (1H, dd, J=1.2 Hz, 8.4 Hz), 8.50 (2H, td, J=2.4 Hz, 9.0 Hz), 8.67 (1H, d, J=3.0 Hz), 12.20 (1H, br s). Elementary Analysis: for C$_{22}$H$_{16}$N$_4$O$_2$ Calcd.: C, 71.73; H, 4.38; N, 15.21. Found: C, 71.39; H, 4.35; N, 15.10.

EXAMPLE 2-186

4-Chloro-3-methyl-1-(2-pyridinylmethyl)-1H-pyrazolo[3,4-b]quinoline

Following the procedures described in Reference Example 2-3 and Example 2-1, the title compound was prepared from 2-(2-oxopropyl)-4H-3,1-benzoxazin-4-one and 2-hydrazinomethylpyridine which was previously prepared from 2-chloromethylpyridine following the method described in Reference Example 2-2 (75% yield).

mp: 113–115° C. (recrystallized from ethyl acetate). NMR (CDCl$_3$) δ: 2.89 (3H, s), 5.88 (2H, s), 6.44 (1H, d, J=7.7 Hz), 7.12–7.20 (1H, m), 7.46–7.62 (2H, m), 7.70–7.80 (1H, m), 8.06 (1H, d, J=8.8 Hz), 8.33–8.40 (1H, m), 8.55–8.61 (1H, m). Elementary Analysis: for C$_{17}$H$_{13}$ClN$_4$ Calcd.: C, 66.13; H, 4.24; N, 18.15; Cl, 11.48. Found: C, 66.27; H, 4.12; N, 18.11; Cl, 11.42.

EXAMPLE 2-187

3-Methyl-1-(2-pyridinylmethyl)-1H-pyrazolo[3,4-b]quinolin-4-ylamine

Following the procedure described in Example 2-2, the title compound was prepared from 4-chloro-3-methyl-1-(2-pyridinylmethyl)-1H-pyrazolo[3,4-b]quinoline (81% yield).

mp: 262–265° C. (recrystallized from ethanol). NMR (DMSO-$d_6$) δ: 2.71 (3H, s), 6.00 (2H, s), 7.52–7.70 (3H, m), 7.95–8.01 (2H, m), 8.10–8.20 (1H, m), 8.65–8.73 (2H, m), hidden (1H). Elementary Analysis: for $C_{17}H_{15}N_5$.2HCl.0.5$H_2O$ Calcd.: C, 55.00; H, 4.89; N, 18.86; Cl, 19.10. Found: C, 55.21; H, 4.89; N, 18.82; Cl, 19.21.

EXAMPLE 2-188

N,N-Dimethyl-N-[3-methyl-1-(2-pyridinylmethyl)-1H-pyrazolo[3,4-b]quinolin-4-yl]amine Following the procedure described in Example 2-8, the title compound was prepared from 4-chloro-3-methyl-1-(2-pyridinylmethyl)-1H-pyrazolo[3,4-b]quinoline and a solution of 2M dimethylamine in tetrahydrofuran (81% yield).

mp: 166–168° C. (recrystallized from ethyl acetate). NMR (CDCl$_3$) δ: 2.78 (3H, s), 3.37 (6H, s), 5.86 (2H, s), 6.98 (1H, d, J=8.1 Hz), 7.10–7.19 (1H, m), 7.25–7.37 (1H, m), 7.49–7.68 (2H, m), 7.98 (1H, dd, J=0.73 Hz, 8.8 Hz), 8.17 (1H, dd, J=0.73 Hz, 8.8 Hz), 8.58 (1H, br d, J=4.8 Hz). Elementary Analysis: for $C_{19}H_{19}N_5$ Calcd.: C, 71.90; H, 6.03; N, 22.07. Found: C, 71.72; H, 6.03; N, 21.90.

EXAMPLE 2-189

3-Methyl-1-(2-pyridinylmethyl)-1,9-dihydro-4H-pyrazolo[3,4-b]quinolin-4-one

Following the procedure described in Example 2-19, the title compound was prepared from 4-chloro-3-methyl-1-(2-pyridinylmethyl)-1H-pyrazolo[3,4-b]quinoline and methanol (23% yield).

mp: 269–272° C. (recrystallized from ethyl acetate/methanol). NMR (DMSO-$d_6$) δ: 2.51 (3H, s), 5.57 (2H, s), 7.14 (1H, d, J=8.1 Hz), 7.25–7.38 (2H, m), 7.55 (1H, d, J=8.1 Hz), 7.65–7.85 (2H, m), 8.23 (1H, d, J=8.1 Hz), 8.52 (1H, d, J=4.8 Hz). Elementary Analysis: for $C_{17}H_{14}N_4O$ Calcd.: C, 70.33; H, 4.86; N, 19.30. Found: C, 70.14; H, 4.80; N, 19.17.

EXAMPLE 2-190

4-Methoxy-3-methyl-1-(2-pyridinylmethyl)-1H-pyrazolo[3,4-b]quinoline

Following the procedure described in Example 2-19, the title compound was prepared from 4-chloro-3-methyl-1-(2-pyridinylmethyl)-1H-pyrazolo[3,4-b]quinoline and methanol (70% yield).

mp: 111–113° C. (recrystallized from ethyl acetate/hexane). NMR (CDCl$_3$) δ: 2.82 (3H, s), 4.26 (3H, s), 5.88 (2H, s), 7.01 (1H, d, J=8.1 Hz), 7.10–7.20 (1H, m), 7.35–7.77 (3H, m), 8.04 (1H, d, J=8.1 Hz), 8.25 (1H, d, J=8.4 Hz), 8.59 (1H, d, J=5.8 Hz). Elementary Analysis: for $C_{18}H_{16}N_4O$ Calcd.: C, 71.04; H, 5.30; N, 18.41. Found: C, 70.97; H, 5.20; N, 18.29.

EXAMPLE 2-191

3-Methyl-1-(3-pyridinylmethyl)-1,9-dihydro-4H-pyrazolo[3,4-b]quinolin-4-one

Following the procedure described in Example 2-12, the title compound was prepared from 2-[[3-methyl-1-(3-pyridinylmethyl)-1H-pyrazol-5-yl]amino]benzoic acid (58% yield).

mp: 285–288° C. (recrystallized from ethyl acetate/methanol). NMR (DMSO-$d_6$) δ: 2.50 (3H, s), 5.53 (2H, s), 7.21–7.73 (5H, m), 8.19 (1H, d, J=8.1 Hz), 8.51 (1H, d, J=4.0 Hz), 8.55 (1H, s), 11.99 (1H, br s). Elementary Analysis: for $C_{17}H_{14}N_4O$.0.1$H_2O$ Calcd.: C, 69.90; H, 4.90; N, 19.18. Found: C, 69.64; H, 5.01; N, 18.95.

EXAMPLE 2-192

3-Methyl-1-(4-pyridinylmethyl)-1,9-dihydro-4H-pyrazolo[3,4-b]quinolin-4-one

Following the procedure described in Example 2-12, the title compound was prepared from 2-[[3-methyl-1-(4-pyridinylmethyl)-1H-pyrazol-5-yl]amino]benzoic acid (85% yield).

mp: 277–280° C. (recrystallized from ethyl acetate/methanol). NMR (DMSO-$d_6$) δ: 2.52 (3H, s), 5.54 (2H, s), 7.13 (2H, d, J=6.0 Hz), 7.21–7.33 (1H, m), 7.50 (1H, d, J=8.4 Hz), 7.60–7.72 (1H, m), 8.20 (1H, dd, J=1.1 Hz, 8.4 Hz), 8.53 (2H, d, J=6.0 Hz), 11.96 (1H, br s). Elementary Analysis: for $C_{17}H_{14}N_4O$ Calcd.: C, 70.33; H, 4.86; N, 19.30. Found: C, 70.26; H, 4.84; N, 19.18.

EXAMPLE 2-193

3-Methyl-1-(2-pyridinyl)-5,6,7,8-tetrahydrocyclopenta[b]pyrazolo[4,3-b]pyridin-4(1H)-one Following the procedure described below in Example 2-194, the title compound was prepared from ethyl 2-oxocyclopentanecarboxylate and 3-methyl-1-(2-pyridinyl)-1H-pyrazol-5-ylamine (17% yield).

mp: 218–219° C. (recrystallized from ethyl acetate). NMR (CDCl$_3$) δ: 2.10–2.25 (2H, m), 2.69 (3H, s), 2.85 (2H, t, J=7.4 Hz), 3.01 (2H, t, J=7.2 Hz), 7.14–7.20 (1H, m), 7.81–7.90 (1H, m), 7.96 (1H, d, J=8.0 Hz), 8.40 (1H, d, J=4.4 Hz), 11.23 (1H, br s). Elementary Analysis: for $C_{15}H_{14}N_4O$.0.1$H_2O$ Calcd.: C, 67.20; H, 5.34; N, 20.90. Found: C, 67.00; H, 5.12; N, 20.77.

EXAMPLE 2-194

3-Methyl-1-(2-pyridinyl)-1,5,6,7,8,9-hexahydro-4H-pyrazolo[3,4-b]quinolin-4-one

A mixture of polyphosphoric acid (4.02 g) and 3-methyl-1-(2-pyridinyl)-1H-pyrazol-5-ylamine (1.75 g, 10.0 mmol) was heated at 130° C. The mixture was stirred at the same temperature, while ethyl 2-cyclohexanone carboxylate(1.70 mL, 10.6 mmol) was added thereto gradually. The mixture was stirred at the same temperature further for 4 hours. The solution was allowed to cool to room temperature, and water was added to the mixture. The solution was neutralized by the addition of a sodium hydroxide solution and the organic matter was extracted with chloroform. The extract was washed with saturated brine and dried over anhydrous sodium sulfate, and the solvent was evaporated under reduced pressure. The residue thus obtained was purified by silica gel column chromatography (chloroform:methanol=100:1 to 50:1 to 20:1), and recrystallized from ethyl acetate to give the title compound (0.39 g, 14% yield).

mp: 172–173° C. (recrystallized from ethyl acetate). NMR (CDCl$_3$) δ: 1.76–2.05 (4H, m), 2.60 (2H, t, J=5.4 Hz), 2.70 (3H, s), 2.73 (2H, t, J=5.6 Hz), 7.13–7.20 (1H, m), 7.81–7.90 (1H, m), 7.96 (1H, d, J=8.0 Hz), 8.40 (1H, dd, J=0.8 Hz, 5.2 Hz), 10.85 (1H, br s). Elementary Analysis: for $C_{16}H_{16}N_4O$.0.75$H_2O$ Calcd.: C, 65.40; H, 6.00; N, 19.07. Found: C, 65.50; H, 6.03; N, 19.08.

EXAMPLE 2-195

3-Methyl-1-(2-pyridinyl)-5,6,7,8,9,10-hexahydrocyclohepta[b]pyrazolo[4,3-e]pyridin-4(1H)-one Following the procedure described in Example 2-194, the title compound was prepared from methyl 2-oxo-1- cycloheptanecarboxylate and 3-methyl-1-(2-pyridinyl)-1H-pyrazol-5-ylamine (15% yield).

mp: 184–185° C. (recrystallized from ethyl acetate-hexane). NMR (CDCl$_3$) δ: 1.53–1.64 (2H, m), 1.77–1.88 (4H, m), 2.71 (3H, s), 2.85–2.90 (4H, m), 7.14–7.21 (1H, m), 7.82–7.90 (1H, m), 7.96 (1H, d, J=8.4 Hz), 8.41 (1H, dd, J=1.0 Hz, 5.3 Hz), 10.97 (1H, br s). Elementary Analysis: for C$_{17}$H$_{18}$N$_4$O.H$_2$O Calcd.: C, 65.37; H, 6.45; N, 17.94. Found: C, 65.38; H, 6.30; N, 18.11.

EXAMPLE 2-196

4-Chloro-3-methyl-1-(2-pyridinyl)-1H-pyrazolo[3,4-b][1, 8]naphthyridine

Following the procedure described in Example 2-1, the title compound was prepared from 2-[[3-methyl-1-(2-pyridinyl)-1H-pyrazol-5-yl]amino]nicotinic acid (69% yield).

mp: 204–205° C. (recrystallized from ethyl acetate/methanol). NMR (CDCl$_3$) δ: 3.03 (3H, s), 7.28 (1H, ddd, J=1.0 Hz, 5.0 Hz, 7.4 Hz), 7.60 (1H, ddd, J=2.0 Hz, 4.2 Hz, 8.6 Hz), 7.97 (1H, ddd, J=1.8 Hz, 7.4 Hz, 8.4 Hz), 8.69 (1H, ddd, J=0.8 Hz, 1.8 Hz, 5.0 Hz), 8.83 (1H, dd, J=2.0 Hz, 8.6 Hz), 9.01 (1H, ddd, J=0.8 Hz, 1.0 Hz, 8.4 Hz), 9.26 (1H, dd, J=2.0 Hz, 4.2 Hz). Elementary Analysis: for C$_{15}$H$_{10}$ClN$_5$.0.25H$_2$O Calcd.: C, 60.01; H, 3.53; N, 23.33; Cl, 11.81. Found: C, 60.30; H, 3.68; N, 23.11; Cl, 11.83.

EXAMPLE 2-197

3-Methyl-1-(2-pyridinyl)-1,9-dihydro-4H-pyrazolo[3,4-b][1,8]naphthylizin-4-one Following the procedure described in Example 2-13, the title compound was prepared from 4-chloro-3-methyl-1-(2-pyridinyl)-1H-pyrazolo[3,4-b][1,8]naphthyridine (50% yield).

mp: >300° C. (recrystallized from chloroform/methanol). NMR (DMSO-d$_6$) δ: 2.59 (3H, s), 7.14 (1H, dd, J=4.4 Hz, 7.8 Hz), 7.22–7.28 (1H, m), 7.92–8.01 (1H, m), 8.48–8.65 (4H, m) , 11.89 (1H, br s). Elementary Analysis: for C$_{15}$H$_{11}$N$_5$O.0.5HCl Calcd.: C, 60.97; H, 3.92; N, 23.70. Found: C, 61.14; H, 3.52; N, 23.70.

REFERENCE EXAMPLE 2-76

4,5-Difluoro-2-[[1-(2-pyridinyl)-1H-pyrazol-5-yl]amino]benzoic acid

A solution of 1-(2-pyridinyl)-1H-pyrazol-5-ylamine (6.94 g, 43.3 mmol), 2-chloro-4,5-difluorobenzoic acid (10.0 g, 51.9 mmol), copper acetate (II) (0.787 g, 4.33 mmol) and potassium carbonate (5.98 g, 43.3 mmol) in N,N-dimethylformamide (40 mL) was heated under reflux under an argon atmosphere for 3 hours. The solution was allowed to cool to room temperature, and poured into water. The solution was made weakly acidic by the addition of 6N hydrochloric acid, and the resulting crude crystals were collected by filtration. The crystals were washed with water and air dried to give the title compound (8.99 g, 55% yield).

mp: 242–245° C. (recrystallized from ethanol). NMR (DMSO-d$_6$) δ: 6.51 (1H, d, J=2.0 Hz), 7.38 (1H, ddd, J=1.0 Hz, 4.8 Hz, 7.2 Hz), 7.51 (1H, dd, J=7.0 Hz, 13.6 Hz), 7.72 (1H, d, J=2.0 Hz), 7.84–7.95 (2H, m), 8.04 (1H, ddd, J=1.8 Hz, 7.2 Hz, 8.4 Hz), 8.47 (1H, ddd, J=0.8 Hz, 1.8 Hz, 4.8 Hz), 12.24 (1H, br s), hidden (1H). Elementary Analysis: for C$_{15}$H$_{10}$F$_2$N$_4$O$_2$.0.2H$_2$O Calcd.: C, 56.32; H, 3.28; N, 17.52. Found: C, 56.32; H, 3.18; N, 17.53.

REFERENCE EXAMPLE 2-77

3-Oxopentanenitrile

A solution of ethyl cyanoacetate (17.0 g, 150 mmol), magnesium chloride (14.4 g, 151 mmol) and triethylamine (42 mL, 301 mmol) in acetonitrile (150 mL) was stirred at 0° C. for 15 minutes. To the solution, propionyl chloride (13.8 g, 150 mmol) was added dropwise over 15 minutes at the same temperature, and subsequently the solution was allowed to warm to room temperature and stirred for 24 hours. After addition of 30% hydrochloric acid (100 mL), the organic matter was extracted with diethylether. The extract was washed with saturated brine and dried over anhydrous magnesium sulfate, and the solvent was evaporated under reduced pressure to give crude ethyl 2-cyano-3-oxopentanoate (24.6 g, 97% yield). The compound (25.4 g, 150 mmol) was dissolved in a mixed solvent of dimethylsulfoxide (50 mL) and water (5 mL), and the solution was stirred at 120° C. for 1.5 hours. The solution was allowed to cool to room temperature and poured into saturated brine, and the organic matter was extracted with dichloromethane. The extract was washed with saturated brine and dried over anhydrous magnesium sulfate, and the solvents were evaporated under reduced pressure to give the title compound (14.6 g, quantitative).

NMR (CDCl$_3$) δ: 1.14 (3H, t, J=7.4 Hz), 2.66 (2H, q, J=7.4 Hz), 3.48 (2H, s).

REFERENCE EXAMPLE 2-78

3-Ethyl-1-(2-pyridinyl)-1H-pyrazol-5-ylamine

To an ice-cold solution of 3-oxopentanenitrile (14.6 g, 150 mmol) and 2-hydrazinopyridine (13.6 g, 125 mmol) in ethanol (150 mL), acetic acid (14.3 mL, 250 mmol) was added and the resulting mixture was heated under reflux for 5 hours. The solution was allowed to cool to room temperature, and concentrated under reduced pressure, and water was added to the residue. The solution was made basic by the addition of an aqueous sodium hydroxide solution, and the organic matter was extracted with ethyl acetate. The extract was washed with saturated brine and water, and dried over anhydrous sodium sulfate, and the solvent was evaporated under reduced pressure. The residue thus obtained was purified by silica gel column chromatography (hexane:ethyl acetate=4:1) to give the title compound (21.1 g, 90% yield). NMR (CDCl$_3$) δ: 1.25 (3H, t, J=7.6 Hz), 2.59 (2H, q, J=7.6 Hz), 5.38 (1H, s), 5.90 (2H, br s), 7.04 (1H, ddd, J=1.2 Hz, 5.0 Hz, 7.4 Hz), 7.75 (1H, ddd, J=2.0 Hz, 7.4 Hz, 8.4 Hz), 7.94 (1H, ddd, J=0.8 Hz, 1.2 Hz, 8.4 Hz), 8.29 (1H, ddd, J=0.8 Hz, 2.0 Hz, 5.0 Hz).

REFERENCE EXAMPLE 2-79

3-Methyl-1-(3-pyridinyl)-1H-pyrazol-5-ylamine dihydrochloride

A solution of aminocrotononitrile (8.21 g, 100 mmol) and 3-hydrazinopyridine dihydrochloride (20.7 g, 114 mmol) in water (50 mL) was mixed with conc. hydrochloric acid (15 mL), and the mixture was heated under reflux for 30 minutes. The solution was allowed to cool to room temperature, and the reaction solvent was evaporated under reduced pressure, and the resulting crystals were collected by filtration. The crystals obtained were washed with water and air dried to give the title compound (13.6 g, 55% yield).

NMR (DMSO-d$_6$) δ: 2.20 (3H, s), 5.61 (1H, s), 7.88 (1H, dd, J=5.0 Hz, 8.4 Hz), 8.41 (1H, ddd, J=1.2 Hz, 2.4 Hz, 8.4 Hz), 8.75 (1H, dd, J=1.2 Hz, 5.0 Hz), 9.00 (1H, d, J=2.4 Hz), hidden (3H).

REFERENCE EXAMPLE 2-80

3-Methyl-1-(4-pyridinyl)-1H-pyrazol-5-ylamine

A mixture of 4-chloropyridine hydrochloride (25.3 g, 169 mmol) and hydrazine monohydrate (40.0 mL, 825 mmol) was heated under reflux for 1 hour. The solution was cooled to 0° C., and the resulting crystals were collected by filtration. The crystals were washed with cold 1-propanol and air dried to give crude 4-hydrazinopyridine (16.1 g, 88% yield). To a solution of the compound (7.64 g, 70.0 mmol) and aminocrotononitrile (5.75 g, 70.0 mmol) in water (30 mL), conc. hydrochloric acid (8 mL) was added and the mixture was heated under reflux for 30 minutes. The solution was allowed to cool to room temperature, made basic by the addition of an aqueous sodium hydroxide solution, and the organic matter was extracted with chloroform. The extract was washed with saturated brine and dried over anhydrous sodium sulfate, and the solvent was evaporated under reduced pressure. The residue thus obtained was purified by silica gel column chromatography (ethyl acetate to 10% methanol/ethyl acetate) to give the title compound (6.20 g, 51% yield)

mp: 109–110° C. (recrystallized from ethyl acetate/hexane). NMR (CDCl$_3$) δ: 2.23 (3H, s), 3.92 (2H, br s), 5.51 (1H, s), 7.64 (2H, dd, J=1.4 Hz, 4.8 Hz), 8.63 (2H, dd, J=1.4 Hz, 4.8 Hz). Elementary Analysis: for C$_9$H$_{10}$N$_4$ Calcd.: C, 62.05; H, 5.79; N, 32.16. Found: C, 62.12; H, 5.93; N, 32.10.

EXAMPLE 2-198

4-Chloro-6,7-difluoro-1-(2-pyridinyl)-1H-pyrazolo[3,4-b]quinoline

A solution of 4,5-difluoro-2-[[1-(2-pyridinyl)-1H-pyrazol-5-yl]amino]benzoic acid (7.00 g, 22.1 mmol) in phosphorous oxychloride (10.3 mL, 111 mmol) was heated under reflux for 1 hour. The solution was allowed to cool to room temperature, and poured into iced water. After neutralization by addition of a sodium hydroxide solution, the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform) to give the title compound (3.99 g, 57% yield).

mp: 167–168° C. (recrystallized from ethyl acetate). NMR (CDCl$_3$) δ: 7.32 (1H, ddd, J=1.0 Hz, 4.8 Hz, 7.4 Hz), 7.93–8.03 (2H, m), 8.12 (1H, dd, J=8.6 Hz, 11.0 Hz), 8.57 (1H, s), 8.65 (1H, ddd, J=0.8 Hz, 1.0 Hz, 8.4 Hz), 8.71 (1H, ddd, J=0.8 Hz, 1.8 Hz, 4.8 Hz). Elementary Analysis: for C$_{15}$H$_7$ClF$_2$N$_4$ Calcd.: C, 56.89; H, 2.23; N, 17.69; Cl, 11.19; F, 12.00. Found: C, 57.00; H, 2.31; N, 17.79; Cl, 11.21; F, 12.02.

EXAMPLE 2-199

6,7-Difluoro-1-(2-pyridinyl)-1,9-dihydro-4H-pyrazolo[3,4-b]quinolin-4-one

To a solution of 4-chloro-6,7-difluoro-1-(2-pyridinyl)-1H-pyrazolo[3,4-b]quinoline (3.17 g, 10.0 mmol) in ethanol (160 mL) was added 6 N hydrochloric acid (8 mL, 48.0 mmol), and the mixture was heated under reflux for 6 hours. The solution was allowed to cool to room temperature, and the resulting crystals were collected by filtration. The crystals were washed with ethanol, air dried, and subsequently recrystallized from ethanol to give the title compound (2.47 g, 83% yield).

mp: >300° C. (recrystallized from ethanol). NMR (DMSO-d$_6$) δ: 7.42–7.49 (1H, m), 7.95 (1H, d, J=8.4 Hz), 8.01–8.05 (2H, m), 8.22 (1H, dd, J=7.0 Hz, 12.4 Hz), 8.37 (1H, s), 8.61–8.64 (1H, m), 12.15 (1H, br s). Elementary Analysis: for C$_{15}$H$_8$F$_2$N$_4$O Calcd.: C, 60.41; H, 2.70; N, 18.79; F, 12.74. Found: C, 60.44; H, 2.73; N, 18.74; F, 12.84.

EXAMPLE 2-200

4-Chloro-3-ethyl-6,7-difluoro-1-(2-pyridinyl)-1H-pyrazolo[3,4-b]quinoline

A solution of 3-ethyl-1-(2-pyridinyl)-1H-pyrazol-5-ylamine (9.41 g, 50.0 mmol), 2-chloro-4,5-difluorobenzoic acid (9.63 g, 50.0 mmol), copper acetate (II) (0.908 g, 5.00 mmol) and potassium carbonate (6.91 g, 50.0 mmol) in N,N-dimethylformamide (50 mL) was heated under reflux under an argon atmosphere for 2 hours. The solution was allowed to cool to room temperature, and poured into water. The solution was made weakly acidic by the addition of 1N hydrochloric acid, and the resulting crude crystals were collected by filtration. The crystals were washed with water and air dried to give crude 4,5-difluoro-2-[[3-ethyl-1-(2-pyridinyl)-1H-pyrazol-5-yl]amino]benzoic acid (11.3 g, 66% yield). A solution of the compound (11.0 g, 31.9 mmol) in phosphorous oxychloride (15 mL, 161 mmol) was heated under reflux for 2 hours. The solution was allowed to cool to room temperature, and poured into iced water. The solution was neutralized by the addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform) to give the title compound (5.50 g, 50% yield).

mp: 160–161° C. (recrystallized from ethyl acetate). NMR (CDCl$_3$) δ: 1.53 (3H, t, J=7.5 Hz), 3.39 (2H, q, J=7.5 Hz), 7.23–7.30 (1H, m), 7.87–7.98 (2H, m), 8.15 (1H, dd, J=8.4 Hz, 11.0 Hz), 8.64–8.71 (2H, m). Elementary Analysis: for C$_{17}$H$_{11}$ClF$_2$N$_4$ Calcd.: C, 59.23; H, 3.22; N, 16.25; Cl, 10.28; F, 11.02. Found: C, 59.09; H, 3.12; N, 16.24; Cl, 10.25; F, 10.93.

EXAMPLE 2-201

3-Ethyl-6,7-difluoro-1-(2-pyridinyl)-1,9-dihydro-4H-pyrazolo[3,4-b]quinolin-4-one To a solution of 4-chloro-3-ethyl-6,7-difluoro-1-(2-pyridinyl)-1H-pyrazolo[3,4-b]quinoline (2.49 g, 7.22 mmol) in ethanol (120 mL), 6N hydrochloric acid (6 mL, 36.0 mmol) was added and the mixture was heated under reflux for 6 hours. The solution was allowed to cool to room temperature, and the resulting crystals were collected by filtration. The crystals were washed with ethanol, air dried, and recrystallized from ethanol to give the title compound (1.73 g, 73% yield).

mp: 247–248° C. (recrystallized from ethanol). NMR (DMSO-d$_6$) δ: 1.33 (3H, t, J=7.4 Hz), 2.98 (2H, q, J=7.4 Hz), 7.41 (1H, ddd, J=1.0 Hz, 5.0 Hz, 7.4 Hz), 7.89 (1H, ddd, J=0.8 Hz, 1.0 Hz, 8.4 Hz), 8.00 (1H, dd, J=9.0 Hz, 11.0 Hz), 8.07 (1H, ddd, J=1.8 Hz, 7.4 Hz, 8.4 Hz), 8.18 (1H, dd, J=7.0 Hz, 12.0 Hz), 8.58 (1H, ddd, J=0.8 Hz, 1.8 Hz, 5.0 Hz), 12.07 (1H, br s). Elementary Analysis: for C$_{17}$H$_{12}$F$_2$N$_4$O Calcd.: C, 62.57; H, 3.71; N, 17.17; F, 11.64. Found: C, 62.40; H, 3.70; N, 17.12; F, 11.62.

EXAMPLE 2-202

4-Chloro-6,7-difluoro-3-methyl-1-(3-pyridinyl)-1H-pyrazolo[3,4-b]quinoline

A solution of 3-methyl-1-(3-pyridinyl)-1H-pyrazol-5-ylamine dihydrochloride (11.0 g, 44.5 mmol), 2-chloro-4,5- difluorobenzoic acid (8.57 g, 44.5 mmol), copper acetate (II) (0.808 g, 4.45 mmol) and potassium carbonate (12.3 g, 89.0 mmol) in N,N-dimethylformamide (50 mL) was heated under reflux under an argon atmosphere for 3 hours. The solution was allowed to cool to room temperature, and poured into water. The solution was made weakly acidic by the addition of 1N hydrochloric acid, and the resulting crude crystals were collected by filtration. The crystals were washed with water and air dried to give crude 4,5-difluoro-2-[[3-methyl-1-(3-pyridinyl)-1H-pyrazol-5-yl]amino] benzoic acid (9.24 g, 63% yield). A solution of the compound (9.24 g, 28.0 mmol) in phosphorous oxychloride (13 mL, 139 mmol) was heated under reflux for 3 hours. The solution was allowed to cool to room temperature, and the reaction solvent was concentrated and evaporated under reduced pressure. The residue was poured into iced water. The solution was neutralized by the addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform) to give the title compound (0.77 g, 8% yield).

mp: 192–194° C. (recrystallized from ethyl acetate). NMR (CDCl$_3$) δ: 2.92 (3H, s), 7.46 (1H, dd, J=4.6 Hz, 8.4 Hz), 7.85 (1H, dd, J=7.6 Hz, 11.2 Hz), 8.09 (1H, dd, J=8.6 Hz, 11.2 Hz), 8.55 (1H, dd, J=1.4 Hz, 4.6 Hz), 8.73 (1H, ddd, J=1.4 Hz, 2.4 Hz, 8.4 Hz), 9.73 (1H, d, J=2.2 Hz). Elementary Analysis: for C$_{16}$H$_9$ClF$_2$N$_4$ Calcd.: C, 58.11; H, 2.74; N, 16.94; Cl, 10.72; F, 11.49. Found: C, 58.18; H, 2.83; N, 17.00; Cl, 10.72; F, 11.34.

EXAMPLE 2-203

6,7-Difluoro-3-methyl-1-(3-pyridinyl)-1,9-dihydro-4H-pyrazolo[3,4-b]quinoline-4-one dihydrochloride To a solution of 4-chloro-6,7-difluoro-3-methyl-1-(3-pyridinyl)-1H-pyrazolo[3,4-b]quinoline (0.70 g, 2.12 mmol) in ethanol (40 mL), 6N hydrochloric acid (2 mL, 12.0 mmol) was added, and the mixture was heated under reflux for 2.5 days. The solution was allowed to cool to room temperature, and the resulting crystals were collected by filtration. The crystals were washed with ethanol and air dried to give the title compound (0.27 g, 33% yield).

mp: >300° C. NMR (DMSO-d$_6$) δ: 2.57 (3H, s), 7.74 (1H, dd, J=6.8 Hz, 11.8 Hz), 7.89 (1H, dd, J=5.0 Hz, 8.4 Hz), 8.02 (1H, dd, J=9.0 Hz, 11.2 Hz), 8.41–8.46 (1H, m), 8.83 (1H, dd, J=1.2 Hz, 5.0 Hz), 9.14 (1H, d, J=2.2 Hz), hidden (1H).

EXAMPLE 2-204

4-Chloro-6,7-difluoro-3-methyl-1-(4-pyridinyl)-1H-pyrazolo[3,4-b]quinoline

A solution of 3-methyl-1-(4-pyridinyl)-1H-pyrazol-5-ylamine (5.80 g, 33.3 mmol), 2-chloro-4,5-difluorobenzoic acid (5.78 g, 30.0 mmol), copper acetate (II) (0.545 g, 3.00 mmol) and potassium carbonate (4.15 g, 30.0 mmol) in N,N-dimethylformamide (30 mL) was heated under reflux under an argon atmosphere for 2 hours. The solution was allowed to cool to room temperature and poured into water. The solution was made weakly acidic by the addition of 1N hydrochloric acid, and the resulting crude crystals were collected by filtration. The crystals were washed with water and air dried to give crude 4,5-difluoro-2-[[3-methyl-1-(4-pyridinyl)-1H-pyrazol-5-yl]amino]benzoic acid (6.44 g, 65% yield). A solution of the compound (5.50 g, 16.7 mmol) in phosphorous oxychloride (10 mL, 107 mmol) was heated under reflux for 3 hours. The solution was allowed to cool to room temperature, and the resulting residue was poured into iced water. The solution was neutralized by the addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform to 1% methanol/chloroform) to give the title compound (0.88 g, 16% yield).

mp: 226–228° C. (recrystallized from ethyl acetate/methanol). NMR (CDCl$_3$) δ: 2.91 (3H, s), 7.91 (1H, dd, J=7.6 Hz, 11.2 Hz), 8.11 (1H, dd, J=8.6 Hz, 11.0 Hz), 8.50 (2H, dd, J=1.6 Hz, 4.8 Hz), 8.72 (2H, dd, J=1.6 Hz, 4.8 Hz). Elementary Analysis: for C$_{16}$H$_9$ClF$_2$N$_4$ Calcd.: C, 58.11; H, 2.74; N, 16.94; Cl, 10.72; F, 11.49. Found: C, 58.02; H, 2.80; N, 16.87; Cl, 10.42; F, 11.75.

EXAMPLE 2-205

6,7-Difluoro-3-methyl-1-(4-pyridinyl)-1,9-dihydro-4H-pyrazolo[3,4-b]quinolin-4-one dihydrochloride To a solution of 4-chloro-6,7-difluoro-3-methyl-1-(4-pyridinyl)-1H-pyrazolo[3,4-b]quinoline (0.80 g, 2.42 mmol) in ethanol (40 mL), 6N hydrochloric acid (2 mL, 12.0 mmol) was added, and the mixture was heated under reflux for 6 hours. The solution was allowed to cool to room temperature, and the resulting crystals were collected by filtration. The crystals were washed with ethanol, air dried and recrystallized from ethanol to give the title compound (0.51 g, 55% yield).

mp: 237–240° C. (recrystallized from ethanol). NMR (DMSO-d$_6$) δ: 2.81 (3H, s), 8.14 (1H, dd, J=7.6 Hz, 11.4 Hz), 8.27 (1H, dd, J=8.8 Hz, 11.2 Hz), 8.82 (2H, d, J=7.0 Hz), 8.94 (2H, d, J=7.0 Hz), hidden (1H). Elementary Analysis: for C$_{16}$H$_{10}$F$_2$N$_4$O.2HCl Calcd.: C, 49.89; H, 3.14; N, 14.54; Cl, 18.41; F, 9.86. Found: C, 49.99; H, 3.14; N, 14.69; Cl, 18.04; F, 9.87.

REFERENCE EXAMPLE 2-81

2-Hydrazino-6-methylpyridine

A mixture of 2-chloro-6-methylpyridine (50.6 g, 397 mmol) and hydrazine hydrate (80 mL, 1.65 mol) was heated under reflux for 20 hours. The reaction solution was allowed to cool to room temperature, and excess hydrazine hydrate was evaporated under reduced pressure, and the residue was poured into water. The solution was made basic by the addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was chilled to crystallize, and the resulting crystals were washed with petroleum ether to give the title compound (31.0 g, 63% yield).

mp: 54–56° C. NMR (CDCl$_3$) δ: 2.40 (3H, s), 3.61 (2H, br s), 5.82 (1H, br s), 6.53 (1H, d, J=8.0 Hz), 6.54 (1H, d, J=7.4 Hz), 7.39 (1H, dd, J=7.4 Hz, 8.0 Hz).

REFERENCE EXAMPLE 2-82

3-Methyl-1-(6-methyl-2-pyridinyl)-1H-pyrazol-5-ylamine

To an ice-cold solution of aminocrotononitrile (20.5 g, 0.25 mol) and 2-hydrazino-6-methylpyridine (31.0 g, 0.252 mol) in ethanol (200 mL), acetic acid (30 g, 0.5 mol) was added and the mixture was heated under reflux for 2 hours. The reaction solution was allowed to cool to room temperature, and the reaction solvent was concentrated and evaporated under reduced pressure, and water was added to the residue. The solution was made basic by the addition of an aqueous sodium hydroxide solution, and the organic matter was extracted with ethyl acetate. The extract was washed with saturated brine and water, dried over anhydrous magnesium sulfate, and the solvent was evaporated under reduced pressure. The residue thus obtained was purified by silica gel column chromatography (ethyl acetate) to give the title compound (41.3 g, 88% yield).

mp: 149–150° C. (recrystallized from ethyl acetate). NMR (CDCl$_3$) δ: 2.22 (3H, s), 2.50 (3H, s), 5.34 (1H, s), 5.95 (2H, br s), 6.90 (1H, dd, J=0.8 Hz, 7.0 Hz), 7.63 (1H, dd, J=7.0 Hz, 8.4 Hz), 7.72 (1H, dd, J=0.8 Hz, 8.4 Hz). Elementary Analysis: for $C_{10}H_{12}N_4$ Calcd.: C, 63.81; H, 6.43; N, 29.77. Found: C, 63.94; H, 6.51; N, 29.90.

EXAMPLE 2-206

1-(2-Pyridinyl)-1,9-dihydro-4H-pyrazolo[3,4-b]quinolin-4-one

To a solution of 4-chloro-1-(2-pyridinyl)-1H-pyrazolo[3,4-b]quinoline (14 g, 0.050 mol) in ethanol (600 mL), 6N hydrochloric acid (30 mL) was added and the mixture was heated under reflux for 12 hours. The reaction solution was allowed to cool to room temperature, and concentrated and evaporated under reduced pressure. The residue was made basic by addition of an aqueous sodium hydroxide solution, and the organic matter was extracted with chloroform. The extract was washed with saturated brine and water, dried over anhydrous magnesium sulfate, and the solvent was evaporated under reduced pressure. The residue thus obtained was purified by silica gel column chromatography (chloroform:methanol=96:4) to give the title compound (10.8 g, 82% yield).

EXAMPLE 2-207

4-Chloro-3-methyl-1-(6-methyl-2-pyridinyl)-1H-pyrazolo[3,4-b]quinoline

A solution of 3-methyl-1-(6-methyl-2-pyridinyl)-1H-pyrazol-5-ylamine (7.03 g, 37.3 mmol), 2-iodobenzoic acid (10.2 g, 41.0 mmol), copper acetate (II) (0.745 g, 4.10 mmol) and potassium carbonate (5.67 g, 41.0 mmol) in N,N-dimethylformamide (30 mL) was heated under reflux under an argon atmosphere for 2 hours. The reaction solution was allowed to cool to room temperature, and the reaction mixture was poured into water. The solution was made weakly acidic by the addition of 1N hydrochloric acid, and the resulting crude crystals were collected by filtration. The crystals were washed with water and air dried to give crude 2-[[3-methyl-1-(6-methyl-2-pyridinyl)-1H-pyrazol-5-yl]amino]benzoic acid (10.6 g, 92% yield). A solution of the compound (9.5 g, 30.8 mmol) in phosphorous oxychloride (15 mL, 161 mmol) was heated under reflux for 1 hour. The reaction solution was allowed to cool to room temperature, and the residue was poured into iced water. The solution was neutralized by the addition of a sodium hydroxide solution, and the organic matter was extracted with chloroform. The extract was washed with saturated brine and water, and dried over anhydrous magnesium sulfate, and the solvent was evaporated under reduced pressure. The residue thus obtained was purified by silica gel column chromatography (chloroform) to give the title compound (2.37 g, 25% yield).

mp: 154° C. (recrystallized from ethyl acetate). NMR (CDCl$_3$) δ: 2.71 (3H, s), 3.01 (3H, s), 7.13 (1H, d, J=7.8 Hz), 7.55–7.63 (1H, m), 7.78–7.87 (2H, m), 8.16 (1H, dd, J=1.0 Hz, 8.8 Hz), 8.38–8.43 (1H, m), 8.58 (1H, d, J=1.0 Hz, 8.4 Hz), 7.69 (1H, d, J=8.0 Hz). Elementary Analysis: for $C_{17}H_{13}ClN_4$ Calcd.: C, 66.13; H, 4.24; N, 18.15; Cl, 11.48. Found: C, 66.19; H, 4.36; N, 18.25; Cl, 11.36.

EXAMPLE 2-208

3-Methyl-1-(6-methyl-2-pyridinyl)-1,9-dihydro-4H-pyrazolo[3,4-b]quinolin-4-one

To a solution of 4-chloro-3-methyl-1-(6-methyl-2-pyridinyl)-1H-pyrazolo[3,4-b]quinoline (2.00 g, 6.48 mmol) in ethanol (90 mL), 6N hydrochloric acid (3 mL, 18.0 mmol) was added and the mixture was heated under reflux for 4 hours. The reaction solution was allowed to cool to room temperature, and the resulting crystals were collected by filtration. The crystals were washed with ethanol, air dried, and recrystallized from ethanol to give the title compound (1.55 g, 82% yield).

mp: 252° C. (recrystallized from ethanol). NMR (DMSO-d$_6$) δ: 2.60 (3H, s), 2.70 (3H, s), 7.23 (1H, d, J=7.6 Hz), 7.29–7.37 (1H, m), 7.66–7.75 (2H, m), 7.83–7.96 (2H, m), 8.21 (1H, dd, J=0.6 Hz, 8.0 Hz), 11.64 (1H, br s). Elementary Analysis: for $C_{17}H_{14}N_4O$ Calcd.: C, 70.33; H, 4.86; N, 19.30. Found: C, 70.29; H, 4.64; N, 19.25.

EXAMPLE 2-209

6,7-Difluoro-3-methyl-1-(6-methyl-2-pyridinyl)-1,9-dihydro-4H-pyrazolo[3,4-b]quinolin-4-one A solution of 3-methyl-1-(6-methyl-2-pyridinyl)-1H-pyrazol-5-ylamine (5.65 g, 30.0 mmol), 2-chloro-4,5-difluorobenzoic acid (6.93 g, 36.0 mmol), copper acetate (II) (0.545 g, 3.00 mmol) and potassium carbonate (4.15 g, 30.0 mmol) in N,N-dimethylformamide (30 mL) was heated under reflux under an argon atmosphere for 2 hours. The solution was allowed to cool to room temperature, and the reaction mixture was poured into water. The solution was made weakly acidic by the addition of 1N hydrochloric acid, and the resulting crude crystals were collected by filtration. The crystals were washed with water and air dried to give crude 4,5-difluoro-2-[[3-methyl-1-(6-methyl-2-pyridinyl)-1H-pyrazol-5-yl]amino]benzoic acid (8.18 g, 79% yield). A solution of the compound (7.00 g, 20.3 mmol) in phosphorus oxychloride (9.73 mL, 104 mmol) was heated under reflux for 30 minutes. The reaction solution was allowed to cool to room temperature, and the residue was poured into iced water. The solution was neutralized by the addition of a sodium hydroxide solution, and the organic matter was extracted with chloroform. The extract was washed with saturated brine and water, dried over anhydrous magnesium sulfate, and the solvent was evaporated under reduced pressure. The residue thus obtained was purified by silica gel column chromatography (chloroform) to give crude 4-chloro-6,7-difluoro-3-methyl-1-(6-methyl-2-pyridinyl)-1H-pyrazolo[3,4-b]quinoline (2.70 g, 39% yield). To a solution of the compound (2.70 g, 36.0 mmol) in ethanol (120 mL), 6N hydrochloric acid (4 mL, 24.0 mmol) was added, and the mixture was heated under reflux for 3 hours. The reaction solution was allowed to cool to room temperature, and the resulting crystals were collected by filtration. The crystals were washed with ethanol, air dried and recrystallized from ethanol to give the title compound (1.68 g, 66% yield).

mp: 301–302° C. (recrystallized from ethanol). NMR (CDCl$_3$:CF$_3$CO$_2$D=50:1) δ: 2.75 (6H, s), 7.23 (1H, d, J=7.4 Hz), 7.37 (1H, dd, J=6.2 Hz, 9.8 Hz), 7.79 (1H, d, J=8.0 Hz), 7.93 (1H, dd, J=7.4 Hz, 8.0 Hz), 8.28 (1H, dd, J=8.2 Hz, 10.4 Hz), 10.85 (1H, br s). Elementary Analysis: for C$_{17}$H$_{12}$F$_2$N$_4$O Calcd.: C, 62.57; H, 3.71; N, 17.17; F, 11.64. Found: C, 62.55; H, 3.58; N, 17.09; F, 11.61.

Structures of the chemical compounds prepared in Examples 2-1 to 2-209 are shown in the following Tables 7 to 14.

TABLE 7

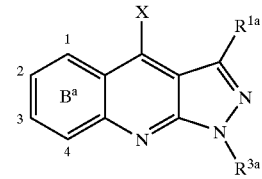

| Example Number | R$^{1a}$ | R$^{3a}$ | X | Substituent of Ring B$^a$ |
|---|---|---|---|---|
| 2-1 | Me | 2-Py | Cl | |
| 2-2 | Me | 2-Py | NH$_2$ | |
| 2-3 | Me | 2-Py | NH$_2$ | |
| 2-4 | Me | 2-Py | MeNH | |
| 2-5 | Me | 2-Py | cyclopropyl-NH | |
| 2-6 | Me | 2-Py | $^n$PrNH | |
| 2-7 | Me | 2-Py | $^n$BuNH | |
| 2-8 | Me | 2-Py | Me$_2$N | |
| 2-9 | Me | 2-Py | $^n$Pr(Me)N | |
| 2-10 | Me | 2-Py | $^n$Bu(Me)N | |
| 2-11 | Me | 2-Py | morpholinyl | |
| 2-15 | Me | 2-Py | MeO | |
| 2-16 | Me | 2-Py | EtO | |
| 2-17 | Me | 2-Py | $^n$PrO | |
| 2-18 | Me | 2-Py | $^i$PrO | |
| 2-19 | Me | 2-Py | $^n$BuO | |
| 2-20 | Me | 2-Py | $^i$BuO | |
| 2-21 | Me | 2-Py | cyclopentyloxy | |
| 2-22 | Me | 2-Py | cyclohexyloxy | |
| 2-23 | Me | 2-Py | PhCH$_2$O | 2: NO$_2$ |
| 2-25 | Me | 2-Py | $^i$PrS | |
| 2-26 | Me | 2-Py | $^i$PrSO | |
| 2-27 | Me | 2-Py | $^n$PrS | |
| 2-28 | Me | 2-Py | $^n$PrSO | |
| 2-29 | Me | 2-Py | Cl | 1: Me |
| 2-30 | Me | 2-Py | NH$_2$ | 1: Me |
| 2-32 | Me | 2-Py | Cl | 2: Me |
| 2-33 | Me | 2-Py | NH$_2$ | 2: Me |
| 2-35 | Me | 2-Py | Cl | 4: Me |
| 2-36 | Me | 2-Py | NH$_2$ | 4: Me |
| 2-37 | Me | 2-Py | NH$_2$ | 4: Me |
| 2-39 | Me | 2-Py | Cl | 2: CF$_3$ |
| 2-41 | Me | 2-Py | Cl | 2: MeO |
| 2-42 | Me | 2-Py | NH$_2$ | 2: MeO |
| 2-44 | Me | 2-Py | Cl | 4: MeO |
| 2-45 | Me | 2-Py | NH$_2$ | 4: MeO |
| 2-46 | Me | 2-Py | Cl | 2, 3: MeO |
| 2-47 | Me | 2-Py | NH$_2$ | 2, 3: MeO |
| 2-49 | Me | 2-Py | Cl | 2: MeS |
| 2-53 | Me | 2-Py | Cl | 2: NO$_2$ |
| 2-57 | Me | 2-Py | Cl | 3: NO$_2$ |
| 2-60 | Me | 2-Py | Cl | 1: CO$_2$Me |
| 2-63 | Me | 2-Py | Cl | 2: CO$_2$Me |
| 2-66 | Me | 2-Py | Cl | 3: CO$_2$Me |
| 2-70 | Me | 2-Py | Cl | 2: Cl |

TABLE 7-continued

| Example Number | R$^{1a}$ | R$^{3a}$ | X | Substituent of Ring B$^a$ |
|---|---|---|---|---|
| 2-71 | Me | 2-Py | NH$_2$ | 2: Cl |
| 2-73 | Me | 2-Py | Cl | 3: Cl |
| 2-75 | Me | 2-Py | Cl | 2, 3: Cl |
| 2-78 | Me | 2-Py | Cl | 1: F |
| 2-80 | Me | 2-Py | Cl | 2: F |
| 2-82 | Me | 2-Py | Cl | 3: F |
| 2-84 | Me | 2-Py | Cl | 4: F |
| 2-86 | Me | 2-Py | Cl | 2: Br |
| 2-88 | Me | 2-Py | Cl | 1, 2: F |
| 2-90 | Me | 2-Py | Cl | 2, 3: F |
| 2-94 | Me | 2-Py | $^n$PrO | 2, 3: F |
| 2-95 | Me | 2-Py | $^i$PrO | 2, 3: F |
| 2-96 | Me | 2-Py | Cl | 2: F, 3: Cl |
| 2-98 | Me | 2-Py | Cl | 2: Cl, 3: F |
| 2-100 | Me | 2-Py | H | |
| 2-101 | Me | 2-Py | Me | |
| 2-102 | Me | 2-Py | Et | |
| 2-103 | Me | 2-Py | $^n$Pr | |
| 2-104 | Me | 2-Py | $^n$Bu | |
| 2-105 | Me | 2-Py | $^i$Bu | |
| 2-106 | Me | 2-Py | $^n$Pentyl | |
| 2-107 | Me | 2-Py | CN | |
| 2-108 | Me | 2-Py | CONH$_2$ | |
| 2-109 | Me | 6-Cl-2-Py | Cl | |
| 2-111 | Me | 6-EtO-2-Py | Cl | |
| 2-113 | Me | 5-Cl-2-Py | Cl | |
| 2-115 | Me | 5-Me-2-Py | Cl | |
| 2-116 | Me | 5-Me-2-Py | NH$_2$ | |
| 2-118 | Me | 3-Me-2-Py | Cl | |
| 2-119 | Me | 3-Me-2-Py | NH$_2$ | |
| 2-121 | Me | 6-EtO-2-Py | Cl | 1: Me |
| 2-123 | Me | 3-Me-2-Py | Cl | 1: Me |
| 2-124 | Me | 3-Me-2-Py | NH$_2$ | 1: Me |
| 2-126 | Me | 6-MeO-2-Py | Cl | 4: Me |
| 2-127 | Me | 6-MeO-2-Py | NH$_2$ | 4: Me |
| 2-128 | Me | 6-EtO-2-Py | Cl | 4: Me |
| 2-129 | Me | 6-EtO-2-Py | NH$_2$ | 4: Me |
| 2-131 | Me | 5-Me-2-Py | Cl | 4: Me |
| 2-132 | Me | 5-Me-2-Py | NH$_2$ | 4: Me |
| 2-133 | Me | 3-Me-2-Py | Cl | 4: Me |
| 2-134 | Me | 3-Me-2-Py | NH$_2$ | 4: Me |
| 2-136 | Me | 3-Py | Cl | |
| 2-137 | Me | 3-Py | NH$_2$ | |
| 2-139 | Me | 3-Py | MeO | |
| 2-140 | Me | 4-Py | Cl | |
| 2-141 | Me | 4-Py | NH$_2$ | |
| 2-142 | Me | 4-Py | Me$_2$N | |
| 2-144 | Me | 2-Pyrimidinyl | Cl | |
| 2-145 | Me | 2-Pyrimidinyl | NH$_2$ | |
| 2-147 | Me | 4,6-Me-Pyrimidinyl | Cl | |
| 2-149 | Me | 1,3-thiazol-2-yl | Cl | |
| 2-150 | Me | 1,3-thiazol-2-yl | NH$_2$ | |
| 2-152 | Me | 2-quinolinyl | Cl | 4: Me |
| 2-153 | Me | 2-quinolinyl | NH$_2$ | 4: Me |
| 2-157 | H | 2-Py | Cl | |
| 2-158 | H | 2-Py | NH$_2$ | |
| 2-160 | H | 2-Py | Cl | 2: Cl |
| 2-162 | H | 2-Py | Cl | 1: F |
| 2-164 | H | 2-Py | Cl | 2: F |
| 2-166 | CF$_3$ | 2-Py | Cl | |
| 2-168 | CH$_2$Br | 2-Py | Cl | |
| 2-169 | Et | 2-Py | Cl | |
| 2-170 | Et | 2-Py | NH$_2$ | |
| 2-172 | $^i$Pr | 2-Py | Cl | |

TABLE 7-continued

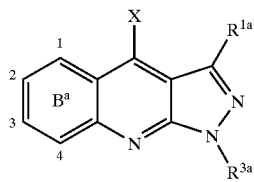

| Example Number | R¹ᵃ | R³ᵃ | X | Substituent of Ring Bᵃ |
|---|---|---|---|---|
| 2-175 | CH₂COOMe | 2-Py | Cl | |
| 2-179 | COOEt | 2-Py | Cl | |
| 2-183 | 4-MeOPh | 2-Py | Cl | |
| 2-184 | 4-MeOPh | 2-Py | NH₂ | |
| 2-186 | Me | 2-Py-CH₂ | Cl | |
| 2-187 | Me | 2-Py-CH₂ | NH₂ | |
| 2-188 | Me | 2-Py-CH₂ | Me₂N | |
| 2-190 | Me | 2-Py-CH₂ | MeO | |
| 2-198 | H | 2-Py | Cl | 2,3: F |
| 2-200 | Et | 2-Py | Cl | 2,3: F |
| 2-202 | Me | 3-Py | Cl | 2,3: F |
| 2-204 | Me | 4-Py | Cl | 2,3: F |
| 2-207 | H | 2-Py | Cl | |

TABLE 11

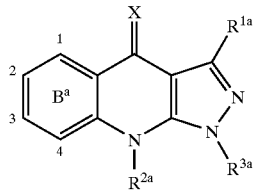

| Example Number | R¹ᵃ | R²ᵃ | R³ᵃ | X | Substituent of Ring A |
|---|---|---|---|---|---|
| 2-12 | Me | H | 2-Py | O | |
| 2-13 | Me | H | 2-Py | O | |
| 2-14 | Me | Me | 2-Py | O | |
| 2-24 | Me | H | 2-Py | S | |
| 2-31 | Me | H | 2-Py | O | 1: Me |
| 2-34 | Me | H | 2-Py | O | 2: Me |
| 2-38 | Me | H | 2-Py | O | 4: Me |
| 2-40 | Me | H | 2-Py | O | 2: CF₃ |
| 2-43 | Me | H | 2-Py | O | 2: MeO |
| 2-48 | Me | H | 2-Py | O | 2, 3: MeO |
| 2-50 | Me | H | 2-Py | O | 2: MeS |
| 2-51 | Me | H | 2-Py | O | 2: MeSO |
| 2-52 | Me | H | 2-Py | O | 2: MeSO₂ |
| 2-54 | Me | H | 2-Py | O | 2: NO₂ |
| 2-55 | Me | H | 2-Py | O | 2: NH₂ |
| 2-56 | Me | H | 2-Py | O | 2: Me₂N |
| 2-58 | Me | H | 2-Py | O | 3: NO₂ |
| 2-59 | Me | H | 2-Py | O | 3: NH₂ |
| 2-61 | Me | H | 2-Py | O | 1: CO₂Me |
| 2-62 | Me | H | 2-Py | O | 1: CO₂H |
| 2-64 | Me | H | 2-Py | O | 2: CO₂Me |
| 2-65 | Me | H | 2-Py | O | 2: CO₂H |
| 2-67 | Me | H | 2-Py | O | 3: CO₂Me |
| 2-68 | Me | H | 2-Py | O | 3: CO₂H |
| 2-69 | Me | H | 2-Py | O | 1: Cl |
| 2-72 | Me | H | 2-Py | O | 2: Cl |
| 2-74 | Me | H | 2-Py | O | 3: Cl |
| 2-76 | Me | H | 2-Py | O | 2, 3: Cl |
| 2-77 | Me | H | 2-Py | O | 2, 4: Cl |
| 2-79 | Me | H | 2-Py | O | 1: F |
| 2-81 | Me | H | 2-Py | O | 2: F |
| 2-83 | Me | H | 2-Py | O | 3: F |
| 2-85 | Me | H | 2-Py | O | 4: F |
| 2-87 | Me | H | 2-Py | O | 2: Br |

TABLE 11-continued

| Example Number | R¹ᵃ | R²ᵃ | R³ᵃ | X | Substituent of Ring A |
|---|---|---|---|---|---|
| 2-89 | Me | H | 2-Py | O | 1, 2: F |
| 2-91 | Me | H | 2-Py | O | 2, 3: F |
| 2-92 | Me | H | 2-Py | O | 2, 3: F |
| 2-93 | Me | ⁿPr | 2-Py | O | 2, 3: F |
| 2-97 | Me | H | 2-Py | O | 2: F, 3: Cl |
| 2-99 | Me | H | 2-Py | O | 2: Cl, 3: F |
| 2-110 | Me | H | 6-Cl-2-Py | O | |
| 2-112 | Me | H | 6-EtO-2-Py | O | |
| 2-114 | Me | H | 5-Cl-2-Py | O | |
| 2-117 | Me | H | 5-Me-2-Py | O | |
| 2-120 | Me | H | 3-Me-2-Py | O | |
| 2-122 | Me | H | 6-EtO-2-Py | O | 1: Me |
| 2-125 | Me | H | 3-Me-2-Py | O | 1: Me |
| 2-130 | Me | H | 6-EtO-2-Py | O | 4: Me |
| 2-135 | Me | H | 3-Me-2-Py | O | 4: Me |
| 2-138 | Me | H | 3-Py | O | |
| 2-143 | Me | H | 4-Py | O | |
| 2-146 | Me | H | 2-Pyrimidinyl | O | |
| 2-148 | Me | H | 4,6-Me-Pyrimidinyl | O | |
| 2-151 | Me | H | 1,3-thiazol-2-yl | O | |
| 2-154 | Me | H | 2-quinolinyl | O | 4: Me |
| 2-159 | H | H | 2-Py | O | |
| 2-161 | H | H | 2-Py | O | 2: Cl |
| 2-163 | H | H | 2-Py | O | 1: F |
| 2-165 | H | H | 2-Py | O | 2: F |
| 2-167 | CF₃ | H | 2-Py | O | |
| 2-171 | Et | H | 2-Py | O | |
| 2-173 | ⁱPr | H | 2-Py | O | |
| 2-174 | ⁱBu | H | 2-Py | O | |
| 2-176 | CH₂COOMe | H | 2-Py | O | |
| 2-177 | CH₂COOH | H | 2-Py | O | |
| 2-178 | CH₂CONH₂ | H | 2-Py | O | |
| 2-180 | COOEt | H | 2-Py | O | |
| 2-181 | COOH | H | 2-Py | O | |
| 2-182 | Ph | H | 2-Py | O | |
| 2-185 | 4-MeOPh | H | 2-Py | O | |
| 2-189 | Me | H | 2-Py-CH₂ | O | |
| 2-191 | Me | H | 3-Py-CH₂ | O | |
| 2-192 | Me | H | 4-Py-CH₂ | O | |
| 2-199 | H | H | 2-Py | O | 2,3: F |
| 2-201 | Et | H | 2-Py | O | 2,3: F |
| 2-203 | Me | H | 3-Py | O | 2,3: F |
| 2-205 | Me | H | 4-Py | O | 2,3: F |
| 2-206 | H | H | 2-Py | O | |
| 2-208 | Me | H | 6-Me-2-Py | O | |
| 2-209 | Me | H | 6-Me-2-Py | O | 2,3: F |

TABLE 14

[Structure: pyrazolo[3,4-b]pyridine core with X at 4-position, CH₃ at 3-position, Ring Bᵃ fused, and 2-pyridyl on N1]

| Example Number | X | Ring Bᵃ |
|---|---|---|
| 2-155 | Cl | thiophene (S, with double bond) |
| 2-156 | OH | dihydrothiophene (S) |
| 2-193 | OH | cyclopentane |
| 2-194 | OH | cyclohexane |
| 2-195 | OH | cycloheptane |
| 2-196 | Cl | pyridine (N) |
| 2-197 | OH | pyridine (N) |

FORMULATION EXAMPLE 2-1

| | |
|---|---|
| (1) The compound obtained in Example 2-1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound obtained in Example 2-1 (10.0 g), lactose (60.0 g), and cornstarch (35.0 g) was sieved through a 1 mm mesh sieve by the use of an aqueous solution of 10 wt % gelatin (30 ml, 3.0 g as gelatin), and the resulting granules were dried at 40° C., and sieved once again. The granules thus obtained were mixed with magnesium stearate (2.0 g) and compressed. The core tablet thus obtained was sugarcoated by the use of an aqueous suspension containing sucrose, titanium dioxide, talc and gum acacia. The coated tablets were glazed with beeswax to give 1000 coated tablets.

FORMULATION EXAMPLE 2-2

| | |
|---|---|
| (1) The compound obtained in Example 2-1 | 10.0 g |
| (2) Lactose | 70.0 g |
| (3) Cornstarch | 50.0 g |
| (4) Soluble starch | 7.0 g |
| (5) Magnesium stearate | 3.0 g |

A mixture of the compound obtained in Example 2-1 (10.0 g) and magnesium stearate (3.0 g) was granulated by the use of an aqueous solution of soluble starch (70 ml, 7.0 g as soluble starch), and the resulting granules were dried, and mixed with lactose (70.0 g) and cornstarch (50.0 g). The mixture was compressed to give 1000 tablets.

EXPERIMENTAL EXAMPLE

The gene manipulation methods described in Experimental Example below are carried out in accordance with the methods described in Maniatis et al., Molecular Cloning (Cold Spring Harbor Laboratory, 1989) or the methods described in the protocols attached to reagents.

Preparation of Microsome Fractions

Preparation of Human COX-1 cDNA Recombinant Baculovirus

A 1.8 kb DNA fragment containing human COX-1 cDNA (FASEB J., vol. 5 (9), p. 2304–2312 (1991)) prepared by the PCR method was inserted into plasmid pFASTBAC1 (CIBCOBRL) to obtain a plasmid pFBCOX1.

Using the plasmid pFBCOX1 and BAC-TO-BAC Baculovirus Expression System (GIBCOBRL), a virus stock BAC-COX1 of the recombinant baculovirus was prepared.

Preparation of Microsome Fractions from COX-1 Expressing Insect Cells

Sf-21 cells were inoculated in 125 mL of Sf-900 II SFM medium (GIBCOBRL) at a concentration of 1×10⁶ cells/mL, and the medium was incubated at 27° C. for 24 hours. 0.75 mL of the virus stock BAC-COX1 of the recombinant baculovirus was added thereto, and the mixture was incubated further for 72 hours. The cells were separated from the medium by centrifugation (3000 rpm, 10 min), and washed with PBS twice. The cells were suspended in 10 mL of a Lysis buffer (0.1M Tris-HCl (pH 7.4), 5 mM EDTA), and were treated with a homogenizer (POLYTRON) three times at 20000 rpm for 20 seconds so that the cells were crushed. The supernatant obtained after centrifugation (2000 rpm, 10 minutes) was further centrifuged (40000 rpm, 45 minutes) to give a precipitate, which was resuspended in a Lysis buffer (0.1M Tris-HCl (pH 7.4), 5 mM EDTA), and the suspension was stored at −80° C.

Preparation of Human COX-2 cDNA Recombinant Baculovirus

A 1.8 kb DNA fragment containing human COX-2 cDNA (Proc. Natl. Acad. Sci. U.S.A., vol. 89 (16), p. 7384–7388 (1992)) prepared by the PCR method was inserted into plasmid pFASTBAC1 (CIBCOBRAL) to obtain a plasmid pFBCOX2.

Using the plasmid pFBCOX2 and BAC-TO-BAC Baculovirus Expression System (GIBCOBRAL), a virus stock BAC-COX2 of the recombinant baculovirus was prepared.

Preparation of Microsome Fractions from COX-2 Expressing Insect Cells

Sf-21 cells were inoculated in 125 mL of LSf-900 II SFM medium (GIBCOBRAL) at a concentration of 1×10⁶ cells/ mL, and the medium was incubated at 27° C. for 24 hours. 0.75 mL of the virus stock BAC-COX2 of the recombinant baculovirus was added thereto, and was incubated further for 72 hours. The cells were separated from the medium by centrifugation (3000 rpm, 10 min), and washed with PBS twice. The cells were suspended in 10 mL of a Lysis buffer (0.1M Tris-HCl (pH 7.4), 5 mM EDTA), and were treated with a homogenizer (POLYTRON), three times at 20000 rpm for 20 seconds so that the cells were crushed. The supernatant thus obtained after centrifugation (2000 rpm, 10 minutes) was further centrifuged (40000 rpm, 45 minutes) to obtain a precipitate, which was resuspended in a Lysis buffer (0.1M Tris-HCl (pH 7.4), 5 mM EDTA), and the suspension was stored at −80° C.

EXPERIMENTAL EXAMPLE 2-1

Determination of COX-1 and COX-2 Inhibitory Activities

To a mixture of 20 µL of a reaction buffer previously concentrated 10 times (1M Tris-HCl (pH8.0), 50 mM EDTA, 1.0% Tween 20, 50 mM luminol, 100 µM hematin), 20 µL of the microsome fractions (COX-1: 40 µg, COX-2: 20 µg), and 55 µL of distilled water, a sample compound dissolved in DMF (5 µL) was added, and the mixture was left at 37° C. for 25 minutes. The reaction was started by the addition of 20 µM arachidonic acid (100 µL), and chemiluminescence amount during the 10-second period after the addition of arachidonic acid was determined by the use of Lumistar (BMG Lab technologies, GmbH). The inhibition rate was calculated, regarding that the enzyme activity when DMF (5 mL) was added was 100%, and the enzyme activity when 4 mM flurbiprofen (5 µL) was added was 0%. The results are shown in Table 15.

TABLE 15

| Compound | Repression rate IC$_{50}$ (µM) | |
|---|---|---|
| (Example No.) | COX-1 | COX-2 |
| 2-6 | 21.7 | 65.1 |
| 2-17 | 7.28 | 49.2 |
| 2-21 | 4.21 | 86.0 |
| 2-61 | 2.00 | 44.0 |
| 2-91 | 0.527 | 0.295 |
| 2-92 | 0.677 | 0.465 |
| 2-99 | 0.263 | 0.213 |
| 2-161 | 0.600 | 0.360 |
| 2-79 | 7.80 | 3.70 |
| 2-159 | 2.66 | 1.37 |

The results in Table 15 indicate that the compound (I) of the present invention has an excellent cyclooxygenase inhibition activity.

EXPERIMENTAL EXAMPLE 2-2

Anti-Inflammatory Activity

Carrageenin Edema Method

Male SD-rats (6 weeks old, CLEA Japan) were used (1 group, n=6). The Carrageenin edema method was performed according to the method of Winter et. al., (Proc. Soc. Exp. Biol. Med., vol. 111, p. 544–547, 1962). After the volume of right hind limb plantar of the rat was determined, a sample was orally administered (1.0 mL, b.w.), and immediately water was orally administered in an amount of 5 mL/rat. Meanwhile, only the solvent of the sample was orally administered to rats in control. After 1 hour, a solution of 1% carrageenin in saline (0.05 mL) was injected into the right hind limb plantar subcutaneously to induce edema. After 2 and 3 hours later from the injection, volumes of the right hind limb plantar were determined. The repression rate (%) of the sample was calculated by comparing the difference of the volumes of the plantar before the carrageenin shot and 2 and 3 hours after the shot between the sample groups and the control groups. The results are shown in Table 16.

TABLE 16

| Compound | Repression rate (%) Dosage 10 mg/kg | |
|---|---|---|
| (Example No.) | 2 hr later | 3 hr later |
| 2-6 | 43** | 35** |
| 2-17 | 45** | 37** |
| 2-21 | 52** | 45** |
| 2-61 | 36* | 28* |
| 2-91 | 51** | 42** |
| 2-99 | 46** | 41** |
| 2-161 | 33** | 33** |
| 2-79 | 37** | 33** |
| 2-159 | 50** | 39 |

**$p < 0.05$, *$p < 0.01$ vs. control.

The results in Table 16 indicate that the compound (I) of the present invention has an excellent anti-inflammatory activity.

EXPERIMENTAL EXAMPLE 2-3

Analgesic Activity

Acetic Acid Rising Method

Male ICR-mice (5 weeks old, CLEA Japan) were used (1 group, n=10), and a sample was orally administered (0.2 mL/10 g, b.w.). After 30 minutes, 0.6% acetic acid solution was injected to mice intraperitoneally (0.1 mL/10 g, b.w.), and the mice were immediately transferred into an observation cage made of a transparent acrylic resin. The number of rising and stretching during the following period of 20 minutes was counted. The repression rate (%) was calculated by comparing the average numbers between the sample groups and the control groups. The results are shown in Table 17.

TABLE 17

| Compound (Example No.) | Repression rate (%) Dosage 10 mg/kg |
|---|---|
| 2-6 | 57** |
| 2-17 | 49* |
| 2-21 | 56** |
| 2-61 | 75** |
| 2-91 | 65** |
| 2-99 | 39* |
| 2-161 | 74** |
| 2-79 | 38** |
| 2-159 | 69** |

**$p < 0.05$, *$p < 0.01$ vs. control.

The results in Table 17 indicate that the compound (I) of the present invention has an excellent analgesic activity.

EXPERIMENTAL EXAMPLE 2-4

Antipyretic Activity in Yeast-Induced Pyrexia

Antipyretic activity was determined using male SD origin male-rats (7 weeks old, CLEA Japan, 1 group: n=6), according to the method of winter et. al. (J. Pharmacol. Exp. Ther., vol. 138, p. 405, 1963). Before 16 hours from measurement of body temperature, a suspension of 15% yeast in saline was injected subcutaneously (10 mL/kg, b.w.) into the rats to induce fever, and simultaneously supply of food was terminated while water was made available all the time. Each of the rats was raised separately. After 16 hours from the yeast shot, a thermistor terminal was inserted at an about 4 cm depth into rectum every hour, and the body temperatures after 30 seconds were recorded. After 18 hours, rats developing fevers consistently were selected, and a sample was orally administered to the rats (5 mL/kg, b.w.), while to the control, only the solvent was administered. After the administration, body temperatures were measured every hour for a period of 6 hours, and the maximum difference in body temperature between the rats in the sample group and in the control group were determined as $\Delta$ (° C.). The results are shown in Table 18.

TABLE 18

| Compound (Example No.) | $\Delta$ (° C.) Dosage 10 mg/kg |
|---|---|
| 2-6 | 0.8** |
| 2-17 | 1.5** |
| 2-18 | 1.7** |
| 2-21 | 1.8** |
| 2-79 | 1.4** |
| 2-91 | 1.5** |
| 2-161 | 1.4** |
| 2-159 | 1.8** |

**$p < 0.05$, *$p < 0.01$ vs. control.

The results in Table 18 indicate that the compound (I) of the present invention has an excellent antipyretic activity.

EXPERIMENTAL EXAMPLE 2-5

Anti-Adjuvant-Arthritic Activity

Male SD origin male-rats (6 weeks old, CLEA Japan, 1 group: n=7) were used. The adjuvant arthritis method was conducted according to the method of Newbould B. B. et. al., (Brit. J. Pharmacol. Chemother., vol. 21, p. 127, 1963). Complete Freund's adjuvant (a suspension of killed tubercule bacillus in liquid paraffin at a concentration of 0.5%, 0.05 mL) was injected into the right hind limb footpad intracutaneouly to induce multiple arthritis. Samples were administered orally (10 mg/kg, b.w.), once a day for 14 days from the day before the injection day 0 to day 13. Volume of the left hind limb (not injected) was determined by the foot-volume measurement apparatus manufactured by Ugo Basile, on the day just before the adjuvant shot (Day 0), Day 10 and Day 14, and repression rate (%) was calculated comparing the values between the sample group and the control group. The results are shown in Table 19.

TABLE 19

| Compound (Example No.) | Repression rate (%) Dosage 10 mg/kg |
|---|---|
| 2-17 | 61* |
| 2-18 | 47 |
| 2-81 | 56 |
| 2-83 | 65* |
| 2-91 | 76** |

**$p < 0.05$, *$p < 0.01$ vs. control

The results in Table 19 indicate that the compound (I) of the present invention has an excellent anti-inflammatory activity.

EXPERIMENTAL EXAMPLE 2-6

Disorder of Gastric Mucosa

Male SD origin male-rats (7 weeks old, CLEA Japan) were used. After 24 hours from the termination of food supply, samples were orally administered (5 mL/kg, b.w.). After 5.5 hours, Evan's Blue (0.5% Evan's Blue/saline) was injected intravenously (1 mL/rat) under no anesthesia. After 30 minutes from the shot, the stomach (with esophagus and duodenum of 1.5 to 2 cm length) was removed by celiotomy, and subsequently, the esophagus terminal was closed with a clip, and a 8 mL of 1% formalin solution was injected into the stomach through the duodenum, which was also closed with a clip after the injection. The stomach was left contacting with the 1% formalin solution for more than 10 minutes, and subsequently cut open from duodenum along the greater curvature of stomach. The stomach was washed and spread on a filter paper, and the length of each of the spots dyed by Evan's Blue (hemorrhagic portion: mucosal ablation to ulcer) was measured under a stereomicroscope, and the total length (mm) was calculated by a counter and recorded. The results are shown in Table 20.

TABLE 20

| Compound (Example No.) | Total length of dyed spots (mm) |
|---|---|
| 2-91 | 0 (1000 mg/kg) |
| 2-92 | 0 (1000 mg/kg) |
| 2-79 | 0 (300 mg/kg) |
| 2-159 | 0 (300 mg/kg) |

EXPERIMENTAL EXAMPLE 2-7

Disorder of Mucosa of Small Intestine

Male SD origin male-rats (7 weeks old, CLEA Japan) were used. To the rats freely fed, samples were administered orally (5 mL/kg, b.w.). After 5.5 hours from the administration, Evan's Blue (0.5% Evan's Blue/saline) was injected (1 mL/rat) intravenously under no anesthesia. After 30 minutes from the shot, the intestine was removed by celiotomy and the area thereof facing mesentery was cut open. After removal of intestinal content, the spots in the intestine dyed by Evan's Blue were measured under a stereomicroscope, and the total length (mm) of the spots was determined by a counter and recorded. The results are shown in Table 21.

TABLE 21

| Compound (Example No.) | Total length of dyed spots (mm) |
|---|---|
| 2-12 | 0 (100 mg/kg) |
| 2-17 | 0 (300 mg/kg) |
| 2-40 | 0 (100 mg/kg) |
| 2-92 | 0 (300 mg/kg) |
| 2-79 | 0 (300 mg/kg) |
| 2-159 | 0 (300 mg/kg) |

INDUSTRIAL APPLICABILITY

The compound (I) of the present invention or the salt thereof (1) suppresses Th2 immune responses by inhibiting production of IL-4, IL-5 and IgE associated with allergic reactions, and consequently controls the balance of Th1 and Th2, and thus provides a novel drug for prevention and/or treatment of allergic diseases, (2) inhibits both cyclooxgenases-1 and -2, and thus has excellent anti-inflammatory, analgesic, and antipyretic activities. It has extremely low possibility of inducing gastrointestinal disorders, compared with the conventional anti-inflammatory and analgesic drugs. Therefore, clinically useful drugs as an anti-inflammatory and analgesic drug are provided. Furthermore, the compound (I) of the present invention or the salt thereof is excellent in pharmacokinetics and also in solubility in water.

What is claimed is:

1. A compound represented by the formula (Ia'):

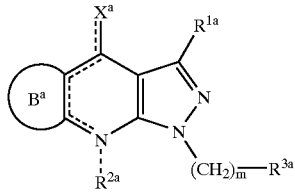

wherein $R^{1a}$ is a hydrogen atom, a hydrocarbon group which may be optionally substituted, or a carboxyl group which may be esterified or amidated; $R^{2a}$ is absent, a hydrogen atom or a hydrocarbon group which may be optionally substituted, $R^{3ab}$ is an unsaturated heterocyclic group containing 1 or 2 nitrogen atoms as the hetero atoms which may be optionally substituted, or an unsaturated monocyclic heterocyclic group containing a nitrogen atom and a sulfur atom as the hetero atoms; $X^a$ is hydrogen, halogen, nitrile, a hydrocarbon group which may be optionally substituted, a carboxyl group which may be optionally esterified or amidated, an acyl group which may be optionally substituted, —$NR^{4a}R^{5a}$, an oxygen atom, —$OR^{4a}$, a sulfur atom, or —$SR^{4a}$($R^{4a}$ and $R^{5a}$ are, respectively, a hydrogen atom, a hydrocarbon group which may be optionally substituted, or both may bind each other to form a cyclic amino group or a heterocyclic group with the nitrogen atom bound thereto); bond portions indicated by both solid and broken lines are either a single bond or a double bond, and bond portions indicated by a broken line are either a single bond or no bond ring $B^a$ is a homocyclic or heterocyclic 5- to 7-membered ring which may be optionally substituted; and m is an integer of 0 or 1, or a salt thereof.

2. The compound according to claim 1, wherein $R^{1a}$ and $R^{2a}$ are, respectively, an alkyl group, an alkenyl group, an alkynyl group, a cycloalkyl group or an aryl group, each of the groups having 1 to 16 carbon atoms, or a salt thereof.

3. The compound according to claim 1, wherein $R^{3ab}$ is pyridinyl which may be optionally substituted by (1) a halogen atom, (2) a lower alkyl group, (3) a cycloalkyl group, (4) a lower alkynyl group, (5) a lower alkenyl group, (6) an aralkyl group, (7) an aryl group, (8) a lower alkoxy group, (9) an aryloxy group, (10) a lower alkanoyl group, (11) an arylcarbonyl group, (12) a lower alkanoyloxy group, (13) an arylcarbonyloxy group, (14) a carboxyl group, (15) a lower alkoxycarbonyl group, (16) an aralkyloxycarbonyl group, (17) a carbamoyl group, (18) a mono-, di- or tri-halogeno-lower alkyl group, (19) an amidino group, (20) an amino group, (21) a mono-lower alkylamino group, (22) a di-lower alkylamino group, (23) a 3- to 6-membered cyclic amino group which may optionally containing 1 to 3 atoms selected from oxygen, sulfur and nitrogen atoms as the hetero atoms as well as carbon atoms and a nitrogen atom, (24) an alkylenedioxy group, (25) a hydroxyl group, (26) a nitro group, (27) a cyano group, (28) a mercapto group, (29) a sulfo group, (30) a sulfino group, (31) a phosphono group, (32) a sulfamoyl group, (33) a monoalkylsulfamoyl group, (34) a dialkylsulfamoyl group, (35) an alkylthio group, (36) an arylthio group, (37) a lower alkylsulfinyl group, (38) an arylsulfinyl group, (39) a lower alkylsulfonyl group, or (40) an arylsulfonyl group, or a salt thereof.

4. The compound according to claim 1, wherein $X^a$ is an oxygen atom or $OR^{4a}$ ($R^{4a}$ is a hydrogen atom or a hydrocarbon group which may be optionally substituted by (1) a halogen atom, (2) a nitro group, (3) a cyano group, (4) a hydroxyl group, (5) a lower alkyl group which may be optionally halogenated, (6) a lower alkoxy group, (7) an amino group, (8) a mono-lower alkylamino group, (9) a di-lower alkylamino group, (10) a carboxyl group, (11) a lower alkylcarbonyl group, (12) a lower alkoxycarbonyl group, (13) a carbamoyl group, (14) a mono-lower alkylcarbamoyl group, (15) a di-lower alkylcarbamoyl group, (16) an arylcarbamoyl group, (17) an aryl group, (18) an aryloxy group or (19) a lower alkylcarbonylamino group which may be optionally halogenated) or a salt thereof.

5. The compound according to claim 1, wherein $R^{3ab}$ is a nitrogen-containing aromatic heterocyclic group, and ring $B^a$ is a benzene ring which may be optionally substituted by (1) a halogen atom, (2) a hydrocarbon group which may be optionally substituted, (3) an amino group which may be optionally substituted, (4) a lower alkoxy group which may be optionally substituted, (5) a lower alkylenedioxy group (6) an aryloxy group, (7) a lower alkanoyl group, (8) an arylcarbonyl, (9) a lower alkanoyloxy group, (10) an arylcarbonyloxy group, (11) a carboxyl group, (12) a lower alkoxycarbonyl group, (13) an aralkyloxycarbonyl group, (14) a carbamoyl group, (15) a mono-, di- or tri-halogeno-lower alkyl group, (16) an amidino group, (17) an amino group, (18) a mono-lower alkylamino group, (19) a di-lower alkylamino group, (20) a 3- to 6-membered cyclic amino group which may contain 1 to 3 atoms selected from the group consisting of oxygen, sulfur and nitrogen atoms as the hetero atom as well as carbon atoms and one nitrogen atom, (21) an alkylenedioxy group, (22) a hydroxyl group, (23) a nitro group, (24) a cyano group, (25) a mercapto group, (26) a sulfo group, (27) a sulfino group, (28) a phosphono group, (29) a sulfamoyl group, (30) a monoalkylsulfamoyl group, (31) a dialkylsulfamoyl group, (32) an alkylsulfanyl group, (33) an arylsulfanyl group, (34) a lower alkylsulfinyl group, (35) an arylsulfinyl group, (36) a lower alkylsulfonyl group, or (37) an arylsulfonyl group, or a salt thereof.

6. The compound according to claim 1, wherein the compound is, 6,7-difluoro-3-methyl-1-(2-pyridinyl)-1,9-dihydro-4H-pyrazolo[3,4-b]quinoline-4-one, 3-methyl-1-(2-pyridinyl)-6-(trifluoromethyl)-1,9-dihydro-4H-pyrazolo[3,4-b]quinoline-4-one, 6-fluoro-3-methyl-1-(2-pyridinyl)-1,9-dihydro-4H-pyrazolo[3,4-b]quinoline-4-one, 7-fluoro-3-methyl-1-(2-pyridinyl)-1,9-dihydro-4H-pyrazolo[3,4-b]quinoline-4-one, 3-ethyl-6,7-difluoro-1-(2-pyridinyl)-1,9-dihydro-4H-pyrazolo[3,4-b]quinoline-4-one, 6,7-difluoro-3-methyl-1-(3-pyridinyl)-1,9-dihydro-4H-pyrazolo[3,4-b]quinoline-4-one, 6,7-difluoro-3-methyl-1-(6-methyl-2-pyridinyl)-1,9-dihydro-4H-pyrazolo[3,4-b]quinolin-4-one, 6,7-difluoro-3-methyl-1-(6-phenyl-2-pyridinyl)-1,9-dihydro-4H-pyrazolo[3,4-b]quinoline-4-one, 5-fluoro-3-methyl-1-(2-pyridinyl)-1,9-dihydro-4H-pyrazolo[3,4-b]quinoline-4-one, or 1-(2-pyridinyl)-1,9-dihydro-4H-pyrazolo[3,4-b]quinoline-4-one, or a salt thereof.

7. A process for producing the compound according to claim 1, which is represented by the formula (Ia"):

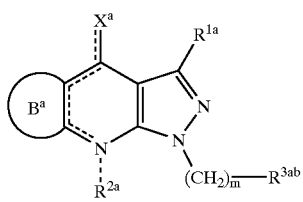

wherein, $R^{1a}$ is a hydrogen atom, a hydrocarbon group which may be optionally substituted, or a carboxyl group which may be optionally esterified or amidated; and $R^{2a}$ is absent, a hydrogen atom, or a hydrocarbon group which may be optionally substituted, and $R^{3ab}$ is an unsaturated heterocyclic group containing 1 or 2 nitrogen atoms as the hetero atoms, which may be optionally substituted, or a unsaturated monocyclic heterocyclic group containing one nitrogen atom and one sulfur atom as the hetero atoms, $X^a$ is hydrogen, halogen, nitrile, a hydrocarbon group which may be optionally substituted, a carboxyl group which may be optionally esterified or amidated, an acyl group which may be optionally substituted, $-NR^{4a}R^{5a}$, an oxygen atom, $-OR^{4a}$ sulfur atom, or $-SR^{4a}$ ($R^{4a}$ and $R^{5a}$ are, respectively, a hydrogen atom, a hydrocarbon group which may be optionally substituted, or may bind to each other to form a cyclic amino group or a heterocyclic group with the nitrogen atom bound thereto); and m is an integer of 0 or 1, or a salt thereof, which comprises subjecting a compound represented by the formula (IIIa):

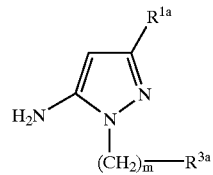

wherein, each symbol is as defined above, or a salt thereof, to a reaction, in the presence of an acidic compound, with a 2-oxocycloalkanecarboxylic ester represented by the formula (X):

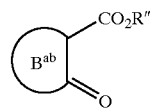

wherein, R" is a hydrocarbon group which may be optionally substituted, and ring $B^{ab}$ is a 5- to 7-membered cycloalkane which may be optionally substituted, or a salt thereof.

* * * * *